(12) United States Patent
Hacohen et al.

(10) Patent No.: US 10,993,997 B2
(45) Date of Patent: May 4, 2021

(54) METHODS FOR PROFILING THE T CELL REPERTOIRE

(71) Applicants: The Broad Institute, Inc., Cambridge, MA (US); Dana-Farber Cancer Institute, Inc., Boston, MA (US); The General Hospital Corporation, Boston, MA (US)

(72) Inventors: Nir Hacohen, Brookline, MA (US); Catherine Ju-Ying Wu, Boston, MA (US); Edward F. Fritsch, Concord, MA (US); Ute E. Burkhardt, Belmont, MA (US)

(73) Assignees: The Broad Institute, Inc., Cambridge, MA (US); Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/537,785

(22) PCT Filed: Dec. 21, 2015

(86) PCT No.: PCT/US2015/067154
§ 371 (c)(1),
(2) Date: Jun. 19, 2017

(87) PCT Pub. No.: WO2016/100977
PCT Pub. Date: Jun. 23, 2016

(65) Prior Publication Data
US 2018/0000913 A1 Jan. 4, 2018

Related U.S. Application Data

(60) Provisional application No. 62/094,859, filed on Dec. 19, 2014.

(51) Int. Cl.
| | |
|---|---|
| *C07K 16/18* | (2006.01) |
| *G01N 33/68* | (2006.01) |
| *G01N 33/50* | (2006.01) |
| *A61K 39/00* | (2006.01) |
| *C12N 15/10* | (2006.01) |
| *A61K 35/17* | (2015.01) |
| *C12Q 1/6881* | (2018.01) |
| *G01N 33/569* | (2006.01) |

(52) U.S. Cl.
CPC .......... *A61K 39/0011* (2013.01); *A61K 35/17* (2013.01); *C12N 15/1093* (2013.01); *C12Q 1/6881* (2013.01); *G01N 33/56972* (2013.01); *A61K 2039/515* (2013.01); *A61K 2039/5158* (2013.01); *A61K 2039/572* (2013.01); *C12Q 2600/158* (2013.01); *C12Q 2600/16* (2013.01); *G01N 2500/10* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 3,870,790 A | 3/1975 | Lowey et al. |
| 4,210,644 A | 7/1980 | Ewing et al. |
| 4,226,859 A | 10/1980 | Stach |
| 4,369,172 A | 1/1983 | Schor et al. |
| 4,379,454 A | 4/1983 | Campbell et al. |
| 4,452,775 A | 6/1984 | Kent |
| 4,588,585 A | 5/1986 | Mark et al. |
| 4,603,112 A | 7/1986 | Paoletti et al. |
| 4,656,127 A | 4/1987 | Mundy |
| 4,675,189 A | 6/1987 | Kent et al. |
| 4,683,195 A | 7/1987 | Mullis et al. |
| 4,683,202 A | 7/1987 | Mullis |
| 4,690,915 A | 9/1987 | Rosenberg |
| 4,722,848 A | 2/1988 | Paoletti et al. |
| 4,743,249 A | 5/1988 | Loveland |

(Continued)

FOREIGN PATENT DOCUMENTS

| | | |
|---|---|---|
| CN | 103180730 A | 6/2013 |
| EP | 2569633 | 5/2011 |

(Continued)

OTHER PUBLICATIONS

Rajasgi et al Systematic identification of personal tumor-specific neoantigens in chronic lymphocytic leukemiaBlood. Jul. 17, 2014; 124(3):453-62.*
Mosmann et al., THI and TH2 Cells: Different Patterns of Lymphokine Secretion Lead to Different Functional Properties Ann. Rev. Innn-nunol. 1989. 7: 145-73.*
Parnini et al Unique Human Tumor Antigens: Immunobiology and Use in Clinical Trials1 J Immunol Feb. 15, 2007, 178 (4) 1975-1979.*
Lennerz et al., The response of autologous T cells to a human melanoma is dominated by mutated neoantigensPNAS Nov. 1, 2005 vol. 102 No. 44 16013-16018 Medical Sciences.*

(Continued)

Primary Examiner — Maria G Leavitt
(74) Attorney, Agent, or Firm — Foley Hoag LLP

(57) ABSTRACT

The present disclosure relates to methods for profiling subject specific and personalized T cell receptor (TCR) repertoires using a single-cell sequencing method. More particularly, disclosed are methods for determining binding of T cell receptors to subject specific neoantigens. In addition, the techniques herein may identify the antigenic targets of T cell receptors in the context of tumor neoantigens. Moreover, the present disclosure enables the discovery of T cell targets in numerous diseases, with implications for understanding the basic mechanisms of the mammalian immune response and for developing antigen-specific diagnostic markers and therapies. Finally, cloned TCRs can be used to formulate personalized immunotherapies for those inflicted with a disease, such as cancer.

41 Claims, 24 Drawing Sheets
Specification includes a Sequence Listing.

(56) References Cited

U.S. PATENT DOCUMENTS

| | | |
|---|---|---|
| 4,751,180 A | 6/1988 | Cousens et al. |
| 4,769,330 A | 9/1988 | Paoletti et al. |
| 4,816,540 A | 3/1989 | Onishi |
| 4,842,866 A | 6/1989 | Horder et al. |
| 4,844,893 A | 7/1989 | Honsik et al. |
| 4,906,169 A | 3/1990 | Chien et al. |
| 4,935,233 A | 6/1990 | Bell et al. |
| 4,973,468 A | 11/1990 | Chiang et al. |
| 5,023,084 A | 6/1991 | Chien et al. |
| 5,035,891 A | 7/1991 | Runkel et al. |
| 5,110,587 A | 5/1992 | Paoletti et al. |
| 5,133,974 A | 7/1992 | Paradissis et al. |
| 5,174,993 A | 12/1992 | Paoletti |
| 5,185,146 A | 2/1993 | Altenburger |
| 5,198,223 A | 3/1993 | Gale et al. |
| 5,204,253 A | 4/1993 | Sanford et al. |
| 5,217,720 A | 6/1993 | Sekigawa et al. |
| 5,279,833 A | 1/1994 | Rose |
| 5,364,773 A | 11/1994 | Paoletti et al. |
| 5,407,686 A | 4/1995 | Patel et al. |
| 5,422,119 A | 6/1995 | Casper |
| 5,494,807 A | 2/1996 | Paoletti et al. |
| 5,541,171 A | 7/1996 | Rhodes et al. |
| 5,580,859 A | 12/1996 | Felgner et al. |
| 5,589,466 A | 12/1996 | Felgner et al. |
| 5,658,785 A | 8/1997 | Johnson |
| 5,686,281 A | 11/1997 | Roberts |
| 5,705,190 A | 1/1998 | Broad et al. |
| 5,736,152 A | 4/1998 | Dunn |
| 5,756,101 A | 5/1998 | Paoletti et al. |
| 5,762,938 A | 6/1998 | Paoletti et al. |
| 5,766,597 A | 6/1998 | Paoletti et al. |
| 5,766,882 A | 6/1998 | Falkner et al. |
| 5,770,212 A | 6/1998 | Falkner et al. |
| 5,811,104 A | 9/1998 | Dale et al. |
| 5,833,975 A | 11/1998 | Paoletti et al. |
| 5,843,728 A | 12/1998 | Seed et al. |
| 5,849,303 A | 12/1998 | Wasmoen et al. |
| 5,849,589 A | 12/1998 | Tedder et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,942,235 A | 8/1999 | Paoletti |
| 5,989,562 A | 11/1999 | Wasmoen et al. |
| 5,990,091 A | 11/1999 | Tartaglia et al. |
| 5,994,136 A | 11/1999 | Naldini et al. |
| 6,004,777 A | 12/1999 | Tartaglia et al. |
| 6,004,811 A | 12/1999 | Seed et al. |
| 6,013,516 A | 1/2000 | Verma et al. |
| 6,090,393 A | 7/2000 | Fischer |
| 6,130,066 A | 10/2000 | Tartaglia et al. |
| 6,156,567 A | 12/2000 | Fischer |
| 6,159,477 A | 12/2000 | Audonnet et al. |
| 6,165,782 A | 12/2000 | Naldini et al. |
| 6,214,353 B1 | 4/2001 | Paoletti et al. |
| 6,228,846 B1 | 5/2001 | Audonnet et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,352,694 B1 | 3/2002 | June et al. |
| 6,392,013 B1 | 5/2002 | Seed et al. |
| 6,406,705 B1 | 6/2002 | Davis et al. |
| 6,410,014 B1 | 6/2002 | Seed et al. |
| 6,428,953 B1 | 8/2002 | Naldini et al. |
| 6,475,769 B1 | 11/2002 | Wilson et al. |
| 6,489,458 B2 | 12/2002 | Hackett et al. |
| 6,534,055 B1 | 3/2003 | June et al. |
| 6,537,540 B1 | 3/2003 | Burstein et al. |
| 6,537,594 B1 | 3/2003 | Paoletti et al. |
| 6,569,457 B2 | 5/2003 | Ullah et al. |
| 6,638,534 B1 | 10/2003 | Ishibashi et al. |
| 6,682,743 B2 | 1/2004 | Mayr |
| 6,713,068 B1 | 3/2004 | Audonnet et al. |
| 6,753,162 B1 | 6/2004 | Seed et al. |
| 6,761,893 B2 | 7/2004 | Chaplin et al. |
| 6,780,407 B1 | 8/2004 | Paoletti et al. |
| 6,780,417 B2 | 8/2004 | Kaslow et al. |
| 6,793,926 B1 | 9/2004 | Rasty et al. |
| 6,797,514 B2 | 9/2004 | Berenson et al. |
| 6,821,515 B1 | 11/2004 | Cleland et al. |
| 6,867,041 B2 | 3/2005 | Berenson et al. |
| 6,869,794 B2 | 3/2005 | Vogels et al. |
| 6,887,466 B2 | 5/2005 | June et al. |
| 6,893,865 B1 | 5/2005 | Lockert et al. |
| 6,905,680 B2 | 6/2005 | June et al. |
| 6,905,681 B1 | 6/2005 | June et al. |
| 6,905,874 B2 | 6/2005 | Berenson et al. |
| 6,913,752 B2 | 7/2005 | Chaplin et al. |
| 6,913,922 B1 | 7/2005 | Bout et al. |
| 6,923,973 B1 | 8/2005 | Cox et al. |
| 6,924,128 B2 | 8/2005 | Allen |
| 6,936,466 B2 | 8/2005 | Feldhaus |
| 6,943,019 B2 | 9/2005 | Wilson et al. |
| 6,953,690 B1 | 10/2005 | Gao et al. |
| 6,955,808 B2 | 10/2005 | Curiel |
| 6,974,695 B2 | 12/2005 | Vogels et al. |
| 6,991,797 B2 | 1/2006 | Andersen et al. |
| 7,029,848 B2 | 4/2006 | Vogels et al. |
| 7,045,313 B1 | 5/2006 | Moss et al. |
| 7,097,842 B2 | 8/2006 | Suter et al. |
| 7,115,391 B1 | 10/2006 | Chen et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,172,893 B2 | 2/2007 | Rabinowitz et al. |
| 7,175,843 B2 | 2/2007 | June et al. |
| 7,189,536 B2 | 3/2007 | Chaplin et al. |
| 7,198,784 B2 | 4/2007 | Kingsman et al. |
| 7,232,566 B2 | 6/2007 | June et al. |
| 7,255,862 B1 | 8/2007 | Tartaglia et al. |
| 7,259,015 B2 | 8/2007 | Kingsman et al. |
| 7,283,337 B2 | 10/2007 | Sakai et al. |
| 7,303,910 B2 | 12/2007 | Bebbington et al. |
| 7,335,364 B2 | 2/2008 | Chaplin et al. |
| 7,351,585 B2 | 4/2008 | Mitrophanous et al. |
| 7,384,644 B2 | 6/2008 | Chaplin et al. |
| 7,445,924 B2 | 11/2008 | Chaplin et al. |
| 7,459,270 B2 | 12/2008 | Chaplin et al. |
| 7,572,631 B2 | 8/2009 | Berenson et al. |
| 7,608,279 B2 | 10/2009 | Parisot et al. |
| 7,628,980 B2 | 12/2009 | Suter et al. |
| 7,705,120 B2 | 4/2010 | Lillie et al. |
| 7,708,949 B2 | 5/2010 | Stone et al. |
| 7,741,465 B1 | 6/2010 | Eshhar et al. |
| 7,767,449 B1 | 8/2010 | Paoletti |
| 7,892,533 B2 | 2/2011 | Suter et al. |
| 7,897,156 B2 | 3/2011 | Ackermann et al. |
| 7,923,017 B2 | 4/2011 | Chaplin et al. |
| 7,939,086 B2 | 5/2011 | Chaplin et al. |
| 7,964,395 B2 | 6/2011 | Chaplin et al. |
| 7,964,396 B2 | 6/2011 | Chaplin et al. |
| 7,964,398 B2 | 6/2011 | Chaplin et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,163,293 B2 | 4/2012 | Chaplin |
| 8,211,422 B2 | 7/2012 | Eshhar et al. |
| 8,227,432 B2 | 7/2012 | Hackett et al. |
| 8,236,560 B2 | 8/2012 | Chaplin et al. |
| 8,268,325 B2 | 9/2012 | Chaplin et al. |
| 8,268,329 B2 | 9/2012 | Chaplin et al. |
| 8,278,036 B2 | 10/2012 | Kariko et al. |
| 8,309,098 B2 | 11/2012 | Howley et al. |
| 8,372,622 B2 | 2/2013 | Suter et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,470,598 B2 | 6/2013 | Chaplin et al. |

(56) References Cited

U.S. PATENT DOCUMENTS

| | | |
|---|---|---|
| 8,557,779 B2 | 10/2013 | Sugiyama |
| 8,697,854 B2 | 4/2014 | Schendel et al. |
| 8,796,414 B2 | 8/2014 | Johnston |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,115,402 B2 * | 8/2015 | Hacohen ............ C12Q 1/6886 |
| 9,909,159 B2 | 3/2018 | Marras et al. |
| 9,962,453 B2 | 5/2018 | Georges |
| 10,202,640 B2 * | 2/2019 | Davis .................. C12Q 1/686 |
| 10,426,824 B1 | 10/2019 | Hacohen et al. |
| 10,801,070 B2 | 10/2020 | Clement et al. |
| 2003/0104008 A1 | 6/2003 | Loosmore et al. |
| 2004/0013648 A1 | 1/2004 | Kingsman et al. |
| 2004/0053304 A1 | 3/2004 | Markowitz |
| 2006/0008468 A1 * | 1/2006 | Chiang ............. A61K 39/0011 424/193.1 |
| 2006/0163385 A1 | 7/2006 | Link et al. |
| 2006/0252077 A1 | 11/2006 | Buzby |
| 2006/0258607 A1 | 11/2006 | Jarosch et al. |
| 2007/0003442 A1 | 1/2007 | Link et al. |
| 2007/0025970 A1 | 2/2007 | Kingsman et al. |
| 2007/0055049 A1 | 3/2007 | Grey et al. |
| 2007/0083334 A1 | 4/2007 | Mintz et al. |
| 2007/0134197 A1 | 6/2007 | Eichner et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014222 A1 | 1/2008 | Simmons et al. |
| 2008/0014589 A1 | 1/2008 | Link et al. |
| 2008/0254008 A1 | 10/2008 | Dropulic et al. |
| 2009/0005254 A1 | 1/2009 | Griffiths et al. |
| 2009/0026082 A1 | 1/2009 | Rothberg et al. |
| 2009/0055944 A1 | 2/2009 | Korman et al. |
| 2009/0111106 A1 | 4/2009 | Mitrophanous et al. |
| 2009/0131543 A1 | 5/2009 | Weitz et al. |
| 2009/0136494 A1 | 5/2009 | Ponath et al. |
| 2009/0186042 A1 | 7/2009 | Johnston et al. |
| 2009/0220980 A1 | 9/2009 | Hoon et al. |
| 2010/0137143 A1 | 6/2010 | Rothberg et al. |
| 2010/0137163 A1 | 6/2010 | Link et al. |
| 2010/0158951 A1 | 6/2010 | Randolph et al. |
| 2010/0203531 A1 | 8/2010 | Sarkaria et al. |
| 2010/0210529 A1 | 8/2010 | van der Burg et al. |
| 2010/0282617 A1 | 11/2010 | Rothberg et al. |
| 2010/0297071 A1 | 11/2010 | Ishibashi et al. |
| 2010/0304989 A1 | 12/2010 | Von Hoff et al. |
| 2011/0097312 A1 | 4/2011 | Molldrem |
| 2011/0257890 A1 | 10/2011 | Weinschenk et al. |
| 2011/0293571 A1 | 12/2011 | Widdowson et al. |
| 2011/0293637 A1 * | 12/2011 | Hacohen ............ C12Q 1/6886 424/173.1 |
| 2012/0082691 A1 | 4/2012 | Rammensee et al. |
| 2012/0219947 A1 | 8/2012 | Yurkovetsky et al. |
| 2012/0244133 A1 | 9/2012 | Rosenberg et al. |
| 2012/0288539 A1 | 11/2012 | Eber |
| 2012/0295960 A1 | 11/2012 | Patti et al. |
| 2013/0071414 A1 | 3/2013 | Dotti et al. |
| 2013/0210014 A1 | 8/2013 | Sharman |
| 2013/0295110 A1 | 11/2013 | Binder et al. |
| 2014/0056986 A1 | 2/2014 | Desai et al. |
| 2014/0178438 A1 | 6/2014 | Sahin et al. |
| 2014/0256595 A1 | 9/2014 | Link et al. |
| 2014/0322716 A1 * | 10/2014 | Robins ................ C12Q 1/6846 435/6.12 |
| 2015/0140041 A1 | 5/2015 | Vitiello |
| 2015/0224182 A1 | 8/2015 | Hunt et al. |
| 2016/0008447 A1 | 1/2016 | Hacohen et al. |
| 2016/0101170 A1 | 4/2016 | Hacohen et al. |
| 2016/0310584 A1 | 10/2016 | Fritsch et al. |
| 2016/0326593 A1 | 11/2016 | Clement et al. |
| 2016/0331822 A1 | 11/2016 | Hacohen et al. |
| 2016/0339090 A1 | 11/2016 | Hacohen et al. |
| 2017/0160269 A1 * | 6/2017 | Linnemann .......... G01N 33/505 |
| 2017/0233821 A1 * | 8/2017 | Lianidou ............ C12Q 1/6858 435/6.11 |
| 2017/0298441 A1 | 10/2017 | Wu et al. |
| 2018/0000913 A1 | 1/2018 | Hacohen et al. |
| 2018/0055922 A1 | 3/2018 | Hacohen et al. |
| 2018/0127803 A1 | 5/2018 | Lei et al. |
| 2018/0153975 A1 | 6/2018 | Fritsch et al. |
| 2019/0060428 A1 | 2/2019 | Fritsch |
| 2019/0060432 A1 | 2/2019 | Hacohen et al. |
| 2019/0099475 A1 | 4/2019 | Benz et al. |
| 2019/0376147 A1 | 12/2019 | Fritsch |
| 2020/0016251 A1 | 1/2020 | Hacohen et al. |
| 2020/0069783 A1 | 3/2020 | Hacohen et al. |

FOREIGN PATENT DOCUMENTS

| | | |
|---|---|---|
| EP | 1680681 B1 | 11/2011 |
| EP | 2390363 A1 | 11/2011 |
| EP | 2569633 A2 | 3/2013 |
| EP | 2574346 A1 | 4/2013 |
| FR | 2650840 A1 | 2/1991 |
| JP | 2003/517274 A | 5/2003 |
| JP | 2003/523365 A | 8/2003 |
| JP | 2003/535024 A | 11/2003 |
| JP | 2005/505271 A | 2/2005 |
| JP | 2005/529187 A | 9/2005 |
| JP | 2006/526628 A | 11/2006 |
| JP | 2009/532664 A | 9/2009 |
| JP | 2012/522500 A | 9/2012 |
| JP | 2013/530943 A | 8/2013 |
| WO | WO-9102087 A1 | 2/1991 |
| WO | WO-9106309 A1 | 5/1991 |
| WO | WO-92/15672 A1 | 9/1992 |
| WO | WO-9215322 A1 | 9/1992 |
| WO | WO-9215712 A1 | 9/1992 |
| WO | WO-9324640 A2 | 12/1993 |
| WO | WO-95/27780 A1 | 10/1995 |
| WO | WO-95/30018 A2 | 11/1995 |
| WO | WO-96/18372 A2 | 6/1996 |
| WO | WO-00/20587 A2 | 4/2000 |
| WO | WO-00/66153 A1 | 11/2000 |
| WO | WO-2001/89788 A2 | 11/2001 |
| WO | WO-2003020763 A2 | 3/2003 |
| WO | WO-2003/057171 A2 | 7/2003 |
| WO | WO-03/086459 A1 | 10/2003 |
| WO | WO-03/106692 A2 | 12/2003 |
| WO | WO-2004/002627 A2 | 1/2004 |
| WO | WO-2004026897 A1 | 4/2004 |
| WO | WO-2004030615 A2 | 4/2004 |
| WO | WO-2004033685 A1 | 4/2004 |
| WO | WO-2004044004 A2 | 5/2004 |
| WO | WO-2004/058801 A2 | 7/2004 |
| WO | WO-2004074322 A1 | 9/2004 |
| WO | WO-2004/091763 A2 | 10/2004 |
| WO | WO-2005/021151 A1 | 3/2005 |
| WO | WO-2005087261 A2 | 9/2005 |
| WO | WO-2005113595 A2 | 12/2005 |
| WO | WO-2005114215 A2 | 12/2005 |
| WO | WO-2006000830 A2 | 1/2006 |
| WO | WO-2006/040551 A2 | 4/2006 |
| WO | WO-2006/040554 A1 | 4/2006 |
| WO | WO-2006/096571 A2 | 9/2006 |
| WO | WO-2006/121168 A1 | 11/2006 |
| WO | WO-2006125962 A2 | 11/2006 |
| WO | WO-2007015540 A1 | 2/2007 |
| WO | WO-2007/059033 A1 | 5/2007 |
| WO | WO-2007/089541 A2 | 8/2007 |
| WO | WO-2007/095033 A2 | 8/2007 |
| WO | WO-2007/101227 A2 | 9/2007 |
| WO | WO-2007/124090 A2 | 11/2007 |
| WO | WO-2007/133710 A2 | 11/2007 |
| WO | WO-2008/011344 A2 | 1/2008 |
| WO | WO-2008038002 A2 | 4/2008 |
| WO | WO-2008039818 A2 | 4/2008 |
| WO | WO-2008063227 A2 | 5/2008 |
| WO | WO-2008/096831 A1 | 8/2008 |

(56) References Cited

FOREIGN PATENT DOCUMENTS

| WO | WO-2008/109075 A2 | 9/2008 |
| --- | --- | --- |
| WO | WO-2009/014708 A2 | 1/2009 |
| WO | WO-2009032477 A2 | 3/2009 |
| WO | WO-2009043520 A1 | 4/2009 |
| WO | WO-2009/126306 A2 | 10/2009 |
| WO | WO-2010033949 A1 | 3/2010 |
| WO | WO-2010/045345 A2 | 4/2010 |
| WO | WO-2011/051489 A2 | 5/2011 |
| WO | WO-2011/079176 A2 | 6/2011 |
| WO | WO-2011/143656 A2 | 11/2011 |
| WO | WO-2011134944 A2 | 11/2011 |
| WO | WO-2011146862 A1 | 11/2011 |
| WO | WO-2012027379 A2 | 3/2012 |
| WO | WO-2012/079000 A1 | 6/2012 |
| WO | WO-2012/095639 A2 | 7/2012 |
| WO | WO-2012/101112 A1 | 8/2012 |
| WO | WO-2012/159643 A1 | 11/2012 |
| WO | WO-2012/159754 A2 | 11/2012 |
| WO | WO-2013/026027 A1 | 2/2013 |
| WO | WO-2013/036201 A1 | 3/2013 |
| WO | WO-2013039889 A1 | 3/2013 |
| WO | WO-2013040371 A1 | 3/2013 |
| WO | WO-2013/086464 A1 | 6/2013 |
| WO | WO-2013/123031 A2 | 8/2013 |
| WO | WO-2013133405 A1 | 9/2013 |
| WO | WO-2013/173223 A1 | 11/2013 |
| WO | WO-2013166321 A1 | 11/2013 |
| WO | WO-2013176915 A1 | 11/2013 |
| WO | WO-2014/009535 A2 | 1/2014 |
| WO | WO-2014/012051 A1 | 1/2014 |
| WO | WO-2014011987 A1 | 1/2014 |
| WO | WO-2014018863 A1 | 1/2014 |
| WO | WO-2014047561 A1 | 3/2014 |
| WO | WO-2014/056986 A1 | 4/2014 |
| WO | WO-2014/059173 A2 | 4/2014 |
| WO | WO-2014/083173 A1 | 6/2014 |
| WO | WO-2014085802 A1 | 6/2014 |
| WO | WO-2014/133567 A1 | 9/2014 |
| WO | WO-2014/133568 A1 | 9/2014 |
| WO | WO-2014/150924 A2 | 9/2014 |
| WO | WO-2014134165 A1 | 9/2014 |
| WO | WO-2014/168874 A2 | 10/2014 |
| WO | WO-2014/172606 A1 | 10/2014 |
| WO | WO-2014/183649 A1 | 11/2014 |
| WO | WO-2014184744 A1 | 11/2014 |
| WO | WO-2014/197369 A1 | 12/2014 |
| WO | WO-2014191128 A1 | 12/2014 |
| WO | WO-2015/085233 A1 | 6/2015 |
| WO | WO-2015/094995 A2 | 6/2015 |
| WO | WO-2015/095811 A2 | 6/2015 |
| WO | WO-2016/020710 A1 | 2/2016 |
| WO | WO-2016/100975 A1 | 6/2016 |
| WO | WO-2016/164833 A1 | 10/2016 |
| WO | WO-2016/201049 A2 | 12/2016 |
| WO | WO-2017/173321 A1 | 10/2017 |
| WO | WO-2017/184590 A1 | 10/2017 |
| WO | PCT/US18/14831 | 1/2018 |
| WO | WO-2018/140391 A1 | 8/2018 |

OTHER PUBLICATIONS

Engler et al A One Pot, One Step, Precision Cloning Method with High Throughput Capability PLoS ONE pp. 1-7.*
Hu et al A cloning and expression system to probe T-cell receptor specificity and assess functional avidity to neoantigens Blood. 2018;132(18):1911-1921).*
DeKosky, B. J. et al. Accurate whole-genome sequencing and haplotyping from 10 to 20 human cells Nature 487, 190-195 (2012).*
Dossinger et al MHC Multimer-Guided and Cell Culture-Independent Isolation of Functional T Cell Receptors from Single Cells Facilitates TCR Identification for Immunotherapy PLOS ONE e61384 pp. 1-10.*
Rosenberg et al., Adoptive cell transfer as personalized immunotherapy for human cancer Science Apr. 3, 2015 • vol. 348 Issue 6230; pp. 62-68.*
Pritchard et al., Exome Sequencing to Predict Neoantigens in Melanoma Cancer Immunol Res, 3:992-998 (2015).*
Turchaninova et al., Pairing of T-cell receptor chains via emulsion PCR. Eur J Immunol. 2013; 43(9):2507-15.*
Han et al., Linking T-cell receptor sequence to functional phenotype at the single-cell level Nat Biotechnol. Jul. 2014 ; 32(7): 684-692.*
Gascoigne et al; Allelic exclusion of the T cell receptor a-chain: developmental regulation of a post-translational event Semin Immunol. 1999; 11:337-347.*
Fillatreau et al Technische Universitat Berlin, Fakultht III—Prozesswissenschaften Direct comparison of T cell receptor avidity of auto-antigen specific conventional and regulatory T cells pp. 1-6; Abstract.*
Fritsch et al Personal Neoantigen Cancer Vaccines: A Road Not Fully Paved •Cancer Innnnunol Res 2020;8:1465-9.*
Single-cell sequencing A brief overview of how to derive a genome or transcriptonne from a single cell. 18 ∛ vol. 11 No. 1 ∛ Jan. 2014 ∛ Nature Methods.*
Carsten Linnemann et al: "High-throughput identification of antigen-specific TCRs by TCR gene capture", Nature Medicine, vol. 19, No. 11, Oct. 13, 2013, pp. 1534-1541.
Andreatta et al., "Gapped sequence alignment using artificial neural networks: application to the MHC class I system," Bioinformatics 32(4):511-517 (2016).
Bassani-Sternberg et al., "Mass Spectrometry of Human Leukocyte Antigen Class I Peptidomes Reveals Strong Effects of Protein Abundance and Turnover on Antigen Presentation," Mol Cell Proteomics, 14:658-673 (2015).
Behrends et al., "Network organization of the human autophagy system," Nature, 466(7302):68-76 (2010).
Berg et al., "Detection of artifacts and peptide modifications in liquid chromatography/mass spectrometry data using two-dimensional signal intensity map data visualization," Rapid Commun Mass Spectrom, 20(10):1558-1562 (2006).
Boen et al., "Identification of T Cell Ligands in a Library of Peptides Covalently Attached to HLA-DR4," J Immunol, 165:2040-2047 (2000).
Boisgerault et al., "Definition of the HLA-A29 peptide ligand motif allows prediction of potential T-cell epitopes from the retinal soluble antigen, a candidate autoantigen in birdshot retinopathy," PNAS, 93:3466-3470 (1996).
Bourdetsky et al., The nature and extent of contributions by defective ribosome products to the HLA peptidome, PNAS, III, E1591-E1599 (2014).
Bremel et al., "An integrated approach to epitope analysis I: Dimensional reduction, visualization and prediction of MHC binding using amino acid principal components and regression approaches," Immunome Res, 6:7 (2010).
Caron et al., "Analysis of MHC immunopeptidomes using mass spectrometry," Mol Cell Proteomics (2015), doi: 10.1074/mcp.OI 15.052431.
Chowell et al., "TCR contact residue hydrophobicity is a hallmark of immunogenic CD8(+) T cell epitopes," PNAS, 112:E1754-E1762 (2015).
Christianson et al., "Defining human ERAD networks through an integrative mapping strategy," Nat Cell Biol, 14:93-105 (2012).
Eichmann et al., "Identification and characterisation of peptide binding motifs of six autoimmune disease-associated human leukocyte antigen-class I molecules including HLA-B*39:06," Tissue Antigens 84(4):378-388 (2014).
Elias et al., Target-decoy search strategy for increased confidence in large-scale protein identifications by mass spectrometry, Nat Meth, 4:207-214 (2007).
Eyers et al., "CONSeQuence: prediction of reference peptides for absolute quantitative proteomics using consensus machine learning approaches," Mol Cell Proteomics (2011); 10(11):M110.003384. doi: 10.1074/mcp.Ml 10.003384. Epub Aug. 3, 2011.
Fruci et al., "Altered expression of endoplasmic reticulum aminopeptidases ERAPI and ERAP2 in transformed non-lymphoid human tissues," J Cell Physiol, 216(3):742-749 (2008).

(56) References Cited

OTHER PUBLICATIONS

Fusaro et al., "Prediction of high-responding peptides for targeted protein assays by mass spectrometry" Nat Biotechnol, 27(2):190-198 (2009).
Guasp et al., "The Peptidome of Behcet's Disease-Associated HLA-B*51 :01 Includes Two Subpeptidomes Differentially Shaped by Endoplasmic Reticulum Aminopeptidase 1," Arthritis Rheumatol, 68:505-515 (2016).
Guruprasad et al., "Correlation between stability of a protein and its dipeptide composition: a novel approach for predicting in vivo stability of a protein from its primary sequence," Protein Eng, 4(2):155-161 (1990).
Harndahl et al., "Peptide-MHC class I stability is a better predictor than peptide affinity of CTL immunogenicity," Eur J Immunol, 42:1405-1416 (2012).
Harndahl et al., "Real-time, High-Throughput Measurements of Peptide-MHC-I Dissociation Using a Scintillation Proximity Assay," J Immunol Methods, 374:5-12 (2011).
Hickman et al., "Toward a Definition of Self: Proteomic Evaluation of the Class I Peptide Repertoire," J Immunol, 172:2944-2952 (2004).
Hoof et al., "NetMHCpan, a method for MHC class I binding prediction beyond humans," Immunogenetics, 61:1-13 (2009).
Hunt et al., "Characterization of peptides bound to the class I MHC molecule HLA-A2.1 by mass spectrometry," Science, 255:1261-1263 (1992).
Ishihama et al., "Exponentially Modified Protein Abundance Index (emPAI) for Estimation of Absolute Protein Amount in Proteomics by the Number of Sequenced Peptides per Protein," Mol Cell Proteomics, 4:1265-1272 (2005).
Jeffery et al., "The Influence of HLA Class I Alleles and Heterozygosity on the Outcome of Human T Cell Lymphotropic Virus Type I Infection," J Immunol, 165:7278-7284 (2000).
Jorgensen et al., "NetMHC stab—predicting stability of peptide-MHC-I complexes; impacts for cytotoxic T lymphocyte epitope discovery," Immunology 141:18-26 (2014).
Keskin et al., "Direct identification of an HPV-16 tumor antigen from cervical cancer biopsy specimens," Front Immunol, 2:75 (2011).
Keskin et al., "Physical detection of influenza a epitopes identifies a stealth subset on human lung epithelium evading natural CD8 immunity," PNAS, 112(7):2151-2156 (2015).
Kesmir et al., "Prediction of proteasome cleavage motifs by neural networks," Protein Eng, 15(4):287-296 (2002).
Kim et al., "Derivation of an amino acid similarity matrix for peptide:MHC binding and its application as a Bayesian prior," BMC Bioinformatics, 10:1-11 (2009).
Kim et al., "Positional Bias of MHC Class I Restricted T-Cell Epitopes in Viral Antigens Is Likely due to a Bias in Conservation," PLoS Comput Biol, 9:e1002884 (2013).
Kronke et al. "Lenalidomide causes selective degradation of IKZFl and IKZF3 in multiple myeloma cells," Science, 343(6168): 301-305 (2014).
Kronke et al. "Lenalidomide induces ubiquitination and degradation of CKla in del(5q) MDS," Nature, 523(7559):183-188 (2015).
Larsen et al., "Large-scale validation of methods for cytotoxic T-Iymphocyte epitope prediction," BMC Bioinformatics, 8:424-424 (2007).
Linnemann et al., "High-throughput epitope discovery reveals frequent recognition of neo-antigens by CD4+ T cells in human melanoma," Nat Med, 21:81-85 (2015).
Lorente et al., "Diversity of Natural Self-Derived Ligands Presented by Different HLA Class I Molecules in Transporter Antigen Processing-Deficient Cells," PLoS ONE 8:e59118 (2013).
Ma, "Novor: Real-Time Peptide de Novo Sequencing Software," J Am Soc Mass Spectrom, 26:1885-1894 (2015).
McMurtrey et al., "Toxoplasma gondii peptide ligands open the gate of the HLA class I binding groove," eLife 5:e12556 (2016).

Milner et al., "The Effect of Proteasome Inhibition on the Generation of the Human Leukocyte Antigen (HLA) Peptidome," Mol Cell Proteomics, 12:1853-1864 (2013).
Milner et al., "The Turnover Kinetics of Major Histocompatibility Complex Peptides of Human Cancer Cells*," Mol Cell Proteomics, 5:357-365 (2006).
Mommen et al., "Expanding the detectable HLA peptide repertoire using electron-transfer/higher-energy collision dissociation (EThcD)," Pnas III, 4507-4512 (2014).
Mommen et al., "Sampling From the Proteome to the Human Leukocyte Antigen-DR (HLA-DR) Ligandome Proceeds Via High Specificity," Mol Cell Proteomics MCP, 15:1412-1423 (2016).
Muntel et al., "Abundance-based Classifier for the Prediction of Mass Spectrometric Peptide Detectability Upon Enrichment (PPA)," Mol Cell Proteomics, 14:430-440 (2015).
Ng et al., "Dereplication and de novo sequencing of nonribosomal peptides," Nat Meth, 6:596-599 (2009).
Nielsen et al., "The role of the proteasome in generating cytotoxic T-cell epitopes: insights obtained from improved predictions of proteasomal cleavage," Immunogenetics, 57:33-41 (2005).
Oates et al., "D(2)P(2): database of disordered protein predictions," Nucleic Acids Res, 41:D508-D516 (2013).
Rappsilber et al., "Protocol for micro-purification, enrichment, pre-fractionation and storage of peptides for proteomics using StageTips," Nat Protoc, 2(8):1896-1906 (2007).
Reche et al., "Elicitation from virus-naive individuals of cytotoxic T lymphocytes directed against conserved HIV-1 epitopes," Med Immunol, 5:1 (2006).
Robinson et al., "The IPD and FMGT/HLA database: allele variant databases," Nucleic Acids Res, 43:D423-D431 (2015).
Rock et al., "Re-examining class-I presentation and the DRiP hypothesis," Trends Immunol, 35(4):144-152 (2014).
Ruggles et al., "An analysis of the sensitivity of proteogenomic mapping of somatic mutations and novel splicing events in cancer," Cell Proteomics, 15(3):1060-1071 (2015).
Saveanu et al., "Concerted peptide trimming by human ERAPI and ERAP2 aminopeptidase complexes in the endoplasmic reticulum," Nat Immunol, 6:689-697 (2005).
Saxova et al., "Predicting proteasomal cleavage sites: a comparison of available methods," Int Immunol, 15:781-787 (2003).
Schumacher et al., "Neoantigens in cancer immunotherapy," Science, 348:69-74 (2015).
Searle et al., "Using Data Independent Acquisition (DIA) to Model High-responding Peptides for Targeted Proteomics Experiments," Mol Cell Proteomics, 14:2331-2340 (2015).
Shimizu et al., "Production of human cells expressing individual transferred HLA-A,-B,-C genes using an HLA-A,-B,-C null human cell line," J Immunol, 142(9):3320-3328 (1989).
Shimizu et al., "Transfer of cloned human class I major histocompatibility complex genes into HLA mutant human lymphoblastoid cells," Mol Cell Biol, 6(4):1074-1087 (1986).
Sidney et al., "Measurement of MHC/Peptide Interactions by Gel Filtration" Curr Prot Immunol, 31(1):18.3.1-18.3.19 (1999).
Sowa et al., "Defining the Human Deubiquitinating Enzyme Interaction Landscape," Cell, 138(2):389-403 (2009).
Trolle et al., "The Length Distribution of Class 1-Restricted T Cell Epitopes Is Determined by Both Peptide Supply and MHC Allele-Specific Binding Preference," J Immunol (2016), doi: 10.4049/jimmunol.1501721.
Tynan et al., "T cell receptor recognition of a "super-bulged" major histocompatibility complex class I-bound peptide," Nat Immunol, 6:1114-1122 (2005).
Udeshi et al., "Methods for quantification of in vivo changes in protein ubiquitination following proteasome and deubiquitinase inhibition," Mol Cell Proteomics, 11:148-159 (2012).
Vita et al., "The immune epitope database (IEDB) 3.0," Nucleic Acids Res, 43:D405-D412 (2015).
Walz et al., "The antigenic landscape of multiple myeloma: mass spectrometry (re)defines targets for T-cell-based immunotherapy," Blood 126:1203-1213 (2015).
Yewdell, "DRiPs solidify: progress in understanding endogenous MHC class I antigen processing," Trends Immunol, 32(11):548-558 (2011).

(56) References Cited

OTHER PUBLICATIONS

Zhang et al., "Dana-Farber repository for machine learning in immunology," J Immunol Methods, 374(1-2):18-25 (2011).
U.S. Appl. No. 16/094,786, filed Oct. 18, 2018, Pending.
U.S. Appl. No. 14/794,449, filed Jul. 8, 2015, 2016-00008447, Published.
U.S. Appl. No. 16/188,737, filed Nov. 13, 2018, Pending.
U.S. Appl. No. 16/381,791, filed Apr. 11, 2019, Pending.
U.S. Appl. No. 14/877,125, filed Oct. 7, 2015, 2016-0101170, Published.
U.S. Appl. No. 15/102,129, filed Jun. 6, 2016, 2016-0310584, Published.
U.S. Appl. No. 15/038,504, filed May 23, 2016, 2016-0326593, Published.
U.S. Appl. No. 15/537,785, filed Jun. 19, 2017, 2018-0000913, Published.
U.S. Appl. No. 15/575,328, filed Nov. 17, 2017, 2018-0153975, Published.
Backed et al., "Immunoinformatics and epitope prediction in the age of genomic medicine," Genome Medicine, 7:119 (2015).
Carreno et al., "A dendritic cell vaccine increases the breadth and diversity of melanoma neoantigen-specific T cells," Science, 348(6239):803-808 (2015).
Chen et al., Molecular Pharmaceutics, 3:109-111 (2010).
Declaration by Professor John Haanen, M.D., Ph.D.
Dössinger et al., "MHC multimer-guided and cell culture-independent isolation of functional T cell receptors from single cells facilitates TCR identification for immunotherapy," PloS one, 8(4):e61384 (2013).
Final Rejection for U.S. Appl. No. 13/108,610, "Compositions and Methods of Identifying Tumor Specific Neoantigens," dated May 12, 2014.
Final Rejection for U.S. Appl. No. 14/794,449, "Compositions and Methods of Identifying Tumor Specific Neoantigens," dated Sep. 13, 2017.
Final Rejection for U.S. Appl. No. 14/877,125, "Compositions and Methods for Personalized Neoplasia Vaccines," dated Oct. 25, 2017.
Final Rejection for U.S. Appl. No. 15/038,504 , "Compositions and Methods for Diagnosing, Evaluating and Treating Cancer by Means of The DNA Methyl," dated Apr. 30, 2018.
Final Rejection for U.S. Appl. No. 15/038,504 , "Compositions and Methods for Diagnosing, Evaluating and Treating Cancer by Means of the DNA Methyl," dated Dec. 21, 2018.
Final Rejection for U.S. Appl. No. 15/102,129, "Formulations for Neoplasia Vaccines," dated Sep. 14, 2018.
Final Rejection for U.S. Appl. No. 15/105,961, "Combination Therapy With Neoantigen Vaccine," dated Jul. 5, 2018.
Final Rejection for U.S. Appl. No. 15/187,174, "Compositions and Methods of Identifying Tumor Specific Neoantigens," dated May 25, 2017.
Final Rejection for U.S. Appl. No. 15/187,174, "Compositions and Methods of Identifying Tumor Specific Neoantigens," dated Oct. 12, 2018.
Gazdar, "Activating and resistance mutations of EGFR in non-small-cell lung cancer: role in clinical response to EGFR tyrosine kinase inhibitors," Oncogene, 28:S24-S31 (2009).
Han et al., "Linking T-Cell Receptor Sequence to Fucntional Phenotype at the Single-Cell Level," Nat Biotechnol, 32:684-692 (2014).
Hombrink et al., "Identification of Biological Relevant Minor Histocompatibility Antigens within the B-lymphocyte—Derived HLA-Ligandome Using a Reverse Immunology Approach," Clin Cancer Res, 21(9):2177-2186 (2015).
Illumina, "Immunotherapy, the Next Generation of Cancer Treatment, NGS-guided assessment of interactions between tumors and the immune system leads to new discoveries in immuno-oncology," (2016).
Jarmalavicius et al., "High Immunogenicity of the Human Leukocyte Antigen Peptidomes of Melanoma Tumor Cells," J Biol Chem, 287(40):33401-33411 (2012).
Johnson et al., "Discovery of Naturally Processed and HLA-Presented Class I Peptides from Vaccinia Virus Infection using Mass Spectrometry for Vaccine Development," Vaccine, 28(1):38-47 (2009).
Kalaora et al., "Use of HLA peptidomics and whole exome sequencing to identify human immunogenic neo-antigens," Oncotarget, 7(5):5110-5117 (2016).
Keskin et al., "Neoantigen vaccine generates intratumoral T cell responses in phase lb glioblastoma trial," Nature, 565(7738):234-239 (2019).
Kim et al., "mTOR inhibitors radiosensitize Pten-deficient non-small-cell lung cancer cells harboring an EGFR activating mutation by inducing autophagy," J Cell Biochem, 114(6):1248-1256 (2013).
Klug et al., "Characterization of MHC Ligands for Peptide Based Tumor Vaccination," Current Pharmaceutical Design, 15(28): 3221-3236 (2009).
Lata et al., "MHCBN 4.0: A database of MHC/TAP binding peptides and T-cell epitopes," BMC Research Notes, 2(1): 61 (2009).
Linardou et al., "Somatic EGFR mutations and efficacy of tyrosine kinase inhibitors in NSCLC," Nat Rev Clin Oncol, 6(6):352-366 (2009).
Llano et al., "Best-Characterized HIV-1 CTL Epitopes: The 2013 Update," HIV Mol Immunol , 3-25 (2013).
Lucas et al., "About human tumor antigens to be used in immunotherapy," Semin Immunol, 20(5):301-307 (2008).
Luo et al. "Machine learning methods for Predicting hLA—Peptide Binding activity," Bioinformatics and Biology Insights, 9(53):21-29 (2015).
Mosmann et al., "TH1 and TH2 Cells: Different Patterns of Lymphokine Secretion Lead to Different Functional Properties," Ann Rev Immunol, 7:145-173 (1989).
Nielsen et al., "NetMHCpan-3.0; improved prediction of binding to MHC class I molecules integrating information from multiple receptor and peptide length datasets," Genome Medicine, 8:33 (2016).
Non-Final Office Action for U.S. Appl. No. 13/108,610, "Compositions and Methods of Identifying Tumor Specific Neoantigens," dated Aug. 15, 2013.
Non-Final Office Action for U.S. Appl. No. 13/108,610, "Compositions and Methods of Identifying Tumor Specific Neoantigens," dated Dec. 3, 2014.
Non-Final Office Action for U.S. Appl. No. 14/794,449, "Compositions and Methods of Identifying Tumor Specific Neoantigens," dated Dec. 29, 2016.
Non-Final Office Action for U.S. Appl. No. 14/794,449, "Compositions and Methods of Identifying Tumor Specific Neoantigens," dated Jul. 24, 2018.
Non-Final Office Action for U.S. Appl. No. 14/877,125, "Compositions and Methods for Personalized Neoplasia Vaccines," dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504 , "Compositions and Methods for Diagnosing, Evaluating and Treating Cancer by Means of the DNA Methyl," dated Sep. 6, 2017.
Non-Final Office Action for U.S. Appl. No. 15/102,129, "Formulations for Neoplasia Vaccines," dated Dec. 17, 2018.
Non-Final Office Action for U.S. Appl. No. 15/102,129, "Formulations for Neoplasia Vaccines," dated Jul. 28, 2017.
Non-Final Office Action for U.S. Appl. No. 15/102,129, "Formulations for Neoplasia Vaccines," dated Mar. 7, 2018.
Non-Final Office Action for U.S. Appl. No. 15/105,961, "Combination Therapy With Neoantigen Vaccine," dated Jan. 8, 2019.
Non-Final Office Action for U.S. Appl. No. 15/105,961, "Combination Therapy With Neoantigen Vaccine," dated Nov. 20, 2017.
Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, "Compositions and Methods of Identifying Tumor Specific Neoantigens," dated Jan. 22, 2018.

(56) References Cited

OTHER PUBLICATIONS

Non-Final Office Action for U.S. Appl. No. 15/513,127, "Use of Clonal Evolution Analysis for Ibrutinib Resistance in Chronic Lymphocytic Leukemia Patients," dated Nov. 26, 2018.
Non-Final Office Action for U.S. Appl. No. 15/537,785, "Methods for Profiling the T Cell Repertoire," dated Dec. 21, 2018.
Non-Final Office Action for U.S. Appl. No. 16/181,098, "Compositions and Methods of Identifying Tumor Specific Neoantigens," dated Jan. 31, 2019.
Notice of Allowance for U.S. Appl. No. 13/108,610, "Compositions and Methods of Identifying Tumor Specific Neoantigens," dated Jun. 11, 2015.
Notice of Allowance for U.S. Appl. No. 13/108,610, "Compositions and Methods of Identifying Tumor Specific Neoantigens," dated May 12, 2015.
Notice of Allowance for U.S. Appl. No. 15/102,129, "Formulations for Neoplasia Vaccines," dated Oct. 12, 2018.
Assignment Register extract (accessed Oct. 20, 2016).
Prints-outs from the UniProtKB database concerning the CEP170, PARVA and FLT3 genes.
Rajasagi et al., "Systematic identification of personal tumor-specific neoantigens in chronic lymphocytic leukemia," Blood, 124(3):453-462 (2014).
Restriction Requirement for U.S. Appl. No. 13/108,610, "Compositions and Methods of Identifying Tumor Specific Neoantigens," dated Mar. 7, 2013.
Restriction Requirement for U.S. Appl. No. 14/794,449, "Compositions and Methods of Identifying Tumor Specific Neoantigens," dated Oct. 26, 2016.
Restriction Requirement for U.S. Appl. No. 14/877,125, "Compositions and Methods for Personalized Neoplasia Vaccines," dated Nov. 18, 2016.
Restriction Requirement for U.S. Appl. No. 15/038,504, "Compositions and Methods for Diagnosing, Evaluating and Treating Cancer by Means of the DNA Methyl," dated Jun. 22, 2017.
Restriction Requirement for U.S. Appl. No. 15/102,129, "Formulations for Neoplasia Vaccines," dated May 8, 2017.
Restriction Requirement for U.S. Appl. No. 15/105,961, "Combination Therapy With Neoantigen Vaccine," dated Jul. 13, 2017.
Restriction Requirement for U.S. Appl. No. 15/187,174, "Compositions and Methods of Identifying Tumor Specific Neoantigens," dated Sep. 9, 2016.
Restriction Requirement for U.S. Appl. No. 15/513,127, "Use of Clonal Evolution Analysis for Ibrutinib Resistance in Chronic Lymphocytic Leukemia Patients," dated Aug. 13, 2018.
Restriction Requirement for U.S. Appl. No. 15/537,785, "Methods for Profiling the T Cell Repertoire," dated Mar. 22, 2018.
Restriction Requirement for U.S. Appl. No. 15/575,328, "Shared Neoantigens," dated Feb. 7, 2019.
Rubin et al., "Mutation patterns in cancer genomes," PNAS, 106(51):21766-21770 (2009).
Sahin et al., "Personalized RNA mutanome vaccines mobilize poly-specific therapeutic immunity against cancer," Nature, 547(7662):222-226 (2017).
Stranzl et al., "NetCTLpan: pan-specific MHC class I pathway epitope predictions," Immunogenetics, 62(6):357-368 (2010).
Sun et al., Material bionics and Thinking Innovation, 176-177 (2012).
Tang et al., "NeoantigenR: An annotation based pipeline for tumor neoantigen identification from sequencing data," bioRxiv preprint first posted online Aug. 8, 2017.
Trolle et al., "Automated benchmarking of peptide-MHC class I binding predictions," Bioinformatics, 31(13):2174-2181 (2015).
Turchaninova et al., "Pairing of T-cell receptor chains via emulsion PCR," Eur J Immunol, 43:2507-2515 (2013).
van Buuren et al., "High sensitivity of cancer exome-based CD8 T cell neo-antigen identification," Oncolmmunology, 3(5):e28836 (2014).
Vogel et al., "Mass Spectrometry Reveals Changes in MHC I Antigen Presentation After Lentivector Expression of a Gene Regulation System," Molecular Therapy—Nucleic Acids, 2:e75 (2013).

Wang et al., Functional Polymeric Material, 1-44 (2010).
Wraith, "The Future of Immunotherapy: A 20-Year Perspective," Front Immunol, 8:1668 (2017).
Zhang et al., Oncology, 1-44 (2005).
Chang et al., "Use of tumor genomic profiling to reveal mechanisms of resistance to the BTK inhibitor ibrutinib in chronic lymphocytic leukemia (CLL)," J Clin Oncol, 31(15S):Abstract 7014 (2013).
Du et al., "The Significance and Therapeutic Potential of GATA3 Expression and Mutation in Breast Cancer: A Systematic Review," Med Res Rev, 35(6):1300-1315 (2015).
Final Rejection for U.S. Appl. No. 14/794,449, "Compositions and Methods of Identifying Tumor Specific Neoantigens," dated Apr. 5, 2019.
Final Rejection for U.S. Appl. No. 14/877,125, "Compositions and Methods for Personalized Neoplasia Vaccines," dated May 24, 2019.
Final Rejection for U.S. Appl. No. 15/513,127, "Use of Clonal Evolution Analysis for Ibrutinib Resistance in Chronic Lymphocytic Leukemia Patients," dated May 17, 2019.
Final Rejection for U.S. Appl. No. 16/181,098, "Compositions and Methods of Identifying Tumor Specific Neoantigens," dated Jun. 17, 2019.
Mackall et al., "Targeting tumor specific translocations in sarcomas in pediatric patients for immunotherapy," Clinical Orthopaedics and Related Research, 373:25-31 (2000).
Mardis, "The impact of next-generation sequencing technology on genetics," Trends in Genetics, 24(3):133-141 (2007).
Non-Final Office Action for U.S. Appl. No. 15/102,129, "Formulations for Neoplasia Vaccines," dated Apr. 26, 2019.
Non-Final Office Action for U.S. Appl. No. 15/575,328, "Shared Neoantigens," dated Jun. 27, 2019.
O'Mahony et al., "A Pilot Study of CTLA-4 Blockade after Cancer Vaccine Failure in Patients with Advanced Malignancy" Clin Canc Res 13(3):958-964 (2007).
Osorio et al., "Stability Analysis of Antimicrobial Peptides in Solvation Conditions by Molecular Dynamics," Adv Comp Bio, 232:127-131 (2014).
Pietras, "Biologic Basis of Sequential and Combination Therapies for Hormone-Responsive Breast Cancer," Oncologist, 11:704-717 (2006).
Restriction Requirement for U.S. Appl. No. 15/537,839, "Molecular Biomarkers for Cancer Immunotherapy," dated Jun. 20, 2019.
Song et al., "Full screening and accurate subtyping of HLA-A*02 alleles through group-specific amplification and mono-allelic sequencing," Cell Mol Immunol, 10:490-496 (2013).
Vita et al., "The Immune Epitope Database 2.0," Nucleic Acids Res, 38:D854-D862 (2010).
"Neon Therapeutics' Personal Neoantigen Vaccine Study Demonstrates Prolonged Progression-Free Survival in Advanced or Metastatic Melanoma, Non-Small Cell Lung and Bladder Cancers," published by Globe Newswire on Jul. 15, 2019 ("Neon Press Release 2019").
Bediaga et al., "DNA methylation epigenotypes in breast cancer molecular subtypes," Breast Cancer Research, 12:R77 (2010).
Cardarella et al., "Clinical, Pathologic, and Biologic Features Associated with Braf Mutations in Non-Small Cell Lung Cancer," Clin Cancer Res, 19(16):4532-4540 (2013).
Dai et al., "Prediction of soluble heterologous protein expression levels in *Escherichia coli* from sequence-based features and its potential in biopharmaceutical process development," Pharmaceutical Bioprocessing, 2(3): 253-266 (2014).
Di Nicolantonio et al., "Wild-Type Is Required for Response to Panitumumab or Cetuximab in Metastatic Colorectal Cancer," Journal of Clinical Oncology, 26(35):5705-5712 (2008).
Donkena et al., "Oxidative Stress and DNA Methylation in Prostate Cancer," Obstetrics and Gynecology International, 2010(Article ID 302051):14 pages (2010).
Dressman et al., "Gene expression profiles of multiple breast cancer phenotypes and response to neoadjuvant chemotherapy," Clin Cancer Res, 12(3):819-826 (2006).
Extended European Search Report for EP Application No. 19219395.1 dated Jul. 23, 2020.

(56) References Cited

OTHER PUBLICATIONS

Final Rejection for U.S. Appl. No. 15/102,129, "Formulations for Neoplasia Vaccines," dated Aug. 15, 2019.
Final Rejection for U.S. Appl. No. 15/105,961, "Combination Therapy With Neoantigen Vaccine," dated Aug. 23, 2019.
Final Rejection for U.S. Appl. No. 15/537,785, "Methods for Profiling the T Cell Repertoire," dated Jul. 18, 2019.
Final Rejection for U.S. Appl. No. 15/537,839, "Molecular Biomarkers for Cancer Immunotherapy," dated May 1, 2020.
Final Rejection for U.S. Appl. No. 15/575,328, "Shared Neoantigens," dated Oct. 23, 2019.
Ganesan et al., "Tumor-Infiltrating Regulatory T Cells Inhibit Endogenous Cytotoxic T Cell Responses to Lung Adenocarcinoma," The Journal of Immunology, 191(4): 2009-2017 (2013).
Goh et al., "Mining the Structural Genomics Pipeline: Identification of Protein Properties that Affect High-throughput Experimental Analysis," Journal of Molecular Biology, 336(1): 115-130 (2004).
Haanen et al., "Immunotherapy of melanoma," Euro J Canc Supp 11:97-105 (2013).
Hamid et al., "Safety and Tumor Responses with Lambrolizumab (Anti-PD-1) in Melanoma," The New England Journal of Medicine, 369(2):134-144 (2013).
IEDB Analysis Resource for MHC-I binding predictions (printed Oct. 2019).
IEDB Analysis Resource for MHC-II binding predictions (printed Oct. 2019).
Jiang et al., "GATA3 Mutations Define a Unique Subtype of Luminal-Like Breast Cancer With Improved Survival," Canc 120:1329-1337 (2014).
Khammari et al., "Treatment of metastatic melanoma with autologous melan-A/mart-1-specific cytotoxic t lymphocyte clones," Journal of Investigative Dermatology, 129(12): 2835-2842 (2009).
Kim et al., "Inactivating mutations of caspase-8 in colorectal carcinomas," Gastroenterology, 125:708-715 (2003).
Kobayashi et al., "DNA methylation profiling reveals novel biomarkers and important roles for DNA methyltransferases in prostate cancer," Genome Research, 21:1017-1027 (2011).
Kreiter et al., "Targeting the tumor mutanome for personalized vaccination therapy," OncoImmunology, 1(5):768-769 (2012).
Loveridge et al., "The genetic contribution to human T-cell receptor repertoire," Immunology, 74:246-250 (1991).
McCleskey et al., "GATA-3 Expression in Advanced Breast Cancer: Prognostic Value and Organ-Specific Relapse," Amer J Clin Pathol 144:756-763 (2015).
Mikeska et al., "The implications of heterogeneous DNA methylation for the accurate quantification of methylation," Epigenomics, 2(4):561-573 (2010).
Niwa et al., "Bimodal protein solubility distribution revealed by an aggregation analysis of the entire ensemble of *Escherichia coli* proteins," PNAS, 106(11): 4201-4206 (2009).
Non-Final Rejection for U.S. Appl. No. 14/877125, " Compositions and Methods for Personalized Neoplasia Vaccines," dated Feb. 3, 2020.
Non-Final Rejection for U.S. Appl. No. 15/038504, "Compositions and Methods for Diagnosing, Evaluating and Treating Cancer by Means of the DNA Methylation Status," dated Feb. 4, 2020.
Non-Final Rejection for U.S. Appl. No. 15/105,961, "Combination Therapy With Neoantigen Vaccine," dated Jun. 2, 2020.
Non-Final Rejection for U.S. Appl. No. 15/513,127, "Use of Clonal Evolution Analysis for Ibrutinib Resistance in Chronic Lymphocytic Leukemia Patients," dated Oct. 29, 2019.
Non-Final Rejection for U.S. Appl. No. 15/537,785, "Methods for Profiling the T Cell Repertoire," dated May 11, 2020.
Non-Final Rejection for U.S. Appl. No. 15/537,839, "Molecular Biomarkers for Cancer Immunotherapy," dated Oct. 8, 2019.
Non-Final Rejection for U.S. Appl. No. 15/735,566, " Formulations for Neoplasia Vaccines and Methods of Preparing Thereof," dated May 28, 2020.
Non-Final Rejection for U.S. Appl. No. 15/800,732, "Compositions and Methods of Identifying Tumor Specific Neoantigens," dated Apr. 10, 2020.
Notice of Allowance for U.S. Appl. No. 15/575328, "Shared Neoantigens," dated Jan. 23, 2020.
Notice of Allowance for U.S. Appl. No. 16/188,737, "Compositions and Methods of Identifying Tumor Specific Neoantigens," dated Jul. 25, 2019.
Ohashi et al., "Lung cancers with aquired resistance to EGFR inhibitors occasionally harbor Braf gene mutations but lack mutations in KRAS, NRAS, or MEKI ," PNAS, E2127-E2133 (2012).
Poster entitled "Disease-related biomarkers are associated with extended progression-free survival after treatment with Neo-PV-01 in combination with anti-PD1 in patients with metastatic cancers" presented at The Society for Immunotherapy of Cancer Annual Meeting Nov. 6-10, 2019 ("SITC 2019 poster").
Sharma et al., "A Chromatin-Mediated Reversible Drug-Tolerant State in Cancer Cell Subpopulations," Cell, 141:69-80 (2010).
Shen et al., "Integrated genetic and epigenetic analysis identifies three different subclasses of colon cancer," PNAS, 104(47):18654-18659 (2007).
Smialowsky et al., "Protein solubility: sequence based prediction and experimental verification," Bioinformatics, 23(19):2356-3542 (2007).
Soung et al., "Capase-8 gene is frequently inactivated by the frameshift somatic mutation 1225_1226delTG in hepatocellular carcinomas," Oncogene, 24:141-147 (2005).
Supplementary Materials from Third Party Observation in EP Application No. 15198284.0.
Thon et al., "Personalized treatment strategies in glioblastoma: MGMT promoter methylation status," Onco Targets and Therapy, 6:1363-1372 (2013).
Topalian et al., "Targeting the PD-1/B7-H1(PD-L1) pathway to activate anti-tumor immunity," Current Opinion in Immunology, 24:207-212 (2012).
Vandrovcova et al., :Somatic BRAF-V600E Mutations in Familial Colorectal Cancer, Cancer Epidemio Biomarkers Prev, 15(11):2270-2273 (2006).
Varley et al., "Intra-tumor heterogeneity of MLH1 promoter methylation revealed by deep single molecule bisulfite sequencing," Nucleic Acids Research, 37(14):4603-4612 (2009).
Yee et al., "Adoptive T cell therapy using antigen-specific CD8 T cell clones for the treatment of patients with metastatic melanoma: In vivo persistence, migration, and antitumor effect of transferred T cells," PNAS, 99(25): 16168-16173 (2002).
U.S. Appl. No. 16/094,786, filed Oct. 18, 2018, 2019-0346442, Pending.
U.S. Appl. No. 13/108,610, filed May 16, 2011, 2011-0293637, U.S. Pat. No. 9,115,402, Granted.
U.S. Appl. No. 14/794,449, filed Jul. 8, 2015, 2016-00008447, Abandoned.
U.S. Appl. No. 15/187,174, filed Jun. 20, 2016, 2016-0331822, Abandoned.
U.S. Appl. No. 15/800,732, filed Nov. 1, 2017, 2018-0055922, Published.
U.S. Appl. No. 16/181,098, filed Nov. 5, 2018, 2019-0060432, Published.
U.S. Appl. No. 16/188,737, filed Nov. 13, 2018, 2016-0101170, U.S. Pat. No. 10,426,824, Granted.
U.S. Appl. No. 16/381,791, filed Apr. 11, 2019, 2020-0069783, Published.
U.S. Appl. No. 16/528,195, filed Jul. 31, 2019, 2020-0016251, Published.
U.S. Appl. No. 14/877,125, filed Oct. 7, 2015, 2016-0101170, Allowed.
U.S. Appl. No. 15/102,129, filed Jun. 6, 2016, 2016-0310584, Abandoned.
U.S. Appl. No. 16/813,371, filed Mar. 9, 2020, Pending.
U.S. Appl. No. 15/038,504, filed May 23, 2016, 2016-0326593, U.S. Pat. No. 10,801,070, Granted.
U.S. Appl. No. 17/017,045, filed Sep. 10, 2020, Pending.
U.S. Appl. No. 15/105,961, filed Jun. 17, 2016, 2016-0339090, Published.

(56) References Cited

OTHER PUBLICATIONS

U.S. Appl. No. 15/537,839, filed Jun. 19, 2017, 2019-0127803, Published.
U.S. Appl. No. 15/575,328, filed Nov. 17, 2017, 2018-0153975, Allowed.
U.S. Appl. No. 16/859,252, filed Apr. 27, 2020, Pending.
U.S. Appl. No. 15/513,127, filed Mar. 21, 2017, 2017-0298441, Published.
U.S. Appl. No. 15/735,566, filed Dec. 11, 2017, 2019-0060428, Published.
U.S. Appl. No. 16/480,535, filed Jul. 24, 2019, 2019-0376147, Published.
Acevedo et al., "Analysis of the mechanisms mediating tumor-specific changes in gene expression in human liver tumors," Cancer Res, 68(8):2641-2651 (2008).
Adams, "Toll-like receptor agonists in cancer therapy," Immunotherapy, 1(6):949-964 (2009).
Akiyama et al., "GATA-4 and GATA-5 transcription factor genes and potential downstream antitumor target genes are epigenetically silenced in colorectal and gastric cancer," Mol Cell Biol, 23:8429-8439 (2003).
Alarcon et al., "DNA vaccines: technology and application as anti-parasite and anti-microbial agents," Advances in Parasitology, 42:343-410 (1999).
Ali et al., "In situ regulation of DC subsets and T cells mediates tumor regression in mice," Cancer Immunotherapy, 1(8):1-10 (2009).
Ali et al., "Infection-mimicking materials to program dendritic cells in situ," Nat Mater, 8:151-8 (2009).
Almeida et al., "CTdatabase: a knowledge-base of high- throughput and curated data on cancer-testis antigens," Nucleic acids research, 37:D816-819 (2008).
Alvarez, "Present and future evolution of advanced breast cancer therapy," Breast Cancer Research, 12(Suppl 2):S1 (2010).
Amara et al., "Control of a mucosal challenge and prevention of AIDS by a multiprotein DNA/MVA vaccine," Science, 292(5514):69-74 (2001).
Amato et al., "Vaccination of metastatic renal cancer patients with MVA-5T4: a randomized, double-blind, placebo-controlled phase III study," Clin Can Res, 16(22):5539-47 (2010).
Amato et al., "Vaccination of renal cell cancer patients with modified vaccinia ankara delivering tumor antigen 5T4 (TroVax) administered with interleukin 2: a phase II trial," Clin Cancer Res, 14(22):7504-10 (2008).
Anders et al., "HTSeq-A Python framework to work with high-throughput sequencing data," Bioinformatics, 31(2):166-169 (2015).
Antoine et al., "The complete genomic sequence of the modified vaccinia Ankara strain: comparison with other orthopoxviruses," Virology, 244(2):365-96 (1998).
Antonis et al., "Vaccination with recombinant modified vaccinia virus Ankara expressing bovine respiratory syncytial virus (bRSV) proteins protects calves against RSV challenge," Vaccine, 25(25):4818-4827 (2007).
Aucouturier et al., "Adjuvants designed for veterinary and human vaccines," Vaccine, 19(17-19):2666-2672 (2001).
Avogadri et al. "Modulation of CTLA-4 and GITR for Cancer Immunotherapy," Curr Top Microbiol Immunol, 344:211 (2011).
Bachem et al., "Superior antigen cross-presentation and XCR1 expression define human CD11c+ CD141+ cells as homologues of mouse CD8+ dendritic cells," Journal of Experimental Medicine, 207(6):1273-1281 (2010).
Baden et al., "First-in-human evaluation of the safety and immunogenicity of a recombinant adenovirus serotype 26 FfIV-1 Env vaccine (IPCAVD 001)," J Infect Dis, 207(2):240-247 (2012).
Balagaan et al., "Stable and efficient intraocular gene transfer using pseudotyped EIAV lentiviral vectors," J Gene Med, 8:275-285 (2005).
Balazsi et al., "Cellular decision making and biological noise: from microbes to mammals," Cell, 144(6):910-925 (2011).
Balch et al., "Final version of 2009 AJCC melanoma staging and classification," Journal of clinical oncology, 27(36):6199-6206 (2009).

Barbie et al., "Systematic RNA interference reveals that oncogenic KRAS-driven cancers require TBK1," Nature, 462:108-112 (2009).
Barretina et al., "The Cancer Cell Line Encyclopedia enables predictive modelling of anticancer drug sensitivity," Nature, 483:603-607 (2012).
Baylin, "A decade of exploring the cancer epigenome-biological and translational implications," Nat Rev Cancer, 11:726-734 (2005).
Baylin, "DNA methylation and gene silencing in cancer," Nat Clin Pract Oncol 2, Suppl 1, S4-11 (2005).
Benson, "Tandem repeats finder: a program to analyze DNA sequences," Nucleic acids research, 27(2):573-580 (1999).
Benton et al., "Screening lambdagt recombinant clones by hybridization to single plaques in situ," Science, 196(4286):180-182 (1977).
Berger et al., "The genomic complexity of primary human prostate cancer," Nature, 470:214-220 (2011).
Berger et al.,"Melanoma genome sequencing reveals frequent PREX2 mutations," Nature, 485(7399):502 (2012).
Berman et al., "Regions of focal DNA hypermethylation and long-range hypomethylation in colorectal cancer coincide with nuclear lamina-associated domains," Nat Genet, 44:40-46 (2012).
Bhardwaj et al., "TLR Agonists: Are They Good Adjuvants?," Cancer J, 16:382-391 (2010).
Bindea et al., "Spatiotemporal dynamics of intratumoral immune cells reveal the immune landscape in human cancer," Immunity, 39:782-795 (2013).
Bird, "DNA methylation patterns and epigenetic memory," Genes Dev, 16:6-21 (2002).
Bishop et al., "APOBEC-mediated editing of viral RNA," Science, 305:645 (2004).
Bisht et al., "Severe acute respiratory syndrome coronavirus spike protein expressed by attenuated vaccinia virus protectively immunizes mice," Proc Natl Aced Sci, 101:6641-46 (2004).
Blanchard et al., "Modified vaccinia virus Ankara undergoes limited replication in human cells and lacks several immunomodulatory proteins: implications for use as a human vaccine," Journal of General Virology, 79(5):1159-1167 (1998).
Bock et al., "BiQ Analyzer: visualization and quality control for DNA methylation data from bisulfite sequencing," Bioinformatics, 21:4067-4068 (2005).
Bock et al., "Reference Maps of human ES and iPS cell variation enable high-throughput characterization of pluripotent cell lines," Cell, 144:439-452 (2011).
Bogunovic et al., "TLR4 engagement during TLR3-induced proinflammatory signaling in dendritic cells promotes IL-10-mediated suppression of antitumor immunity," Cancer Res, 71(16):5467-5476 (2011).
Boller et al. "Characterization of the antibody response specific for the human endogenous retrovirus HTDV/HERV-K," Journal of virology, 71(6):4581-4588 (1997).
Boni et al. "Adoptive transfer of allogeneic tumor-specific T cells mediates effective regression of large tumors across major histocompatibility barriers," Blood, 112(12):4746-4754 (2008).
Boquest et al., "Isolation and transcription profiling of purified uncultured human stromal stem cells: alteration of gene expression after in vitro cell culture," Molecular biology of the cell, 16(3):1131-1141 (2005).
Boscardin et al., "Antigen targeting to dendritic cells elicits long-lived T cell help for antibody responses," Journal of Experimental Medicine, 203(3):599-606 (2006).
Boyle et al., "Gel-free multiplexed reduced representation bisulfite sequencing for large-scale DNA methylation profiling," Genome Biol, 13:R92 (2012).
Boyle et al., "Tapasin-related protein TAPBPR is an additional component of the MHC class I presentation pathway," Proceedings of the National Academy of Sciences, 110: 3465-3470 (2013).
Bozic et al., "Dynamics of targeted cancer therapy," Trends Mol Med, 18:311-316 (2012).
Bozic et al., "Evolutionary dynamics of cancer in response to targeted combination therapy," Elife, 2:e00747 (2013).
Brahmer et al., "Safety and activity of anti-PD-L1 antibody in patients with advanced cancer," N Engl J Med, 366(26):2455-2465 (2012).

(56) References Cited

OTHER PUBLICATIONS

Brochier et al., "Large-scale eradication of rabies using recombinant vaccinia-rabies vaccine," Nature, 354:520-552 (1991).
Brown et al., "Integrative genomic analysis implicates gain of PIK3CA at 3g26 and MYC at 8q24 in chronic lymphocytic leukemia," Clin Cancer Res, 8:3791-802 (2012).
Buchschacher et al., "Human immunodeficiency virus vectors for inducible expression of foreign genes." Journal of virology, 66(5):2731-2739 (1992).
Buller et al., "Decreased virulence of recombinant vaccinia virus expression vectors is associated with a thymidine kinase-negative phenotype," Nature, 317:813-815 (1985).
Buller et al., "Deletion of the vaccinia virus growth factor gene reduces virus virulence," Journal of virology, 62(3):866-874 (1988).
Burger et al., "B cell receptor signaling in chronic lymphocytic leukemia," Trends Immunol, 34:592-601 (2013).
Buser et al., "Unique composite hematolymphoid tumor consisting of a pro-T lymphoblastic lymphoma and an indeterminate dendritic cell tumor: evidence for divergent common progenitor cell differentiation," Pathobiology, 81:199-205 (2014).
Byrd et al., "Targeting BTK with ibrutinib in relapsed chronic lymphocytic leukemia," The New England journal of medicine, 369:32-42 (2013).
Bystryn et al., "Double-blind trial of a polyvalent, shed-antigen, melanoma vaccine," Clin Cancer Res, 7(7):1882-1887 (2001).
Böhme al., DNA vector constructs that prime hepatitis B surface antigen-specific cytotoxic T lymphocyte and antibody responses in mice after intramuscular injection. Journal of immunological methods 193(1): 29-40 (1996).
Cahill et al., "450K-array analysis of chronic lymphocytic leukemia cells reveals global DNA methylation to be relatively stable over time and similar in resting and proliferative compartments," Leukemia, 27:150-158 (2013).
Cancer Genome Atlas Network, "Comprehensive molecular characterization of human colon and rectal cancer," Nature, 487:330-337 (2012).
Cancer Genome Atlas Network, "Comprehensive molecular portraits of human breast tumours," Nature, 490:61-70 (2012).
Cancer Genome Atlas Research Network, "Comprehensive genomic characterization defines human glioblastoma genes and core pathways," Nature, 455(7216):1061-1068 (2008).
Cancer Genome Atlas Research Network, "Comprehensive genomic characterization of squamous cell lung cancers," Nature, 489, 519-525 (2012).
Cancer Genome Atlas Research Network, "Comprehensive molecular characterization of clear cell renal cell carcinoma," Nature, 499:43-49 (2013).
Cancer Genome Atlas Research Network, "Comprehensive molecular characterization of gastric adenocarcinoma," Nature, 513:202-209 (2014).
Cancer Genome Atlas Research Network, "Genomic and epigenomic landscapes of adult de novo acute myeloid leukemia," New England Journal of Medicine, 368(22):2059-2074 (2013).
Cancer Genome Atlas Research Network, "Integrated genomic analyses of ovarian carcinoma," Nature, 474: 609-615 (2011).
Carreno et al., "IL-12p70-producing patient DC vaccine elicits Tcl-polarized immunity," Journal of Clinical Investigation, 123(8):3383-94 (2013).
Carter et al., "Absolute quantification of somatic DNA alterations in human cancer," Nat Biotechnol, 30:413-21 (2012).
Carter et al., "Accurate estimation of homologue-specific DNA concentration-ratios in cancer samples allows long-range haplotyping," Nature Precedings, 59-87 (2011).
Caskey et al., "Synthetic double-stranded RNA induces innate immune responses similar to a live viral vaccine in humans," The Journal of experimental medicine, 208(12):2357-2366 (2011).
Castle et al., "Exploiting the mutanome for tumor vaccination," Cancer research, 72(5):1081-1091 (2012).
Chang et al., "Immune selection of hot-spot beta 2-microglobulin gene mutations, HLA-A allospecificity loss, and antigen-processing machinery component down-regulation in melanoma cells derived from recurrent metastases following immunotherapy," Journal of immunology, 174:1462-1471 (2005).
Chapman et al., "Initial genome sequencing and analysis of multiple myeloma," Nature, 471:467-472 (2011).
Cheever, "Twelve immunotherapy drugs that could cure cancers," Immunological reviews, 222:357-368 (2008).
Chen et al., "Impact of replication timing on non-CpG and CpG substitution rates in mammalian genomes," Genome Res, 20:447-457 (2010).
Chen et al., "Langerhans Cell Sarcoma Arising from Chronic Lymphocytic Lymphoma/Small Lymphocytic Leukemia: Lineage Analysis and BRAF V600E Mutation Study," N Am J Sci, 5:386-91 (2013).
Chen et al., "Molecular mechanisms of T cell co-stimulation and co-inhibition," Nature reviews Immunology, 13:227-242 (2013).
Chen et al., "Recombinant modified vaccinia virus Ankara expressing the spike glycoprotein of severe acute respiratory syndrome coronavirus induces protective neutralizing antibodies primarily targeting the receptor binding region," Journal of virology, 79.5:2678-2688 (2005).
Chen et al., "Induction of CD8+ T cell responses to dominant and subdominant epitopes and protective immunity to Sendai virus infection by DNA vaccination," The Journal of Immunology, 160(5):2425-2432 (1998).
Child et al., "Insertional inactivation of the large subunit of ribonucleotide reductase encoded by vaccinia virus is associated with reduced virulence in vivo," Virology, 174(2):625-629 (1990).
Chim et al., "Epigenetic dysregulation of the Wnt signalling pathway in chronic lymphocytic leukaemia," J Clin Pathol, 61:1214-1219 (2008).
Chiron et al., "Cell-cycle reprogramming for PI3K inhibition overrides a relapse-specific C4815 BTK mutation revealed by longitudinal functional genomics in mantle cell lymphoma," Cancer Discov, 4:1022-35 (2014).
Chroboczek et al., "The Sequence of the Genome of Adenovirus Type 5 and Its Comparison with the Genome of Adenovirus Type 2," Virology, 186:280-285 (1992).
Church, "Genomes for all," Sci Am, 294(1):46-54 (2006).
Cibulskis et al., "ContEst: estimating cross-contamination of human samples in next-generation sequencing data," Bioinformatics, 27:2601-2602 (2011).
Cibulskis et al., "Sensitive detection of somatic point mutations in impure and heterogeneous cancer samples," Nat Biotechnol, 31:213-9 (2013).
Cleveland, "LOWESS: A program for smoothing scatterplots by robust locally weighted regression," The American Statistician, 35:54 (1981).
Conlon et al., "Mouse, but not Human STING, Binds and Signals in Response to the Vascular Disrupting Agent 5,6-Dimethylxanthenone-4-Acetic Acid," Journal of Immunology, 190:5216-25 (2013).
Corbett et al., "Aerosol immunization with NYVAC and MVA vectored vaccines is safe, simple, and immunogenic," Proc Natl Acad Sci, 105(6):2046-51 (2008).
Coulie et al., "A mutated intron sequence codes for an antigenic peptide recognized by cytolytic T lymphocytes on a human melanoma," Proc Natl Acad Sci USA, 92(17):7976-7980 (1995).
Cox et al., "Induction of cytotoxic T lymphocytes by recombinant canarypox (ALVAC) and attenuated vaccinia (NYVAC) viruses expressing the HIV-1 envelope glycoprotein," Virology, 195(2):845-850 (1993).
Crozat et al., "The XC chemokine receptor 1 is a conserved selective marker of mammalian cells homologous to mouse CD8α+ dendritic cells," Journal of Experimental Medicine, 207(6):1283-1292 (2010).
Daheshia et al., "Suppression of ongoing ocular inflammatory disease by topical administration of plasmid DNA encoding IL-10," The Journal of Immunology 159(4):1945-1952 (1997).
De et al., "Aberration in DNA methylation in B-cell lymphomas has a complex origin and increases with disease severity," PLoS Genet. 9:e1003137 (2013).

(56) References Cited

OTHER PUBLICATIONS

De Magalhaes et al., "Next-generation sequencing in aging research: emerging applications, problems, pitfalls and possible solutions," Ageing Research Reviews, 9(3):315-323 (2010).
DeLuca et al., "RNA-SeQC: RNA-seq metrics for quality control and process optimization," Bioinformatics, 28:1530-2 (2012).
DePristo et al., "A framework for variation discovery and genotyping using next-generation DNA sequencing data," Nature Genetics, 43:491-498 (2011).
Di Stasi et al., "Inducible apoptosis as a safety switch for adoptive cell therapy," New England Journal of Medicine, 365(18):1673-1683 (2011).
Didierlaurent et al., "Attenuated poxviruses expressing a synthetic HIVprotein stimulate HLA-A2-restricted cytotoxic T-cell responses," Vaccine, 22(25-26):3395-3403 (2004).
Ding et al., "Somatic mutations affect key pathways in lung adenocarcinoma," Nature, 455:1069-1075 (2008).
Dohner et al., "Genomic aberrations and survival in chronic lymphocytic leukemia," The New England journal of medicine, 343:1910-1916 (2000).
Doody et al., "PRDMI/BLIMP-1 Modulates IFN—Dependent Control of the MHC Class I Antigen-Processing and Peptide-Loading Pathway," The Journal of Immunology, 179:7614-7623 (2007).
Dreicer et al., "MVA-MUC1-IL2 vaccine immunotherapy (TG4010) improves PSA doubling time in patients with prostate cancer with biochemical failure," Investigational new drugs, 27(4):379-386 (2009).
Dubey et al., "The immunodominant antigen of an ultraviolet-induced regressor tumor is generated by a somatic point mutation in the DEAD (SEQ ID No. 62) box helicase p68," The Journal of experimental medicine, 185(4):695-705 (1997).
DuPage et al., "Expression of tumour-specific antigens underlies cancer immunoediting," Nature, 482(7385):405-409 (2012).
Earl et al., "Immunogenicity of a highly attenuated MVA smallpox vaccine and protection against monkeypox," Nature, 428:182 (2004).
Eckhardt et al., "DNA methylation profiling of human chromosomes 6, 20 and 22," Nat Genet, 38:1378-1385 (2006).
Eden et al., "Discovering motifs in ranked lists of DNA sequences," PLoS computational biology, 3, e39 (2007).
Eden et al., "GOrilla: a tool for discovery and visualization of enriched GO terms in ranked gene lists," BMC bioinformatics, 10:48 (2009).
Eggermont et al., "Ulceration and stage are predictive of interferon efficacy in melanoma: results of the phase III adjuvant trials EORTC 18952 and EORTC 18991," Eur J Cancer, 48(2):218-225 (2012).
Ehrlich, "DNA hypomethylation in cancer cells," Epigenomics, 1:239-259 (2009).
Escobar et al., "Bayesian density estimation and inference using mixtures," Journal of the American Statistical Association, 90:577-588 (1995).
Esteban, "Attenuated poxvirus vectors MVA and NYVAC as promising vaccine cadidates against HIV/AIDS," Human vaccines, 5(12):867-871 (2009).
Fais et al., "Chronic lymphocytic leukemia B cells express restricted sets of mutated and unmutated antigen receptors," The Journal of clinical investigation, 102:1515-25 (1998).
Fan et al., "The multi substrate adapter Gabl regulates hepatocyte growth factor (scatter factor)-c-Met signaling for cell survival and DNA repair," Molecular and cellular biology, 21:4968-4984 (2001).
Fantom Consortium et al., "A promoter-level mammalian expression atlas," Nature, 507:462-470 (2014).
Farsaci et al., "Consequence of dose scheduling of sunitinib on host immune response elements and vaccine combination therapy," Int J Cancer, 130:1948-1959 (2012).
Feigner et al., "Lipofection: a highly efficient, lipid-mediated DNA-transfection procedure," PNAS, 84(21):7413-7414 (1987).
Ferrier-Rembert et al., "Short-and long-term immunogenicity and protection induced by non-replicating smallpox vaccine candidates in mice and comparison with the traditional 1st generation vaccine," Vaccine, 26(14):1794-1804 (2008).
Finke et al., "Sunitinib Reverses Type-1 Immune Suppression and Decreases T-Regulatory Cells in Renal Cell Carcinoma Patients," Clin Cancer Res, 14(20):6674-6682 (2008).
Fisher et al., "A scalable, fully automated process for construction of sequence-ready human exome targeted capture libraries," Genome Biol, 12:R1 (2011).
Flaherty et al., "From genes to drugs: targeted strategies for melanoma," Nat Rev Cancer, 12(5):349-361 (2012).
Flexner et al., "Prevention of vaccinia virus infection in imiminodeficient mice by vector-directed IL-2 expression," Nature, 330(6145):259-262 (1987).
Flynn et al., "Immunization with HIV Gag targeted to dendritic cells followed by recombinant New York vaccinia virus induces robust T-cell immunity in nonhuman primates," Proc Natl Acad Sci, 108(17):7131-7136 (2011).
Forconi et al., "Genome-wide DNA analysis identifies recurrent imbalances predicting outcome in chronic lymphocytic leukaemia with 17p deletion," British journal of haematology, 143:532-6 (2008).
Fransen et al., "Controlled local delivery of CTLA-4 blocking antibody induces CD8+ T-cell-dependent tumor eradication and decreases risk of toxic side effects," Clin Cancer Res, 19(19):5381-5389 (2013).
Frederick et al., "BRAF inhibition is associated with enhanced melanoma antigen expression and a more favorable tumor microenvironment in patients with metastatic melanoma," Clin Cancer Res, 19:1225-1231 (2013).
Friedberg et al., "Inhibition of Syk with fostamatinib disodium has significant clinical activity in non-Hodgkin lymphoma and chronic lymphocytic leukemia," Blood, 115:2578-2585 (2011).
Fritsch et al., "Translational repression of MCL-1 couples stress-induced elF2 alpha phosphorylation to mitochondrial apoptosis initiation," The Journal of biological chemistry, 282:22551-62 (2007).
Furman et al., "Ibrutinib resistance in chronic lymphocytic leukemia," The New England journal of medicine, 370(24):2352 (2014).
Furman et al., "Idelalisib and rituximab in relapsed chronic lymphocytic leukemia," The New England journal of medicine, 370:997-1007 (2014).
Fynan et al., "DNA vaccines: protective immunizations by parenteral, mucosal, and gene-gun inoculations," PNAS, 90 (24): 11478-82 (1993).
Gallego-Gomez et al., "Differences in virus-induced cell morphology and in virus maturation between MVA and other strains (WR, Ankara, and NYCBH) of vaccinia virus in infected human cells," Journal of virology, 77(19):10606-10622 (2003).
Gallois et al., "A needle in the 'cancer vaccine' haystack," Nature medicine, 16(8):854-856 (2010).
Gao et al., "Integrative analysis of complex cancer genomics and clinical profiles using the cBioPortal," Science signaling, 6(269):pi1 (2013).
Garimella et al., "Identification of novel molecular regulators of tumor necrosis factor-related apoptosis-inducing ligand (TRAIL)-induced apoptosis in breast cancer cells by RNAi screening," Breast cancer research, 16(2):R41 (2014).
Garofalo et al., "miR-221&222 regulate TRAIL resistance and enhance tumorigenicity through PTEN and TIMP3 downregulation," Cancer Cell, 16(6):498-509 (2009).
Garraway et al., "Lessons from the cancer genome," Cell, 153:17-37 (2013).
Gaucher et al., "Yellow fever vaccine induces integrated multilineage and polyfunctional immune responses," The Journal of experimental medicine, 205(13):3119-3131 (2008).
Gevaert et al., "Protein identification methods in proteomics," Electrophoresis: An International Journal, 21(6):1145-1154 (2000).
Gherardi et al., "Prime-boost immunization schedules based on influenza virus and vaccinia virus vectors potentiate cellular immune responses against human immunodeficiency virus Env protein systemically and in the genitorectal draining lymph nodes," Journal of virology, 77(12):7048-7057 (2003).
Ghiringhelli et al., "Metronomic cyclophosphamide regimen selectively depletes CD4+CD25+ regulatory T cells and restores T and NK effector functions in end stage cancer patients," Cancer Immunol Immunother, 56:641-648 (2007).

(56) References Cited

OTHER PUBLICATIONS

Giannopoulos et al., "Peptide vaccination elicits leukemia-associated antigen-specific cytotoxic CD8+ T-cell responses in patients with chronic lymphocytic leukemia," Leukemia, 24(4):798-805 (2010).
Gibbs et al., "Abundant quantitative trait loci exist for DNA methylation and gene expression in human brain," PLoS genetics, 6:e1000952 (2010).
Goebel et al., "The complete DNA sequence of vaccinia virus," Virology, 179(1):247-266 (1990).
Gomez et al., "Efficient CD8+ T cell response to the HIV-env V3 loop epitope from multiple virus isolates by a DNA prime/vaccinia virus boost (rWR and rMVA strains) immunization regime and enhancement by the cytokine IFN-γ," Virus research, 105:11-22 (2004).
Gomez et al., "Head-to-head comparison on the immunogenicity of two HIV/AIDS vaccine candidates based on the attenuated poxvirus strains MVA and NYVAC co-expressing in a single locus the HIV-1 BX08 gp120 and Hiv-1IIIB Gag-Pol-Nef proteins of clade B," Vaccine, 25(15):2863-2885 (2007).
Gomez et al., "MVA and NYVAC as vaccines against emergent infectious diseases and cancer," Current gene therapy, 11(:3):189-217 (2011).
Gomez et al., "The poxvirus vectors MVA and NYVAC as gene delivery systems for vaccination against infectious diseases and cancer," Current gene therapy, 8(2):97-120 (2008).
Gomez et al., "Virus distribution of the attenuated MVA and NYVAC poxvirus strains in mice," Journal of General Virology, 88(9):2473-2478 (2007).
Greco et al., "Improving the safety of cell therapy with the TK-suicide gene," Front Pharmacol, 6:95 (2015).
Greenman et al., "Patterns of somatic mutation in human cancer genomes," Nature, 446:153-158 (2007).
Gregoriadis et al., "Improving the therapeutic efficacy of peptides and proteins: A role for polysialic acids," Int J Pharmaceutics, 300(1-2):125-30 (2005).
Gros et al., "PD-1 identifies the patient-specific CD8+ tumor-reactive repertoire infiltrating human tumors," The Journal of clinical investigation, 124(5):2246-2259 (2014).
Grunstein et al., "Colony hybridization: a method for the isolation of cloned DNAs that contain a specific gene," PNAS, 72(10):3961-3965 (1975).
GTEx Consortium, The Genotype-Tissue Expression (GTEx) project, Nature genetics, 45:580-585 (2013).
Guo et al., "Droplet microfluidics for high-throughput biological assays," Lab Chip, 12:2146-55 (2012).
Guthals et al., "Shotgun Protein Sequencing with Meta-contig Assembly," Molecular and Cellular Proteomics, 1(10):1084-96 (2012).
Hadrup et al., "Parallel detection of antigen-specific T-eeil responses by multidimensional encoding of MHC multimers," Nature Methods, 6(7):520-26 (2009).
Halabi et al., "Prognostic model for predicting survival in men with hormone-refractory metastatic prostate cancer," Journal of Clinical Oncology, 21(7):1232-1237 (2003).
Hall, "Advanced sequencing technologies and their wider impact in microbiology," Journal of experimental biology, 210(9):1518-1525 (2007).
Hanahan et al., "Hallmarks of cancer: the next generation," Cell, 144:646-674 (2011).
Hansen et al., "Increased methylation variation in epigenetic domains across cancer types," Nat Genet, 43:768-775 (2011).
Hanzelmann et al., "GSVA: gene set variation analysis for microarray and RNA-Seq data," BMC bioinformatics, 14:7 (2013).
Harris et al., "Comparison of sequencing-based methods to profile DNA methylation and identification of monoallelic epigenetic modifications," Nat Biotechnol, 28:1097-1105 (2010).
Harris et al., "RNA editing enzyme APOBECl and some of its homologs can act as DNA mutators," Molecular cell, 1095):1247-1253 (2002).

Heemskerk et al., "The cancer antigenome," EMBO Journal, 32(2):194-203 (2013).
Hel et al., "Potentiation of simian immunodeficiency virus (SIV)-specific CD4+ and CD8+ T cell responses by a DNA-SIV and NYVAC-SIV prime/boost regimen," The Journal of Immunology, 167(12):7180-7191 (2001).
Herbeuval et al., "HAART reduces death ligand but not death receptors in lymphoid tissue of HIV-infected patients and simian immunodeficiency virus-infected macaques," AIDS, 23:35-40 (2009).
Herman et al., "ibrutinib-induced lymphocytosis in patients with chronic lymphocytic leukemia: correlative analyses from a phase II study," Leukemia, 28:2188 (2014).
Hinrichs et al., "Exploiting the curative potential of adoptive T-cell therapy for cancer," Immunological reviews, 257:56-71 (2014).
Hombrink et al., "High-Throughput Identification of Potential Minor Histocompatibility Antigens by MHC Tetramer-Based Screening: Feasibility and Limitations," Plos One, 6(8):1-11 (2011).
Honigberg et al., "The Bruton tyrosine kinase inhibitor PCI-32765 blocks B-cell activation and is efficacious in models of autoimmune disease and B-cell malignancy," PNAS, 107:13075-13080 (2010).
Honig et al., "Phase 1 clinical trial of a recombinant canarypoxvirus (ALVAC) vaccine expressing human carcinoembryonic antigen and the B7.1 co- stimulatory molecule," Cancer Immunol Immunother, 49:504-514 (2000).
Huang et al., "Mucosal priming with replicative Tiantan vaccinia and systemic boosting with DNA vaccine raised strong mucosal and systemic HIV-specific immune responses," Vaccine, 25(52):8874-8884 (2007).
Hutchings et al., "Combination of protein and viral vaccines induces potent cellular and humoral immune responses and enhanced protection from murine malaria challenge," Infect Immun, 75(12):5819-26 (2007).
Illingworth et al., "Orphan CpG islands identify numerous conserved promoters in the mammalian genome," PLoS Genet, 6(9):e1001134 (2010).
Inokuchi et al., "DCC protein expression in hematopoietic cell populations and its relation to leukemogenesis," J Clin Invest, 97:852-857 (1996).
Itoh et al., "Personalized peptide vaccines: A new therapeutic modality for cancer," Cancer Sci, 97:970-976 (2006).
Izeradjene et al., "Casein kinase II (CK2) enhances death-inducing signaling complex (DISC) activity in TRAIl-induced apoptosis in human colon carcinoma cell lines," Oncogene, 24:2050-2058 (2005).
Jaatinen et al., "Global gene expression profile of human cord blood-derived CD133+ cells," Stem Cells, 24:631-641 (2006).
Jemal et al., "Cancer statistics, 2007," CA: a cancer journal for clinicians, 57:43-66 (2007).
Jennewein et al., "Sumoylation of peroxisome proliferator-activated receptor gamma by apoptotic cells prevents lipopolysaccharide-induced NCoR removal from kappaB binding sites mediating transrepression of proinflammatory cytokines," Journal of immunology, 181:5646-5652 (2008).
Jensen et al., "Design and implementation of adoptive therapy with chimeric antigen receptor-modified T cells," Immunol Rev, 257(1):127-144 (2014).
Johann et al., "GLVR1, a receptor for gibbon ape leukemia virus, is homologous to a phosphate permease of Neurospora crassa and is expressed at high levels in the brain and thymus," Journal of Virology, 66(3)1 635-1640 (1992).
Johnson et al., "Single-cell perforin and granzyme expression reveals the anatomical localization of effector CD8+ T cells in influenza virus-infected mice," PNAS, 100:2657-2662 (2003).
Jones et al., "Functions of DNA methylation: islands, start sites, gene bodies and beyond," Nat Rev Genet, 13:484-492 (2012).
Jones et al., "InterProScan 5: genome-scale protein function classification," Bioinformatics, 30:1236-1240 (2014).
Jones et al., "The epigenomics of cancer," Cell, 128:683-692 (2007).
Kandoth et al., "Mutational landscape and significance across 12 major cancer types," Nature, 502:333-339 (2013).
Kannan et al., "Vaccination strategies in follicular lymphoma," Current hematologic malignancy reports, 4(4):189-195 (2009).

(56) References Cited

OTHER PUBLICATIONS

Kantoff et al. "Overall survival analysis of a phase II randomized controlled trial of a Poxviral-based PSA-targeted immunotherapy in metastatic castration-resistant prostate cancer," Journal of Clinical Oncology, 28(7):1099-1105 (2010).
Karanikas et al., "High frequency of cytolytic T lymphocytes directed against a tumor-specific mutated antigen detectable with HLA tetramers in the blood of a lung carcinoma patient with long survival," Cancer Res, 61:3718-3724 (2001).
Karnani et al., "Pan-S replication patterns and chromosomal domains defined by genome-tiling arrays of ENCODE genomic areas," Genome research, 17:865-876 (2007).
Karolchik et al., "The UCSC Table Browser data retrieval tool," Nucleic acids research, 32:D493-496 (2004).
Kaufman et al., "Phase II randomized study of vaccine treatment of advanced prostate cancer (E7697): a trial of the Eastern Cooperative Oncology Group," Journal of Clinical Oncology, 22(11):2122-2132 (2004).
Kawai et al., "TLR signaling," Seminars in immunology, 19(1):24-32 (2007).
Kenter et al., "Vaccination against HPV-16 oncoproteins for vulvar intraepithelial neoplasia," New England Journal of Medicine, 361(19):1838-1847 (2009).
Khong et al., "Natural selection of tumor variants in the generation of "tumor escape" phenotypes," Nature immunology, 3:999-1005 (2002).
Kim et al., "A Myc network accounts for similarities between embryonic stem and cancer cell transcription programs," Cell, 143:313-324 (2010).
Kim et al., "Anticancer flavonoids are mouse-selective STING agonists," ACS chemical biology, 8(7):1396-1401 (2013).
Kim et al., "TopHat2: accurate alignment of transcriptomes in the presence of insertions, deletions and gene fusions," Genome biology, 14:R36 (2013).
Kim et al., "TroVax, a recombinant modified vaccinia Ankara virus encoding 5T4: lessons learned and future development," Human vaccines, 6(10):784-791 (2010).
Kimmel et al., "[54] Identification and characterization of specific clones: Strategy for confirming the validity of presumptive clones," Methods in enzymology, 152:507-511 (1987).
Kirkwood et al., "High- and Low-dose Interferon Alpha-2b in High-isk Melanoma: First Analysis of Intergroup Trial E1690/S9111/C9190," J Clin Oncol, 18:2444-2458 (2000).
Kirkwood et al., "Interferon alfa-2b Adjuvant Therapy of High-Risk Resected Cutaneous Melanoma: The Eastern Cooperative Oncology Group Trial EST 1684," J Clin Oncol, 14:7-17 (1996).
Klebanoff et al., "Therapeutic cancer vaccines:are we there yet?," Immunol Rev, 239(1):27-44 (2011).
Kloor et al., "Immune evasion of microsatellite unstable colorectal cancers," International journal of cancer, 127:1001-1010 (2010).
Kobayashi et al., "Peptide epitope identification for tumor-reactive CD4 T cells," Current opinion in immunology, 20(2):221-227 (2008).
Kotwal et al., "Vaccinia virus encodes two proteins that are structurally related to members of the plasma serine protease inhibitor superfamily," Journal of virology, 63(2):600-606 (1989).
Kreiter et al., "Mutant MHC Class II epitopes drive therapeutic immune responses to cancer," Nature, 520:692 (2015).
Kreso et al., "Variable clonal repopulation dynamics influence chemotherapy response in colorectal cancer," Science, 339:543-548 (2013).
Krieg, "Therapeutic potential of Toll-like receptor 9 activation," Nature reviews Drug discovery, 5(6):471-484 (2006).
Kulis et al., "Epigenomic analysis detects widespread gene-body DNA hypomethylation in chronic lymphocytic leukemia," Nat Genet, 44:1236-1242 (2012).
Kyte et al., "Telomerase Peptide Vaccination Combined with Temozolomide: A Clinical Trial in Stage IV Melanoma Patients," Clin Cancer Res, 17(13):4568-4580 (2011).
Landan et al., "Epigenetic polymorphism and the stochastic formation of differentially methylated regions in normal and cancerous tissues," Nat Genet, 44:1207-1214 (2012).
Landau et al., "Clonal evolution in hematological malignancies and therapeutic implications," Leukemia, 28:34-43 (2014).
Landau et al., "Evolution and impact of subclonal mutations in chronic lymphocytic leukemia," Cell, 152(4):714-726 (2013).
Langmead et al., "Fast gapped-read alignment with Bowtie 2," Nature methods, 9:357-359 (2012).
Langmead et al., "Ultrafast and memory-efficient alignment of short DNA sequences to the human genome," Genome Biology, 10:R25 (2009).
Lawrence et al., "Discovery and saturation analysis of cancer genes across 21 tumour types," Nature, 505:495-501 (2014).
Lawrence et al., "Mutational heterogeneity in cancer and the search for new cancer-associated genes," Nature, 499:214-218 (2013).
Le et al., "Evaluation of Ipilimumab in combination with allogeneic pancreatic tumor cells transfected with a GM-CSF gene in previously treated pancreatic cancer," J Immunother, 36(7):382-389 (2013).
Le Mercier et al., "Beyond CTLA-4 and PD-1, the generation Z of negative checkpoint regulators," Front Immunol, 6:418 (2015).
Leffers et al., "Immunization with a P53 synthetic long peptide vaccine induces P53□specific immune responses in ovarian cancer patients, a phase II trial," Int J Cancer, 125(9):2104-2113 (2009).
Leffers et al., "Long□term clinical and immunological effects of p53□SLP® vaccine in patients with ovarian cancer," Int J Cancer, 130(1)105-112 (2012).
Leitner et al., "Immune responses induced by intramuscular or gene gun injection of protective deoxyribonucleic acid vaccines that express the circumsporozoite protein from Plasmodium berghei malaria parasites," J Immunol, 159(12):6112-6119 (1997).
Lemay et al., "Dok-3, a Novel Adapter Molecule Involved in the Negative Regulation of Immunoreceptor Signaling," Mol Cell Biol, 20:2743-2754 (2000).
Lennerz et al, "The response of autologous T cells to a human melanoma is dominated by mutated neoantigens," PNAS, 102(44)1 6013-16018 (2005).
Lewintre et al., "Analysis of chronic lymphotic leukemia transcriptomic profile: differences between molecular subgroups," Leuk Lymphoma, 50:68-79 (2009).
Lewis et al., "DNA Vaccines: A Review," Advances in Virus Research, 54:129-88 (1999).
Li et al., "Fast and accurate short read alignment with Burrows-Wheeler Transform," Bioinformatics, 25(14):1754-1760 (2009).
Li et al., "Inactivating mutations of the chromatin remodeling gene ARID2 in hepatocellular carcinoma," Nature Genetics, 43:828-829 (2011).
Li et al., "Mapping short DNA sequencing reads and calling variants using mapping quality scores," Genome Res, 18:1851-1858 (2008).
Li et al., "RSEM: accurate transcript quantification from RNA-Seq data with or without a reference genome," BMC Bioinformatics,12:323 (2011).
Li et al., "The Sequence Alignment/Map format and SAMtools," Bioinformatics, 25(16):2078-2079 (2009).
Li et al.,"Fast and accurate long-read alignment with Burrows-Wheeler transform," Bioinformatics, 26(5):589-595 (2010).
Liggins et al., "MORC4, a novel member of the MORC family, is highly expressed in a subset of diffuse large B-cell lymphomas," Brit J Haematol, 138:479-486 (2007).
Lim et al., "Transcriptome analyses of mouse and human mammary cell subpopulations reveal multiple conserved genes and pathways," Breast Cancer Res, 12:R21 (2010).
Lin et al., "Relevance of the immunoglobulin VH somatic mutation status in patients with chronic lymphocytic leukemia treated with fludarabine, cyclophosphamide, and rituximab (FCR) or related chemoimmunotherapy regimens," Blood, 113:3168-71 (2009).
Lindhout et al., "Site-specific enzymatic polysialylation of therapeutic proteins using bacterial enzymes," PNAS, 108(18):7397-7402 (2011).
Link et al., "Electric control of droplets in microfluidic devices," Angew Chem Int Ed Engl, 45(16):2556-2560 (2006).

(56) References Cited

OTHER PUBLICATIONS

Liu et al., "Systematic identification of type I and type II interferon-induced antiviral factors," PNAS, 109(11):4239-4244 (2012).
Livak et al. "Methods for qPCR gene expression profiling applied to 1440 lymphoblastoid single cells," Methods, 59(1):71-79 (2013).
Llobet et al., "CK2 controls TRAIL and Fas sensitivity by regulating FLIP levels in endometrial carcinoma cells," Oncogene, 27:2513-2524 (2008).
Lohr et al., "Discovery and prioritization of somatic mutations in diffuse large B-cell lymphoma (DLBCL) by whole-exome sequencing," PNAS, 109(10):3879-3884 (2012).
Lu et al., "Mutated regions of nucleophosmin 1PPP1R3B Is Recognized by T Cells Used To Treat a Melanoma Patient Who Experienced a Durable Complete Tumor Regression," J Immunol, 190(12):6034-6042 (2013).
Lund et al., "Coordination of early protective immunity to viral infection by regulatory T cells," Science, 320(5880):1220-1224 (2008).
Lundegaard et al., "Prediction of epitopes using neural network based methods," J Immunol Methods, 374(1-2):26-34 (2011).
Mackett et al., "Vaccinia virus: a selectable eukaryotic cloning and expression vector," PNAS, 79:7415-7419 (1982).
Maegawa et al., "Age-related epigenetic drift in the pathogenesis of MDS and AML," Genome Res, 24:580-591 (2014).
Mandl et al., "Immunotherapy with MVA-BN®-HER2 induces HER-2-specific Th1 immunity and alters the intratumoral balance of effector and regulatory T cells," Cancer Immunol Immunother, 61(1):19-29 (2012).
Manghera et al, "Endogenous retrovirus-K promoter: a landing strip for inflammatory transcription factors?," Retrovirol, 10:16 (2013).
Marabelle et al., "Depleting tumor-specific Tregs at a single site eradicates disseminated tumors," J Clin Invest, 1123(6):2447-2463(2013).
Maratea et al. "Deletion and fusion analysis of the phage φX174 lysis gene E," Gene 40(1):39-46 (1985).
Marcais et al., "A fast, lock-free approach for efficient parallel counting of occurrences of k-mers," Bioinformatics, 27(6):764-770 (2011).
Marshall et al., "Phase I Study in Cancer Patients of a Replication-Defective Avipox Recombinant Vaccine That Expresses Human Carcinoembryonic Antigen," J Clin Oncol, 17:332-337 (1999).
Matsushita et al., "Cancer Exome Analysis Reveals a T Cell Dependent Mechanism of Cancer Immunoediting," Nature, 482(7385):400-404 (2012).
Maus et al., "Adoptive Immunotherapy for Cancer or Viruses," Annual Review of Immunology, 32:189-225 (2014).
Mayer et al., "A revised nomenclature for transcribed human endogenous retroviral loci," Mobile DNA, 2:7 (2011).
Mayr et al., "Abstammung, Eigenschaften und Verwendung des attenuierten Vaccinia-Stammes MVA (Translated Summary)," Infection, 3(1):6-14 (1975).
Mayr, "The smallpox vaccination strain MVA: marker, genetic structure, experience gained with the parenteral vaccination and behavior in organisms with a debilitated defence mechanism (author's transl)," Zentralbl Bakteriol 167(5-6):375-9 (1978).
Mazutis et al., "Single-cell analysis and sorting using droplet-based microfluidics," Nat Protoc, 8:870-891 (2013).
McCormack et al., "HLA-A*3101 and Carbamazepine-Induced Hypersensitivity Reactions in Europeans," New Engl J Med, 364:1134-1143 (2011).
McCurdy et al., "Modified Vaccinia Ankara: Potential as an Alternative Smallpox Vaccine," Clin Infect Dis, 38:1749-1753 (2004).
McDermott et al., "Immune Therapy for Kidney Cancer: A Second Dawn?," Semin Oncol, 40(4):492-498 (2013).
McFadden et al., "Genetic and clonal dissection of murine small cell lung carcinoma ression by genome sequencing," Cell, 156(6):1298-1311 (2014).
McKenna et al., "The Genome Analysis Toolkit: a MapReduce framework for analyzing next-generation DNA sequencing data," Genome Res, 20(9):1297-1303 (2010).
Medema et al., "Immune Escape of Tumors In Vivo by Expression of Cellular Flice-Inhibitory Protein," J Exp Med, 190:1033-1038 (1999).
Meissner et al., "Genome-scale DNA methylation maps of pluripotent and differentiated cells," Nature, 454:766-770 (2008).
Melief et al., "Immunotherapy of established (pre)malignant disease by synthetic long peptide vaccines," Nature Rev Cancer, 8:351-360 (2008).
Menke et al., "Genetic interactions between the Wilms' tumor 1 gene and the p53 gene," Cancer Res, 62(22):6615-6620 (2002).
Mermel et al., "GISTIC2.0 facilitates sensitive and confident localization of the targets of focal somatic copy-number alteration in human cancers," Genome Biol, 12:R41 (2011).
Merrifield, "Solid Phase Peptide Synthesis. I. The Synthesis of a Tetrapeptide," J Am Chem Soc, 85(14):2149-2154 (1963).
Messmer et al., "In vivo measurements document the dynamic cellular kinetics of chronic lymphocytic leukemia B cells," J Clin Invest, 115(3):755-764 (2005).
Meyer et al., "Mapping of deletions in the genome of the highly attenuated vaccinia virus MVA and their influence on virulence," J Gen Virol, 72:1031-1038 (1991).
Midgley, "Vaccinia virus strain NYVAC induces substantially lower and qualitatively different human antibody responses compared with strains Lister and Dryvax," J Gen Virol, 89:2992-2997 (2008).
Miller et al., "Construction and properties of retrovirus packaging cells based on gibbon ape leukemia virus," Virol, 65:2220-2224 (1991).
Missale et al., "HLA-A31- and HLA-Aw68-restricted cytotoxic T cell responses to a single hepatitis B virus nucleocapsid epitope during acute viral hepatitis," J Exp Med, 177(3):751-762 (1993).
Mocellin et al., "Interferon Alpha Adjuvant Therapy in Patients With High-Risk Melanoma: A Systematic Review and Meta-analysis," JNCI, 102(7):493-501 (2010).
Mooij, "Differential CD4+ versus CD8+ T-Cell Responses Elicited by Different Poxvirus-Based Human Immunodeficiency Virus Type 1 Vaccine Candidates Provide Comparable Efficacies in Primates," J Virol, 82(6):2975-2988 (2008).
Mor et al., "Complexity of the cytokine and antibody response elicited by immunizing mice with Plasmodium yoelii circumsporozoite protein plasmid DNA," J Immunol, 155(4):2039-2046 (1995).
Morison et al., "A census of mammalian imprinting," Trends Genet, 21(8):457-465 (2005).
Morozov et al., "The Transmembrane Protein of the Human Endogenous Retrovirus—K (HERV-K) Modulates Cytokine Release and Gene Expression," PloS one 8(8):e70399 (2013).
Morton et al., "Prolonged Survival of Patients Receiving Active Immunotherapy With Canvaxin Therapeutic Polyvalent Vaccine After Complete Resection of Melanoma Metastatic to Regional Lymph Nodes," Ann Surg, 236(4):438-448 (2002).
Moss, "Reflections on the early development of poxvirus vectors," Vaccine, 31(39): 4220-4222 (2013).
Murphy et al., "Genetic construction, expression, and melanoma-selective cytotoxicity of a diphtheria toxin-related alpha-melanocyte-stimulating hormone fusion protein," PNAS, 83:8258-8262 (1986).
Musey et al., "HIV-1 Vaccination Administered Intramuscularly Can Induce Both Systemic and Mucosal T Cell Immunity in HIV-1-Uninfected Individuals," J Immunol, 171(2):1094-1101 (2003).
Najera et al., "Cellular and Biochemical Differences between Two Attenuated Poxvirus Vaccine Candidates (MVA and NYVAC) and Role of the C7L Gene," J Virol, 80(12):6033-6047 (2006).
Nam et al., "Different contribution of co-stimulatory molecules B7.1 and B7.2 to the immune response to recombinant modified vaccinia virus ankara vaccine expressing prM/E proteins of Japanese encephalitis virus and two hepatitis B virus vaccines," Acta Virol, 51:125-30 (2007).
Nielsen et al., "NetMHCpan, a Method for Quantitative Predictions of Peptide Binding to Any HLA-A and -B Locus Protein of Known Sequence," PloS one, 2:e796 (2007).
Nishimura et al, "Distinct Role of Antigen-Specific T Helper Type 1 (Th1) and Th2 Cells in Tumor Eradication in Vivo," J Ex Med, 190(5):617-27 (1999).

(56) References Cited

OTHER PUBLICATIONS

Nocentini et al., "A new member of the tumor necrosis factor/nerve growth factor receptor family inhibits T cell receptor-induced apoptosis," PNAS, 94(12):6216-6221 (1997).
Novershtern et al., "Densely Interconnected Transcriptional Circuits Control Cell States in Human Hematopoiesis," Cell, 144(2):296-309 (2011).
Oh et al., "Neutrophil isolation protocol," J Vis Exp (2008).
Ohnishi et al., "Premature Termination of Reprogramming In Vivo Leads to Cancer Development through Altered Epigenetic Regulation," Cell, 156(4):663-677 (2014).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma," J Clin Oncol, 29(3):330-336 (2011).
Oshiumi et al., "DEAD/H BOX 3 (DDX3) helicase binds the RIG-I adaptor IPS-1 to up-regulate IFN-beta-inducing potential," Eur J Immunol, 40:940-948 (2010).
Ott et al., "CTLA-4 and PD-1/PD-L1 Blockade: New Immunotherapeutic Modalities with Durable Clinical Benefit in Melanoma Patients," Clin Cancer Res, 19(19):5300-5309 (2013).
Oudard et al., "A phase II study of the cancer vaccine TG4010 alone and in combination with cytokines in patients with metastatic renal clear-cell carcinoma: clinical and immunological findings," Cancer Immunol Immunother, 60(2):261-71 (2011).
Page et al., "Immune Modulation in Cancer with Antibodies," Annu Rev Med, 65:185-202 (2014).
Pages, et al., "Effector Memory T Cells, Early Metastasis, and Survival in Colorectal Cancer," New Engl J Med, 353:2654-2666 (2005).
Panicali et al., "Construction of live vaccines by using genetically engineered poxviruses: biological activity of recombinant vaccinia virus expressing influenza virus hemagglutinin," PNAS, 80(17):5364-5368 (1983).
Panicali et al., "Construction of poxviruses as cloning vectors: insertion of the thymidine kinase gene from herpes simplex virus into the DNA of infectious vaccinia virus," 79(16):4927-4931 (1982).
Pantaleo et al., "Poxvirus vector-based HIV vaccines," Curr Opin HIV-AIDS, 5:391-396 (2010).
Paoletti, "Applications of pox virus vectors to vaccination: an update," PNAS, 93(21):11349-53 (1996).
Pei et al., "Genome-wide DNA methylation analysis reveals novel epigenetic changes in chronic lymphocytic leukemia," Epigenetics, 7:567-578 (2012).
Peng et al., "DOK3 Negatively Regulates LPS Responses and Endotoxin Tolerance," PloS one 7:e39967 (2012).
Perez et al., "A new era in anticancer peptide vaccines," Cancer, 116(9):2071-2080 (2010).
Perez et al., "p63 consensus DNA-binding site: identification, analysis and application into a p63MH algorithm," Oncogene, 26:7363-7370 (2007).
Perkvs et al., "Poxvirus based vaccine candidates for cancer, AIDS, and other infectious diseases," J Leukocyte Biol, 58(1):1-13 (1995).
Perreau et al., "DNA/NYVAC Vaccine Regimen Induces HIV-Specific CD4 and CD8 T-Cell Responses in Intestinal Mucosa," J Virol, 85(19):9854-9862 (2011).
Petsch et al., "Protective efficacy of in vitro synthesized, specific mRNA vaccines against influenza a virus infection," Nat Biotechnol, 30(12):1210-1216 (2012).
Pieters et al., "On guard: coronin proteins in innate and adaptive immunity," Nat Rev Immunol, 13:510-518 (2013).
Pirard et al., "Interferon Alpha as Adjuvant Postsurgical Treatment of Melanoma: A Meta-Analysis," Dermatology, 208(1):43-48 (2004).
Poirot et al., "Multiplex genome edited T-cell manufacturing platform for "off-the-shelf" adoptive T-cell immunotherapies," Cancer Res, 75(18):3853 (2015).

Poulet, "Development and registration of recombinant veterinary vaccines: the example of the canarypox vector platform," Vaccine, 25(30):5606-5612 (2007).
Powell et al., "NCoR1 Mediates Papillomavirus E8^E2C Transcriptional Repression," J Virol, 84:4451-4460 (2010).
Pujadas et al., "Regulated noise in the epigenetic landscape of development and disease," Cell, 148(6):1123-1131 (2012).
Qin et al., "Soft lithography for micro- and nanoscale patterning," Nat Protoc, 5:491-502 (2010).
Quesada et al., "Exome sequencing identifies recurrent mutations of the splicing factor SF3B1 gene in chronic lymphocytic leukemia," Nat Genet, 44:47-52 (2012).
Quezeda et al.,"CTLA4 blockade and GM-CSF combination immunotherapy alters the intratumor balance of effector and regulatory T cells," J Clin Invest, 116(7):1935-1945 (2006).
Ramos et al., "An Inducible Caspase 9 Suicide Gene to Improve the Safety of Mesenchymal Stromal Cell Therapies," Stem Cells, 28(6):1107-1115 (2010).
Ramskold et al., "Full-length mRNA-Seq from single-cell levels of RNA and individual circulating tumor cells," Nat Biotechnol, 30:777-782 (2012).
Rassenti et al., "Relative value of ZAP-70, CD38, and immunoglobulin mutation status in predicting aggressive disease in chronic lymphocytic leukemia," Blood, 112:1923-1930 (2008).
Raval et al., "Downregulation of Death-Associated Protein Kinase 1 (DAPK1) in Chronic Lymphocytic Leukemia," Cell, 129(5):879-890 (2007).
Ravi et al., "Sensitization of Tumor Cells to Apo2 Ligand/TRAIL-induced Apoptosis by Inhibition of Casein Kinase II," Cancer Res, 62(15):4180-4185 (2002).
Restifo et al., "Adoptive immunotherapy for cancer: harnessing the T cell response," Nat Rev Immunol, 12(4):269-281 (2015).
Richter et al., "Mechanistic Determinants of Biotherapeutics Absorption Following SC Administration," The AAPS Journal, 14(3):559-568 (2012).
Rini et al., "Biology and Treatment of Advanced Renal Cell Carcinoma: A Global Perspective," Semin Oncol, 40(4):419-420 (2013).
Robbins et al., "Mining exomic sequencing data to identify mutated antigens recognized by adoptively transferred tumor-reactive T cells," Nat Med, 19(6):747-752 (2013).
Robinson et al., "A phase I-II trial of multiple-dose polyriboinosic-polyribocytidylic acid in patieonts with leukemia or solid tumors," J Natl Cancer Inst, 57(3):599-602 (1976).
Robinson et al., "DNA vaccines for viral infections: Basic studies and applications," Adv Virus Res, 55:1-74 (2000).
Robinson et al., "edgeR: a Bioconductor package for differential expression analysis of digital gene expression data," Bioinformatics, 26(1):139-140 (2010).
Robinson et al., "Integrative genomics viewer," Nat Biotechnol, 29:24-26 (2011).
Rolph et al., "Recombinant viruses as vaccines and immunological tools," Curr Opin Immunol, 9(4):517-524 (1997).
Ronchetti et al., "Frontline:GITR, a member of the TNF receptor superfamily,is costimulatory to mouse T lymphocytesubpopulations," Eur J Immunol, 34(3):613-622 (2004).
Rosenberg et al., "Adoptive cell transfer as personalized immunotherapy for human cancer," Science, 348(6230):62-68 (2015).
Rosenberg, "Raising the Bar: The Curative Potential of Human Cancer Immunotherapy," Sci Transl Med, 4(127):127p5128 (2012).
Rossi et al., "Integrated mutational and cytogenetic analysis identifies new prognostic subgroups in chronic lymphocytic leukemia," Blood, 121:1403-1412 (2013).
Rubio-Moscardo et al., "Characterization of 8p21.3 chromosomal deletions in B-cell lymphoma: TRAIL-R1 and TRAIL-R2 as candidate dosage-dependent tumor suppressor genes," Blood, 106:3214-3222 (2005).
Rupprecht et al., "Oral immunization and protection of raccoons (*Procyon lotor*) with a vaccinia-rabies glycoprotein recombinant virus vaccine," PNAS, 83:7947-7950 (1986).
Rutledge et al., "Tumor-Infiltrating Lymphocytes in Glioblastoma Are Associated with Specific Genomic Alterations and Related to Transcriptional Class," Clin Cancer Res, 19:4951-4960 (2013).

(56) References Cited

OTHER PUBLICATIONS

Sabado et al., "Preparation of Tumor Antigen-loaded Mature Dendritic Cells for Immunotherapy," J Vis Exp, 78:50085 (2013).
Sadelain, "Eliminating Cells Gone Astray," New Engl J Med, 365:1735-1737 (2011).
Salem et al., "Defining the Antigen-Specific T-Cell Response to Vaccination and Poly(I:C)/TLR3 Signaling: Evidence of Enhanced Primary and Memory CD8 T-Cell Responses and Antitumor Immunity," J Immunother, 28(3):220-228 (2005).
Sampson et al., "Greater chemotherapy-induced lymphopenia enhances tumor-specific immune responses that eliminate EGFRvIII-expressing tumor cells in patients with glioblastoma," Neuro-Oncology, 13(3):324-333 (2011).
Sampson et al., "Immunologic Escape After Prolonged Progression-Free Survival With Epidermal Growth Factor Receptor Variant III Peptide Vaccination in Patients With Newly Diagnosed Glioblastoma," J Clin Oncol, 28(31):4722-4729 (2010).
Samuels et al., "Oncogenic PI3K and its role in cancer," Curr Opin Oncol, 18:77-82n (2006).
Sancho, "The Block in Assembly of Modified Vaccinia Virus Ankara in HeLa Cells Reveals New Insights into Vaccinia Virus Morphogenesis," J Virol, 76(16):8313-8334 (2002).
Sato et al., "Discovery of Novel Targets for Aberrant Methylation in Pancreatic Carcinoma Using High-Throughput Microarrays," Cancer Res, 63(13):3735-3742 (2003).
Saturno et al., "Combining TRAIL with PI3 Kinase or HSP90 inhibitors enhances apoptosis in colorectal cancer cells via suppression of survival signaling," Oncotarget, 4(8):1185-1198 (2013).
Saunders et al., "Strelka: accurate somatic small-variant calling from sequenced tumor-normal sample pairs," Bioinformatics, 28(14):1811-1817 (2012).
Schmitt et al., "Transcriptional Profiling of Human Endogenous Retrovirus Group HERV-K(HML-2) Loci in Melanoma," Genome Biol Evol, 5(2):307-328 (2013).
Schneider et al, "Induction of CD8+ T cells using heterologous prime-boost immunisation strategies," Immunol Rev, 170(1):29-38 (1999).
Schreiber et al., "Cancer Immunoediting: Integrating Immunity's Roles in Cancer Suppression and Promotion," Science, 331(6024):1565-1570 (2011).
Schumacher et al., "Prognostic Significance of Activated CD8+ T Cell Infiltrations within Esophageal Carcinomas," Cancer Res, 61(10):3932-3936 (2001).
Schuster et al., "Vaccination With Patient-Specific Tumor-Derived Antigen in First Remission Improves Disease-Free Survival in Follicular Lymphoma," J Clin Oncol, 29(20):2787-2794 (2011).
Scriba et al., "Modified vaccinia Ankara expressing Ag85A, a novel tuberculosis vaccine, is safe in adolescents and children, and induces polyfunctional CD4+ T cells," Eur J Immunol, 40(1):279-290 (2010).
Secchiero et al., "Aberrant expression of TRAIL in B chronic lymphocytic leukemia (B-CLL) cells," J Cell Physiol, 205(2):246-252 (2005).
Sedegah et al., "Protection against malaria by immunization with plasmid DNA encoding circumsporozoite protein," PNAS, 91(21):9866-9870 (1994).
Sensi et al., "Unique tumor antigens: evidence for immune control of genome integrity and immunogenic targets for T cell-mediated patient-specific immunotherapy," Clin Cancer, Res 12:5023-5032 (2006).
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, 2(2):117-125 (2002).
Shalek et al., "Single-cell RNA-seq reveals dynamic paracrine control of cellular variation," Nature, 510(7505):363-369 (2014).
Shannon, "A Mathematical Theory of Communication," Bell System Technical Journal, 27(3):379-423 (1948).

Shao et al., "Clonally related histiocytic/dendritic cell sarcoma and chronic lymphocytic leukemia/small lymphocytic lymphoma: a study of seven cases," Mod Pathol, 24:1421-1432 (2011).
Sharei et al., "Ex Vivo Cytosolic Delivery of Functional Macromolecules to Immune Cells," PLOS ONE, 10(4):e0118803 (2015).
Shendure et al., "Next-generation DNA sequencing," Nat Biotechnol, 26(10):1135-1145 (2008).
Shida, "Effects and virulences of recombinant vaccinia viruses derived from attenuated strains that express the human T-cell leukemia virus type I envelope gene," J Virol, 62(12):4474-4480 (1988).
Shipony et al., "Dynamic and static maintenance of epigenetic memory in pluripotent and somatic cells," Nature, 513:115-119 (2014).
Sidney et al., "HLA class I supertypes: a revised and updated classification," BMC Immunol, 9:1 (2008).
Siegel et al., "Cancer statistics, 2013," CA, 63(1):11-30 (2013).
Simmons et al., "Local secretion of anti-CTLA-4 enhances the therapeutic efficacy of a cancer immunotherapy with reduced evidence of systemic autoimmunity," Cancer Immunol Immunother, 57(8)1263-1270 (2008).
Simpson et al., "Cancer/testis antigens, gametogenesis and cancer," Nat Rev Cancer, 5:615-625 (2005).
Simpson et al., "Fc-dependent depletion of tumor-infiltrating regulatory T cells co-defines the efficacy of anti-CTLA-4 therapy against melanoma," J Exp Med, 210(9)1695-1710 (2013).
Sizemore, "Attenuated Shigella as a DNA Delivery Vehicle for DNA-Mediated Immunization," Science, 270(5234):299-303 (1995).
Slingluff et al., "Immunologic and Clinical Outcomes of a Randomized Phase II Trial of Two Multipeptide Vaccines for Melanoma in the Adjuvant Setting," Clin Cancer Res, 13(21):6386-6395 (2007).
Slingluff et al., "Randomized Multicenter Trial of the Effects of Melanoma-Associated Helper Peptides and Cyclophosphamide on the Immunogenicity of a Multipeptide Melanoma Vaccine," J Clin Oncol, 29(21):2924-2932 (2011).
Smith et al., "Comparison of biosequences," Adv Appl Math, 2(4):482-489 (1981).
Smith et al., "Construction and characterization of an infectious vaccinia virus recombinant that expresses the influenza hemagglutinin gene and induces resistance to influenza virus infection in hamsters," PNAS, 80(23):7155-7159 (1983).
Smith et al., "Infectious vaccinia virus recombinants that express hepatitis B virus surface antigen," Nature, 302:490-495 (1983).
Smoley et al., "Standardization of fluorescence in situ hybridization studies on chronic lymphocytic leukemia (CLL) blood and marrow cells by the CLL Research Consortium," Cancer Genet Cytogenet, 203(2):141-148 (2010).
Soares et al. "A subset of dendritic cells induces CD4+ T cells to produce IFN-gamma by an IL-12-independent but CD70-dependent mechanism in vivo," J Exp Med, 2215(11):1095-1106 (2007).
Sommerfelt et al., "Receptor interference groups of 20 retroviruses plating on human cells," Virol, 176:58-69 (1990).
Song et al., "c-Cbl acts as a mediator of Src-induced activation of the PI3K-Akt signal transduction pathway during TRIAL treatment," Cellular Signalling, 22(3):377-385 (2010).
Sosman et al., "A phase 2 trial of complete resection for stage IV melanoma: results of Southwest Oncology Group Clinical Trial S9430," Cancer, 117(20):4740-4706 (2011).
Speetjens et al., "Induction of p53-Specific Immunity by a p53 Synthetic Long Peptide Vaccine in Patients Treated for Metastatic Colorectal Cancer," Clin Cancer Res, 15(3):1086-1095 (2009).
Speiser et al., "Molecularly defined vaccines for cancer immunotherapy, and protective T cell immunity," Semin Immunol, 22(3):144-154 (2010).
Spencer et al., "Non-genetic origins of cell-to-cell variability in TRAIL-induced apoptosis," Nature, 459:428-432 (2009).
Spranger et al., "Up-regulation of PD-LI, IDO, and Tregs in the melanoma tumor microenvironment is driven by CD8+ T cells," Sci Transl Med, 5(200):200ra116 (2013).
Staehler et al., "An open label study to evaluate the safety and immunogenicity of the peptide based cancer vaccine IMA901," ASCO meeting 2007; Abstract No. 3017.

(56) References Cited

OTHER PUBLICATIONS

Stahl-Hennig et al., "Synthetic double-stranded RNAs are adjuvants for the induction of T helper 1 and humoral immune responses to human papillomavirus in rhesus macaques," PLoS pathogens, 5(4):e1000373 (2009).
Stransky et al., "The Mutational Landscape of Head and Neck Squamous Cell Carcinoma," Science, 333:1157-1160 (2011).
Su et al., "Next-generation sequencing and its applications in molecular diagnostics" Exp Rev Mol Diagn, 11(3):333-343 (2011).
Subramanian et al., "Gene set enrichment analysis: a knowledge-based approach for interpreting genome-wide expression profiles," PNAS, 102:15545-15550 (2005).
Sullivan et al., "Expression and Characterization of Herpes Simplex Virus Type 1 (HSV-1) Glycoprotein G (gG) by Recombinant Vaccinia Virus: Neutralization of HSV-1 Infectivity with Anti-gG Antibody," Gen Vir, 68:2587-2598 (1987).
Suzuki et al., "A Novel Glycosylphosphatidyl Inositol-Anchored Protein on Human Leukocytes: A Possible Role for Regulation of Neutrophil Adherence and Migration," J Immunol, 162(7):4277-4284 (1999).
Sykulev et al., "Evidence that a Single Peptide-MHC Complex on a Target Cell Can Elicit a Cytolytic T Cell Response," Immunity, 4:565-571 (1996).
Tang et al., "The landscape of viral expression and host gene fusion and adaptation in human cancer," Nat Commun, 4:2513 (2013).
Tartaglia et al., "NYVAC: A highly attenuated strain of vaccinia virus," Virology, 188(1):217-232 (1992).
ten Bosch et al., "Keeping Up With the Next Generation: Massively Parallel Sequencing in Clinical Diagnostics," J Mol Diagn, 10(6):484-492 (2008).
Teng et al., "A human TAPBP (TAPASIN)-related gene, TAPBP-R," Eur J Immunol, 32:1059-1068 (2002).
Testori et al., "Phase III comparison of vitespen, an autologous tumor-derived heat shock protein gp96 peptide complex vaccine, with physician's choice of treatment for stage IV melanoma: the C-100-21 Study Group," J Clin Oncol, 26(6):955-962 (2008).
Textor et al., "Human NK cells are alerted to induction of p53 in cancer cells by upregulation of the NKG2D ligands ULBPI and ULBP2," Cancer Res, 71:5998-6009 (2011).
Timp et al., "Cancer as a dysregulated epigenome allowing cellular growth advantage at the expense of the host," Nat Rev Cancer, 13:497-510 (2013).
Tjoa et al., "Follow-up evaluation of prostate cancer patients infused with autologous dendritic cells pulsed with PSMA peptides," The Prostate, 32(4):272-278 (1997).
Topalian et al., "Safety, Activity, and Immune Correlates of Anti-PD-1 Antibody in Cancer," N Engl J Med, 366(26):2443-2454 (2012).
Topalian et al., "Survival, Durable Tumor Remission, and Long-Term Safety in Patients With Advanced Melanoma Receiving Nivolumab," J Clin Oncol, 32(10):1020-1030 (2014).
Tough et al., "Induction of bystander T cell proliferation by viruses and type I interferon in vivo," Science, 272(5270):1947-1950 (1996).
Tran et al., "Cancer Immunotherapy Based on Mutation-Specific CD4+ T Cells in a Patient with Epithelial Cancer," Science, 344(6184):641-645 (2014).
Trumpfheller et al., "Intensified and protective CD4+ T cell immunity in mice with anti-dendritic cell HIV gag fusion antibody vaccine," J Exp Med, 203(3):607-617 (2006).
Trumpfheller et al., "The microbial mimic poly IC induces durable and protective CD4+ T cell immunity together with a dendritic cell targeted vaccine," PNAS, 105(7):2574-2579 (2008).
Tucker et al., "Massively Parallel Sequencing:The Next Big Thing in Genetic Medicine," Am J Hum Genet, 85(2):142-154 (2009).
Uderhardt et al., "12/15-lipoxygenase orchestrates the clearance of apoptotic cells and maintains immunologic tolerance," Immunity, 36(5):834-846 (2012).
Ushijima et al., "Fidelity of the methylation pattern and its variation in the genome," Genome research, 13:868-874 (2005).

Uyttenhove et al., "Evidence for a tumoral immune resistance mechanism based on tryptophan degradation by indoleamine 2,3-di oxygenase," Nature medicine, 9:1269-1274 (2003).
Vaishampayan et al., "Active immunotherapy of metastatic melanoma with allogeneic melanoma lysates and interferon alpha," Clin Cancer Res, 8(12):3696-3701 (2002).
Van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," Journal of Experimental Medicine, 190(3):355-366 (1999).
Van Poelgeest et al., "HPV16 synthetic long peptide (HPV16-SLP) vaccination therapy of patients with advanced or recurrent HPV16-induced gynecological carcinoma, a phase II trial," J Transl Med, 11:88 (2013).
Van Rooij et al., "Tumor exome analysis reveals neoantigen-specific T-cell reactivity in an ipilimumab-responsive melanoma," Journal of clinical oncology: official journal of the American Society of Clinical Oncology, 31:32 (2013).
Verardi et al., "A vaccinia virus renaissance: new vaccine and immunotherapeutic uses after smallpox eradication," Human vaccines & immunotherapeutics, 8(7):961-970 (2012).
Vermeij et al., "Potentiation of a p53-SLP vaccine by cyclophosphamide in ovarian cancer: a single-arm phase II study," Int J Cancer, 131(5):E670-680 (2012).
Von Krempelhuber et al., "A randomized, double-blind, dose-finding Phase II study to evaluate immunogenicity and safety of the third generation smallpox vaccine candidate IMVAMUNE®," Vaccine, 28(5):1209-1216 (2010).
von Mehren et al., "Pilot study of a dual gene recombinant avipox vaccine containing both carcinoembryonic antige (CEA.) and B7.1 transgenes in patients with, recurrent CEA-expressing adenocarcinomas," Clin Cancer Res, 6:2219-28 (2000).
Wahl et al., "[43] Molecular hybridization of immobilized nucleic acids: Theoretical concepts and practical considerations," Methods in enzymology, Academic Press, 152:399-407 (1987).
Walter et al., "Multipeptide immune response to cancer vaccine IMA901 after single-dose cyclophosphamide associates with longer patient survival," Nature medicine, 18(8):1254 (2012).
Wang et al., "Role of protein kinase CK2 in the regulation of tumor necrosis factor-related apoptosis inducing ligand-induced apoptosis in prostate cancer cells," Cancer research, 66:2242-2249 (2006).
Wang et al., "SF3B1 and other novel cancer genes in chronic lymphocytic leukemia," N Engl J Med, 365:2497-2506 (2011).
Wang et al., "Widespread plasticity in CTCF occupancy linked to DNA methylation," Genome Res, 22:1680-1688 (2012).
Watson et al., "SHP-1: the next checkpoint target for cancer immunotherapy?," Biochem Soc Trans, 44(2):356-362 (2016).
Webster et al., "Enhanced T cell-mediated protection against malaria in human challenges by using the recombinant poxviruses FP9 and modified vaccinia virus Ankara," Proceedings of the National Academy of Sciences, 102(13):4836-4841 (2005).
Weiner et al., "Genetic vaccines," Scientific American, 281(1):50-57 (1999).
Welters et al., "Induction of tumor-specific CD4+ and CD8+ T-cell immunity in cervical cancer patients by a human papillomavirus type 16 E6 and E7 long peptides vaccine," Clinical cancer research, 14(1):178-187 (2008).
Welters et al., "Success or failure of vaccination for HPV16-positive vulvar lesions correlates with kinetics and phenotype of induced T-cell responses," PNAS, 107(26):11895-11899 (2010).
Weyer et al., "Generation and evaluation of a recombinant modified vaccinia virus Ankara vaccine for rabies," Vaccine, 25(21):4213-4222 (2007).
Weyer et al., "Poxvirus-vectored vaccines for rabies-a review," Vaccine, 27(51):7198-7201 (2009).
Wheatley et al., "Does adjuvant interferon-alpha for high-risk melanoma provide a worthwhile benefit? A meta-analysis of the randomised trials," Cancer treatment reviews, 29(4):241-252 (2003).
Whelan et al., "Safety and immunogenicity of boosting BCG vaccinated subjects with BCG: comparison with boosting with a new TB vaccine, MVA85A," PLoS One, 4(6):e5934 (2009).

(56) References Cited

OTHER PUBLICATIONS

Widschwendter et al., "Epigenetic stem cell signature in cancer," Nat Genet, 39:157-158 (2007).
Wierda et al., "Multivariable model for time to first treatment in patients with chronic lymphocytic leukemia," J Clin Oncol, 29:4088-4095 (2011).
Wiktor et al., "Protection from rabies by a vaccinia virus recombinant containing the rabies virus glycoprotein gene," Proceedings of the National Academy of Sciences, 81(22):7194-7198 (1984).
Wilson et al., "Formation of infectious hybrid virions with gibbon ape leukemia virus and human T-cell leukemia virus retroviral envelope glycoproteins and the gag and pol proteins of Moloney murine leukemia virus," Journal of virology, 63(5):2374-2378 (1989).
Wolchok et al., "Nivolumab plus ipilimumab in advanced melanoma," N Engl J Med, 369(2):122-133 (2013).
Wong et al., "Module map of stem cell genes guides creation of epithelial cancer stem cells," Cell Stem Cell, 2:333-344 (2008).
Woodfine et al., "Quantitative analysis of DNA methylation at all human imprinted regions reveals preservation of epigenetic stability in adult somatic tissue," Epigenetics & chromatin, 4:1 (2011).
Woyach et al., "Resistance mechanisms for the Bruton's tyrosine kinase inhibitor ibrutinib," The New England journal of medicine, 370:2286-94 (2014).
Wyatt et al., "Marker rescue of the host range restriction defects of modified vaccinia virus Ankara," Virology, 251(2):334-342 (1998).
Wyatt et al., "Multiprotein HIV type 1 clade B DNA and MVA vaccines: construction, expression, and immunogenicity in rodents of the MVA component," AIDS research and human retroviruses, 20(6):645-653 (2004).
Xi et al., "BSMAP: whole genome bisulfite sequence MAPping program," BMC bioinformatics, 10:232 (2009).
Xie et al., "Stepwise reprogramming of B cells into macrophages," Cell, 117(5):663-676 (2004).
Yan et al., "PBAF chromatin-remodeling complex requires a novel specificity subunit, BAF200, to regulate expression of selective interferon-responsive genes," Genes & development, 19(14):1662-1667 (2005).
Yang et al., "Meta-analysis followed by replication identifies loci in or near CDKN1B, TET3, CD80, DRAM1, and ARID5B as associated with systemic lupus erythematosus in Asians," American journal of human genetics, 92:41-51 (2013).
Yilma, "Prospects for the total eradication of rinderpest," Vaccine, 7(6):484-485 (1989).
Yoshihara et al., Inferring tumour purity and stromal and immune cell admixture from expression data,: Nature communications 4:2612 (2013).
Yoshitake et al., "Cross☐linking of GPI☐80, a possible regulatory molecule of cell adhesion, induces up☐regulation of CD11b/CD18 expression on neutrophil surfaces and shedding of L☐selectin," Journal of leukocyte biology, 71(2):205-211 (2002).
Young et al., "Resurrection of endogenous retroviruses in antibody-deficient mice," Nature, 491(7426):774 (2012).
Yu et al., "Nucleic acid-sensing Toll-like receptors are essential for the control of endogenous retrovirus viremia and ERV-induced tumors," Immunity, 37(5):867-879 (2012).
Yuille et al., "TCL1 is activated by chromosomal rearrangement or by hypomethylation," Genes, Chromosomes and Cancer, 30(4):336-341 (2001).
Zeestraten et al., "Addition of interferon-alpha to the p53-SLP(R) vaccine results in increased production of interferon-gamma in vaccinated colorectal cancer patients: a phase 1/11 clinical trial," Int J Cancer, 132(7):1581-1591 (2013).
Zhang et al., "Machine learning competition in immunology-prediction of HLA class I binding peptides," J Immunol Methods 374:1-4 (2009).
Zhang et al., "The impact of next-generation sequencing on genomics," J Genet Genomics, 38(3):95-109 (2011).
Zhou et al., "A hypermorphic missense mutation in PLCG2, encoding phospholipase Cgamma2, causes a dominantly inherited autoinflammatory disease with immunodeficiency," Am J Hum Genet, 91:713-20 (2012).
Zhou et al., "Long-term outcome after haploidentical stem cell transplant and infusion of T cells expressing the inducible caspase 9 safety transgene," Blood, 123(25):3895-3905 (2014).
Zhu et al., "Toll like receptor-3 ligand poly-ICLC promotes the efficacy of peripheral vaccinations with tumor antigen-derived peptide epitopes in murine CNS tumor models," Journal of translational medicine, 5:10 (2007).
Ziller et al., "Charting a dynamic DNA methylation landscape of the human genome," Nature, 500:477-481 (2013).
Zitvogel et al., "Immunological aspects of cancer chemotherapy," Nature reviews immunology, 8:59 (2008).
Zorn et al., "A natural cytotoxic T cell response in a spontaneously regressing human melanoma targets a neoantigen resulting from a somatic point mutation," Eur J Immunol, 29(2):592-601 (1999).
Zwaveling et al., "Established human papillomavirus type 16-expressing tumors are effectively eradicated following vaccination with long peptides," J Immunol, 169(1):350-358 (2002).
"CT-011 and p53 Genetic Vaccine for Advance Solid Tumor," National Library of Medicine, updated:Jun. 30, 2011, XP002738554, https://clinicaltrials.gov/archive/NCT01386502/2011_06_30, Clinical Trials Identifier NCT01386502.
"Monoclonal Antibody Therapy and Vaccine Therapy in Treating Patients with Stage IV Melanoma That Has Been Removed By Surgery," National Library of Medicine, 2010, XP002738553, https:clinicaltrials.gov/archive/NCT01176474/2010_08_05.
Acknowledgment of Receipt dated Jun. 28, 2017 for Response to Notices of Opposition of EP2569633.
Albert et al., "Direct Selection of Human Genomic Loci by Microarray Hybridization," Nat Methods, 4(11): 903-905 (2007).
Allison, "The Mode of Action of Immunological Adjuvants," Dev Biol Stand, 92: 3-11 (1998).
Altman et al., "Phenotypic analysis of antigen-specific T lymphocytes," Science, 274(5284):94-6 (1996).
Alyea et al., "Toxicity and Efficacy of Defined Doses of CD4+ Donor Lymphocytes for Treatment of Relapse After Allogeneic Bone Marrow Transplant," Blood, 91(10):3671-3680 (1998).
Andersen et al., "Parallel detection of antigen-specific T cell responses by combinatorial encoding of MHC multimers," Nature protocols, 7(5):891-902 (2012).
Anderson et al., "Next Generation DNA Sequencing and the Future of Genomic Medicine," Genes, 1: 38-69 (2010).
Annunziata et al., "Frequent Engagement of the Classical and Alternative NF-KB Pathways by Diverse Genetic Abnormalities in Multiple Myeloma," Cancer Cell, 12(2):115-130 (2007).
Applicant's Authorization and Release Form of the Massachusetts General Hospital, Aug. 12, 2008; and Supplemental Release to Applicant of the Partners Healthcare System, Aug. 13, 2008.
Attia et al., "Autoimmunity Correlates With Tumor Regression in Patients With Metastatic Melanoma Treated with Anti-Cytotoxic T-Lymphocyte Antigen-4," J Clin Oncol, 23.(25): 6043-6053 (2005).
Austen et al., "Mutations in the ATM Gene Lead to Impaired Overall and Treatment-Free Survival that is Independent of IGVH Mutation Status in Patients with B-CLL," Blood, 106(9): 3175-3182 (2005).
Ausubel, "A botanical macroscope," Proceedings of the National Academy of Sciences, 106(31):12569-12570 (2009).
Azvolinsky et al., "PD-1 Inhibitor MK-3475 Again Shows Promise in Advanced Melanoma," Cancer Network, 2013. [Retrieved online] http://www.cancernetwork.com/melanoma/pd-1-inhibitor-mk-3475-again-shows-promise-advanced-melanoma.
Bachireddy et al., "Reversal of in situ T cell exhaustion during effective human anti-leukemia responses to donor lymphocyte infusion," Blood, 123(9):1412-1421 (2013).
Balakrishnan et al, "Novel Somatic and Germline Mutations in Cancer Candidate Genes in Glioblastoma, Melanoma, and Pancreatic Carcinoma," Cancer Res, 67: 3545-3550 (2007).
Baskar et al., "Autologous Lymphoma Vaccines Induce Human T Cell Responses Against Multiple, Unique Epitopes," J Clin Invest, 113:1498-1510 (2004).

(56) References Cited

OTHER PUBLICATIONS

Baurain et al., "High Frequency of Autologous Anti-Melanoma CTL Directed Against an Antigen Generated by a Point Mutation in a New Helicase Gene," J Immunol, 164: 6057-6066 (2000).
Beck et al., "Enterocolitis in Patients With Cancer After Antibody Blockade of Cytotoxicity TLymphocyte-Associated Antigen 4," J Clin Oncol, 24(15): 2283-2289 (2006).
Bellucci et al., "Complete Response to Donor Lymphocyte Infusion in Multiple Myeloma is Associated with Antibody Responses to Highly Expressed Antigens," Blood, 103: 656-663 (2004).
Bentley et al., "Accurate Whole Human Genome Sequencing using Reversible Terminator Chemistry," Nature, 456(7218): 53-59 (2008).
Bettelli et al., "TH-17 cells in the circle of immunity and autoimmunity," Nat Immunol, 8:345-350 (2007).
Birrell et al., "A genome-wide screen in *Saccharomyces cerevisiae* for genes affecting UV radiation sensitivity," Proceedings of the National Academy of Sciences 98(22):12608-12613 (2001).
Boisguerin et al., "Translation of genomis-guided RNA-based personalised cancer vaccaines: towards the bedside," British J Cancer, 111:1469-1475 (2014).
Boon et al., "Human T Cell Responses Against Melanoma," Annu Rev Immunol, 24: 175-208 (2006).
Boon, "Toward a Genetic Analysis of Tumor Rejection Antigens," Adv Cancer Res, 58:177-210 (1992).
Bowerman et al., "Engineering the binding properties of the T cell receptor:peptide:MHC ternary complex that governs T cell activity," Mol Immunol, 46(15):3000-3008 (2009).
Brendle et al., "A Mutated HLA-A2 Molecule Recognized by Autologous Cytotoxic T Lymphocytes on a Human Renal Cell Carcinoma," J Exp Med, 183: 2501-2508 (1996).
Brinckerhoff et al., "Melanoma Vaccines," Curr Opin Oncol, 12:163-173 (2000).
Broad Institute Article, Jan. 29, 2009, "Turning Cancer's Strength Into Weakness," (2009).
Brown et al., "Neo-antigens predicted by tumor genome meta-analysis correlate with increased patient survival," Genome Res, 24(5):743-750 (2014).
Brunsvig et al., "Telomerase Peptide Vaccination: A Phase I/II Study in Patients with Non-Small Cell Lung Cancer," Cancer Immunol Immunother, 55(12): 1553-1564 (2006).
Buckwalter et al., "'It is the antigen(s), stupid' and other lessons from over a decade of vaccitherapy of human cancer," Seminar in Immunology, 20(5):296-300 (2008).
Burger et al., "Safety and activity of ibrutinib plus rituximab for patients with high-risk chronic lymphocytic leukaemia: a single-arm, phase 2 study," Lancet Oncology, 15(10)1090-1099 (2014).
Burkhardt et al., "Autologous CLL cell vaccination early after transplant induces leukemia-specific T cells," The Journal of clinical investigation, 123(9):3756-3765 (2013).
Cai et al., "Mutated BCR-ABL Generates Immunogenic T-Cell Epitopes in CML Patients," Clinical Cancer Research, 18(20):5761-5772 (2012).
Cai et al., "Peptides Derived From Mutated BCR-ABL Elicit T Cell Immunity in CML Patients," Blood, 116(21): 388-388 (2010).
Carpten et al., "A transforming mutation in the pleckstrin homology domain of AKT1 in cancer," Nature, 448(26):439-444 (2004).
Carter et al., "Identification and validation of cell surface antigens for antibody targeting in oncology," Endocrine-Related Cancer, 11:659-687 (2004).
CBOL Plant Working Group, "A DNA barcode for land plants," PNAS, 106(31):12794-12797 (2009).
Certified Priority Document for U.S. Appl. No. 61/334,866, filed May 14, 2010.
Chang et al., "Peptide length-based prediction of peptide-MHC class II binding," Bioinformatics, 22(22): 2761-2767 (2006).
Chatila, "The Regulatory T Cell Transcriptosome: E Pluribus Unum," Immunity, 27(5):693-695 (2007).
Chianese-Bullock et al., "Multi-peptide vaccines vialed as peptide mixtures can be stable reagents for use in peptide-based immune therapies," Vaccine, 27(11):1764-1770 (2009).

Chiari et al., "Two Antigens Recognized by Autologous Cytolytic T Lymphocytes on a Melanoma Result from a Single Point Mutation in an Essential Housekeeping Gene," Cancer Res, 59: 5785-5792 (1999).
Chinese Office Action dated Jun. 12, 2017 in corresponding CN Application No. 2014800322910.
Christian et al., "Targeting DNA double-strand breaks with TAL effector nucleases," Genetics, 186(2):757-761 (2010).
Ciofani et al., "A Validated Regulatory Network for Th17 Cell Specification," Cell, 151(2):289-303 (2012).
Clinical trial NCT 01970358, Patrick Ott, A Phase I Study With a Personalized NeoAntigen Cancer Vaccine in Melanoma, p. 1-6, Retrieved from https://clinicaltrials.gov/ct2/show/NCT01970358 downloaded Jun. 20, 2017.
Coffman et al., "Vaccine Adjuvants: Putting Innate Immunity to Work," Immunity 33:492-503 (2010).
Consolidated Table of Documents filed in Opposition to date in Response to Notices of Opposition of EP2569633 dated Jun. 28, 2017.
De Plaen et al., "Immunogenic (tum-) Variants of Mouse Tumor P815: Cloning of the Gene of Tum- Antigen P91A and Identification of the Tum-Mutation," PNAS, 85: 2274-2278 (1988).
Declaration by Stephen Johnston filed during the prosecution of granted U.S. Pat. No. 8,796,414 Nov. 20, 2013.
Declaration of Dr Nir Hacohen on Feb. 16, 2014.
Declaration of Dr. John C. Castle executed on Nov. 9, 2016.
Dengjel et al., "Glycan side chains on naturally presented MHC class II ligands," J. Mass Spectrom, 40:100-104 (2005).
Dermer et al., "Another Anniversary for the War on Cancer," Biotech, 12:320 (1994).
Ding et al., "Genome remodelling in a basal-like breast cancer metastasis and xenograft," Nature, 464:999-1005 (2010).
Dudley et al., "Cancer Regression and Autoimmunity in Patients After Clonal Repopulation with Antitumor Lymphocytes," Science, 298: 850-854 (2002).
Dupuis et al., "Dendritic Cells Internalize Vaccine Adjuvant after Intramuscular Injection," Cell Immunol, 186(1): 18-27 (1998).
Engelhard, "Structure of peptides associated with MHC class I molecules," Curr Opin Immunol, 6(1):13-23 (1994).
Engler et al., "A one pot, one step, precision cloning method with high throughput capability," PloS one 3(11):e3647 (2008).
Engler et al., "Golden gate shuffling: a one-pot DNA shuffling method based on type IIs restriction enzymes," PloS one, 4(5):e5553 (2009).
Erlich et al., "Next-generation sequencing for HLA typing of class I loci," BMC Genomics, 12:42 (2011).
Estep et al., "Mutation Analysis of BRAF, MEK1 and MEK2 in 15 Ovarian Cancer Cell Lines: Implications for Therapy," PLOS ONE, 12:e1279 (2007).
Extended European Search Report dated Apr. 11, 2016, which issued during prosecution of EP Application No. 15198284.0.
Extended European Search Report received for EP patent application No. EP11781409, dated Apr. 10, 2014.
Extended Search Report in Corresponding European Application No. 11781409.5, dated Apr. 14, 2014.
Extracts from the USPTO patent register.
Ezzell, "Cancer 'Vaccines': An idea whose time has come?," J NIH Res, 7:46 (1995).
Feigner et al., "Lipofection: A Highly Efficient, Lipid-Mediated DNA-Transfection Procedure," PNAS, 84(21): 7413-7417 (1987).
Fritsch et al., "HLA-Binding Properties of Tumor Neoepitopes in Humans," Cancer Immunol Res, 2(6):522-529 (2014).
Fritsch et al., "Personal neoantigen cancer vaccines: The momentum builds," Oncoimmunology, 3(6):e29311 (2014).
Gabrilovich et al., "IL-12 and Mutant P53 Peptide-Pulsed Dendritic Cells for the Specific Immunotherapy of Cancer," J Immunother Emphasis Tumor Immunol, 19(6): 414-418 (1996).
Garcia-Marco et al., "Frequent Somatic Deletion of the 13q12.3 locus Encompassing BRCA2 in Chronic Lymphocytic Leukemia," Blood, 88: 1568-1575 (1996).
Giaever et al., "Functional profiling of the Saccharomyces cerevisiae genome," Nature, 418(6896):387-391 (2002).

(56) References Cited

OTHER PUBLICATIONS

Gibney et al., "Safety and efficacy of adjuvant anti-PD1 therapy (nivolumab) in combination with vaccine in resected high-risk metastatic melanoma.," J Clin Oncol, Abstract 9056 (2013).
Gilboa, "The Makings of a Tumor Rejection Antigen," Immunity, 11: 263-270 (1999).
Gluzman, "SV40-transformed simian cells support the replication of early SV40 mutants," Cell, 23:175-182 (1981).
Gnirke et al., "Solution Hybrid Selection with Ultra-Long Oligonucleotides for Massively Parallel Targeted Sequencing," Nat Biotechnol, 27(2): 182-189 (2009).
Gotter et al., "Medullary Epithelial Cells of the Human Thymus Express a Highly Diverse Selection of Tissue-specific Genes Colocalized in Chromosomal Clusters," J Exp Med, 199(2): 155-166 (2004).
Goya et al., "SNVMix:predicting single nucleotide variants from next-generation sequencing of tumors," Bioinformatics, Original Paper, 26(6): 730-736 (2010).
Gubin et al., "Checkpoint blockade cancer immunotherapy targets tumor-specific mutant antigens," Nature, 515:577-581 (2014).
Gueguen et al., "An Antigen Recognized by Autologous CTLs on a Human Bladder Carcinoma," J Immunol, 160(12): 6188-6194 (1998).
Guo et al., "Different length peptides bind to HLA-Aw68 similarity at their ends but bulge on in the middle," Nature, 360:364-366 (1992).
Hacohen et al., "Getting Personal with Neoantigen-Based Therapeutic Cancer Vaccines," Cancer Immunol. Res, 1(1):11-15 (2013).
Herbst et al., "Predictive Correlates of Response to the Anti-PD-L1 Antibody MPDL3280A in Cancer Patients," Nature, 515(7528):563-567 (2014).
Herman et al., "Differences in the Recognition by Ctl of Peptides Presented by the HLAB*4402 and the HLA-B*4403 Molecules Which Differ by a Single Amino Acid," Tissue Antigens, 53: 111-121 (1999).
Hersey et al., "Phase I/II study of treatment with dendritic cell vaccines in patient with disseminated melanoma," Cancer Immunol Immunoother, 53:125-134 (2004).
Hocker et al., "Ultraviolet Radiation and Melanoma: A Systematic Review and Analysis of Reported Sequence Variants," Hum Mutat, 28(6): 578-588 (2007).
Hodi et al., "Biologic Activity of Cytotoxic T Lymphocyte-Associated Antigen 4 Antibody Blockade in Previously Vaccinated Metastatic Melanoma and Ovarian Carcinoma Patients," PNAS, 100: 4712-4717 (2003).
Hodi et al., "Immunologic and Clinical Effects of Antibody Blockade of Cytotoxic T Lymphocyte-Associated Antigen 4 in Previously Vaccinated Cancer Patients," PNAS, 105: 3005-3010 (2008).
Hodi et al., "Improved Survival with Ipilimumab in Patients with Metastatic Melanoma," New Engl J Med, 363:711-723 (2010).
Huang et al., "T Cells Associated With Tumor Regression Recognize Frameshifted Products of the CDKN2A Tumor Suppressor Gene Locus and a Mutated HLA Class I Gene Product," J Immunol, 172(10):6057-6064 (2004).
Humphries et al., "Lineage tracing reveals multipotent stem cells maintain human adenomas and the pattern of clonal expansion in tumor evolution," PNAS, 110(27):e2490-e2499 (2013).
Intellectual Property Policy for Partners-Affiliated Hospitals and Institutions, Aug. 15, 2002.
International Preliminary Report on Patentability for International Application No. PCT/US2011/036665 dated Nov. 20, 2012.
International Preliminary Report on Patentability for International Application No. PCT/US2014/033185 dated Oct. 22, 2015.
International Preliminary Report on Patentability for International Application No. PCT/US2014/067146 dated May 31, 2016.
International Preliminary Report on Patentability for International Application No. PCT/US2014/068746 dated Jun. 7, 2016.
International Preliminary Report on Patentability for International Application No. PCT/US2014/068893 dated Jun. 7, 2016.
International Preliminary Report on Patentability for International Application No. PCT/US2014/071707 dated Jun. 21, 2016.
International Preliminary Report on Patentability for International Application No. PCT/US2015/067143 dated Jun. 20, 2017.
International Search Report and Written Opinion for International Application No. PCT/US/2015/051340 dated Dec. 21, 2015.
International Search Report and Written Opinion for International Application No. PCT/US/2016/033452 dated May 20, 2016.
International Search Report and Written Opinion for International Application No. PCT/US/2016/036605 dated Jan. 16, 2017.
International Search Report and Written Opinion for International Application No. PCT/US2011/036665 dated Jul. 2, 2012.
International Search Report and Written Opinion for International Application No. PCT/US2014/033185 dated Nov. 5, 2014.
International Search Report and Written Opinion for International Application No. PCT/US2014/067146 dated Mar. 31, 2015.
International Search Report and Written Opinion for International Application No. PCT/US2015/067143 dated Apr. 12, 2016.
International Search Report for International Application No. PCT/US2014/068746 dated Mar. 23, 2015.
International Search Report for International Application No. PCT/US2014/068893 dated Apr. 9, 2015.
International Search Report for International Application No. PCT/US2014/071707 dated Sep. 10, 2015.
Invention Agreement of the Dana-Farber Cancer Institute, Jul. 1, 1997.
Japanese Office Action dated Jan. 22, 2018, which issured during prosecution of JP 2016-507587.
Japanese Office Action from Application No. 2013-510360 dated Apr. 28, 2015.
Ji et al., "An immune-active tumor microenvironment favors clinical response to ipilimumab," Cancer Immunol Immunother, 61(7):1019-1031 (2011).
Jocham et al., "Adjuvant Autologous Renal Tumour Cell Vaccine and Risk of Tumour Progression in Patients with Renal-Cell Carcinoma After Radical Nephrectomy: Phase III, Randomised Controlled Trial," Lancet, 363: 594-599 (2004).
Jun et al., "Progress in T cell adoptive Immunotherapy for Malignant Solid Tumors," Chin Med Biotechnol, 3(1):1-7 (2008).
Kanduri et al., "Differential genome-wide array-based methylation profiles in prognostic subsets of chronic lymphocytic leukemia," Blood, 115(2):296-305 (2010).
Kanzler et al., "Therapeutic Targeting of Innate Immunity with Toll-like Receptor Agonists and Antagonists," Nat Med, 13: 552-559 (2007).
Kawakami et al., "Identification of human tumor antigens and its implications for diagnosis and treatment of cancer," Cancer Sci, 95(10): 784-791 (2004).
Keats et al., "Promiscuous Mutations Activate the Noncanonical NF-KB Pathway in Multiple Myeloma," Cancer Cell, 12: 131-144 (2007).
Kenter et al., "Phase I Immunotherapeutic Trial with Long Peptides Spanning the E6 and E7 Sequences of High- Risk Human Papillomavirus 16 in End-Stage Cervical Cancer Patients Show Low Toxicity and Robust Immunogenicity," Clin. Cancer Research, 14(1):169-177 (2008).
Keogh et al., "Identification of New Epitopes from Four Different Tumor-Associated Antigens: Recognition of Naturally Processed Epitopes Correlates with HLA-A□0201-Binding Affinity," J Immunol, 167:787-796 (2001).
Kessler et al., "Identification of T-cell epitopes for cancer immunotherapy," Leukemia, 21:1859-1874 (2007).
Khalili et al., "In silico prediction of tumor antigens derived from functional missense mutations of the cancer gene census," Oncoimmunology, 1(8):1281-1289 (2012).
Klein et al., "Droplet Barcoding for Single-Cell Transcriptomics Applied to Embryonic Stem Cells," Cell, 161:1187-1201 (2015).
Koch, "Combining morphology and DNA barcoding resolves the taxonomy of Western Malagasy Liotrigona Moure, 1961," African Invertebrates, 51(2):413-421 (2010).
Koh et al., "Immunological consequences of using three different clinical/laboratory techniques of emulsifying peptide-based vaccines in incomplete Freund's adjuvant," J Translational Med, 4:42 (2006).

(56) References Cited

OTHER PUBLICATIONS

Komarova et al., "Evolution of Ibrutinib Resistance in Chronic Lymphcytic Leukemia (CLL)," Proceedings of the National Academy of Sciences, 111(38):13906-13911 (2014).
Kornher et al., "Mutation Detection Using Nucleotide Analogs That Alter Electrophoretic Mobility," Nucleic Acids Res, 17(19): 7779-7784 (1989).
Kress et al., "DNA barcodes: Genes, genomics, and bioinformatics," PNAS, 105(8):2761-2762 (2008).
Kress et al., "Use of DNA barcodes to identify flowering plants," PNAS, 102(23):8369-8374 (2005).
Kronenberger et al., "A Polyvalent Cellular Vaccine Induces T-cell Responses Against Specific Self-antigens Overexpressed in Chronic Lymphocytic B-cell Leukemia," J Immunother, 31(8): 723-730 (2008).
Kuppuswamy et al., "Single Nucleotide Primer Extension to Detect Genetic Diseases: Experimental Application to Hemophilia B (Factor IX) and Cystic Fibrosis Genes," PNAS, 88(4): 1143-1147 (1991).
Ladetto et al., "Real-Time Polymerase Chain Reaction in Multiple Myeloma: Quantitative Analysis of Tumor Contamination of Stem Cell Harvests," Exp Hematol, 30: 529-536 (2002).
Lahaye et al., "DNA barcoding the floras of biodiversity hotspots," PNAS, 105(8):2923-2928 (2008).
Landau et al., "Chronic lymphocytic leukemia: molecular heterogeneity revealed by high-throughput genomics," Genome Med, 5:47 (2013).
Landau et al., "Evolution and Impact of Subclonal Mutations in Chronic Lymphocytic Leukemia," Cell, 152:714-726 (2013).
Landau et al., "Increased Local Disorder of DNA Methylation Forms the Basis of High Intra-Leukemic Epigenetic Heterogeneity and Enhances CLL Evolution," Blood, 122:596 (2013).
Le et al., "Next-Generation Cancer Vaccine Approaches: Integrating Lessons Learned From Current Successes With Promising Biotechnologic Advances," J Natl Compr Cancer Network, 11:766-772 (2013).
Lee et al., "Sequential amplification of cloned DNA as tandem multimers using class-IIS restriction enzymes," Genetic Analysis: Biomolecular Engineering, 13(6):139-145 (1996).
Lemmel et al., "Differential quantitative analysis of MHC ligands by mass spectrometry using stable isotope labeling," Nature Biotechnology, 22(4):450-454 (2004).
Lennerz et al., "The Response of Autologous T Cells to a Human Melanoma is Dominated by Mutated Neoantigens," PNAS, 102(44):16013-10618 (2005).
Letter from Mathys & Squire dated Jun. 28, 2017 accompanying Response to Notices of Opposition of EP2569633.
Letter from Mathys & Squire dated Jun. 29, 2017+B245:B256.
Lewin et al., "DNA is the Genetic Material: Mutations Change the Sequence of DNA," Genes IV, 4:68-69 (1990).
Ley et al., "DNA sequencing of a cytogenetically normal acute myeloid leukaemia genome," Nature, 456: 66-72 (2008).
Ley et al., "DNMT3A Mutations in Acute Myeloid Leukemia", The New England Journal of Medicine, 363: 2423-2433 (2010).
Li et al., "Cancer Genome Sequencing and Its Implications for Personalized Cancer Vaccines," Cancers 3(4):4191-4211 (2011).
Lin et al., "Evaluation of MHC-II Peptide Binding Prediction Servers: Applications for Vaccine Research," BMC Bioinformatics, 9: S22 (2008).
Linard et al., "A ras-Mutated Peptide Targeted by CTL Infiltrating a Human Melanoma Lesion," J Immunol, 168:4802-4808 (2002).
Liu et al., "Athlates:accurate typing of human leukocyte antigen through exome sequencing," Nucleic Acids Res, 41(14):e142 (2013).
Luckow et al.,"Trends in the Development of Baculovirus Expression Vectors," Nat Biotechnol, 6:47-55 (1988).
Lundegaard et al., "NetMHC-3.0: accurate web accessible predictions of human, mouse and monkey MHC class I affinities for peptides of length 8-11," Nucleic Acids Research, 36: W509.W512 (2008).
Lundegaard et al., "State of the art and challenges in sequence based T-cell epitope prediction," Immunome Research, 6(Suppl 2): S3 (2010).
Macconaill et al., Profiling Critical Cancer Gene Mutations in Clinical Tumor Samples, PLoS One, 4(11):e7887 (2009).
Machiels et al., "Peptide-Based Cancer Vaccines," Seminars in Oncology, 29(5):494-502 (2002).
Macosko et al., "Highly Parallel Genome-wide Expression Profiling of Individual Cells Using Nanoliter Droplets," Cell, 161(5):1202-1214 (2015).
Maeurer et al., "New treatment options for patients with melanoma: review of melanoma-derived T-cell epitopebased peptide vaccines," Melanom Research, 6:11-24 (1996).
Maker et al., "Intrapatient Dose Escalation of Anti-CTLA-4 Antibody in Patients With Metastatic Melanoma," J Immunother, 29: 455-463 (1997).
Malavota et al., "Interpretation of the dissolution of insoluble peptide sequences based on the acid☐base properties of the solvent," Protein Sci, 15(6):1476-1488 (2006).
Malcikova et al., "Identification of somatic hypermutations in the TP53 gene in B-cell chronic lymphocytic leukemia," Molecular Immunol, 45(5):1525-1529 (2008).
Mandelboim et al., "Regression of Established Murine Carcinoma Metastases Following Vaccination with Tumor-Associated Antigen Peptides," Nature Medicine, 1(11):1179-1183 (1995).
Mandruzzato et al., "A CASP-8 Mutation Recognized by Cytolytic T Lymphocytes on a Human Head and Neck Carcinoma," J Exp Med, 186: 785-793 (1997).
Mannino et al., "Liposome Mediated Gene Transfer," Biotechniques, 6(7): 682-690 (1988).
Mardis et al., "Cancer genome sequencing: a review," Human Molecular Genetics, 18(2): R163-R168 (2009).
Mardis et al., "Recurring Mutations Found by Sequencing an Acute Myeloid Leukemia Genome," New Engl J Med, 361:1058-1066 (2009).
Margulies et al., "Genome Sequencing in Open Microfabricated High Density Picoliter Reactors," Nature, 15:437(7057): 376-380 (2005).
Marijt et al., "Hematopoiesis-Restricted Minor Histocompatibility Antigens HA-1- or HA -2-specific T Cells can Induce Complete Remissions of Relapsed Leukemia," PNAS, 100: 2742-2747 (2003).
Marina et al., "Serologic Markers of Effective Tumor Immunity Against Chronic Lymphocytic Leukemia Include Nonmutated B-Cell Antigens," Cancer Res, 70(4): 1344-1355 (2010).
Mark et al., "Site-specific mutagenesis of the human fibroblast interferon gene," PNAS, 81(18):5662-5666 (1984).
Men et al., "Assessment of Immunogenicity of Human Melan-A Peptide Analogues in HLA-A*0201/Kb Transgenic Mice," J Immunol, 162:3566-3573 (1999).
Meyerson et al., "Advances in understanding cancer genomes through second-generation sequencing," Nat Rev Genetics, 11:685-696 (2010).
Mullally et al., "Beyond HLA: The Significance of Genomic Variation for Allogeneic Hematopoietic Stem Cell Transplantation," Blood, 109: 1355-1362 (2007).
Murphy et al., "Antigen Presentation to T Lymphocytes," Janeway's Immunobiology, 7th Edition, 5:182-83 & 197 (2008).
Murphy et al., "Phase I Clinical Trial: T-Cell Therapy for Prostate Cancer Using Autologous Dendritic Cells Pulsed with HLA-A0201-Specific Peptides from Prostate-Specific Membrane Antigen," Prostate, 29(6): 371-380 (1996).
Notice of Opposition to European Patent No. EP2569633—Agenus Inc. (Opponent) dated Nov. 9, 2016.
Notice of Opposition to European Patent No. EP2569633—Dr. Christian Muller (Opponent) dated Nov. 9, 2016.
Notice of Opposition to European Patent No. EP2569633—Gritstone Oncology, Inc. (Opponent) dated Nov. 7, 2016.
Notice of Opposition to European Patent No. EP2569633—James Poole Limited (Opponent) dated Nov. 9, 2016.
Notice of Opposition to European Patent No. EP2569633—Strawman Limited (Opponent) dated Nov. 10, 2016.

(56) References Cited

OTHER PUBLICATIONS

Novellino et al., "A listing of human tumor antigens recognized by T cells: Mar. 2004 update," Cancer Immunol Immunother, 54(3):187-207 (2005).
Nyren et al., "Solid Phase DNA Minisequencing by an Enzymatic Luminometric Inorganic Pyrophosphate Detection Assay," Anal Biochem, 208(1): 171-175 (1993).
O'Shea et al., "Signal transduction and Th17 cell differentiation," Microbes Infect, 11(5):599-611 (2009).
Oakes et al., "Evolution of DNA Methylation Is Linked to Genetic Aberrations in Chronic Lymphocytic Leukemia," Cancer Discov, 4(3):348-361 (2014).
Oakes et al., "Heterogeneity and Evolution of DNA Methylation in Chronic Lymphocyctic Leukemia," Blood, 122(21):1626 (2013).
Ofran et al., "Identification of Human Minor Histocompatibility Antigens (MHA) by Combining Bioinformatic Prediction of Peptide Epitopes with Validation of T Cell Reactivity in Patient Blood Samples after Allogeneic Hematopoietic Stem Cell Transplantation," Biol Bone Marrow Transplant, 14:1 (Abstract #2) (2008).
Opaysky et al., CpG Island Methylation in a Mouse Model of Lymphoma Is Driven by the Genetic Configuration of Tumor Cells, PLOS Genetics, 3(9):e167 (2007).
Opposition Letter—Agenus Inc. (Opponent) in European Patent 2569633, dated Nov. 9, 2016.
Opposition Letter—Dr. Christian Muller (Opponent) in European Patent No. 2569633, dated Nov. 9, 2016.
Opposition Letter—Gritstone Oncology Inc. (Opponent) in European Application No. 11781409.5 dated Nov. 7, 2016.
Opposition Letter—James Poole Limited (Opponent) in European Patent No. 2569633, dated Nov. 9, 2016.
Opposition Letter—Strawman Limited (Opponent) in European Patent No. 2569633 dated Nov. 10, 2016.
Ott et al., "An Immunogenic personal neoantigen vaccine for patients with melanoma," Nature, 547:217-221 (2017).
Ott et al., "Vaccines and Melanoma," Hematol Oncol Clin N Am, 28(3):559-569 (2014).
Padgett et al., "Creating seamless junctions independent of restriction sites in PCR cloning," Gene, 168:31-35 (1996).
Screenshot Patent Assignment Abstract of Title of U.S. Appl. No. 13/108,610, filed May 16, 2011.
Pan et al., "Epigenomic Evaluation in diffuse Large B-Cell Lymphomas," Blood, Nov. 15, 2013, 122(21) XP55174946.
Parker et al., "Scheme for Ranking Potential HLA-A2 Binding Peptides Based on Independent Binding of Individual Peptide Side-Chains," J Immunol, 152(1): 163-175 (1994).
Parkhurst et al., "Improved induction of melanoma-reactive CTL with peptides from the melanoma antigen gp100 modified at HLA-A *0201-binding residues", The Journal of Immunology, 157: 2539-2548 (1996).
Parmiani et al., "Unique Human Tumor Antigens: Immunobiology and Use in Clinical Trials," J Immunol, 178: 1975-1979 (2007).
Pasmant et al., "Characterization of a Germ-Line Deletion, Including the Entire INK4/ARF Locus, in a Melanoma-Neural System Tumor Family: Identification of ANRIL, an Antisense Noncoding RNA Whose Expression Coclusters with ARF," Cancer Res, 67(8):3963-3969 (2007).
Peters et al., "The Immune Epitope Database and Analysis Resource: From Vision to Blueprint," PLoS Biol, 3(3): e91 (2005).
Peters et al., "The many faces of TH-17 Cells," Curr Opin Immunol, 23(6):702-706 (2011).
Phan et al., "Cancer regression and autoimmunity induced by cytotoxic T lymphocyte-associated antigen 4 blockade in patients with metastatic melanoma," PNAS, 100(14):8372-8377 (2003).
Pilla et al., "Multipeptide vaccination in cancer patient," Expert Opin Biol Ther, 9(8):1043-1055 (2009).
Piros et al., "Market Opportunity for Molecular Diagnostics in Personalized Cancer Therapy," Handbook of Clinical Nanomedicine: Law, Business, Regulation, Safety and Risk, Chapter 14: 1-29 (2016).
Pleasance et al., "A comprehensive catalogue of somatic mutations from a human cancer genome," Nature, 463:191-196 (2010).
Pleasance et al., "A small-cell lung cancer genome with complex signatures of tobacco exposure," Nature, 463: 184-190 (2010).
Policy Reallocating Ownership of Intellectual Property Covered by the Intellectual Property Policy, Sep. 18, 2002.
Prezant et al., "Trapped-Oligonucleotide Nucleotide Incorporation (TONI) Assay, a Simple Method for Screening Point Mutations," Hum Mutat, 1(2): 159-164 (1992).
Provan et al., "Eradication of Polymerase Chain Reaction-Detectable Chronic Lymphocytic Leukemia Cells is Associated with Improved Outcome After Bone Marrow Transplantation," Blood, 88: 2228-2235 (1996).
Public Assignment Data Screenshot of U.S. Appl. No. 61/334,866, filed May 14, 2010.
Rajasagi et al., "Systematic Identification of Personal Mutated Tumor-Specific Neoantigens in CLL," Blood, 120(21):954 (2012).
Rajasagi et al., "Systematic identification of personal tumor-specific neoantigens in chronic lymphocytic leukemia," Blood, 124(3): 453 (2014).
Rammensee et al., "Cancer Vaccines: Some Basic Considerations," Genomic and Personalized Medicine, 5:573-589 (2009).
Rammensee et al., "MHC ligands and peptide motifs: first listing," Immunogenetics, 41:178 (1995).
Rammensee et al., "SYFPEITHI: Database for MHC Ligands and Peptide Motifs," Immunogenetics, 50(3-4): 213-219 (1999).
Rammensee et al., "Towards Patient-Specific Tumor Antigen Selection for Vaccination," Immunological Reviews, Blackwell Publishing Munksgaard, 188:164-176 (2002).
Reifenberger et al., "Frequent Alterations of Ras Signaling Pathway Genes in Sporadic Malignant Melanomas," Int J Cancer, 109: 377-384 (2004).
Response to Notices of Opposition of EP2569633, dated Jun. 28, 2017.
Ressing et al., "Human CTL epitopes encoded by human papillomavirus type 16 E6 and E7 identified through in vivo and in vitro immunogenicity studies of HLA-A*0201-binding peptides.," J Immunol, 154(11):5934-5943 (1995).
Ribas et al., "Antitumor Activity in Melanoma and Anti-Self Responses in a Phase I Trial with the Anti-Cytotoxic T Lymphocyte-Associated Antigen 4 Monoclonal Antibody CP-675,206," J Clin Oncol, 23(35): 8968-8977 (2005).
Rifenberger et al., "Frequent Alterations of Ras Signaling Pathway Genes in Sporadic Malignant Melanomas," Int J Cancer, 109:377-384 (2004).
Rizvi et al., "Mutational landscape determines sensitivity to PD-1 blockade in non-small cell lung cancer," Science, 348(6230):124-128 (2015).
Robbins et al., "A mutated beta-catenin gene encodes a melanoma-specific antigen recognized by tumor infiltrating lymphocytes," J Exp Med, 183(3):1185-1192 (1996).
Rondon et al., "Graft-versus-Leukemia Effect After Allogeneic Bone Marrow Transplantation for Chronic Lymphocytic Leukemia," Bone Marrow Transplant, 18: 669-672 (1996).
Rooney et al., "Molecular and Genetic Properties of Tumors Associated with Local Immune Cytolytic Activity," Cell, 160(1-2):48-61 (2015).
Rosenberg et al., "Cancer Immunotherapy: Moving Beyond Current Vaccines," Nat Med, 10: 909-915 (2004).
Rubinfeld et al., "Stabilization of Beta-Catenin by Genetic Defects in Melanoma Cell Lines," Science, 275(5307):1790-1792 (1997).
Sabbatini et al., "Phase I trial of overlapping long peptides from a tumor self-antigen and Poly-ICLC shows rapid induction of integrated immune response in ovarian cancer patients," Clin Cancer Res, 18:6497-6508 (2012).
Sampson et al., "An epidermal growth factor receptor variant III-targeted vaccine is safe and immunogenic in patients with glioblastomas multiforme," Mol Cancer Ther, 8(10):2773-2779 (2009).
Sanderson et al., "Autoimmunity in a Phase I Trial of a Fully Human Anti-Cytotoxic T-Lymphocyte Antigen-4 Monoclonal Antibody With Multiple Melanoma Peptides and Montanide ISA 51 for Patients With Resected Stages III and IV Melanoma," J Clin Oncol, 23(4):741-750 (2005).

(56) References Cited

OTHER PUBLICATIONS

Saterdal et al., "Frameshift-mutation-derived peptides as tumor-specific antigens in inherited and spontaneous colorectal cancer," Proceedings of the National Academy of Sciences 98(23): 13255-13260 (2001).
Sato et al., "Intraepithelial CD8+ tumor-infiltrating lymphocytes and a high CD8+/regulatory T cell ratio are associated with favorable prognosis in ovarian cancer," PNAS, 102(51):1838-18543 (2005).
Schaffner et al., "Somatic ATM Mutations Indicate a Pathogenic Role of ATM in B-Cell Chronic Lymphocytic Leukemia," Blood, 94: 748-753 (1999).
Scheibenbogen et al., "Analysis of the T Cell Response to Tumor and Viral Peptide Antigens by an IFNγ-ELISPOT Assay," Int. J. Cancer, 71:932-936 (1997).
Schietinger et al., "Specificity in cancer immunotherapy," Semin. Immunol, 20(5)276-285 (2008).
Schuh et al., "Monitoring chronic lymphocytic leukemia progression by whole genome sequencing reveals heterogeneous clonal evolution patterns," Blood, 120(20):4191-4196 (2012).
Schwitalle et al., "Immunogenic peptides generated by frameshift mutations in DNA mismatch repair-deficient cancer cells," Cancer Immunity, 4(1):14 (2004).
Seberg et al., "How Many Loci Does it Take to DNA Barcode a Crocus?," PLoS One 4(2):e4598 (2009).
Segal et al., "Epitope Landscape in Breast and Colorectal Cancer," Cancer Res, 68: 889-892 (2008).
Sensi et al., "Unique Tumor Antigenesis: Evidence for Immune Control of Genome Integrity and Immunogenic for T Cell-Mediated Patient-Specific Immunotherapy," Clin Cancer Res, 12(7): :5023-5032 (2006).
Sette et al., "Peptide binding to the most frequent HLA-A class I alleles measured by quantitative molecular binding assays," Molecular Immunology, 31(11): 813-822 (1994).
Sette et al., "The relationship between class I binding affinity and immunogenicity of potential cytotoxic T cell epitopes," J Immunol, 153:5586-5592 (1994).
Shames et al., "A Genome-Wide Screen for Promoter Methylation in Lung Cancer Identifies Novel Methylation Markers for Multiple Malignancies," PLOS Med, 3(12):e486 (2006).
Sharma et al., "Novel cancer immunotherapy agents with survival benefit: recent successes and next steps," Nat Rev Cancer, 11(11):805-812 (2011).
Shastri et al., "Presentation of endogenous peptide/MHC class I complexes is profoundly influenced by specific C-terminal flanking residues," J Immunol, 155:4339 (1995).
Shukla et al., "Topics in Cancer Genomics," Graduate Theses and Dissertations, Paper 13796 (2014). [accessed online] https://search.proquest.com/docview/1558874754.
Sidney et al., "Measurement of MHC/Peptide Interactions by Gel Filtration or Monoclonal Antibody Capture," Curr Protoc Immunol: 18.3.1-18.3.36 (2013).
Siegmund et al., "Inferring clonal expansion and cancer stem cell dynamics from DNA methylation patterns in colorectal cancers," PNAS, 106(12):4828-4833 (2009).
Singh-Jasuga et al., "Correlation of T-cell response, clinical activity and regulatory T-cell levels in renal cell carcinoma patients treated with IMA901, a novel multi-peptide vaccine," J Clin Conology, 25:18S, Abstract #3017 (2007).
Sjoblom et al., "The Consensus Coding Sequences of Human Breast and Colorectal Cancers," Science, 314(5797):268-274 (2006).
Snyder et al., "Genetic Basis for Clinical Response to CTLA-4 Blockade in Melanoma," New Engl J Med, 371(23):2189-2199 (2014).
Snyder et al., "Immunogenic peptide discovery in cancer genomes," Cuff Opin Genet Dev, 30: 7-16 (2015).
Soiffer et al., "Vaccination with irradiated autologous melanoma cells engineered to secrete human granulocyte-macrophage colony-stimulating factor generates potent antitumor immunity in patients with metastatic melanoma," PNAS, 95(22):13141-13146 (1998).

Soiffer et al., "Vaccination With Irradiated, Autologous Melanoma Cells Engineered to Secrete Granulocyte-Macrophage Colony-Stimulating Factor by Adenoviral-Mediated Gene Transfer Augments Antitumor Immunity in Patients With Metastatic Melanoma," J Clin Oncol, 21(17):3343-3350 (2003).
Soininen et al., "Analysing diet of small herbivores: the efficiency of DNA barcoding coupled with high-throughput pyrosequencing for deciphering the composition of complex plant mixtures," Front Zool, 6:16 (2009).
Sokolov., "Primer Extension Technique for the Detection of Single Nucleotide in Genomic DNA," Nucleic Acids Res. 18(12): 3671 (1990).
Spitler, "Cancer Vaccines: The Interferon Analogy," Cancer Biother, 10:1-3 (1995).
Srivastava et al., "Modeling the Repertoire of True Tumor-Specific MHC I Epitopes in a Human Tumor," PLOS ONE, 4(7):e6094 (2009).
Srivastava, "Therapeutic Cancer Vaccines," Curr Opin Immunol, 18: 201-205 (2006).
Stankovic et al., "Microarray Analysis Reveals that TP53- and ATM-Mutant B-CLLs Share a Defect in Activating Proapoptotic Responses after DNA Damage but are Distinguished byMajor Differences in Activating Prosurvival Responses," Blood, 103: 291-300 (2004).
Stover et al., "New Use of BCG for Recombinant Vaccines," Nature, 351(6326): 456-460 (1991).
Stratton et al., "The Cancer Genome," Nature, 458(7239):719-724 (2009).
Su et al., "Immunological and Clinical Responses in Metastatic Renal Cancer Patients Vaccinated with Tumor RNA-Transfected Dendritic Cells," Cancer Res, 63: 2127-2133 (2003).
Submission in opposition proceedings of EP 2569633, dated Jun. 28, 2017.
Syvanen et al., "A Primer-Guided Nucleotide Incorporatiopn Assay in the Genotyping of Apoliprotein E," Genomics, 8(4): 684-692 (1990).
Syvanen et al., "Identification of Individuals by Analysis of Biallelic DNA Markers, Using PCR and Solid-Phase Minisequencing," Am J Hum. Genet, 52(1): 46-59 (1993).
Table S4 Somatic mutations Identified in Breast or Colorectal Cancers filed on Nov. 7, 2016 in Notice of Opposition by Gritstone Oncology Inc. to EP 2569633.
Table S5 Breast CAN-genes, filed on Nov. 7, 2016, in Notice of Opposition by Gritstone Oncology Inc., to EP Patent No. 2569633.
Table S6 Colorectal CAN-genes, filed on Nov. 7, 2016 in Notice of Opposition by Gritstone Oncology Inc. to EP Patent No. 2569633.
Thomas et al., "High-Throughput Oncogene Mutation Profiling in Human Cancer," Nat Genet, 39: 347-351 (2007).
Thompson et al., "Aberrations of the B-Cell Receptor B29 (CD79b) Gene in Chronic Lymphocytic Leukemia," Blood, 90(4):1387-1394 (1997).
Thornton et al., "Characterisation of TP53 Abnormalities in Chronic Lymphocytic Leukaemia," Hematol J, 5: 47-54 (2004).
Timmerman et al., "Idiotype-Pulsed Dendritic Cell Vaccination for B-Cell Lymphoma: Clinical and Immune Responses in 35 Patients," Blood, 99: 1517-1526 (2002).
Tjoa et al., "Follow-Up Evaluation of Prostate Cancer Patients Infused with Autologous Dendritic Cells Pulsed with PSMA Peptides," Prostate, 32(4): 272-278 (1997).
Tong et al., "Methods and protocols for prediction of immunogenic epitopes", Briefings in Bioinformatics, 8(2): 96-108 (2008).
Tourdot et al., "A general strategy to enhance immunogenicity of low-affinity HLA-A2.1-associated peptides: implication in the identificatiioonn of cryptic tumor epitopes," Eur. J. Immunol, 30:3411-3421 (2000).
Toze et al., "Myeloablative Allografting for Chronic Lymphocytic Leukemia: Evidence for Potent Graft-versus-Leukemia Effect Associated with Graft-versus-Host Disease," Bone Marrow Transplant, 36: 825-830 (2005).
Tumeh et al., "PD-1 blockade induces responses by inhibiting adaptive immune resistance," Nature, 515(7528):568-571 (2014).
U.S. Final Office Action dated May 25, 2017 and issued in U.S. Appl. No. 15/187,174.

(56) References Cited

OTHER PUBLICATIONS

U.S. Final Rejection dated Sep. 13, 2017 and issued in U.S. Appl. No. 14/794,449.
U.S. Non-Final Office Action dated Jan. 22, 2018 and issued in U.S. Appl. No. 15/187,174.
U.S. Non-Final Office Action dated Dec. 5, 2016 and issued in U.S. Appl. No. 15/187,174.
U.S. Non-Final Office Action dated Dec. 29, 2016 and issued in U.S. Appl. No. 14/794,449.
Ueda et al., "Germ Line and Somatic Mutations of BRAF V599E in Ovarian Carcinoma," Int J Gynecol Cancer, 17: 794-797 (2007).
Ugozzoli et al., "Detection of Specific Alleles by Using Allele-Specific Primer Extension Followed by Capture on Solid Support," Genet Anal Tech AppL, 9(4): 107-112 (1992).
UniProtKB Printouts—Q5SW79 filed on Nov. 2016 in Muller Opposition to EP 2569633.
Van de Roemer et al., "P1737:IVAC: Individualized vaccines for cancer," Immunology 137(Suppl. 1):715, Sep. 2012.
Van Den Broeke et al., "Identification and Eiptope Enhancement of a PAX-FKHR Fusion Protein Breakpoint Epitope in Alveolar Rhabdomyosarcoma Cells Created by a Tumorigenic Chromosomal Translocation Inducing CTL Capable of Lysing Human Tumors," American Association for Cancer Research, 66(3):1818-1823 (2006).
Van der Bruggen et al., "A Gene Encoding an Antigen Recognized by Cytolytic T Lymphocytes on a Human Melanoma," Science, 254: 1643-1647 (1991).
Van Pel et al., "Tumor Cell Variants Obtained by a Mutageneis of a Lewis Lung Carcinoma Cell Line: Immune Rejection by Syngeneic Mice," PNAS, 76(10): 5282-5285 (1979).
Van Rooij et al., "Tumor Exome Analysis Reveals Neoantigen-Specific T-Cell Reactivity in an 1pilimumab- Responsive Melanoma," Journal of Clinical Oncology, 31(32):e439-e442 (2013).
Van Trappen et al., "Somatic Mitochondrial DNA Mutations in Primary and Metastatic Ovarian Cancer," Gynecol Oncol, 104: 129-133 (2007).
Verhoef et al., "Des-enkephalin-γ-endorphin (DEγE): Biotransformation in rat, dog and human plasma," Eur J Drug Metab Ph, 11(4):291-302 (1986).
Vogelstein et al., "Cancer Genome Landscapes," Science, 339(6127): 1546-1558 (2013).
Volpe et al., "Alternative BCR/ANL Splice Variants in Philadelphia Chromosome-Positive Leukemias Result in Novel Tumor-Specific Fusion Proteins that May Represent Potential Targets for Immunotherapy Approaches," Cancer Res, 67(11):5300-5307 (2007).
Walter et al., "DNA Methylation Profiling Defines Clinically Relevant Biological Subsets of Non-small Cell Lung Cancer," Clin Cancer Res, 18(8):2360-2373 (2012).
Wang, "Tumor Antigens Discovery: Perspectives for Cancer Therapy", Molecular Medicine, 3(11): 716-731 (1997).
Weber et al., "Assembly of Designer TAL Effectors by Golden Gate Cloning," PLoS ONE, 6:e19722 (2001).
Weber et al., "Safety, Efficacy, and Biomarkers of Nivolumab With Vaccine in Ipilimumab-Refractory or -Naive Melanoma," J Clin Oncol, 31:4311-4318 (2013).
Weinschenk et al., "Integrated Functional Genomics Approach for the Design of Patientindividual Antitumor Vaccines," Cancer Res, 62: 5818-5827 (2002).
Willmore-Payne et al., "Human Malignant Melanoma: Detectection of BRAF- and c-kit-Activating Mutations by High-Resolution Amplicon Melting Analysis," Hum Pathol, 36: 486-493 (2005).
Winzeler et al., "Functional characterization of the *S. cerevisiae* genome by gene deletion and parallel analysis," science, 285(5429):901-906 (1999).
Wolfel et al., "A p16INK4a-insensitive CDK4 mutant targeted by cytolytic T lymphocytes in a human melanoma," Science, 269(5228):1281-1284 (1995).
Wolff et al., "Direct Gene Transfer into Mouse Muslce in Vivo," Science, 247(4949):1465-1468 (1990).
Wood et al., "The Genomic Landscapes of Human Breast and Colorectal Cancers," Science, 318: 1108-1113 (2007).
Woodbury et al., "Introduction to Macromolecular Binding Equilibria," CRC Press, 13:978 (2007).
Wu et al., "Detection of a potent humoral response asscoiated with immune-induced remission of chronic myelogenous leukemia," J Clin Invest, 106(5):705-714 (2000).
Wu et al., "Graft-versus-Leukemia Target Antigens in Chronic Myelogenous Leukemia Are Expressed on Myeloid Progenitor Cells," Clin Cancer Res, 11(12):4504-4511 (2005).
Wu et al., "Induction of Tumor Immunity Following Allogeneic Stem Cell Transplantation," Adv Immunol, 90: 133-173 (2006).
Wu et al., "Mouse Model of Human Ovarian Endometrioid Adenocarcinoma Based on Somatic Defects in the Wnt/6-Catenin and PI3K/Pten Signaling Pathways," Cancer Cell, 11: 321-333 (2007).
Wu et al., "Reconstitution of T-Cell Receptor Repertoire Diversity Following T-Cell Depleted Allogeneic Bone Marrow Transplantation is Related to Hematopoietic Chimerism," Blood, 95: 352-359 (2000).
Xu et al., "Design of 240,000 orthogonal 25mer DNA barcode probes," Proceedings of the National Academy of Sciences, pnas-0812506106 (2009).
Yang et al. "CML66, a broadly immunogenic tumor antigen, elicits a humoral immune response associated with remission of chronic myelogenous leukemia," PNAS, 98(13):7492-7497 (2001).
Yao et al., "Advances in targeting cell surface signalling molecules for immune modulation," Nature Rev Drug Discov, 12:130-146 (2013).
Yokoyama et al., "Matrilysin (MMP-7) Is a Novel Broadly Expressed Tumor Antigen Recognized by Antigen- Specific T Cells," Clin Cancer Res, 14(17): 5503-5511 (2008).
Yosef et al., "Dynamic regulatory network controlling TH17 cell differentiation," Nature, 496(7446):461-468 (2013).
You et al., "Understanding Prediction Systems for HLA-Binding Peptides and T-Cell Epitope Identification," Pattern Recognition in Bioinformatics, Lecture Notes in Computer Science, 4474: 337-348 (2007).
Zhang et al., "Graft-versus-Leukemia Antigen CML66 Elicits Coordinated B-Cell and T-Cell Immunity after Donor Lymphocyte Infusion," Clin Cancer Res, 16: 2729-2739 (2010).
Zhang et al., "Intratumoral T Cells, recurrence, and survival in epithelial ovarian cancer," New Engl J Med, 348(3):203-213 (2003).
Zhou et al., "Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine," Cancer Res, 65: 1079-1088 (2005).
Zhou et al., "Transcriptional regulatory networks in Th17 cell differentiation," Curr Opin Immunol, 21(2):146-152 (2009).
Zhou et al., Persistance of Multiple Tumor-Specific T-Cell Clones is Associated with Complete Tumor Regression in a Melanoma Patient Receiving Adoptive Cell transfer Therapy, J Immunother, 28(1):53-62 (2005).

* cited by examiner

Reporter assay

1. Transduce TCR sequence into parental reporter cell line

2. Stimulate with APC pulsed to present neoantigen

3. Detect mCherry expression if TCR is specific for neoantigen

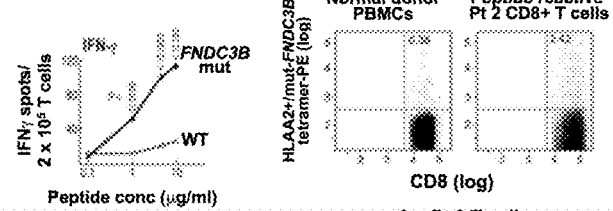
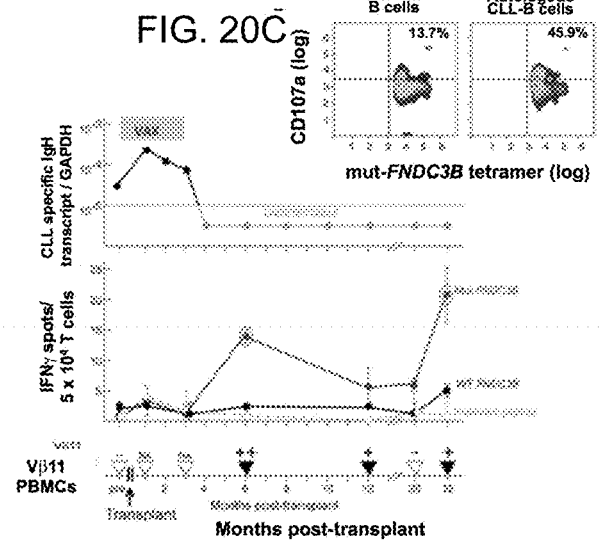
FIG. 20A
FIG. 20B
FIG. 20C
FIG. 20D

METHODS FOR PROFILING THE T CELL REPERTOIRE

RELATED APPLICATIONS AND INCORPORATION BY REFERENCE

This application claims benefit of and priority to U.S. provisional patent application Ser. No. 62/094,859, filed Dec. 19, 2014. Reference is also made to U.S. Pat. No. 9,115,402.

FEDERAL FUNDING LEGEND

This invention was made with government support under Grant No. CA155010 awarded by the National Institutes of Health. The government has certain rights in the invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present disclosure relates to methods for profiling the T cell receptor repertoire of single subjects in need thereof and preparing subject specific treatments based on the T cell receptors.

BACKGROUND OF THE INVENTION

The T cell receptor (TCR) is a molecule found on the surface of T lymphocytes (i.e. T cells) that is responsible for recognizing antigens bound to major histocompatibility complex (MHC) molecules. The TCR is a heterodimer composed of two different protein chains. In most T cells (about 95%), these two protein chains are termed the alpha ($\alpha$) and beta ($\beta$) chains. However, in a small percentage of T cells (about 5%), these two protein chains are termed the gamma and delta ($\gamma/\delta$) chains. The ratio of TCRs comprised of $\alpha/\beta$ chains versus $\gamma/\delta$ chains may change during a diseased state. When the TCR engages with antigenic peptide and MHC (peptide/MHC), the T lymphocyte is activated through a series of biochemical events mediated by associated enzymes, co-receptors, specialized adaptor molecules, and activated or released transcription factors.

The genetically programmed variability of TCRs and immunoglobulins (Ig) underlies immune recognition of diverse antigens. The selection of antigen-specific T and B cells under different pressures—such as infections, vaccines, autoimmune diseases, allergy, and tumors—can dramatically alter the repertoire in individuals either transiently or permanently. However, since the active receptor consists of paired chains (e.g., TCR$\alpha$/TCR$\beta$ or IgH/IgL) within single cells, determination of active paired chains requires the sequencing of single cells.

The immune system is a vital component in preventing and eliminating cancer. Cytotoxic T cells (CTL) and natural killer cells (NK) have potent ability to kill tumor cells and numerous studies show that effector T cells at the tumor site predict favorable outcome across many cancers. Additionally, tumors vary greatly between each individual, requiring subject specific T cells targeting subject specific tumor antigens to kill a tumor.

Methods for sequencing TCR receptors have been described. Linnemann, et al., describe a method for identifying unpaired TCR sequences using genomic DNA from a large number of samples and assemble a library of TCRs (Nature Medicine 2013 November; 19(11):1534-41). The library was proposed to be used for autologous TCR gene therapy without knowledge of antigen specificity. Dössinger, et al., describe isolation of paired full-length TCR sequences from non-expanded antigen-specific T cells using a PCR-based method (TCR-SCAN) (PLoS One. 2013 Apr. 26; 8(4):e61384). The method allowed isolation of TCRs of known oncogenes. Seitz, et al., describes a method to identify TCR$\alpha\beta$ pairs from archival tissue (Proc Natl Acad Sci USA. 2006 Aug. 8; 103(32):12057-62). However, TCR transfected cells were not reactive to the antigens assayed.

Personalized treatments based on the matching of neoantigens to T cells has not been previously described. Thus, there remains an unmet need in the art to develop methods to treat cancer patients in need thereof with a personalized immunotherapy.

Citation or identification of any document in this application is not an admission that such document is available as prior art to the present invention.

SUMMARY OF THE INVENTION

The present disclosure relates to methods for profiling the T cell repertoire of individual subjects and matching of TCR pairs with subject specific neoepitopes. Specifically, T cell receptors are identified that can recognize a subject specific tumor. Therefore, it is an object of the present invention to treat a subject in need thereof with T cells expressing personalized T cell receptors to provide a subject specific and effective therapy.

In a first aspect TCRs from individual T cells are identified. In one embodiment the TCR repertoire is quantified to determine the number of cells expressing a subject specific TCR. In one embodiment T cells are obtained from a subject with cancer. In another embodiment T cells are obtained that have infiltrated a subjects tumor. In another embodiment T cells are isolated from blood. In another embodiment T cells are isolated from peripheral blood mononuclear cells (PBMC). In one embodiment T cells are enriched by binding of a ligand to T cell specific markers. In one embodiment, the markers may be CD3, CD4, CD8, CD28, or any combination therewith. In one embodiment the markers are CD3/CD28. In one embodiment the ligands are antibodies. In one embodiment the antibodies are conjugated to beads. In one embodiment the antibodies are fluorescently labeled. In one embodiment the cells are separated by cell sorting.

In one embodiment single T cells are sequenced. In one embodiment single T cells are diluted such that each well of a plate contains a single cell. In one embodiment the single T cells are expanded in tissue culture. In one embodiment the nucleic acid from the single expanded T cell clones are sequenced. In one embodiment the nucleic acid from the single cells is sequenced without expanding the cells.

In another embodiment single cells are sequenced using a microfluidic system. Single cells may be selected for and then sequenced using a microfluidic system. In one embodiment single T cells are selected by FACS and then sequenced. Single cells may be encapsulated in droplets. The droplets may include reagents for synthesizing nucleic acids. The droplets may include individual markers to identify that the nucleic acid present in the droplet originated from a single cell. The individual marker may be a barcode. The barcode may be a polynucleotide with a unique sequence. The barcode may be introduced on a bead that is incorporated into the droplet.

In one embodiment, the present disclosure relates to methods for a platform for profiling the T cell receptor repertoire using single-cell bar-coded droplets (SCBD). In one embodiment a high-throughput single cell analysis system that integrates micron-scale engineered emulsions (droplets), novel molecular barcoding, hydrogel materials, and massively parallel sequencing techniques is used. This technology enables, a general method for the capture of single cell genomic information, including the pairing of multiple amplicon sequences per individual cell from an extremely large cell population ($>10^6$). SCBD may be used to profile the T cell repertoire and to quantify the relative abundance of each T cell clone within a population. In addition, methods are provided to identify the antigenic targets of T cell receptors in the context of tumor neoantigens.

In a second aspect neoantigens are identified for single subjects. In addition to identifying individual TCRs present in a subject with cancer, neoantigens targeted by T cells expressing the TCRs are identified. In one embodiment neoantigens are determined by whole exome sequencing. In one embodiment neoantigens are determined based on individual HLA type of a subject. In one embodiment molecular modeling is used to determine the TCR that binds to a neoantigen.

The invention comprehends performing methods as in U.S. patent application No. 20110293637, incorporated herein by reference, e.g., a method of identifying a plurality of at least 4 subject-specific peptides and preparing a subject-specific immunogenic composition that upon administration presents the plurality of at least 4 subject-specific peptides to the subject's immune system, wherein the subject has a tumor and the subject-specific peptides are specific to the subject and the subject's tumor, said method comprising:
(i) identifying, including through
nucleic acid sequencing of a sample of the subject's tumor and
nucleic acid sequencing of a non-tumor sample of the subject,
a plurality of at least 4 tumor-specific non-silent mutations not present in the non-tumor sample; and
(ii) selecting from the identified non-silent mutations the plurality of at least 4 subject-specific peptides, each having a different tumor neo-epitope that is an epitope specific to the tumor of the subject, from the identified plurality of tumor specific mutations,
wherein each neo-epitope is an expression product of a tumor-specific non-silent mutation not present in the non-tumor sample, each neo-epitope binds to a HLA protein of the subject, and selecting includes
determining binding of the subject-specific peptides to the HLA protein, and
(iii) formulating the subject-specific immunogenic composition for administration to the subject so that upon administration the plurality of at least 4 subject-specific peptides are presented to the subject's immune system,
wherein the selecting or formulating comprises at least one of:
including in the subject-specific immunogenic composition a subject-specific peptide that includes an expression product of an identified neo-ORF, wherein a neo-ORF is a tumor-specific non-silent mutation not present in the non-tumor sample that creates a new open reading frame, and
including in the subject-specific immunogenic composition a subject-specific peptide that includes an expression product of an identified point mutation and has a determined binding to the HLA protein of the subject with an IC50 less than 500 nM,
whereby, the plurality of at least 4 subject-specific peptides are identified, and the subject-specific immunogenic composition that upon administration presents the plurality of at least 4 subject-specific peptides to the subject's immune system, wherein the subject-specific peptides are specific to the subject and the subject's tumor, is prepared; or a method of identifying a neoantigen comprising:
a. identifying a tumor specific mutation in an expressed gene of a subject having cancer;
b. wherein when said mutation identified in step (a) is a point mutation:
  i. identifying a mutant peptide having the mutation identified in step (a), wherein said mutant peptide binds to a class I HLA protein with a greater affinity than a wild-type peptide;
  and has an IC50 less than 500 nm;
c. wherein when said mutation identified in step (a) is a splice-site, frameshift, read-through or gene-fusion mutation:
  i. identifying a mutant polypeptide encoded by the mutation identified in step (a), wherein said mutant polypeptide binds to a class I HLA protein; or a method of inducing a tumor specific immune response in a subject comprising administering one or more peptides or polypeptides identified and an adjuvant; or a method of vaccinating or treating a subject for cancer comprising:
a. identifying a plurality of tumor specific mutations in an expressed gene of the subject wherein when said mutation identified is a:
  i. point mutation further identifying a mutant peptide having the point mutation; and/or
  ii. splice-site, frameshift, read-through or gene-fusion mutation further identifying a mutant polypeptide encoded by the mutation;
b. selecting one or more mutant peptides or polypeptides identified in step (a) that binds to a class I HLA protein;
c. selecting the one or more mutant peptides or polypeptides identified in step (b) that is capable of activating anti-tumor CD8 T cells; and
d. administering to the subject the one or more peptides or polypeptides, autologous dendritic cells or antigen presenting cells pulsed with the one or more peptides or polypeptides selected in step (c); or preparing a pharmaceutical composition comprising one identified peptide(s), and performing method(s) as herein discussed. Thus, the neoplasia vaccine or immunogenic composition herein can be as in U.S. patent application No. 20110293637.

In a third aspect the present invention provides for functional analysis of subject specific TCRs. In one embodiment the TCRs are cloned into a vector that allows expression. In one embodiment the TCRs are cloned into a plasmid. In another embodiment the TCRs are cloned into a viral vector. In another embodiment the TCRs are expressed in T cells. In one embodiment the T cells are transformed with a plasmid.

In another embodiment the T cells are transduced with a virus. In one embodiment TCRs are expressed in cells that do not express endogenous TCRs. In one embodiment TCRs are transduced into a mouse cell line. In one embodiment TCRs are transduced into a human cell line. In one embodiment the T cell can release IL2. In one embodiment the T cells can express the cellular machinery to function in cytolytic killing of a tumor cell. In one embodiment the cells are BW5147 cells. In one embodiment the cells are peripheral blood lymphocytes. In one embodiment the T cells expressing cloned TCRs are used to assay cytolytic activity against subject specific tumor cells in vitro. In one embodiment T cells expressing cloned TCRs are used to assay binding to tumor cells obtained from a subject. In one embodiment TCRs that bind neoantigens are determined. In one embodiment the TCRs identified in a subject are used to model binding to the neoantigens present in the subject. In one embodiment T cells expressing cloned TCRs are used to assay binding to subject specific neoantigens. In one embodiment soluble recombinant TCRs are used to bind subject specific neoantigens. In another embodiment T cells expressing subject specific TCRs are incubated with antigen presenting cells that present subject specific neoantigens to the engineered T cells. In one embodiment at least one reporter is used to detect binding of TCRs to antigen. In one embodiment the T cell line includes a polynucleotide sequence encoding a reporter gene. The reporters may be expressed in the T cells that express the cloned TCRs. In another embodiment the expression of cytokines is used to assay TCR binding to antigen.

In another embodiment the TCRs present in a subject are monitored before, after and/or simultaneously with the administration of an immunogenic composition that includes neoantigens. TCRs may be monitored by PCR using primers specific to each T cell receptor pair.

In a fourth aspect the present invention provides a personalized treatment for a subject using the identified T cell repertoire. In one embodiment identification of the T cell repertoire is used to determine an immunogenic composition or vaccine to be administered to a subject in need thereof. In one embodiment the immunogenic composition is a neoantigen vaccine. In another embodiment the neoantigen vaccine may comprise subject specific neoantigen peptides. In one embodiment neoantigen peptides to be included in a neoantigen vaccine are selected based on the quantification and identity of subject specific TCRs. In one embodiment the neoantigen peptides are selected based on the binding affinity of the peptide to a TCR. In one embodiment the selecting is based on a combination of both the quantity and the binding affinity. Not being bound by a theory, a TCR that binds strongly to a neoantigen in a functional assay, but that is not highly represented in the TCR repertoire is a good candidate for a neoantigen vaccine because T cells expressing the TCR would be advantageously amplified.

In one embodiment the subject in need thereof is treated with T cells expressing T cell receptors. In one embodiment the T cell receptors are autologous. In one embodiment T cells are transduced with subject specific TCRs. In one embodiment T cells are obtained from the subject being treated. In another embodiment the T cell receptors target neoantigens. In one embodiment the T cells are administered to a subject. In one embodiment the T cells are administered after immunoablation. Not being bound by a theory this may be an effective treatment because the drug regimen used to treat a patient may have killed the majority of the tumor cells and an immunotherapy that includes T cells can be effective to remove any remaining cells. In another embodiment the T cells are administered within a standard of care for a cancer.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 20A-D Illustrates that post-HSCT/vaccination T cells of Patient 2 are (A) specifically reactive to mutated-but not wild-type-FNDC3B peptide (ELISPOT), and (B) these neoantigen-reactive T cells are detectable by neoantigen-specific tetramers, and express the cytolytic marker CD107a (C). (D) The kinetics of the mutated-FNDC3B specific T cell response in relation to molecular tumor burden.

DETAILED DESCRIPTION OF THE INVENTION

Figure 1:
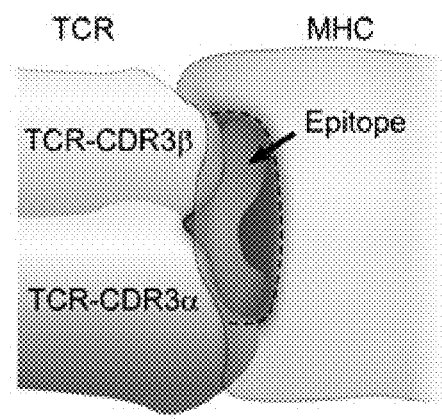
FIG. 1 is an exemplary schematic showing that recognition of MHC-bound peptide by the combined TCRβ and TCRα proteins occurs primarily in the CDR3 regions.

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

By "agent" is meant any small molecule chemical compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a tumor specific neo-antigen polypeptide analog retains the biological activity of a corresponding naturally-occurring tumor specific neo-antigen polypeptide, while having certain biochemical modifications that enhance the analog's function relative to a naturally-occurring polypeptide. Such biochemical modifications could increase the analog's protease resistance, membrane permeability, or half-life, without altering, for example, ligand binding. An analog may include an unnatural amino acid.

By "control" is meant a standard or reference condition.

By "disease" is meant any condition or disorder that damages or interferes with the normal function of a cell, tissue, or organ.

The terms "droplet library" or "droplet libraries" are also referred to herein as an "emulsion library" or "emulsion libraries." These terms are used interchangeably throughout the specification.

By "fragment" is meant a portion of a polypeptide or nucleic acid molecule. This portion contains, preferably, at least 5%, 10%, 20%, 30%, 40%, 50%, 60%, 70%, 80%, or 90% of the entire length of the reference nucleic acid molecule or polypeptide. A fragment may contain 5, 10, 20, 30, 40, 50, 60, 70, 80, 90, or 100, 200, 300, 400, 500, 600, 700, 800, 900, 1000 or more nucleotides or amino acids.

The terms "frequency" or "frequencies" refer to the rate at which microdroplets of certain species are delivered to a specific location. Moreover, this frequency or rate is a number per unit time, typically several hundred to tens of thousands per second. Furthermore the terms "frequency" or "frequencies" refers to the number of times at which droplets of certain species are delivered to a specific location.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The term "hydrogel" as used herein refers to a gel in which water is the dispersion medium. Non-limiting examples of hydrogels include cellulose gels, such as agarose and derivatized agarose (e.g., low melting agarose, monoclonal anti-biotin agarose, and streptavidin derivatized agarose); xanthan gels; synthetic hydrophilic polymers, such as crosslinked polyethylene glycol, polydimethyl acrylamide, polyacrylamide, polyacrylic acid (e.g., cross-linked with dysfunctional monomers or radiation cross-linking), and micellar networks; and combinations thereof By "immune response" is meant any cellular or humoral response against an antigen.

By "isolated polynucleotide" is meant a nucleic acid (e.g., a DNA) that is free of the genes which, in the naturally-occurring genome of the organism—or in the genomic DNA of a neoplasia/tumor derived from the organism—the nucleic acid molecule of the disclosure is derived. The term therefore includes, for example, a recombinant DNA (e.g., DNA coding for a neoORF, read-through, or InDel derived polypeptide identified in a patient's tumor) that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the disclosure that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the disclosure may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The CEF Control Peptides are 8-12 amino acids in length, with sequences derived from the human Cytomegalovirus, Epstein-Barr Virus and Influenza Virus (CEF). These peptides are used in the stimulation of IFNg release from CD8+ T cells in individuals with defined HLA types, they are useful in applications such as ELISPOT, intracellular cytokine and CTL assays.

A "ligand" is to be understood as meaning a molecule which has a structure complementary to that of a receptor and is capable of forming a complex with the receptor. According to the invention, a ligand is to be understood as meaning a peptide or peptide fragment that has a suitable length and suitable binding motifs in its amino acid sequence, so that the peptide or peptide fragment is capable of forming a complex with proteins of MHC class I or MHC class II.

"Mutation" for the purposes of this document means a DNA sequence found in the tumor DNA sample of a patient that is not found in the corresponding normal DNA sample of that same patient. "Mutation" may also refer to patterns in the sequence of RNA from a patient that are not attributable to expected variations based on known information for an individual gene and are reasonably considered to be novel variations in, for example, the splicing pattern of one or more genes that has been specifically altered in the tumor cells of the patient.

"Neo-antigen" or "neo-antigenic" means a class of tumor antigens that arises from a tumor-specific mutation(s) which alters the amino acid sequence of genome encoded proteins.

By "neoplasia" is meant any disease that is caused by or results in inappropriately high levels of cell division, inappropriately low levels of apoptosis, or both. For example, cancer is an example of a neoplasia. Examples of cancers include, without limitation, leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

The term "neoplasia vaccine" is meant to refer to a pooled sample of neoplasia/tumor specific neoantigens, for example at least two, at least three, at least four, at least five, or more neoantigenic peptides. A "vaccine" is to be understood as meaning a composition for generating immunity for the prophylaxis and/or treatment of diseases (e.g., neoplasia/tumor). Accordingly, vaccines are medicaments which comprise antigens and are intended to be used in humans or animals for generating specific defence and protective substance by vaccination. A "neoplasia vaccine composition" can include a pharmaceutically acceptable excipient, carrier or diluent.

Unless specifically stated or obvious from context, as used herein, the term "or" is understood to be inclusive. Unless specifically stated or obvious from context, as used herein, the terms "a," "an," and "the" are understood to be singular or plural.

The term "patient" or "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" of pooled tumor specific neo-antigens as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the pooled tumor specific neo-antigens provided herein, including those listed by *Remington's Pharmaceutical Sciences,* 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

By "polypeptide" is meant any chain of amino acids, regardless of length or post-translational modification.

As used herein, the terms "prevent," "preventing," "prevention," "prophylactic treatment," and the like, refer to reducing the probability of developing a disease or condition in a subject, who does not have, but is at risk of or susceptible to developing a disease or condition.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

"Proteins or molecules of the major histocompatibility complex (MHC)," "MHC molecules," "MHC proteins" or "HLA proteins" are to be understood as meaning, in particular, proteins capable of binding peptides resulting from the proteolytic cleavage of protein antigens and representing potential T cell epitopes, transporting them to the cell surface and presenting them to specific cells there, in particular naïve T cells, cytotoxic T-lymphocytes or T-helper cells. The major histocompatibility complex in the genome comprises the genetic region whose gene products are expressed on the cell surface and are important for binding and presenting endogenous and/or foreign antigens, and thus for regulating immunological processes. The major histocompatibility complex is classified into two gene groups coding for different proteins: molecules of MHC class I and MHC class II. The molecules of the two MHC classes are specialized for different antigen sources. The molecules of MHC class I typically present but are not restricted to endogenously synthesized antigens, for example viral proteins and tumor antigens. The molecules of MHC class II present protein antigens originating from exogenous sources, for example bacterial products. The cellular biology and the expression patterns of the two MHC classes are adapted to these different roles.

MHC molecules of class I consist of a heavy chain and a light chain and are capable of binding a peptide of about 8 to 11 amino acids, but usually 9 or 10 amino acids, if this peptide has suitable binding motifs, and presenting it to naïve and cytotoxic T-lymphocytes. The peptide bound by the MEW molecules of class I typically but not exclusively originates from an endogenous protein antigen. The heavy chain of the MHC molecules of class I is preferably an HLA-A, HLA-B or HLA-C monomer, and the light chain is β-2-microgobulin.

MHC molecules of class II consist of an α-chain and a β-chain and are capable of binding a peptide of about 15 to 24 amino acids if this peptide has suitable binding motifs, and presenting it to T-helper cells. The peptide bound by the MEW molecules of class II usually originates from an extracellular or exogenous protein antigen. The α-chain and the β-chain are in particular HLA-DR, HLA-DQ and HLA-DP monomers.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A "receptor" is to be understood as meaning a biological molecule or a molecule grouping capable of binding a ligand. A receptor may serve, to transmit information in a cell, a cell formation or an organism. The receptor comprises at least one receptor unit and frequently contains two or more receptor units, where each receptor unit may consist of a protein molecule, in particular a glycoprotein molecule. The receptor has a structure that complements the structure of a ligand and may complex the ligand as a binding partner. Signaling information may be transmitted by conformational changes of the receptor following binding with the ligand on the surface of a cell. According to the invention, a receptor may refer to particular proteins of MHC classes I and II capable of forming a receptor/ligand complex with a ligand, in particular a peptide or peptide fragment of suitable length.

A "receptor/ligand complex" is also to be understood as meaning a "receptor/peptide complex" or "receptor/peptide fragment complex," in particular a peptide- or peptide fragment-presenting MHC molecule of class I or of class II.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of, or the entirety of, a specified sequence; for example, a segment of a full-length cDNA or genomic sequence, or the complete cDNA or genomic sequence. For polypeptides, the length of the reference polypeptide sequence will generally be at least about 10-2,000 amino acids, 10-1,500, 10-1,000, 10-500, or 10-100. Preferably, the length of the reference polypeptide sequence may be at least about 10-50 amino acids, more preferably at least about 10-40 amino acids, and even more preferably about 10-30 amino acids, about 10-20 amino acids, about 15-25 amino acids, or about 20 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

By "specifically binds" is meant a compound or antibody that recognizes and binds a polypeptide of the invention, but which does not substantially recognize and bind other molecules in a sample, for example, a biological sample.

Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 35% formamide, 1% SDS, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "subject" is meant a mammal, such as a human patient or an animal (e.g., a rodent, bovine, equine, porcine, ovine, canine, feline, or other domestic mammal).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

A "T cell epitope" is to be understood as meaning a peptide sequence that can be bound by MEW molecules of class I or II in the form of a peptide-presenting MEW molecule or MEW complex and then, in this form, be recognized and bound by naïve T cells, cytotoxic T-lymphocytes or T-helper cells.

By "tumor specific T cell" is meant a T cell with special affinity for a tumor antigen and whose function is restricted to a tumor.

The present invention relates to methods for profiling subject specific T cell receptor (TCR) repertoires. More particularly, the present invention relates to methods for determining binding of T cell receptors to subject specific neoantigens and for determining cytolytic activity targeting the individual subject's tumor using a single-cell sequencing method. The techniques described herein enable, for the first time, a transformative and general method to profile the T cell repertoire and to quantify the relative abundance of each T cell clone within a population. In addition, the techniques herein may identify the antigenic targets of T cell receptors in the context of tumor neoantigens. Additionally, the present disclosure enables the discovery of T cell targets in numerous diseases, with implications for understanding the basic mechanisms of the mammalian immune response and for developing antigen-specific diagnostic markers and therapies (whether immunizing or tolerizing). Finally, cloned TCRs can be used to formulate personalized immunotherapies for those inflicted with cancer.

As noted herein, T cells express specific TCR pairs that determine the target of a T cell. The immune system can be classified into two functional subsystems: the innate and the acquired immune system. The innate immune system is the first line of defense against infections, and most potential pathogens are rapidly neutralized by this system before they can cause, for example, a noticeable infection. The acquired immune system reacts to molecular structures, referred to as antigens, of the intruding organism. There are two types of acquired immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in particular T cells, of the body. Cytotoxic T cells recognize these antigens and kill the cells that harbor the antigens.

The molecules that transport and present peptides on the cell surface are referred to as proteins of the major histocompatibility complex (MHC). MHC proteins are classified into two types, referred to as MHC class I and MHC class II. The structures of the proteins of the two MHC classes are very similar; however, they have very different functions. Proteins of MHC class I are present on the surface of almost all cells of the body, including most tumor cells. MHC class I proteins are loaded with antigens that usually originate from endogenous proteins or from pathogens present inside cells, and are then presented to naïve or cytotoxic T-lymphocytes (CTLs). MHC class II proteins are present on dendritic cells, B-lymphocytes, macrophages and other antigen-presenting cells. They mainly present peptides, which are processed from external antigen sources, i.e. outside of the cells, to T-helper (Th) cells. Most of the peptides bound by the MHC class I proteins originate from cytoplasmic proteins produced in the healthy host cells of an organism itself, and do not normally stimulate an immune reaction. Accordingly, cytotoxic T-lymphocytes that recognize such self-peptide-presenting MHC molecules of class I are deleted in the thymus (central tolerance) or, after their release from the thymus, are deleted or inactivated, i.e. tolerized (peripheral tolerance). MHC molecules are capable of stimulating an immune reaction when they present peptides to non-tolerized T-lymphocytes. Cytotoxic T-lymphocytes have both T cell receptors (TCR) and CD8 molecules on their surface. T cell receptors are capable of recognizing and binding peptides complexed with the molecules of MHC class I. Each cytotoxic T-lymphocyte expresses a unique T cell receptor which is capable of binding specific MHC/peptide complexes.

The peptide antigens attach themselves to the molecules of MHC class I by competitive affinity binding within the endoplasmic reticulum, before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines.

T cells play an important role in numerous diseases, and yet in most cases, the critical TCR heterodimers and their cognate antigens have not been identified. Furthermore, the principles underlying thymic positive and negative selection, generation of regulatory T cells, and induction of peripheral anergy are not well understood. Accordingly, there is a great need to identify the TCRs within single T cells and monitor the dynamics of the TCR repertoire during these processes. Using such an approach, it should be feasible to derive the rules of self vs, non-self antigen recognition and the evolution of the repertoire and to identify the TCRs that drive disease. For example, the ability to systematically discover the functional CD8 T cell TCRs that target tumor antigens may make it possible to develop more rational cancer vaccines. Moreover, T cells expressing TCRs that have potent cytolytic activity can be expanded and used for cancer therapies. Finally, TCRs that have high affinity for a tumor can be expressed in T cells and administered as a therapy.

The highly polymorphic TCR is generated by joining of non-contiguous gene segments (Vβ, Dβ, Jβ for TCRβ and Vα, Jα for TCRα) together with deletion/insertion of random sequences at junctions and Recombination Signal Sequences (RSS) to form the highly variable CDR3 regions. The recognition of MHC-bound peptide by the combined TCRβ and TCRα proteins occurs primarily by the CDR3 regions (see e.g., FIG. 1; Robins et al., 2010 Sci Transl Med. 2:47ra64; Krogsgaard et al., 2005; Nicholson et al., 2005). Although there is a theoretical possibility of forming as many as $5\times10^{11}$ unique TCRβ chains, the actual number of unique TCRβ genes found in humans is closer to 0.1% of this estimate (Robins et al., 2010). Without being bound by theory, this reduction in complexity may be due to thymic education (positive/negative selection) and antigen exposure (e.g. pathogens, tumors, self antigens), processes that select specific T cell clones. The techniques described herein will facilitate understanding of the evolution of the repertoire, and also identify functional TCRs.

Identifying TCR Pairs from Individual Subject Specific T Cells

In a first aspect, T cell receptors that are expressed on individual T cells in a subject are identified. In one embodiment a source of T cells is obtained from a subject. The term "subject" is intended to include living organisms in which an immune response can be elicited (e.g., mammals). The present disclosure provides, at least in part, a method for comprehensive analysis of the TCR repertoire. In an exemplary embodiment, the present disclosure provides a platform that would include both TCR and immunoglobulin sequencing and cloning into vectors. Advantageously, the exemplary platform disclosed herein is generalizable to any disease setting (human or animal) in which the TCR repertoire and antigen specificity are important to study, including tumors, infections, autoimmunity, transplant and allergy/asthma.

In one embodiment T cells that have infiltrated a tumor are isolated. T cells may be removed during surgery. T cells may be isolated after removal of tumor tissue by biopsy. T cells may be isolated by any means known in the art. In one embodiment the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell soiling and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease as described herein. In one embodiment neoepitopes are determined for a subject and T cells specific to these antigens are isolated. In certain embodiments, antigen-specific T cells can be induced by vaccination of a subject with a particular antigen, either alone or in conjunction with an adjuvant or pulsed on dendritic cells. In one embodiment a subject is vaccinated with a neoantigen identified as described herein. Antigen-specific cells for use in expansion may also be generated in vitro using any number of methods known in the art, for example, as described in U.S. Patent Publication No. US 20040224402 entitled, Generation And Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., *Science*. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. In a preferred embodiment, neoantigens are used. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment antigen-specific T cells are isolated by contacting the T cells with antibodies specific for T cell activation markers. Antibodies that can be used with the methods of the present invention include, but are not limited to, anti-CD25, anti-CD54, anti-CD69, anti-CD38, anti-CD45RO, anti-CD49d, anti-CD40L, anti-CD137, anti-IFN-γ, IL-2, IL-4, and other activation induced cytokines, and anti-CD134 antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

Once T cells are isolated the TCRs present on individual cells may be determined. Many approaches have been used to analyze the TCR repertoire previously. In one embodiment the present invention determines the TCRs of single cells by subcloning primary T cells in culture. After subcloning, each clonal population is sequenced. In a preferred embodiment the TCR pairs are amplified by PCR and then sequenced.

Single cells may be sequenced by any method known in the art. The present invention utilizes single cell sequencing to identify TCR pairs. In one embodiment T cells are sorted into single wells of a plate and each well is sequenced individually. As described herein, specific sets of primers may be used to amplify TCR pairs for sequencing. The T cells may be sorted by FACS. The T cells may be sorted based on IFNγ or any other cell surface marker.

In another embodiment, single cell analysis is performed by digital polymerase chain reactions (PCR), e.g., Fluidigm C. Digital polymerase chain reaction (digital PCR, DigitalPCR, dPCR, or dePCR) is a refinement of conventional polymerase chain reaction methods that can be used to directly quantify and clonally amplify nucleic acids including DNA, cDNA or RNA. The key difference between dPCR and traditional PCR lies in that PCR carries out one reaction per single sample and dPCR carries out a single reaction within samples separated into a large number of partitions wherein the reactions are carried out in each partition individually. A sample is partitioned so that individual nucleic acid molecules within the sample are localized and concentrated within many separate regions. The capture or isolation of individual nucleic acid molecules may be effected in micro well plates, capillaries, the dispersed phase of an emulsion, and arrays of miniaturized chambers, as well as on nucleic acid binding surfaces.

In a preferred embodiment single cell sequencing is performed using microfluidics. Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947 and PCT publication No. WO2014085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment single cell analysis is performed in droplets using methods according to WO 2014085802. Each of these patents and publications is herein incorporated by reference in their entireties for all purposes.

In one embodiment RNA from single cells is used to make cDNA within the droplet. In one embodiment the reagents are delivered to the droplet during droplet formation. In one embodiment the reagents for producing cDNA cause the single cells to be lysed within a droplet. In one embodiment the cDNA from single cells is attached to a barcode. In one embodiment the barcode is attached to a bead. In one embodiment the beads are hydrogel beads. In one embodiment droplets are formed to include a single cell, a single barcoded bead, and reagents for producing cDNA. In one embodiment the reagents include primers specific for all TCR α and β chains. In another embodiment the cDNA is sequenced by any method of sequencing known to one of ordinary skill. In a preferred embodiment massively parallel sequencing or a next generation sequencing platform is used. Not being bound by a theory single cell sequencing allows the ability to tag the desired nucleic acids in each droplet with a unique computationally designed sequencing-compatible barcode, allowing droplets to be subsequently broken and their contents pooled for sequencing. After sequencing, the unique barcodes representing individual cells (droplets) are then re-associated in silico.

Single T cells of the present invention may be divided into single droplets using a microfluidic device. RNA and/or DNA in single cells in such droplets may be further labeled with a barcode. In this regard reference is made to Macosko et al., 2015, "Highly Parallel Genome-wide Expression Profiling of Individual Cells Using Nanoliter Droplets" Cell 161, 1202-1214 and Klein et al., 2015, "Droplet Barcoding for Single-Cell Transcriptomics Applied to Embryonic Stem Cells" Cell 161, 1187-1201 all the contents and disclosure of each of which are herein incorporated by reference in their entirety.

Barcoding may be performed based on any of the compositions or methods disclosed in patent publication WO 2014047561 A1, Compositions and methods for labeling of agents, incorporated herein in its entirety. The term "barcode" as used herein, refers to any unique, non-naturally occurring, nucleic acid sequence that may be used to identify the originating source of a nucleic acid fragment. Such barcodes may be sequences including but not limited to, TTGAGCCT, AGTTGCTT, CCAGTTAG, ACCAACTG, GTATAACA or CAGGAGCC.

Although it is not necessary to understand the mechanism of an invention, it is believed that the barcode sequence provides a high-quality individual read of a barcode associated with a viral vector, shRNA, or cDNA such that multiple species can be sequenced together.

DNA barcoding is a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a *crocus*?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31): 12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

Identifying TCR Pairs Induced by Neoantigens

In a second aspect, neoantigens are identified that bind to subject specific TCRs. Neoantigens are a unique class of tumor antigen characterized by their potential to generate high avidity T cells and their exquisite tumor-specificity. Abundant evidence in mouse and man supports the role of neoantigens in cancer control (reviewed in Hacohen et al, CIR 2013; Fritsch et al, CIR 2014). A complementary approach to the identification of and immunization with neoantigens is an understanding of the interacting T cell receptors (TCR). The repertoire of TCRs within tumor infiltrating lymphocytes, prior to or following immunotherapy, is a measure of T cell responsiveness and reflects the repertoire of epitopes against which these T cells react. These epitopes could be derived from predicted neoantigens, from neoantigens missed by the prediction algorithm, or from other tumor-associated antigens active in the tumor. In one embodiment a subject is immunized with at least one antigen before identifying TCRs. In another embodiment the antigen is a neoantigen. In another embodiment the subject is immunized with a neoplasia vaccine that includes at least one neoantigen. In one embodiment tumor specific T cells are enriched by stimulation with autologous tumor ex vivo (Burkhardt et al., J Clin Invest. 2013; 123(9):3756-3765). Whole genome/exome sequencing may be used to identify all, or nearly all, mutated neoantigens that are uniquely present in a neoplasia/tumor of an individual patient, and that this collection of mutated neoantigens may be analyzed to identify a specific, optimized subset of neoantigens for use as a personalized cancer vaccine or immunogenic composition for treatment of the patient's neoplasia/tumor. For example, a population of neoplasia/tumor specific neoantigens may be identified by sequencing the neoplasia/tumor and normal DNA of each patient to identify tumor-specific mutations, and the patient's HLA allotype can be identified. The population of neoplasia/tumor specific neoantigens and their cognate native antigens may then be subject to bioinformatics analysis using validated algorithms to predict which tumor-specific mutations create epitopes that could bind to the patient's HLA allotype. Based on this analysis, a plurality of peptides corresponding to a subset of these mutations may be designed and synthesized for each patient, and pooled together for use as a cancer vaccine or immunogenic composition in immunizing the a subject. TCRs may be identified after an initial vaccination or any time after the initial vaccination. TCRs may be identified after a boosting dose. TCRs may be identified after a second boosting dose. TCRs may be identified before vaccination and after vaccination. The TCRs identified before and after vaccination can be compared in order to determine new TCRs present in the T cell repertoire. Additionally, TCRs may be found to be present before and after vaccination, however, the amount of a TCR pair may be increased after vaccination. In one embodiment new TCRs are determined. In another embodiment TCR pairs are quantified to determine a change in their representation in the T cell repertoire.

In another embodiment TCRs are determined by incubating PBMCs with neoantigens followed by sequencing of the TCR repertoire as described herein.

Functional Analysis of TCR Pairs

In a third aspect, the identified TCR pairs are used in functional assays. In a first embodiment a nucleic acid encoding the TCR pairs are cloned. A further embodiment provides a nucleic acid (e.g., a polynucleotide) encoding protein of interest (e.g., a TCRα chain, a TCRβ chain, a TCR pair, a tumor neoantigen, and the like), which may be used to produce the protein in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. A still further embodiment of the disclosure provides an expression vector capable of expressing a polypeptide according to the invention. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

In one embodiment, the TCR pairs are cloned using the Golden Gate assembly method as described further herein (Engler, C. et al (2008). *PLoS ONE*. 3: e3647; Engler, C. et al (2009). *PLoS ONE*. 4: e5553; Lee, J. H. et al (1996). *Genetic Analysis: Biomolecular Engineering*. 13; 139-145; Padgett, K. A. and Sorge, J. A. (1996). *Gene*. 168, 31-35; Weber, E. et al (2001). *PLoS ONE*. 6; e19722; and Christian, M. et al (2010). *Genetics*. 186, 757-761). A library of all Vα and Vβ segments is synthesized. For a particular sequenced pair of TCRα and TCRβ genes in a T cell, the appropriate segments are mixed with a synthesized CDR3 segment, and assembled into a final vector that expresses both TCRα and TCRβ.

The disclosure further embraces variants and equivalents which are substantially homologous to the identified tumor TCR pairs or neo-antigens described herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art.

The disclosure also includes expression vectors comprising the isolated polynucleotides, as well as host cells containing the expression vectors. It is also contemplated within the scope of the disclosure that the polynucleotides may be provided in the form of RNA or cDNA molecules encoding the desired TCR peptides. The disclosure also provides that the one or more TCR peptides of the disclosure may be encoded by a single expression vector. The disclosure also provides that the one or more TCR peptides of the disclosure may be encoded and expressed in vivo using a viral based system (e.g., an adenovirus, AAV, or retrovirus described in more detail herein).

The term "polynucleotide encoding a polypeptide" encompasses a polynucleotide which includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides can comprise the coding sequence for the TCR peptide fused in the same reading frame to a marker sequence that allows, for example, for purification of the encoded polypeptide. For example, the marker sequence can be a hexa-histidine tag (SEQ ID NO: 1) supplied by a pQE-9 vector to provide for purification of the mature polypeptide fused to the marker in the case of a bacterial host, a molecular barcode, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, molecular barcodes, and the like.

In embodiments, the present disclosure provides isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a TCR peptide of the present invention.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The isolated TCR peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., *Proc. Nat'l. Acad. Sci. USA* 81:5662-5066 (1984) and U.S. Pat. No. 4,588,585.

Once assembled (e.g., by synthesis, site-directed mutagenesis, or another method), the polynucleotide sequences encoding a particular isolated polypeptide of interest will be inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors may be used to amplify and express DNA encoding the TCR peptides. Recombinant expression vectors are replicable DNA constructs which have synthetic or cDNA-derived DNA fragments encoding a subject or tumor specific TCR or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail herein. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., *Cloning Vectors: A Laboratory Manual*, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Additionally, T cell lines as described herein may be used in order to determine binding of a T cell to a tumor or antigen. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine (SEQ ID NO: 1), maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In certain embodiments nucleic acids encoding T cell receptors are introduced into a cell for expression of the T cell receptor. Transfection can be carried out using calcium phosphate, by electroporation, by cell squeezing or by mixing a cationic lipid with the material to produce liposomes, which fuse with the cell membrane and deposit their cargo inside. In one embodiment the TCR is transfected into a cell by using a plasmid. In other embodiments a viral vector is used to transduce a TCR into a cell. In one embodiment the viral vectors include AAV, adenovirus, or a retrovirus. Plasmids that can be used for adeno associated virus (AAV), adenovirus, and lentivirus delivery have been described previously (see e.g., U.S. Pat. Nos. 6,955,808 and 6,943,019, and U.S. Patent application No. 20080254008, hereby incorporated by reference).

Among vectors that may be used in the practice of the invention, integration in the host genome of a T cell is possible with retrovirus gene transfer methods, often resulting in long term expression of the inserted transgene. In a preferred embodiment the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Additionally, cell type specific promoters can be used to target expression in specific cell types. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Separate retroviral vectors can be used for each TCR chain. A bi-cistronic retroviral vector to express both chains may also be used. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), multi-cistronic murine stem cell virus (MSCV) and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700; and Engels et al., (2003) Hum Gene Ther 14, 1155-1168).

Also useful in the practice of the invention is a minimal non-primate lentiviral vector, such as a lentiviral vector based on the equine infectious anemia virus (EIAV) (see, e.g., Balagaan, (2006) J Gene Med; 8: 275-285, Published online 21 Nov. 2005 in Wiley InterScience (www.interscience.wiley.com). DOI: 10.1002/jgm.845). The vectors may have cytomegalovirus (CMV) promoter driving expression of the target gene. Accordingly, the invention contemplates amongst vector(s) useful in the practice of the invention: viral vectors, including retroviral vectors and lentiviral vectors.

Also useful in the practice of the invention is an adenovirus vector. One advantage is the ability of recombinant adenoviruses to efficiently transfer and express recombinant genes in a variety of mammalian cells and tissues in vitro and in vivo, resulting in the high expression of the transferred nucleic acids. Further, the ability to productively infect quiescent cells, expands the utility of recombinant adenoviral vectors. In addition, high expression levels ensure that the products of the nucleic acids will be expressed to sufficient levels to determine function in infected cells (see e.g., U.S. Pat. No. 7,029,848, hereby incorporated by reference).

Also useful in the practice of the invention is an adenovirus associated virus (AAV) vector. AAV is advantageous over other viral vectors due to low toxicity and low probability of causing insertional mutagenesis because it doesn't integrate into the host genome. AAV has a packaging limit of 4.5 or 4.75 Kb. Constructs larger than 4.5 or 4.75 Kb result in significantly reduced virus production. There are many promoters that can be used to drive nucleic acid molecule expression. AAV ITR can serve as a promoter and is advantageous for eliminating the need for an additional promoter element. For ubiquitous expression, the following promoters can be used: CMV, CAG, CBh, PGK, SV40, Ferritin heavy or light chains, etc. Promoters used to drive RNA can include: Pol III promoters such as U6 or H1. The use of a Pol II promoter and intronic cassettes can also be used to express TCRs.

In one embodiment purified recombinant TCRs are used in in vitro assays. In one embodiment in vitro binding assays to antigens are performed. TCRs in a soluble form can be made by methods known in the art (Boulter et al. (2003), Protein Engineering 16; 9: 707-711). Additionally binding assays such as Biacore have been previously described (Laugel et al., (2005), The Journal of Biological Chemistry 280; 3: 1882-1892; Gadola et al., (2006), Journal of Experimental Medicine 203: 699-710; Cole et al., (2007), The Journal of Immunology 178: 5727-5734; Sami et al., (2007), Protein Engineering, Design & Selection 20; 8: 397-403; Cole et al., (2008), Molecular Immunology 45: 2700-2709).

In one embodiment T cell lines are transfected or transduced with the subject specific TCRs of the invention for use in functional assays. In one embodiment T cell lines are deficient for endogenous TCRs. In one embodiment mammalian cells are used. In one embodiment the T cells are murine cells. In one embodiment the T cells are human cells. In one embodiment the T cells respond to antigen stimulation. In one embodiment the T cells have cytolytic activity. In one embodiment the cells are peripheral blood lymphocytes (PBLs). In one embodiment the PBLs are from a healthy subject that has not had cancer previously and does not have a tumor. In another embodiment the PBLs are from a subject with a different HLA type than the subject where the subject specific TCRs were cloned. This would assure that TCRs present on the PBL would not react with antigens that are presented by the subject specific HLA proteins. In one embodiment the cells are BW5147.3 (ATCC TIB-47; BW) cells. In one embodiment the T cells are the human TCR-deficient Jurkat76 cells (Heemskerk, M. H., et al., (2003) Blood 102, 3530-3540).

In one embodiment functional assays are performed using T cells that express subject specific TCRs. In one embodiment neoantigens are presented by antigen presenting cells in functional assays. In one embodiment neoantigens are presented that were used to immunize the subject. In one embodiment sequence analysis of the TCRs determines the antigens to be presented. In one embodiment autologous tumor cells are presented to T cells. In one embodiment cytolytic activity is determined. In another embodiment TCR binding to antigen is determined.

Assays for detection of CTLs have relied on direct determination of cell lysis as measured by the classical assay for CTL activity namely the chromium release assay (Walker et al., (1987) Nature: 328:345-348; Scheibenbogen et al., (2000) J Immunol Methods: 244(1-2):81-89.). Effector Cytotoxic T Lymphocytes (CTL) bind targets bearing antigenic peptide on Class I MHC and signal the targets to undergo apoptosis. If the targets are labeled with $^{51}$Chromium before the CTL are added, the amount of $^{51}$Cr released into the supernatant is proportional to the number of targets killed. Antigen-specific lysis is calculated by comparing lysis of target cells expressing disease or control antigens in the presence or absence of patient effector cells, and is usually expressed as the %-specific lysis. Percent specific cytotoxicity is calculated by (specific release−spontaneous release)÷(maximum release−spontaneous release) and may be 20%-85% for a positive assay. Percent specific cytotoxicity is usually determined at several ratios of effector (CTL) to target cells (E:T). Additionally, the standard lytic assay is qualitative and must rely on a limiting dilution analysis (LDA) for quantitative results, and the LDA frequently underestimates the true level of CTL response. Although CTL can each kill many targets in vivo, in vitro this assay requires numbers of CTL equal to or greater than the number of targets for detectable killing. In one embodiment CTL responses are measured by the chromium release assay, monitoring the ability of T cells (Effector cells) to lyse radiolabelled HLA matched "target cells" that express the appropriate antigen-MHC complex.

Another method of measuring cytotoxicity, is the ELISPOT assay where the CD8+ CTL response, which can be assessed by measuring IFN-γ production by antigen-specific effector cells, is quantitated by measuring the number of Spot Forming Units (SFU) under a stereomicroscope (Rininsland et al., (2000) J Immunol Methods: 240(1-2):143-155.). In this assay, antigen-presenting cells (APC) are immobilized on the plastic surface of a micro titer well, and effector T cells are added at various effector:target ratios. Antigen presenting cells are preferably B cells or dendritic cells. More preferably the B cells or dendritic cells are from the subject wherein the TCRs expressed on the effector T cells were identified. The binding of APC's by antigen-specific effector cells triggers the production of cytokines including IFN-γ by the effector cells (Murali-Krishna et al., (1998) Adv Exp Med Biol.: 452:123-142). In one embodiment subject specific T cells are used in the ELISPOT assay.

Another method for quantifying the number of circulating antigen-specific CD8+ T cells is the tetramer assay that is used to measure CTL activity. In this assay, a specific epitope is bound to synthetic tetrameric forms of fluorescent labeled MHC Class I molecules. Since CD8+ T cells recognize antigen in the form of short peptides bound to Class I molecules, cells with the appropriate T cell receptor will bind to the labeled tetramers and can be quantified by flow cytometry. Although this method is less time-consuming than the ELISPOT assay, the tetramer assay measures only binding, not function. Not all cells that bind a particular antigen necessarily become activated.

In another embodiment cytolytic activity is determined by FACS. In one embodiment target cells are incubated with T cells. The target cells may be incubated with agents that stain activated apoptotic proteins such as caspases. The target cells may also be incubated with stains that indicate cell death, such as 7-AAD. Analysis of the cells by FACS indicates the level of cytolytic activity. The present invention can use any commercially available assay to detect cytolytic activity. FACS based assays for cytolytic activity are well known in the art and have been described previously (Lee-MacAry et al., (2001). J. Immunology. Met 252, 83-92; Gogoy-Ramirez et al., (2000). Journal of Immunology. Met 239, 35-44; Goldberg et al., (1999). Journal of Immunology. Methods 224, 1; Hatam et al., (1994). Cytometry 16, 59; De Clerck et al., (1994) J. Immunol. Meth. 172, 115; Bronner-Fraser, J. Cell Biol. 101, 610 (1985); Rabinovitch et al., (1986) J. Immunol. 136, 2769 (1986); Su, X., J. (1996) Immunol. 156, 156, 4198).

In another embodiment TCRs will be expressed on any of the T cells described herein and further incorporating a reporter gene. The reporter gene may be activated upon binding of the TCR to antigen. The reporter gene may express a fluorescent protein. Transcription of the reporter gene may be activated upon activation of a signalling cascade initiated by TCR binding to antigen. In a preferred embodiment the reporter gene is controlled by the nuclear factor of activated T cells (NFAT) (Szymczak et al., Nat Biotechnol. 2004; 22:589-594; Jones et al., Hum Gene Ther. 2009; 20:630-640.). In one embodiment fluorescence indicates TCR binding to an antigen. In another embodiment T cells are analysed by FACS after activation of the reporter.

Treatment of Patients with Personalized TCR Therapy

In a fourth aspect a subject in need thereof is treated based on the TCR repertoire of the subject. In one embodiment a neoantigen vaccine is selected based on the TCRs. In another embodiment a subject is treated with T cells expressing subject specific TCRs. The ability to effectively profile the TCR repertoire and to link individual T cells containing specific TCRs to an epitope thereby provides an essential approach to the identification of therapy-critical T cell targets. Once identified, such TCRs provide molecular reagents to prove the functionality of epitope-specific T cells against tumor targets and to follow highly specific T cells longitudinally in a patient and also enable adoptive therapy with T cells engineered to contain these epitope-specific TCRs.

In one embodiment a neoantigen immunogenic composition or vaccine is selected based on the TCRs identified. In one embodiment identification of the T cell repertoire and testing in functional assays as described herein is used to determine an immunogenic composition or vaccine to be administered to a subject in need thereof. In one embodiment the immunogenic composition is a neoantigen vaccine. In another embodiment the neoantigen vaccine may comprise subject specific neoantigen peptides. In one embodiment neoantigen peptides to be included in a neoantigen vaccine are selected based on the quantification of subject specific TCRs that bind to the neoantigens. In one embodiment the neoantigen peptides are selected based on the binding affinity of the peptide to a TCR. In one embodiment the selecting is based on a combination of both the quantity and the binding affinity. Not being bound by a theory, a TCR that binds strongly to a neoantigen in a functional assay, but that is not highly represented in the TCR repertoire is a good candidate for a neoantigen vaccine because T cells expressing the TCR would be advantageously amplified.

Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).In one embodiment TCRs are selected for administering to a subject based on binding to neoantigens as described herein. In one embodiment T cells are expanded using the methods described herein. Expanded T cells that express tumor specific TCRs may be administered back to a subject. In another embodiment PBMCs are transduced or transfected with polynucleotides for expression of TCRs and administered to a subject. T cells expressing TCRs specific to neoantigens are expanded and administered back to a subject. In one embodiment T cells that express TCRs that result in cytolytic activity when incubated with autologous tumor tissue are expanded and administered to a subject. In one embodiment T cells that express TCRs that when used in the functional assays described herein result in binding to neoantigens are expanded and administered to a subject. In another embodiment TCRs that have been determined to bind to subject specific neoantigens are expressed in T cells and administered to a subject.

Aspects of the invention involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; and, Restifo et al., 2015, Adoptive immunotherapy for cancer: harnessing the T cell response. Nat. Rev. Immunol. 12(4): 269-281). Various strategies may for example be employed to genetically modify T cells by altering the specificity of the T cell receptor (TCR) for example by introducing new TCR $\alpha$ and $\beta$ chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, or CD28 signaling domains (for example scFv-CD28-4-1BB-CD3g or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to threat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoreponsive cell, thereby treating or preventing the disease (such as a neoplasia, a pathogen infection, an autoimmune disorder, or an allogeneic transplant reaction). Dosing in CAR T cell therapies may for example involve administration of from $10^6$ to $10^9$ cells/kg, with or without a course of lymphodepletion, for example with cyclophosphamide.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation. In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6): 1107-15 (2010)). In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853).

Cell therapy methods often involve the ex-vivo activation and expansion of T-cells. In one embodiment T cells are activated before administering them to a subject in need thereof. Activation or stimulation methods have been described herein and is preferably required before T cells are administered to a subject in need thereof. Examples of these type of treatments include the use tumor infiltrating lymphocyte (TIL) cells (see U.S. Pat. No. 5,126,132), cytotoxic T-cells (see U.S. Pat. Nos. 6,255,073; and 5,846,827), expanded tumor draining lymph node cells (see U.S. Pat. No. 6,251,385), and various other lymphocyte preparations (see U.S. Pat. Nos. 6,194,207; 5,443,983; 6,040,177; and 5,766,920). These patents are herein incorporated by reference in their entirety.

For maximum effectiveness of T-cells in cell therapy protocols, the ex vivo activated T-cell population should be in a state that can maximally orchestrate an immune response to cancer, infectious diseases, or other disease states. For an effective T-cell response, the T-cells first must be activated. For activation, at least two signals are required to be delivered to the T-cells. The first signal is normally delivered through the T-cell receptor (TCR) on the T-cell surface. The TCR first signal is normally triggered upon interaction of the TCR with peptide antigens expressed in conjunction with an MHC complex on the surface of an antigen-presenting cell (APC). The second signal is normally delivered through co-stimulatory receptors on the surface of T-cells. Co-stimulatory receptors are generally triggered by corresponding ligands or cytokines expressed on the surface of APCs.

Due to the difficulty in maintaining large numbers of natural APC in cultures of T-cells being prepared for use in cell therapy protocols, alternative methods have been sought for ex-vivo activation of T-cells. One method is to by-pass the need for the peptide-MHC complex on natural APCs by instead stimulating the TCR (first signal) with polyclonal activators, such as immobilized or cross-linked anti-CD3 or anti-CD2 monoclonal antibodies (mAbs) or superantigens. The most investigated co-stimulatory agent (second signal) used in conjunction with anti-CD3 or anti-CD2 mAbs has been the use of immobilized or soluble anti-CD28 mAbs. The combination of anti-CD3 mAb (first signal) and anti-CD28 mAb (second signal) immobilized on a solid support such as paramagnetic beads (see U.S. Pat. No. 6,352,694, herein incorporated by reference in its entirety) has been used to substitute for natural APCs in inducing ex-vivo T-cell activation in cell therapy protocols (Levine, Bernstein et al., 1997 Journal of Immunology:159:5921-5930; Garlie, LeFever et al., 1999 J Immunother. July; 22(4):336-45; Shibuya, Wei et al., 2000 Arch Otolaryngol Head Neck Surg. 126(4):473-9).

It is contemplated that the T cells obtained by the inventive methods can be used in methods of treating or preventing cancer. In this regard, the invention provides a method of treating or preventing cancer in a subject, comprising administering to the subject the pharmaceutical compositions or cell populations obtained by any of the inventive methods described herein in an amount effective to treat or prevent cancer in the subject. Another embodiment of the invention provides a method of treating or preventing cancer in a subject, comprising administering a cell population enriched for tumor-reactive T cells to a subject by any of the inventive methods described herein in an amount effective to treat or prevent cancer in the mammal.

For purposes of the inventive methods, wherein populations of cells are administered, the cells can be cells that are allogeneic or autologous to the subject. In one embodiment the T cells are autologous and the TCRs are allogeneic. In one embodiment the TCRs are autologous and the T cells are allogeneic. In one embodiment the TCRs are autologous and the T cells are autologous. Preferably, the cells are autologous to the subject.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of cancer in a mammal.

Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

With respect to the inventive methods, the cancer can be any cancer, including any of sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head-neck cancer, acute lymphocytic cancer, acute myeloid leukemia, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer (e.g., colon carcinoma), esophageal cancer, cervical cancer, gastrointestinal cancer (e.g., gastrointestinal carcinoid tumor), hypopharynx cancer, larynx cancer, liver cancer, lung cancer, malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, renal cancer, small intestine cancer, soft tissue cancer, stomach cancer, testicular cancer, thyroid cancer, ureter cancer, and urinary bladder cancer.

The method may comprise combining the cell population of tumor-reactive T cells expressing subject specific TCRs with a pharmaceutically acceptable carrier to obtain a pharmaceutical composition comprising a personalized cell population of tumor-reactive T cells. Preferably, the carrier is a pharmaceutically acceptable carrier. With respect to pharmaceutical compositions, the carrier can be any of those conventionally used for the administration of cells. Such pharmaceutically acceptable carriers are well-known to those skilled in the art and are readily available to the public. It is preferred that the pharmaceutically acceptable carrier be one which has no detrimental side effects or toxicity under the conditions of use. A suitable pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

The T cells can be administered by any suitable route as known in the art. Preferably, the T cells are administered as an intra-arterial or intravenous infusion, which preferably lasts approximately 30-60 min. Other examples of routes of administration include intraperitoneal, intrathecal and intralymphatic. T cells may also be administered by injection. T cells may be introduced at the site of the tumor.

For purposes of the invention, the dose, e.g., number of cells in the inventive cell population expressing subject specific TCRs, administered should be sufficient to effect, e.g., a therapeutic or prophylactic response, in the subject over a reasonable time frame. For example, the number of cells should be sufficient to bind to a cancer antigen, or detect, treat or prevent cancer in a period of from about 2 hours or longer, e.g., 12 to 24 or more hours, from the time of administration. In certain embodiments, the time period could be even longer. The number of cells will be determined by, e.g., the efficacy of the particular cells and the condition of the subject (e.g., human), as well as the body weight of the subject (e.g., human) to be treated.

Many assays for determining an administered number of cells from the inventive cell population expressing subject specific TCRs are known in the art. For purposes of the invention, an assay, which comprises comparing the extent to which target cells are lysed or one or more cytokines such as, e.g., IFN-γ and IL-2 are secreted upon administration of a given number of such cells to a subject, could be used to determine a starting number to be administered to a mammal. The extent to which target cells are lysed, or cytokines such as, e.g., IFN-γ and IL-2 are secreted, upon administration of a certain number of cells, can be assayed by methods known in the art. Secretion of cytokines such as, e.g., IL-2, may also provide an indication of the quality (e.g., phenotype and/or effectiveness) of a cell preparation.

The number of the cells administered from the inventive cell population expressing subject specific TCRs may also be determined by the existence, nature and extent of any adverse side effects that might accompany the administration of a particular cell population.

Typically, the attending physician will decide the number of the cells with which to treat each individual patient, taking into consideration a variety of factors, such as age, body weight, general health, diet, sex, route of administration, and the severity of the condition being treated. By way of example and not intending to limit the invention, the number of cells can be about $10 \times 10^6$ to about $10 \times 10^{10}$ cells per infusion, about $10 \times 10^9$ cells to about $10 \times 10^{10}$ cells per infusion, or $10 \times 10^7$ to about $10 \times 10^9$ cells per infusion. The cell populations obtained by the inventive methods may, advantageously, make it possible to effectively treat or prevent cancer. Likewise, any suitable dose of T cells can be administered. Preferably, from about $2.3 \times 10^{10}$ T cells to about $13.7 \times 10^{10}$ T cells are administered, with an average of around $7.8 \times 10^{10}$ T cells, particularly if the cancer is melanoma. With respect to the alternative method, preferably, from about $1.2 \times 10^{10}$ to about $4.3 \times 10^{10}$ T cells are administered.

An embodiment of the invention further comprises lymphodepleting the subject prior to administering any of the T cells obtained by any of the inventive methods described herein. Examples of lymphodepletion include, but may not be limited to, nonmyeloablative lymphodepleting chemotherapy, myeloablative lymphodepleting chemotherapy, total body irradiation, etc.

In another embodiment, the T cell therapy described herein provides selecting the appropriate point to administer the therapy in relation to and within the standard of care for the cancer being treated for a subject in need thereof. The therapy described herein can be effectively administered even within the standard of care that includes surgery, radiation, or chemotherapy. The standards of care for the most common cancers can be found on the website of National Cancer Institute (http://www.cancer.gov/cancer-topics). The standard of care is the current treatment that is accepted by medical experts as a proper treatment for a certain type of disease and that is widely used by healthcare professionals. Standard of care is also called best practice, standard medical care, and standard therapy. Standards of Care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T cell therapy. The therapy described herein can be incorporated within the standard of care. The therapy described herein may also be administered where the standard of care has changed due to advances in medicine.

Incorporation of the T cell therapy described herein may depend on a treatment step in the standard of care that causes the immune system to be suppressed. Such treatment steps may include irradiation, high doses of alkylating agents and/or methotrexate, steroids such as glucosteroids, surgery, such as to remove the lymph nodes, imatinib mesylate, high doses of TNF, and taxanes (Zitvogel et al., 2008). The therapy may be administered before such steps or may be administered after.

In one embodiment the T cell therapy may be administered after bone marrow transplants and peripheral blood stem cell transplantation. Bone marrow transplantation and peripheral blood stem cell transplantation are procedures that restore stem cells that were destroyed by high doses of chemotherapy and/or radiation therapy. After being treated with high-dose anticancer drugs and/or radiation, the patient receives harvested stem cells, which travel to the bone marrow and begin to produce new blood cells. A "mini-transplant" uses lower, less toxic doses of chemotherapy and/or radiation to prepare the patient for transplant. A "tandem transplant" involves two sequential courses of high-dose chemotherapy and stem cell transplant. In autologous transplants, patients receive their own stem cells. In syngeneic transplants, patients receive stem cells from their identical twin. In allogeneic transplants, patients receive stem cells from their brother, sister, or parent. A person who is not related to the patient (an unrelated donor) also may be used. In some types of leukemia, the graft-versus-tumor (GVT) effect that occurs after allogeneic BMT and PBSCT is crucial to the effectiveness of the treatment. GVT occurs when white blood cells from the donor (the graft) identify the cancer cells that remain in the patient's body after the chemotherapy and/or radiation therapy (the tumor) as foreign and attack them. Immunotherapy with the T cell therapy described herein can take advantage of this by introducing T cells expressing subject tumor specific TCRs after a transplant.

In another embodiment T cells expressing subject specific TCRs are administered to a subject in need thereof that has not received a treatment resulting in immunoablation. In one embodiment T cells expressing subject specific TCRs are administered after surgery to remove a tumor. Not being bound by a theory, for tumors that are localized and where the standard of care is surgical removal followed by adjuvant therapy to remove any tumor cells that are present as micrometastases, introducing T cells expressing subject specific TCRs can facilitate removal of any remaining tumor cells.

In another embodiment TCR expressing cells that were transplanted into a subject are monitored to quantify each T cell clone at various time points following transplant, whole tumor cell vaccination, or immunization with a neoantigen immunogenic composition. Monitoring may be by PCR of nucleic acids isolated from subjects during treatment. The PCR may use TCR specific primers. The TCR primers may hybridize to constant regions of each TCR chain and a unique region specific to a particular TCR chain.

In another embodiment identified subject specific TCRs are administered by a gene therapy method. TCRs may be cloned and expressed using a vector. The vector can be introduced into a subject. The vector may be a viral vector. The vector preferably targets T cells. The T cells preferably express the TCR. More preferably the T cell is activated. In a preferred embodiment the vector allows expression of the TCR and activation of the target T cell.

In one embodiment a lentivirus is used. Preferably the lentivirus is administered with about 10 μl of recombinant lentivirus having a titer of $1 \times 10^9$ transducing units (TU)/ml by an intrathecal catheter. These sort of dosages can be adapted or extrapolated to use of a retroviral or lentiviral vector in the present invention.

In an embodiment herein the delivery is via an adenovirus, which may be at a single dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10$-$1 \times 10^{11}$ particles or about $1 \times 10^8$-$1 \times 10^{12}$ particles), and most preferably at least about $1 \times 10^9$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{50}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. In a preferred embodiment, AAV is used with a titer of about $2 \times 10^{13}$ viral genomes/milliliter, and each of the striatal hemispheres of a mouse receives one 500 nanoliter injection. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

The main advantage of the methods described herein are that TCRs that are subject specific and tumor specific are identified and these TCRs are matched to subject specific neoantigens. The identification allows the formulation of a subject specific immunotherapy that can be coordinated with an immunotherapy that includes a neoantigen immunogenic composition or can help guide the proper neoantigen immunogenic composition.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Figure 2:
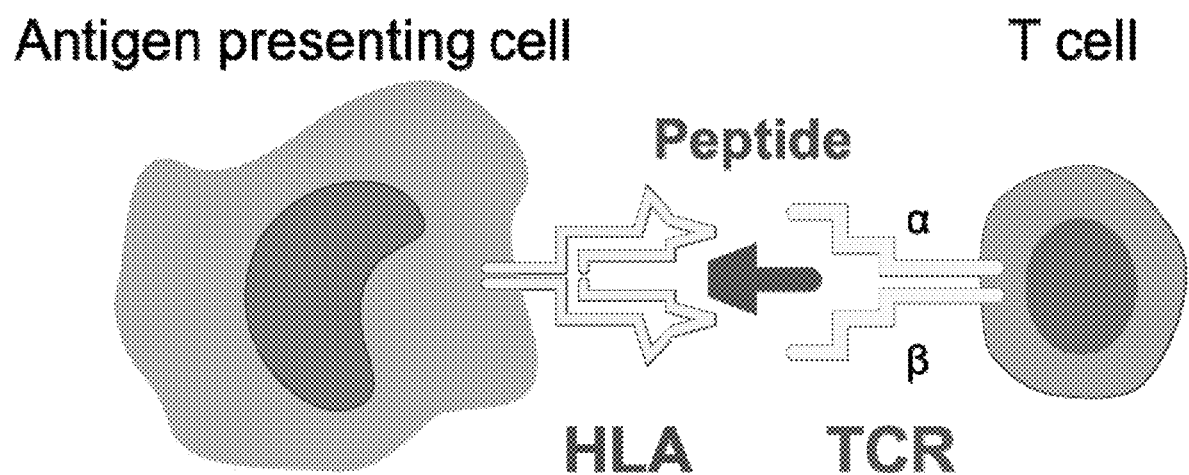
FIG. 2 illustrates that a T cell receptor (TCR) recognizes a specific peptide presented on HLA.

Combined TCRα/TCRβ Chains within Single Cells are Responsible for T Cell Specificity The highly polymorphic TCR is generated by joining of non-contiguous gene segments (Vβ,Dβ,Jβ for TCRβ and Vα, Jα for TCRα) together with deletion/insertion of random sequences to form the CDR3 regions. Although there is a theoretical possibility of forming as many as $5 \times 10^{11}$ unique TCRβ chains, the actual number of unique TCRβ genes found in humans is closer to 0.1% of this estimate (Brahmer et al., N Engl J Med. 2012; 366:2455-2465). The recognition of MHC-bound peptide by the combined TCRβ and TCRα proteins occurs primarily by the CDR3 regions (FIGS. 1 and 2; Topalian et al., N Engl J Med. 2012; 366:2443-2454; and Wolchok et al., N Engl J Med. 2013; 369:122-133). During thymic education (positive/negative selection) and antigen exposure (e.g. pathogens), specific T cell clones are selected and alter the actual repertoire. Since antigen-specific T cells with high-avidity TCRs (e.g. against tumor neoantigens) are rare relative to the large repertoire of T cells, it remains critical to develop a method to comprehensively characterize the TCR repertoire and thus enable discovery of TCRs and their target tumors antigens.

Example 2

Isolation and Sequencing of T Cell Receptors from T Cells Associated with Tumor

Figure 3:
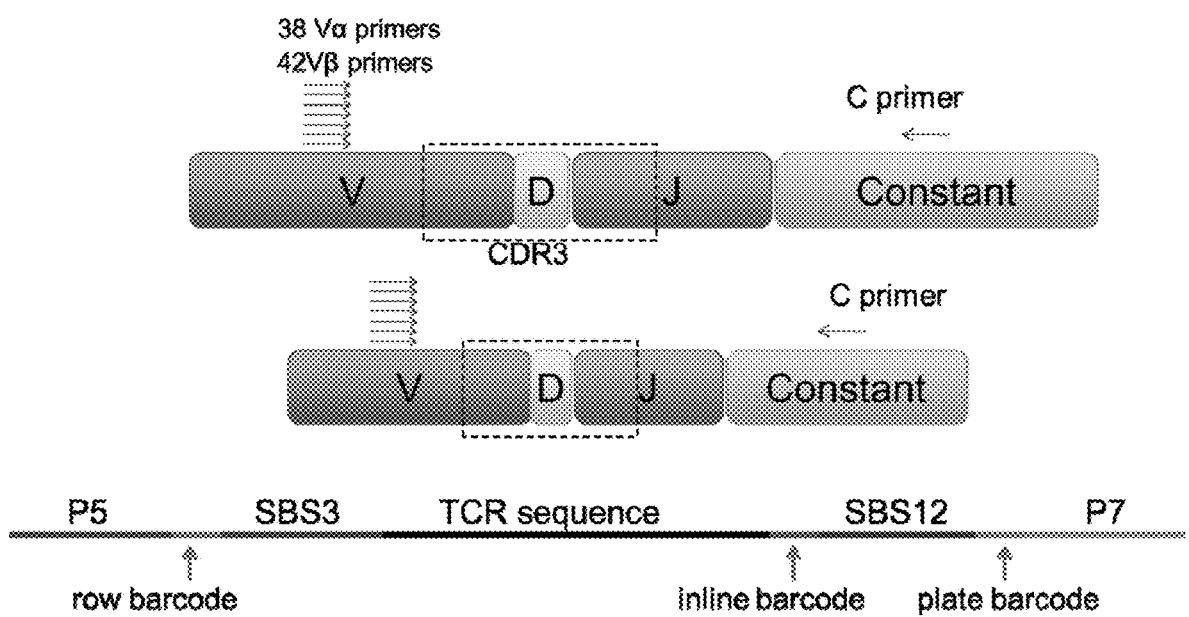
FIG. 3 illustrates the amplification of the CDR3 region and addition of sequencing adaptors by RT-PCR and PCR. Sequences P5 and P7 are configured to bind to a flow cell and sequences SBS3 and SBS12 are configured to bind sequencing primers.

Applicants generate RNA-sequencing libraries from single T cells from a patient sample. Applicants can dissociate cells and generate single cell RNA-sequencing libraries from all T cells in a biopsy. While the synthesis of genome-wide RNA-seq libraries uses oligo-dT primers, this may not always amplify the TCR genes. Since Applicants need to guarantee amplification and sequencing of the TCR genes, and are not concerned with quantifying TCR transcript numbers, Applicants add to the reaction mixture a pool of 38 Vα and 36 Vβ primers to amplify the 45 and 48 TCRα and TCRβ variable regions, respectively, together with primers in the constant region of TCRα and TCRβ (FIG. 3). Amplification productions are sequenced in parallel and deconvoluted based on barcodes that tag transcripts from each cell. Applicants analyze the resulting sequences to identify the Vα and Vβ regions, including the CDR3, of each cell. If Applicants sequence ~1000 T cells per biopsy, Applicants expect to identify clones with frequencies of 0.3% at 90% power (and lower when isolating and sequencing higher numbers of T cells).

Figure 4:
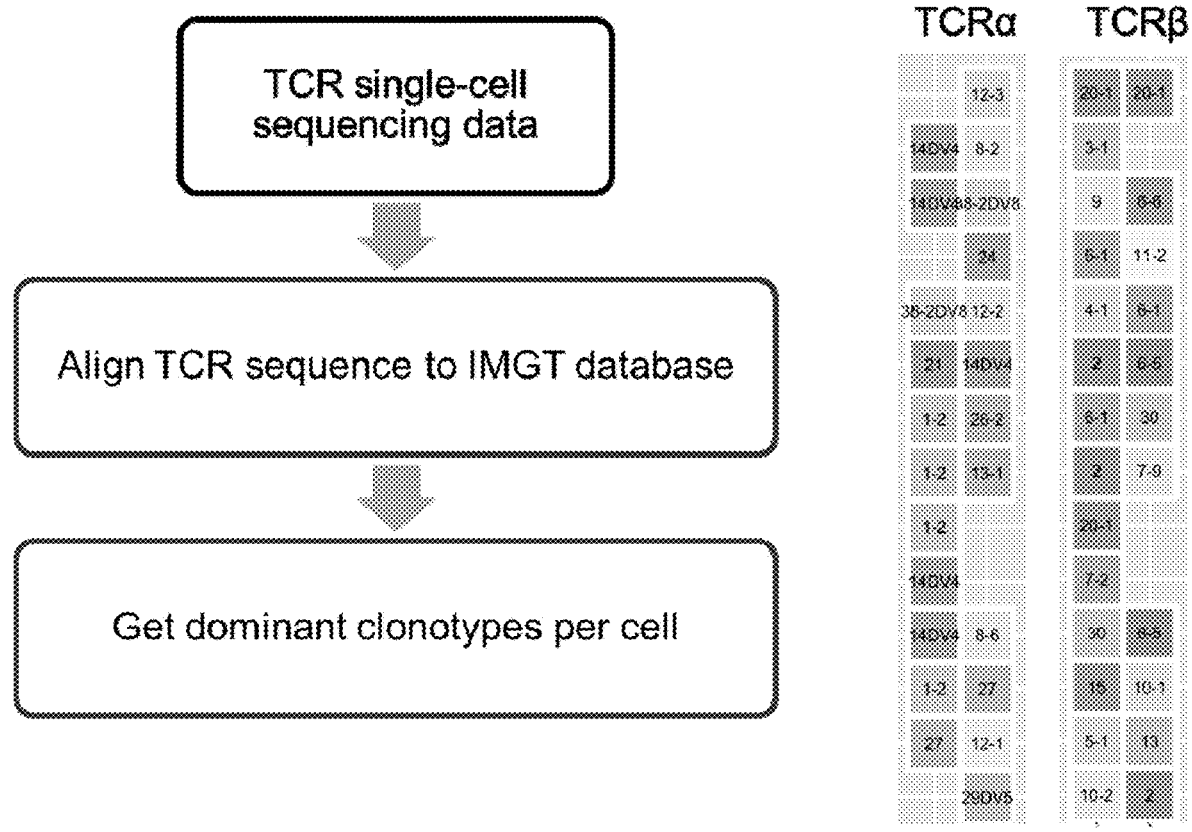
FIG. 4 illustrates TCRαβ sequencing data analysis.

Single cells are sequenced by any method described herein. The TCR single cell sequencing data is aligned to a database to get dominant clonotypes per cell (FIG. 4).

Applicants use an approach for amplifying and sequencing paired CDR3-Vα and -Vβ chain sequences from single T cells using a 'multiprimer approach': a modified version of a recently described method, in which 36 T cell receptor TCRα V primers and 36 TCRβ V primers were used to perform multiplexed amplification of TCR gene sequences (FIG. 3; Han et. al., Nature Biotechnology, Vol 32:7, 2014). Primers of reaction 1 and 2 for TRAV and TRBV are shown (Table 1 and Table 2).

TABLE 1

| oligo name | reaction1 | SEQ ID NO: | reaction2 | SEQ ID NO: |
| --- | --- | --- | --- | --- |
| TRAV1 | CTGCACGTACCAGACATCTGGGTT | 2 | AGGTCGTTTTTCTTCATTCCTTAGTC | 40 |
| TRAV2 | GGCTCAAAGCCTTCTCAGCAGG | 3 | ACGATACAACATGACCTATGAACGG | 41 |
| TRAV3 | GGATAACCTGGTTAAAGGCAGCTA | 4 | CTTTGAAGCTGAATTTAACAAGAGCC | 42 |
| TRAV4 | GGATACAAGACAAAAGTTACAAACGA | 5 | CTCCCTGTTTATCCCTGCCGAC | 43 |
| TRAV5 | GCTGACGTATATTTTTCAAATATGGA | 6 | AAACAAGACCAAAGACTCACTGTTC | 44 |
| TRAV6 | GGAAGAGGCCCTGTTTTCTTGCT | 7 | AAGACTGAAGGTCACCTTTGATACC | 45 |
| TRAV7 | GCTGGATATGAGAAGCAGAAAGGA | 8 | ACTAAATGCTACATTACTGAAGAATGG | 46 |
| TRAV8 | AGGACTCCAGCTTCTCCTGAAGTA | 9 | GCATCAACGGTTTTGAGGCTGAATTTAA | 47 |

TABLE 1-continued

| oligo name | reaction1 | SEQ ID NO: | reaction2 | SEQ ID NO: |
|---|---|---|---|---|
| TRAV9 | GTATGTCCAATATCCTGGAGAAGGT | 10 | GAAACCACTTCTTTCCACTTGGAGAA | 48 |
| TRAV10 | CAGTGAGAACACAAAGTCGAACGG | 11 | TACAGCAACTCTGGATGCAGACAC | 49 |
| TRAV12-1 | CCTAAGTTGCTGATGTCCGTATAC | 12 | GAAGATGGAAGGTTTACAGCACA | 50 |
| TRAV12-2 | GGGAAAAGCCCTGAGTTGATAATGT | 13 | GAAGATGGAAGGTTTACAGCACA | 50 |
| TRAV12-3 | GCTGATGTACACATACTCCAGTGG | 14 | GAAGATGGAAGGTTTACAGCACA | 50 |
| TRAV13-1 | CCCTTGGTATAAGCAAGAACTTGG | 15 | GACATTCGTTCAAATGTGGGCGAA | 51 |
| TRAV13-2 | CCTCAATTCATTATAGACATTCGTTC | 16 | GGCAAGGCCAAAGAGTCACCGT | 52 |
| TRAV14 | GCAAAATGCAACAGAAGGTCGCTA | 17 | TCCAGAAGGCAAGAAAATCCGCCA | 53 |
| TRAV16 | TAGAGAGAGCATCAAAGGCTTCAC | 18 | GCTGACCTTAACAAAGGCGAGACA | 54 |
| TRAV17 | CGTTCAAATGAAAGAGAGAAACACAG | 19 | TTAAGAGTCACGCTTGACACTTCCA | 55 |
| TRAV18 | CCTGAAAAGTTCAGAAAACCAGGAG | 20 | GCAGAGGTTTTCAGGCCAGTCCT | 56 |
| TRAV19 | GGTCGGTATTCTTGGAACTTCCAG | 21 | TCCACCAGTTCCTTCAACTTCACC | 57 |
| TRAV20 | GCTGGGGAAGAAAAGGAGAAAGAAA | 22 | GCCACATTAACAAAGAAGGAAAGCT | 58 |
| TRAV21 | GTCAGAGAGCAAACAAGTGGAA | 23 | GCCTCGCTGGATAAATCATCAGGA | 59 |
| TRAV22 | GGACAAAACAGAATGGAAGATTAAGC | 24 | ACGACTGTCGCTACGGAACGCTA | 60 |
| TRAV23 | CCAGATGTGAGTGAAAAGAAAGAAG | 25 | CACAATCTCCTTCAATAAAGTGCCA | 61 |
| TRAV24 | GACTTTAAATGGGGATGAAAAGAAGA | 26 | ACGAATAAGTGCCACTCTTAATACCA | 62 |
| TRAV25 | GGAGAAGTGAAGAAGCAGAAAAGAC | 27 | GTTTGGAGAAGCAAAAAGAACAGCT | 63 |
| TRAV26-1 | CCAATGAAATGGCCTCTCTGATCA | 28 | CAGAAGACAGAAAGTCCAGCACCT | 64 |
| TRAV26-2 | GCAATGTGAACAACAGAATGGCT | 29 | ATCGCTGAAGACAGAAAGTCCAGT | 65 |
| TRAV27 | GGTGGAGAAGTGAAGAAGCTGAAG | 30 | ACTAACCTTTCAGTTGGTGATGCAA | 66 |
| TRAV29 | GGATAAAAATGAAGATGGAAGATTCAC | 31 | CTTAAACAAAAGTGCCAAGCACCTC | 67 |
| TRAV30 | CCTGATGATATTACTGAAGGGTGGA | 32 | AATATCTGCTTCATTTAATGAAAAAAGC | 68 |
| TRAV34 | GGTGGGGAAGAGAAAAGTCATGAA | 33 | CCAAGTTGGATGAGAAAAAGCAGCA | 69 |
| TRAV35 | GGTGAATTGACCTCAAATGGAAGAC | 34 | CTCAGTTTGGTATAACCAGAAAGGA | 70 |
| TRAV36 | GCTAACTTCAAGTGGAATTGAAAAGA | 35 | GGAAGACTAAGTAGCATATTAGATAAG | 71 |
| TRAV38 | GAAGCTTATAAGCAACAGAATGCAAC | 36 | CTGTGAACTTCCAGAAAGCAGCCA | 72 |
| TRAV39 | GGAGCAGTGAAGCAGGAGGGAC | 37 | CCTCACTTGATACCAAAGCCCGT | 73 |
| TRAV40 | GAGAGACAATGGAAAACAGCAAAAAC | 38 | AGGCGGAAATATTAAAGACAAAAACTC | 74 |
| TRAV41 | GCTGAGCTCAGGGAAGAAGAAGC | 39 | GATTAATTGCCACAATAAACATACAGG | 75 |

TABLE 2

| oligo name | reaction1 | SEQ ID NO: | reaction2 | SEQ ID NO: |
|---|---|---|---|---|
| TRBV2 | CTGAAATATTCGATGATCAATTCTCAG | 76 | GCCTGATGGATCAAATTTCACTCTG | 112 |
| TRBV3-1 | TCATTATAAATGAAACAGTTCCAAATCG | 77 | TCTCACCTAAATCTCCAGACAAAGCT | 113 |
| TRBV4 | AGTGTGCCAAGTCGCTTCTCAC | 78 | CCTGAATGCCCCAACAGCTCTC | 114 |
| TRBV5-1 | GAGACACAGAGAAACAAAGGAAACTTC | 79 | CGATTCTCAGGGCGCCAGTTCTCT | 115 |
| TRBV5-4 | CAGAGGAAACTYCCCTCCTAGATT | 80 | CTCTGAGCTGAATGTGAACGCCT | 116 |

TABLE 2-continued

| oligo name | reaction1 | SEQ ID NO: | reaction2 | SEQ ID NO: |
|---|---|---|---|---|
| TRBV5-8 | CAGAGGAAACTYCCCTCCTAGATT | 80 | CTCTGAGCTGAATGTGAACGCCT | 116 |
| TRBV6-1 | GGTACCACTGACAAAGGAGAAGTCC | 81 | TGGCTACAATGTCTCCAGATTAAACAA | 117 |
| TRBV6-2 | GAGGGTACAACTGCCAAAGGAGAGGT | 82 | CCCTGATGGCTACAATGTCTCCAGA | 118 |
| TRBV6-3 | GAGGGTACAACTGCCAAAGGAGAGGT | 82 | CCCTGATGGCTACAATGTCTCCAGA | 118 |
| TRBV6-4 | GGCAAAGGAGAAGTCCCTGATGGTT | 83 | GTGTCTCCAGAGCAAACACAGATGATT | 119 |
| TRBV6-5 | AAGGAGAAGTCCCSAATGGCTACAA | 84 | GTCTCCAGATCAACCACAGAGGAT | 120 |
| TRBV6-6 | AAGGAGAAGTCCCSAATGGCTACAA | 84 | GTCCAGATCAACCACAGAGGAT | 120 |
| TRBV6-8 | CTGACAAAGAAGTCCCCAATGGCTAC | 85 | GTCTCTAGATTAAACACAGAGGATTTC | 121 |
| TRBV6-9 | CACTGACAAAGGAGAAGTCCCCGAT | 86 | GGCTACAATGTATCCAGATCAAACA | 122 |
| TRBV7-2 | AGACAAATCAGGGCTGCCCAGTGA | 87 | TCGCTTCTCTGCAGAGAGGACTGG | 123 |
| TRBV7-3 | GACTCAGGGCTGCCCAACGAT | 88 | CGGTTCTTTGCAGTCAGGCCTGA | 124 |
| TRBV7-4 | GGTTCTCTGCAGAGAGGCCTGAG | 89 | TCTCCACTCTGAMGATCCAGCGCA | 125 |
| TRBV7-6 | GGTTCTCTGCAGAGAGGCCTGAG | 89 | TCTCCACTCTGAMGATCCAGCGCA | 125 |
| TRBV7-7 | GGCTGCCCAGTGATCGGTTCTC | 90 | GCAGAGAGGCCTGAGGGATCCAT | 126 |
| TRBV7-8 | CCAGAATGAAGCTCAATCAGACAA | 91 | CCAGTGATCGCTTCTTTGCAGAAA | 127 |
| TRBV7-9 | GACTTACTTCCAGAATGAAGCTCAACT | 92 | CTGCAGAGAGGCCTAAGGGATCT | 128 |
| TRBV9 | GAGCAAAAGGAAACATTCTTGAACGATT | 93 | CTCCGCACAACAGTTCCCTGACTT | 129 |
| TRBV10-1 | GGCTRATCCATTACTCATATGGTGTT | 94 | CAGATGGCTAYAGTGTCTCTAGATCAAA | 130 |
| TRBV10-2 | GATAAAGGAGAAGTCCCCGATGGCT | 95 | GTTGTCTCCAGATCCAAGACAGAGAA | 131 |
| TRBV10-3 | GGCTRATCCATTACTCATATGGTGT | 94 | CAGATGGCTAYAGTGTCTCTAGTCAAA | 130 |
| TRBV11 | GATTCACAGTTGCCTAAGGATCGAT | 96 | GCAGAGAGGCTCAAAGGAGTAGACT | 132 |
| TRBV12-3 | GATTCAGGGATGCCCGAGGATCG | 97 | GCTAAGATGCCTAATGCATCATTCTC | 133 |
| TRBV12-4 | GATTCAGGGATGCCCGAGGATCG | 97 | GCTAAGATGCCTAATGCATCATTCTC | 133 |
| TRBV12-5 | GATTCGGGGATGCCGAAGGATCG | 98 | CTCAGCAGAGATGCCTGATGCAACT | 134 |
| TRBV13 | GCAGAGCGATAAAGGAAGCATCCCT | 99 | TCTCAGCTCAACAGTTCAGTGACTA | 135 |
| TRBV14 | TCCGGTATGCCCAACAATCGATTCT | 100 | GCTGAAAGGACTGGAGGGACGTAT | 136 |
| TRBV15 | GATTTTAACAATGAAGCAGACACCCCT | 101 | GATAACTTCCAATCCAGGAGGCCG | 137 |
| TRBV16 | GATGAAACAGGTATGCCCAAGGAAAG | 102 | GCTAAGTGCCTCCCAAATTCACCC | 138 |
| TRBV18 | TATCATAGATGAGTCAGGAATGCCAAAG | 103 | GGAACGATTTTCTGCTGAATTTCCCA | 139 |
| TRBV19 | GACTTTCAGAAAGGAGATATAGCTGAA | 104 | GGTACAGCGTCTCTCGGGAGAAGA | 140 |
| TRBV20-1 | CAAGGCCACATACGAGCAAGGCGTC | 105 | GGACAAGTTTCTCATCAACCATGCAA | 141 |
| TRBV24-1 | CAAAGATATAAACAAAGGAGAGATCTCT | 106 | TGGATACAGTGTCTCTCGACAGGC | 142 |
| TRBV25-1 | AGAGAAGGGAGATCTTTCCTCTGAGT | 107 | CAACAGTCTCCAGAATAAGGACGGA | 143 |
| TRBV27-1 | GACTGATAAGGGAGATGTTCCTGAAG | 108 | TACAAAGTCTCTCGAAAAGAGAAGAGGA | 144 |
| TRBV28 | GGCTGATCTATTTCTCATATGATGTTAA | 109 | GGGGTACAGTGTCTCTAGAGAGA | 145 |
| TRBV29 | GCCACATATGAGAGTGGATTTGTCATT | 110 | GTTTCCCATCAGCCGCCCAAACCTA | 146 |
| TRBV30 | GGTGCCCCAGAATCTCTCAGCCT | 111 | CAGACCCCAGGACCGGCAGTTCAT | 147 |

Example 3

Cloning of Full TCRα and TCRβ into Expression Vector

Figure 5:
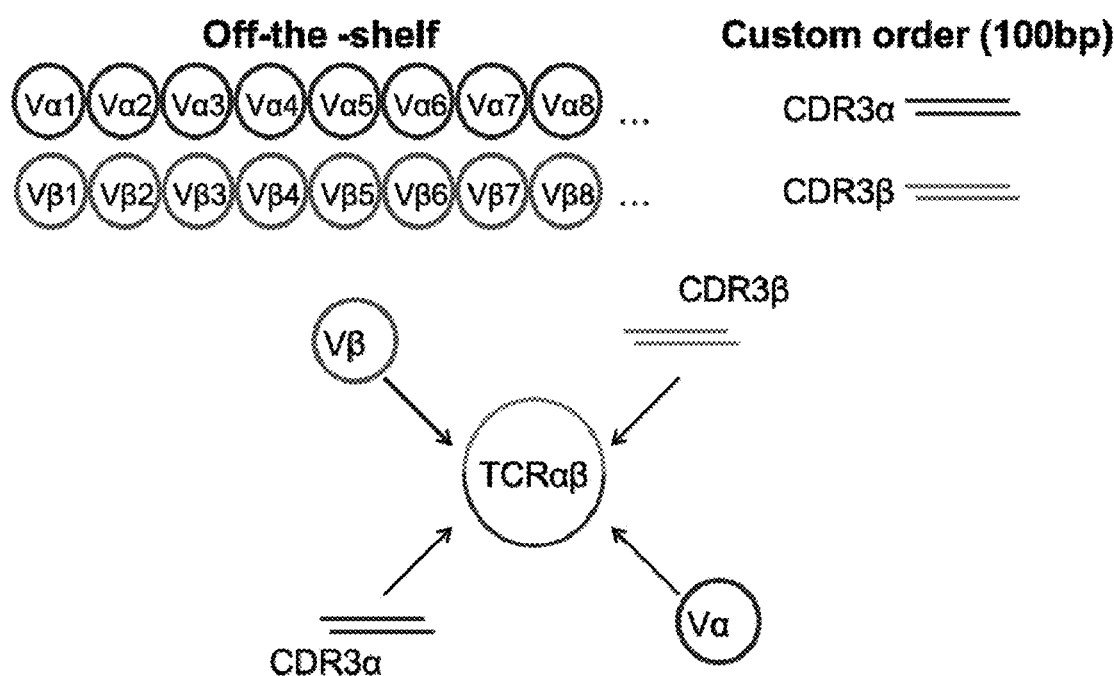
FIG. 5 illustrates generating TCRαβ constructs using a pre-assembled library of Vα and Vβ chains (SEQ ID NOS 259 and 260, respectively, in order of appearance).
Figure 6:
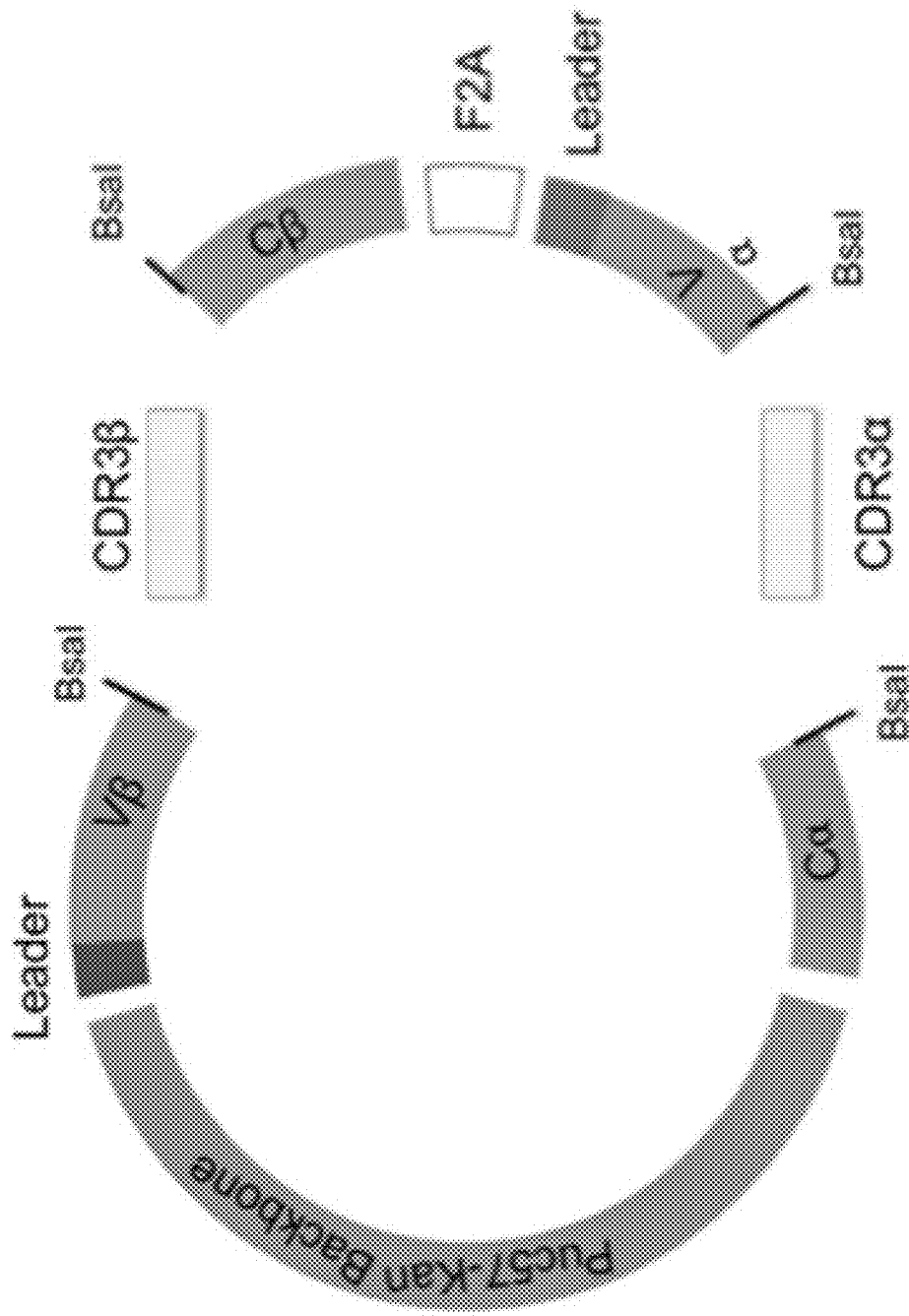
FIG. 6 illustrates a Golden Gate Assembly of TCRα/β vectors. A pre-made library of Vβ and Vα plasmids is linked to a synthesized CDR3.

In order to probe the functional activity of TCR sequences obtained from single cell sequencing, Applicants clone and express any pair of TCRs for functional analysis. Because TCRs are generated through recombination of pre-fixed modules, Applicants have created a fixed plasmid library in which each plasmid contains one of ~48 Vβ or ~45 Vα regions. In addition, each plasmid also contains the constant region of the other TCR, a leader sequence for surface expression, and BsaI restriction sites for seamless assembly into a complete TCR by Golden Gate assembly methods. In the assembled constructs a 2A-peptide sequence separates the TCRα and TCRβ chains, and is cleaved following translation to allow simultaneous expression of both genes at equal levels. Finally, the CDR3 sequences are synthesized as oligos for both TCRs and co-assembled (FIG. 5,6). As describe herein, Applicants have generated a synthetic library of all V, D, and J components, so that any TCR plasmid construct can be readily generated through multi-component DNA assembly (e.g., Golden Gate assembly) to include discovered CDR3 Vα and -Vβ sequences. The sequences for segments in the pre-made library are shown in the sequence listing. The pre-made library consists of the TRAV sequences inserted in "master pUC57-Kan Cb1-F2A" and "master pUC57-Kan Cb2-F2A", and the TRBV sequences inserted in "master pUC57-Kan Ca short" or "master pUC57-Kan Ca." TRBV sequences in "master pUC57-Kan Ca" are: TRBV5-6, 5-8, 6-8, 6-9, 7-4, 7-8, 10-2, 11-1, 11-2, 11-3, 16, 19, 29-1. The rest are ALL in "master pUC57-Kan Ca short"

Example 4

Expression of TCR in TCR-Deleted T Cells

Figure 7:
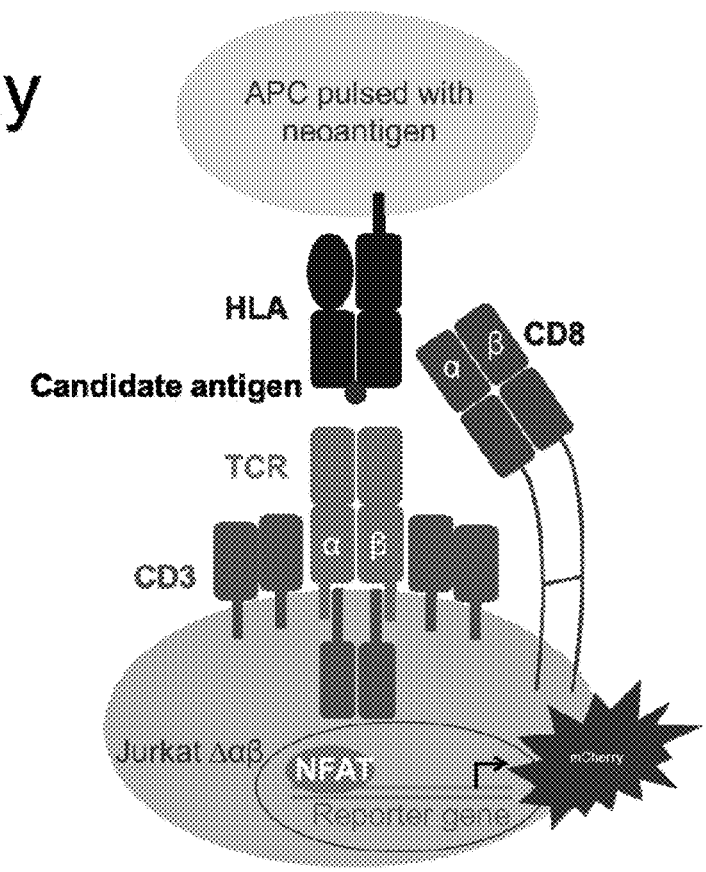
FIG. 7 illustrates a reporter assay for detecting a TCR specific for a neoantigen.

The plasmids containing both TCR sequences are transfected or infected (by producing lentiviruses) into a Jurkat ΔαβT cell line (FIG. 7). Expression is verified by antibody surface staining for TCR. The Jurkat cells also express CD8 and Thy1.1 under control of an NFAT promoter to respond to TCR stimulation. If the patient tumor expresses MHC Class II, Applicants also use Jurkat cells expressing CD4.

Example 5

A Library of Candidate Antigens to Screen for TCR Reactivity

Candidate sets of neoantigens are selected from 2 groups: (i) predicted neoantigens from each patient's tumor using our MHC Class I prediction pipeline and also MHC class II binding prediction if a tumor expresses MHC class II; (ii) neoantigen peptides identified on tumors by mass spectrometry, some of which may not be predicted by predictive algorithms. In addition, Applicants test native tumor antigen peptides observed by mass spectrometry, and published tumor antigen peptides corresponding to patient-specific HLAs. Applicants then test hundreds of neoantigens and other antigens for identifying cognate TCRs that bind these neoantigens bound to autologous HLA proteins. Applicants create a library of antigens as an expression library in lentiviral vectors, and infect the library into immortalized B cells generated from the blood of the same patient (for candidate class II antigens, Applicants also insert the antigens into a separate lentiviral vector for antigen fusion with ATG8/LC3 to enhancer antigen trafficking to the MHC Class II compartment Schmid, et al., Immunity. 2007 January; 26(1):79-92. Epub 2006 Dec. 21).

Example 6

Screening TCRs for Reactivity Against Neoantigens

Applicants screen for TCR recognition of tumor antigens using the assembled library of TCR-expressing T cells and a library of antigen-expressing B cells. First, Applicants incubate all transgenic T cells with B cells expressing each of the neoantigens in separate wells and sort out reactive T cells from positive wells using the TCR-induced molecules, such as CD83 or CD69 on the surface of cells, or by a surface of fluorescent reporter downstream of NFTA binding sites (that is activated by TCR stimulation). Applicants focus on CD8 T cells, but add CD4 T cells if MHC Class II is expressed on tumor cells. Second, Applicants then incubate reactive T cells with tumor cells to determine if T cells recognize antigen endogenously presented by tumor cells.

Example 7

Tracking Tumor-Specific TCRs in the Blood

Using the subset of TCRs that detect tumors, Applicants use bulk TCR sequencing of longitudinal blood samples to monitor anti-tumor immunity. This allows for a correlation of changes in tumor-reactive clones over the short and long term with tumor growth and spread.

Example 8

Proof of Concept with Known TCR Sequences

Figure 8:
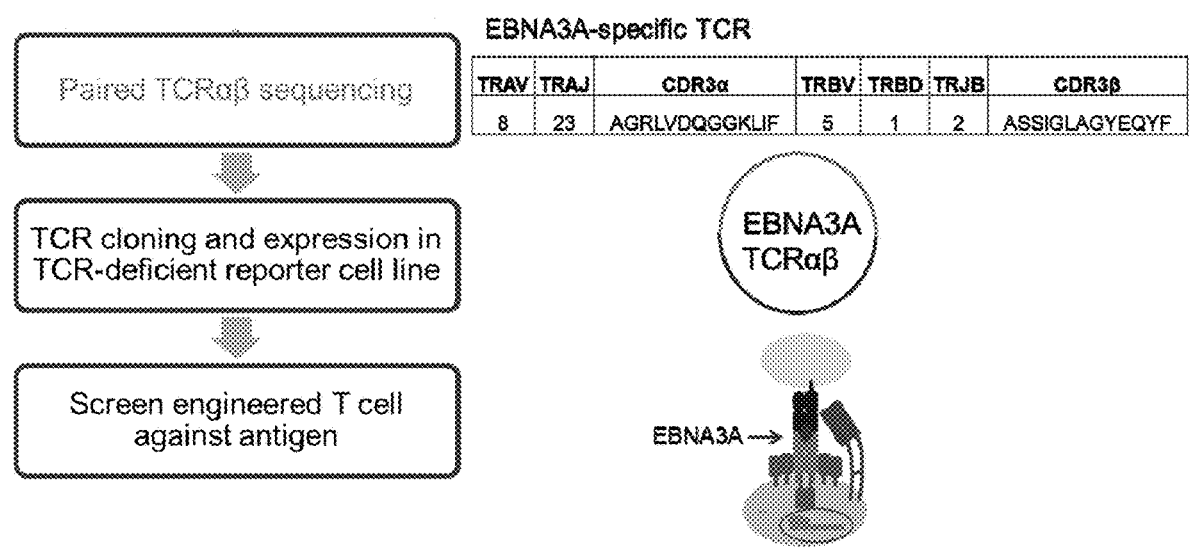
FIG. 8 illustrates a workflow of a proof of concept experiment for obtaining specific TCRs using known TCR sequences. A TCR specific for EBNA3A is shown (SEQ ID NOS 259 and 260, respectively, in order of appearance).
Figure 9:
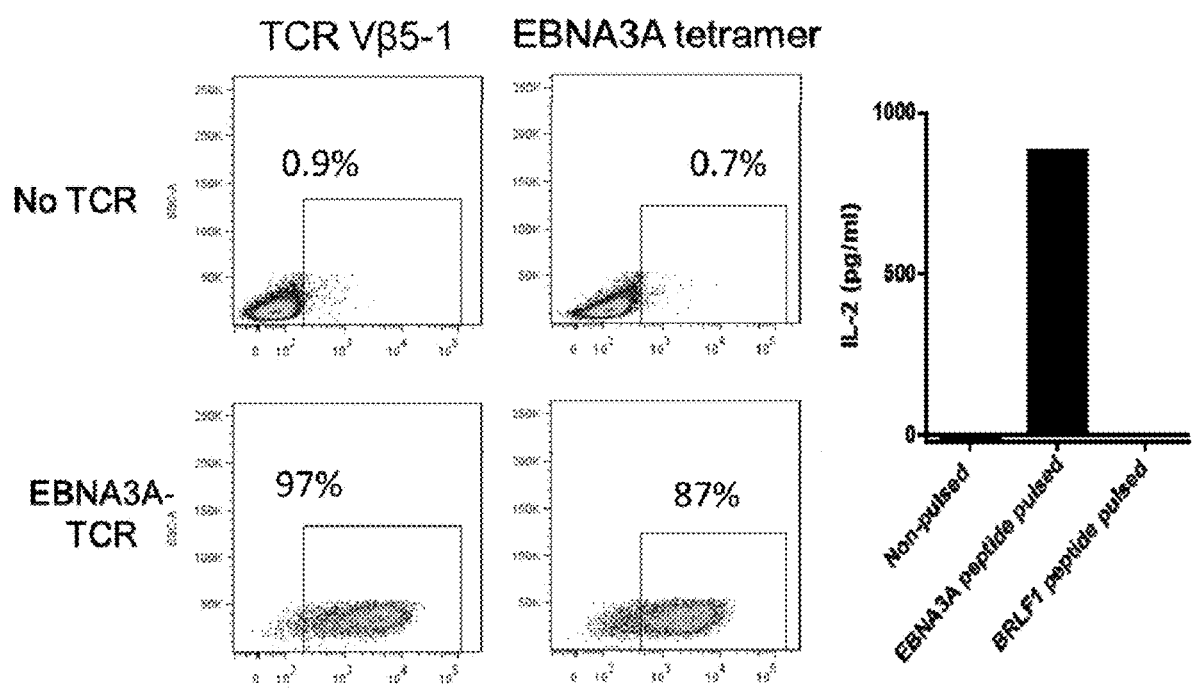
FIG. 9 illustrates expression of EBNA3A-specific TCRαβ in JurkatΔαβ cells and the specificity of the T cells for EBNA3A. Shown are three methods of detecting TCR specificity.
Figure 10:
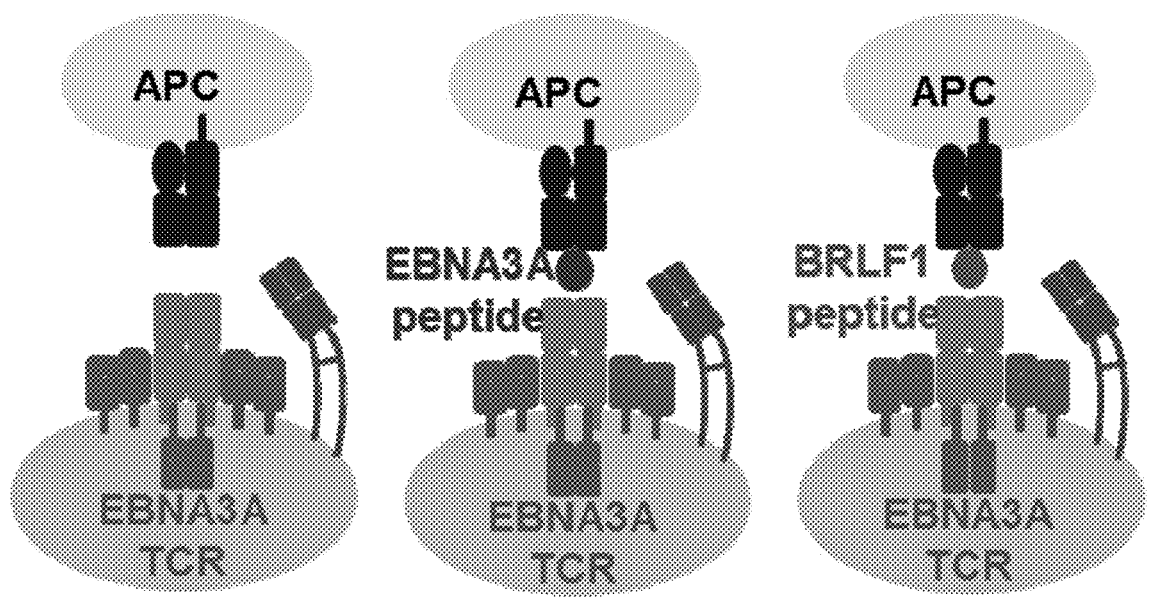
FIG. 10 illustrates functional analysis of EBNA3A-specific TCR expressing JurkatΔαβ cells using antigen presenting cells loaded with no peptide, EBNA3A peptide or BRLF1 peptide.

As proof of principle, Applicants have cloned the EBNA3A-specific TCR pair by Golden Gate assembly into a lentiviral vector (FIGS. 8, 9 and 10). Expression of EBNA3A-specific TCRα3 on JurkatΔαβ is shown by binding of TCR Vβ5-1 antibody, EBNA3A tetramer binding and IL-2 release. Additionally, the reporter T cells may be stimulated with antigen presenting cells loaded with EBNA3A peptide or control peptide.

Example 9

Proof of Concept for Isolation of TCR Sequences Specific for Peptides from CMV, EBV and Influenza (CEF)

Figure 11:
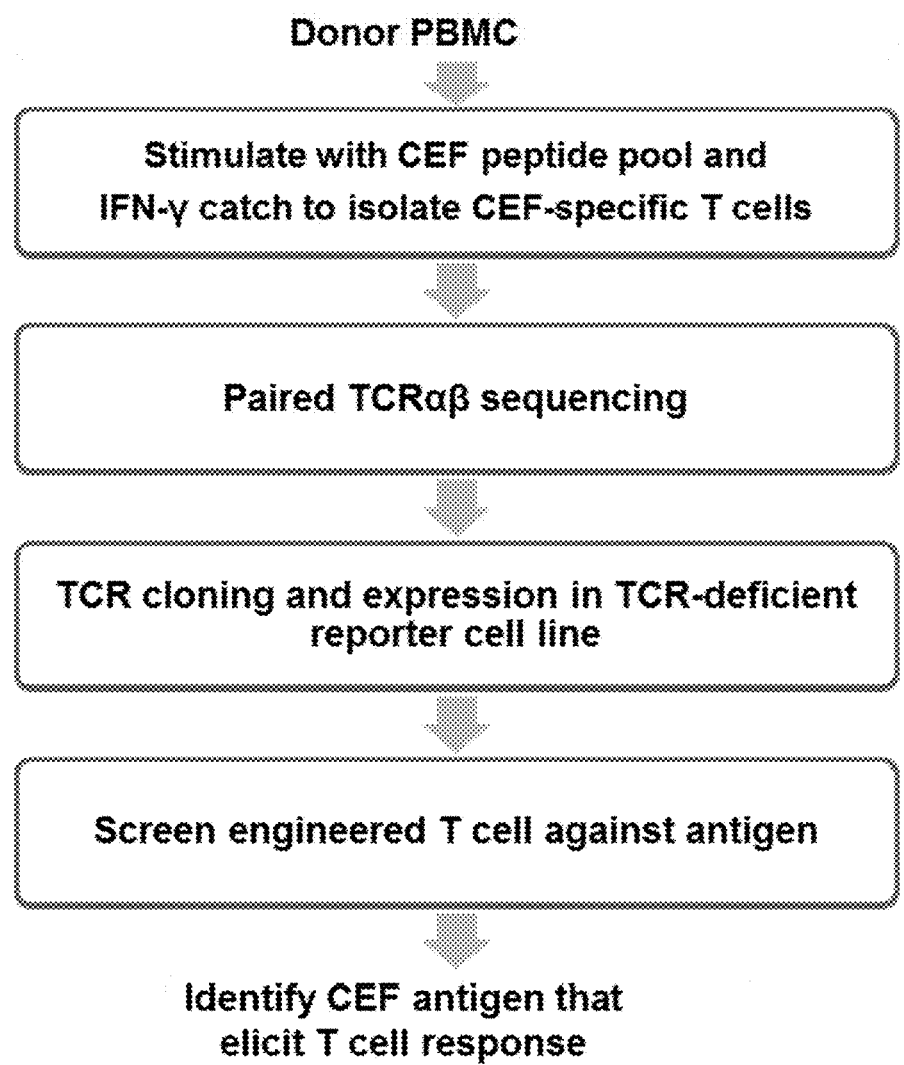
FIG. 11 illustrates a workflow of a proof of concept experiment for isolating antigen-specific TCRs against a known pool of antigens (CEF).
Figure 12:
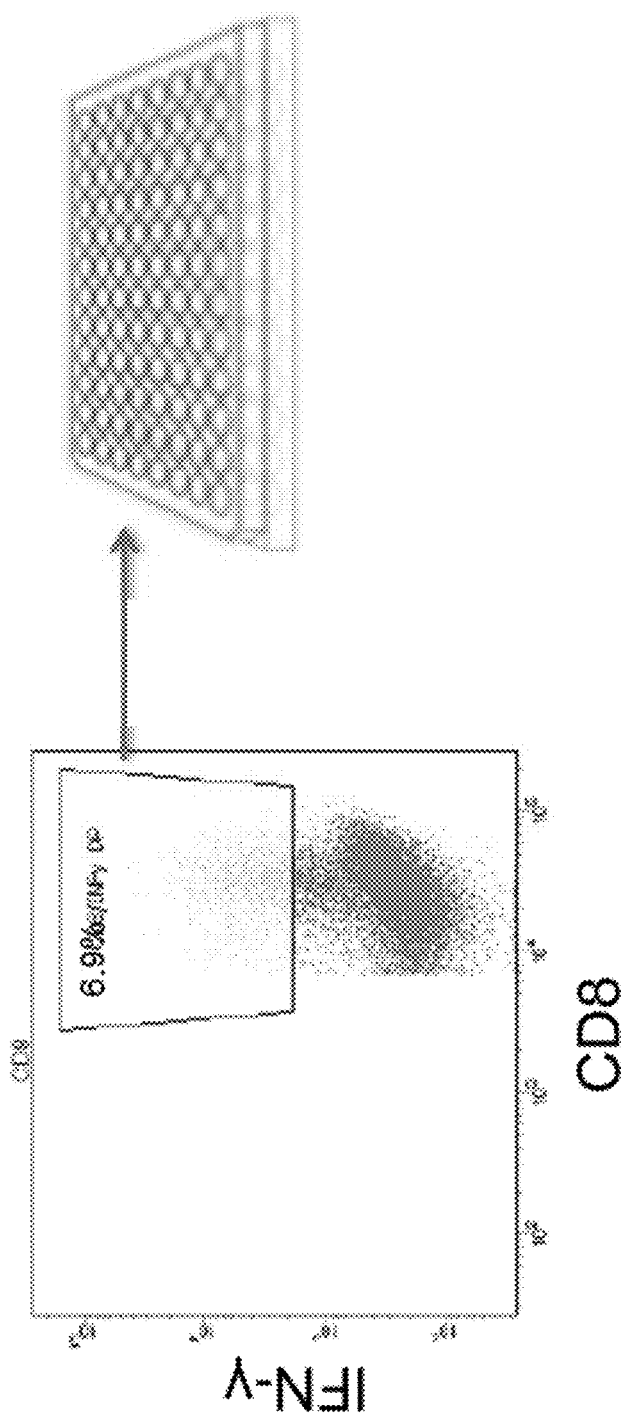
FIG. 12 illustrates the expansion and isolation of CEF-specific T cells.
Figure 13:
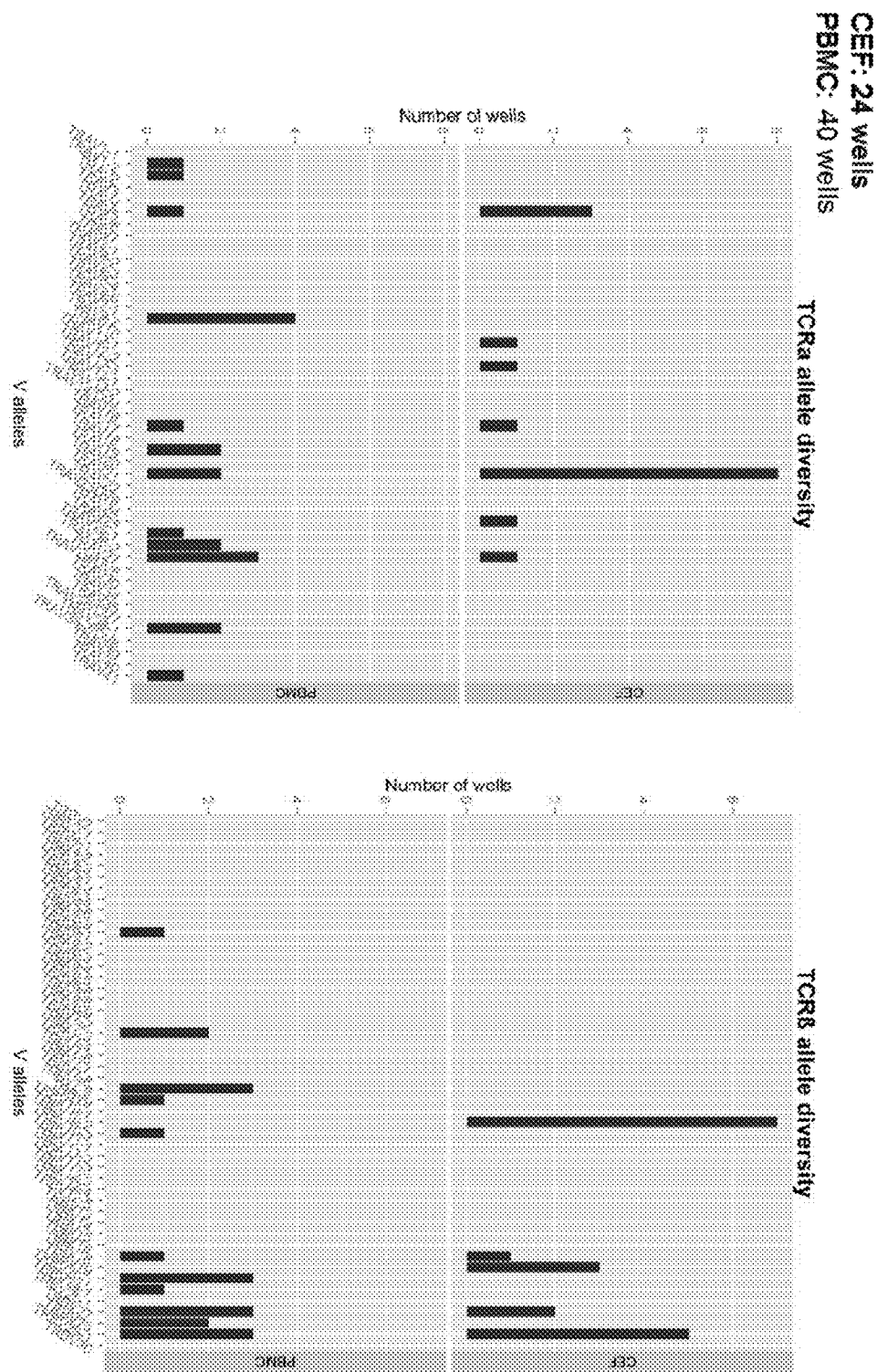
FIG. 13 illustrates TCR sequencing of CEF-specific T cells.
Figure 14:
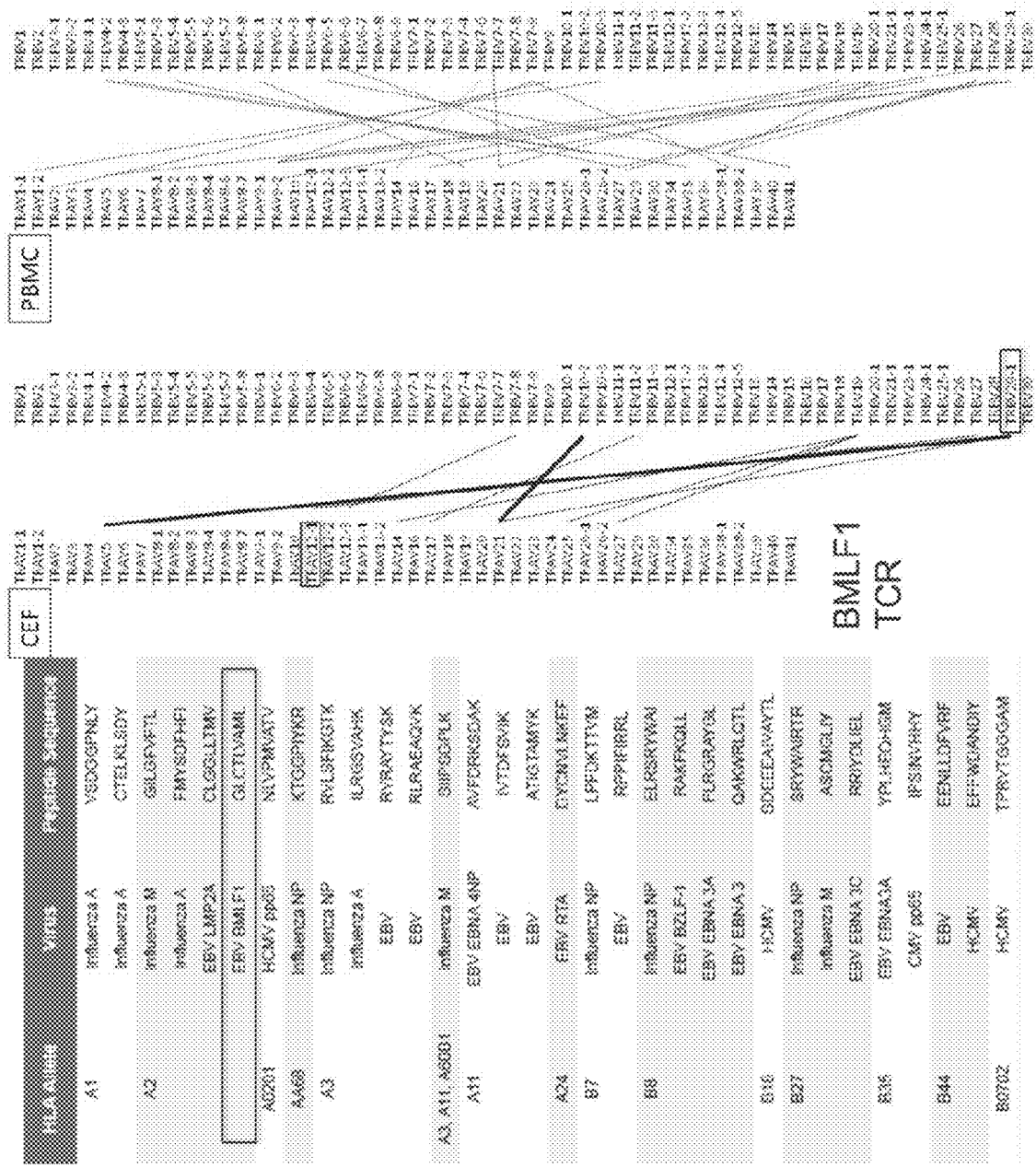
FIG. 14 illustrates TCRαβ pairs in PBMCs and PMBCs stimulated with CEF peptides (SEQ ID NOS 261-262, 148 and 263-291, respectively, in order of appearance). Shown are the CEF peptides and enrichment of TCRαβ pairs specific for BMLF1.
Figure 15:
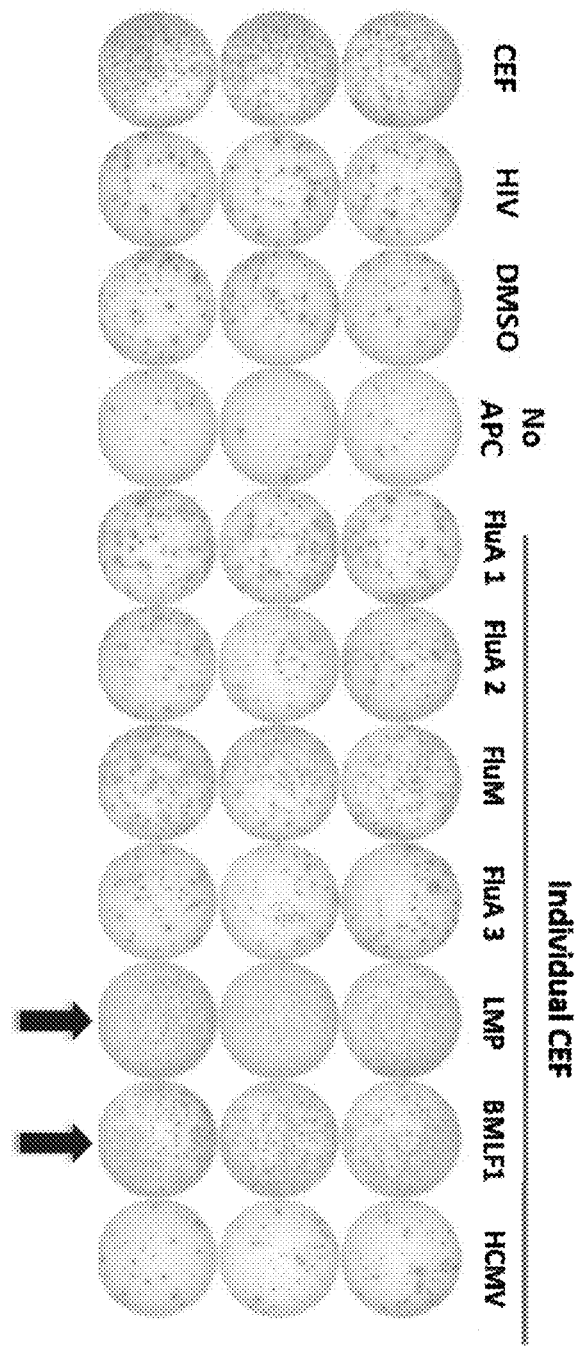
FIG. 15 illustrates IFN-γ elispot experiments with T cells from the same donor stimulated with CEF and then tested against individual antigens to confirm the pipeline of sequencing to antigen screening.

Applicants have cloned a library of TCR pairs in T cells from patients expanded with peptides from CMV, EBV and influenza (CEF). A workflow is described in FIG. 11. Expansion and isolation of CEF-specific T cells is performed by stimulation of healthy donor PBMCs with the CEF peptide pool, culturing for 10 days to expand CEF-specific T cells, performing an IFN-γ catch assay to isolate CEF-specific T cells, and FACS sorting IFN-γ$^+$CD8$^+$ T cells into 384 well plates (FIG. 12). T cells stimulated with CEF peptides have more dominant TCRα and TCRβ chains (FIG. 13). Comparison of the TCRα and TCRβ pairs between CEF treated and PBMCs shows less diversity and dominant TCR pairs (FIG. 14). Applicants also found a published TCR pair specific for the BMLF1 peptide that is included in the CEF peptide pool. Applicants use IFN-γ elispot to confirm the screening pipeline (FIG. 15). Stimulation with individual CEF peptides shows signal above background in T cells re-stimulated with BMLF1. Thus, Applicants have developed a method to isolate TCR sequences specific for antigens.

Example 10

Screening Patient T Cells

Figure 16:
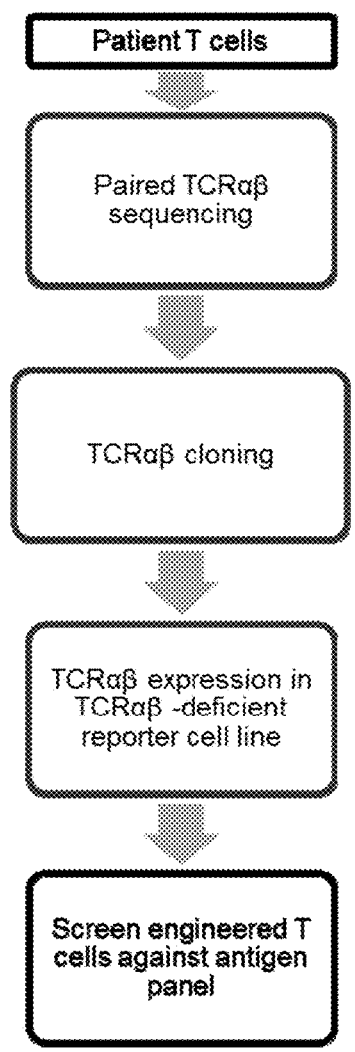
FIG. 16 illustrates a workflow for isolating T cell receptors with specificity for an antigen panel.
Figure 17:
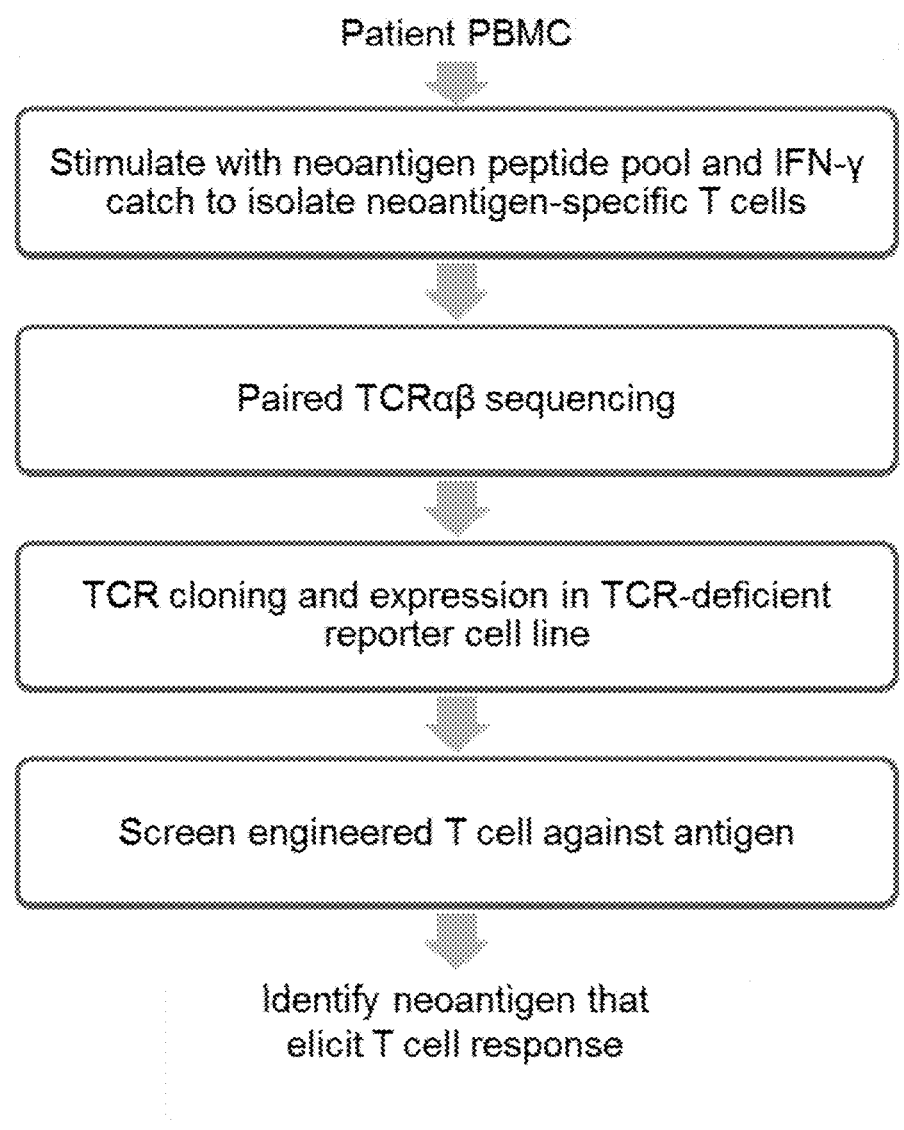
FIG. 17 illustrates a workflow for stimulating T cells with a neoantigen peptide pool and isolating T cell receptors with specificity for a neoantigen.

Applicants have developed a pipeline to screen patient T cells for T cell pairs with specificity against an antigen panel, such as a neoantigen panel (FIG. 16). T cell pairs are sequenced, cloned and assayed against the panel. The TCR pairs may then be used in a therapeutic such as adoptive transfer of transgenic T cells. Additionally, neoantigen peptides reactive to T cells may be used in a neoantigen immunogenic composition. Applicants further developed another pipeline to isolate TCR pairs reactive to a neoantigen peptide pool (FIG. 17). Applicants stimulate patient PBMCs with a neoantigen peptide pool (or transfection with plasmids or infection with viruses to express neoantigens), followed by IFN-γ catch (or other method to capture activated T cells) to isolate neoantigen-specific T cells. The paired TCRαβs are sequenced in single cells, and screened against the individual neoantigens in a reporter cell line. The isolated TCR pairs that are shown to recognize patient tumor neoantigens may then be used as a therapeutic such as adoptive transfer of transgenic T cells.

Example 11

Multi-Epitope Personal Vaccines for CLL is an Effective Therapeutic Strategy

Figure 18:
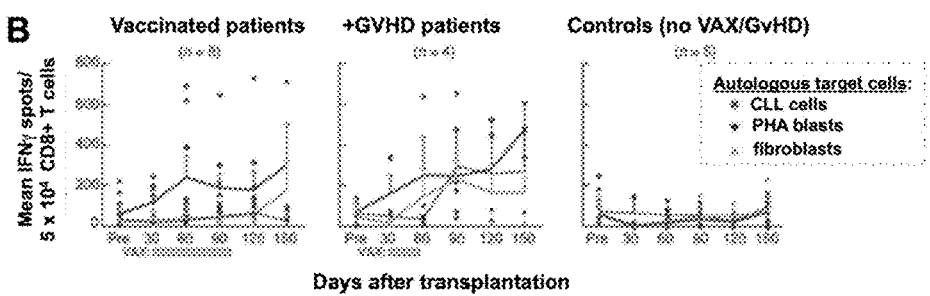
FIG. 18 illustrates CLL-specific CD8+ T cell immunity in CLL patients following allo-HSCT/whole tumor cell vaccination. (A) Target cell panel and expected reactivity pattern. (B) Mean tumor- or alloantigen-specific IFNγ spot production of CD8+ T cells isolated from vaccinated, GvHD or control patients. (C) Number of T cell clones specifically recognizing CLL-associated antigens per patient.

The curative basis of allogeneic hematopoietic stem cell transplantation (HSCT) relies on the immunologic recognition and elimination of malignant cells by normal donor cells that have reconstituted the hematopoietic system of the host (called the graft-versus-leukemia effect [GvL]) (Smith et al., Nat Protoc. 2009; 4:372-384; Wu et al., Nat Methods. 2014; 11:41-46). Strong evidence in support of the potency of GvL comes from (1) durable remissions observed following donor lymphocyte infusion (DLI) by which lymphocytes from the original donor are infused in the absence of further chemotherapy or radiotherapy, and in which remissions have been observed in 80% of patients with chronic myeloid leukemia (CML) and 15-40% of patients with CLL (Wu et al., Nat Methods. 2014; 11:41-46); and, (2) long-term remissions following reduced-intensity HSCT, where it is acknowledged that the intensity of the conditioning regimen alone is insufficient to generate durable leukemia control, and hence GvL is presumed to underly the clinically evident responses (DeKosky et al., Nat Biotechnol. 2013; 31:166-169; Mazutis et al., Nat Protoc. 2013; 8:870-891; Abate-Daga et al., PLoS One. 2014; 9:e93321). Based on these concepts, Applicants devised and tested a strategy to enhance GvL by vaccinating 18 patients with advanced CLL with irradiated autologous whole-tumor cells, administered early following reduced-intensity HSCT (between days 30-45) (Burkhardt et al., J Clin Invest. 2013; 123(9):3756-3765; Horowitz et al., Blood. 1990; 75:555-562). In addition to promising clinical activity (an estimated 2-year progression-free and overall survival rate of 82% and 88%, respectively), Applicants also observed CD8+ T cells from vaccinated patients, but not non-vaccinated patients, to consistently react against autologous tumor (with increased secretion of the effector cytokine IFNγ) but not to autologous alloantigen-bearing cells (FIG. 18A,B). Applicants further confirmed that approximately 15-30% of CD8+ T cell clones isolated from 4 vaccinated patients by limiting dilution solely reacted against CLL-associated antigens (FIG. 18C). These studies support the existence of CLL-specific antigens and that targeting of these antigens is associated with cancer control.

Figure 19:
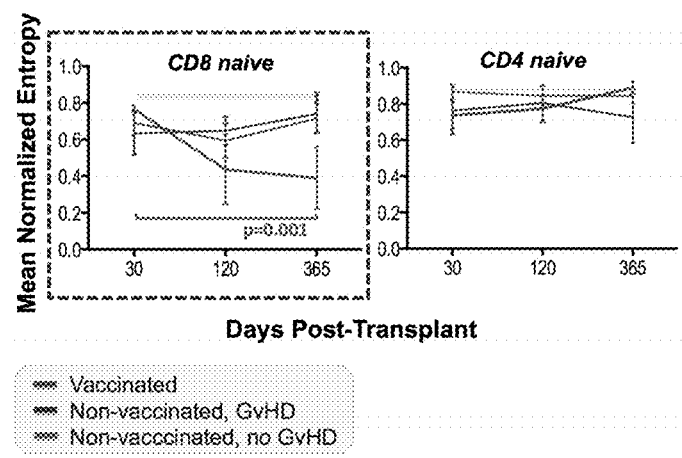
FIG. 19 illustrates CD8+ naïve TCR diversity increases from post-transplant day 30 to 365 in vaccinated patients. The statistical measure 'normalized entropy' characterizes the shape of distribution of TCRβ clonotype frequencies within the TCRβ repertoire. Values close to 1 indicate a relatively even distribution of TCRβ clonotypes.

In ongoing studies, Applicants have analyzed whether perturbation by vaccination in the early post-transplant period impacts immune reconstitution. Applicants isolated naïve and memory CD4+ and CD8+ T cells from peripheral blood mononuclear cells (PBMC) of 14 patients with advanced CLL who underwent a reduced-intensity allo-HSCT. Time points included post-transplant day 30, day 120 (a time point informative for thymic-independent T cell immune recovery) and day 365 (a time point informative for thymic-dependent immune recovery). From these T cell subpopulations, genomic DNA was extracted and a template library for sequencing on an Illumina GA2 system was generated through PCR amplification of the TCRβ CDR3 region using an established panel of 45 Vβ- and 13 Jβ-specific primers (Adaptive Biotechnologies, Seattle, Wash.). Applicants obtained a median of 394,872 (range 0-26,426, 784) productive reads across 168 samples. As a comparison group, Applicants further studied repertoire data from naïve and memory CD4+ and CD8+ T cells collected from 9 healthy adult volunteers. Analyses revealed that CD8+ naïve T cells exhibited greater TCR diversity, as defined by a clonality measure, at post-transplant day 365 in vaccinated compared to non-vaccinated/non graft-versus-host disease (GvHD) individuals (FIG. 19; Burkhardt et al CIMT presentation). These results suggest that immunologic intervention early following hematopoietic stem cell infusion can indeed alter the T cell repertoire diversity of patients.

Example 12

Development of a Tumor Neoantigen Discovery Pipeline.

Neoantigens are a highly valuable class of tumor-expressed antigens generated as a result of somatic mutation. To systematically define CLL neoantigens, Applicants developed a pipeline that incorporates existing Broad Institute bioinformatic algorithms that have been used and validated in large-scale cancer genome projects such as the TCGA to precisely identify the tens to thousands of protein-coding changes in the DNA of each tumor (Wu et al., Adv Immunol. 2006; 90:133-173; Brown et al., Leukemia. 2013; 27:362-369; and NetMHCpan, one of the top rated prediction algorithms for HLA binding). Using recently reported results of large-scale whole-exome sequencing (WES) of CLL (Wang et al, NEJM 2011; Landau et al, Cell 2013:29, 30) Applicants used NetMHCpan to predict candidate CLL-specific peptides generated from missense mutations with the potential to bind personal class-I HLA proteins. Applicants predicted an average of ~22 binding epitopes (IC50<500 nM) per CLL patient and evaluated the binding affinity of more than 100 predicted peptides using a competitive class I binding assay (Burkhardt et al., J Clin Invest. 2013; 123:3756-3765) to understand the boundaries of accurate predictivity.

Example 13

Identification of the CLL Neoantigen FNDC3B

Applicants further established that this approach could identify neoantigens which were immunogenic in vivo. In one CLL patient who achieved long-term remission following HSCT/whole tumor cell vaccination, Applicants found CTLs that were reactive to a predicted neoantigen peptide (from mutated but not wild-type FNDC3B). These mutFNDC3B-specific T cells could be detected by neoantigen-specific tetramers (FIG. 20B) and were found to be cytolytic to autologous tumor (based on CD107a staining, FIG. 20C), were long-lived (>32 months) and Vβ11 restricted (FIG. 20D).

Example 14

Developing the Pipeline and Prioritization Criteria for Selecting Neoepitopes to Include in a Personalized Neoantigen-Based Vaccination Study Leveraging publicly-available TCGA WES, Applicants used the pipeline to predict missense mutation-generated neoepitopes across 13 cancer types, including CLL. Applicants predicted 10's-1000's of neoantigens per tumor, suggesting that neoantigens are frequent.

Applicants retrospectively applied NetMHCpan to 40 neoepitopes identified as spontaneously occurring targets of T cells isolated from cancer patients, most of whom had regressing or long-term stable disease. This analysis demonstrated that all neoepitopes naturally observed in cancer patients would have been predicted by NetMHCpan and thus establishing criteria for epitope prioritization based on bona fide human T cell responses (Fritsch et al, Cancer Immunol Res 2014, June; 2(6):522-9).

Example 15

Figure 21:
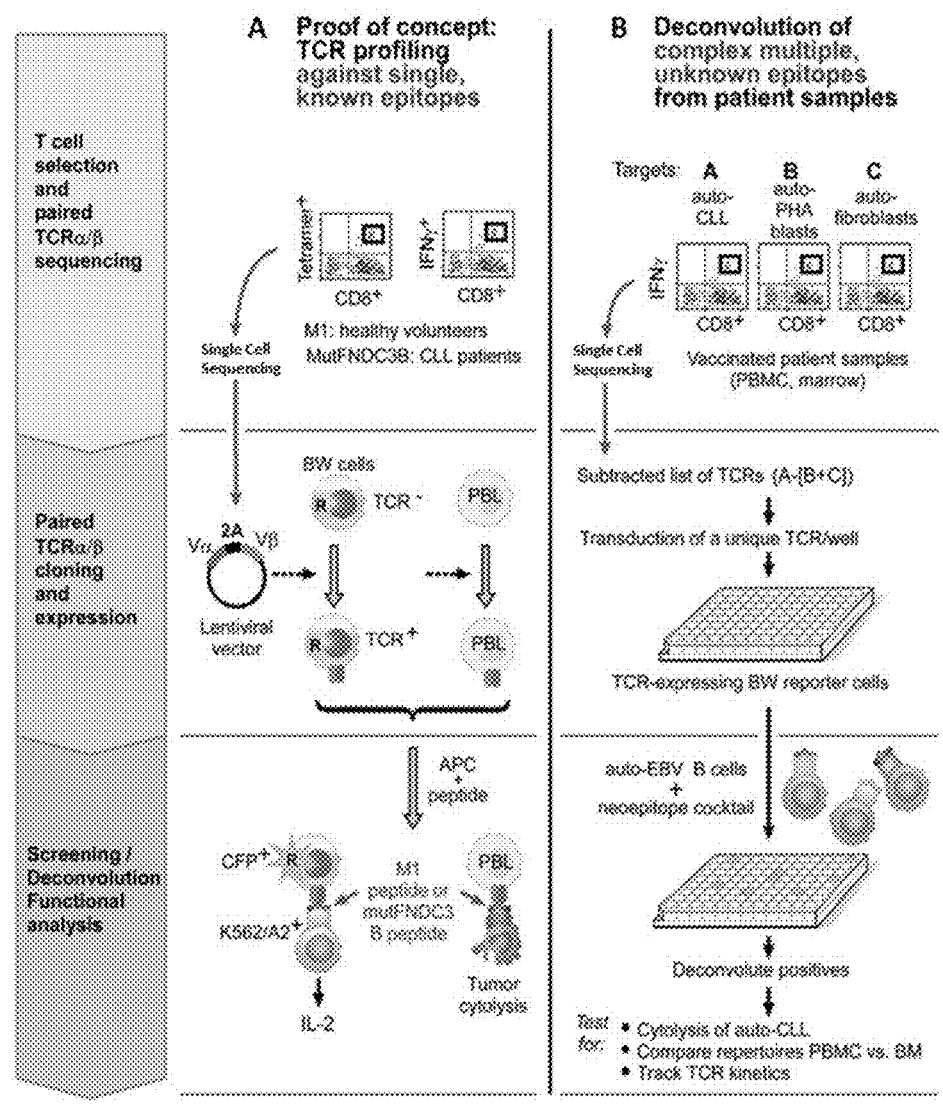
FIG. 21 illustrates an experimental work flow for functionally analysing the TCR repertoire.

Exemplary Workflow to Directly Identify the Paired α and β Chains of the TCR Complex in Individual T Cells Following Epitope Recognition An experimental workflow is shown to directly identify the paired α and β chains of the TCR complex in individual T cells following epitope recognition (FIG. 21). TCRα/TCRβ pairs of individual tumor-reactive T cells and their reactivity against predicted personal neoepitopes is described. The experiments described in panel A shows the methodology to identify the known and novel TCRα/β pairs for two distinct target antigens (differing significantly in TCRs). Additionally, a T cell reporter cell line is generally applicable to the analysis of all isolated TCRα/β pairs to demonstrate antigen specificity. In panel B the tools in panel A are applied to identify the neoantigens associated with the tumor-specific T cell responses observed in the recently reported study of whole CLL cell vaccination following allotransplant (Rajasagi et al., Blood 2014, Jul. 17; 124(3): 453-62; Horowitz et al., Blood. 1990; 75:555-562).

Well-characterized primers specific for the 3' constant region and for each of the 5' Vα and Vβ gene segments has been described (Robins et al., Sci Transl Med. 2010; 2:47ra64). Validation of the primer set includes amplifying CDR3 using a primer in the constant region and specific primers from each Vα and Vβ segment. The primers generate amplicons corresponding to all of the Vα and Vβ families. The products are sequenced on an Illumina MiSeq with 250 nt paired end reads. This strategy can be compared to an alternative 5'-RACE approach that does not require 5' V primers but rather uses a template switching oligonucleotide for second strand synthesis; while the downside of this latter approach is reduced efficiency, it requires only a single primer for RT to capture each TCR.

PCR primers are validated by confirming the ability to correctly identify known TCRα/β pairs by performing multiplex amplification and sequencing of single T cells with known paired TCRs (i.e. Jurkat and HuT78 cell lines).

Panel A shows a schematic representation of single cell sequencing being used to sequence the TCRs from T cells that recognize a known viral antigen (influenza M1) and a single tumor neoantigen (mutated FNDC3B from CLL) (FIG. 21A).

To generate M1-specific T cells, PBMCs are collected from HLA-A2+ healthy adult volunteers after generating M1-reactive T cells by standard stimulation with the HLA-A2-restricted M1 (GILGFVFTL (SEQ ID NO: 148)) peptide (as performed in Naito et al, Cancer Immunol Immunother 2013, February; 62(2):347-57; Sidney et al., Curr Protoc Immunol. 2013; Chapter 18:Unit 18 13). About 10,000 $CD8^+$ M1-tetramer$^+$ cells may be isolated by flow sorting and analyzed by TCRα and TCRβ amplification and sequencing. In addition, M1-responsive CD8+ T cells may be isolated based on IFNγ secretion (IFNγ Catch Assay, Miltenyi) to compare the TCR repertoire with that identified by tetramer sorting.

To generate tumor mutated FND3CB neoepitope specific T cells, PBMCs from a well-characterized CLL patient are stimulated with the mutFNDC3B peptide. About 10,000 tetramer+ CD8+ T cells may be isolated (NIH Tetramer Core Facility at Emory; see FIG. 4B) for TCRα and TCRβ amplification and sequencing.

Reads are aligned with the IMGT database of germline TCR genes to reveal the identity and abundance of paired TCRα/β chains. One example of how the Illumina MiSeq paired-end reads are analyzed are:

(i) Each read is queried against the IMGT-curated library of V, D, and J gene sequences using IgBlast (a well-established algorithm to align TCR). Paired-end reads are kept if at least one read aligns to the V gene with high confidence ($p<10^{-6}$). This read end is assumed to map upstream in the pair.

(ii) Each (upstream) read is then superimposed upon its assigned germline V gene segment. In cases of mismatch, the sequenced base is preferred if the quality score is high (Phred>30). In addition, algorithms may be developed to utilize unique molecular identifiers to determine sequence accuracy.

(iii) The reconstructed V segments are tested for overlap with their corresponding paired end read. If the overlap (≥10 nts) fails, 1 base will be deleted from the 3' end of the reconstructed V segment and retried (to account for chewback) up to 5 times before giving up. When successful overlap occurs, the reconstructed V segment and the paired read are fused to form a fully reconstructed sequence.

(iv) Each fully reconstructed sequence is then queried using IgBlast. Sequences with V-gene and J-gene assignments both scoring $p<10e^{-6}$ are retained, and their IgBlast-identified CDR3 sequences are recorded as long as all CDR3 bases have a Phred score >30.

(v) The most frequent CDR3 reconstruction is designated as a motif, and all reconstructions within a Hamming distance of 1 are assigned to that motif. This process is repeated on the remaining reconstructions until fewer than 2 sequences can be assigned to a motif.

(vi) Sequence and abundance of unique TCR sequences are reported based on CDR3 assignments.

Panel A also describes a TCR-deficient reporter cell for expression of identified antigen-specific TCRα/TCRβ pairs for functional analysis. The reporter is activated upon binding to antigen. The reactivity of the TCRs to cognate antigen are tested by introducing them into a TCR-deficient reporter cell that can be used to test for antigen responsiveness.

The identified TCRα/β paired chains are cloned and expressed in the reporter T cell line. An expression vector containing the distinct paired specific TCRα and β chains linked by a 2A-peptide encoding sequence (~60 bp); the 2A peptide is cleaved following translation and allows reliable simultaneous expression of both genes at equal levels (Boria et al., BMC Immunol. 2008; 9:50). The ~1.8 kb insert consists of fixed sequences (Cα and C β—the invariant portions of each TCR chain) as well as the linking region. Only the ~400 bp variable regions require synthesis or PCR-based insertion to construct the complete vector. The expression cassette is cloned as a TCRα/β cassette into the lentiviral vector pRRLSIN.cPPT.PGK-GFP.WPRE (Addgene, Cambridge, Mass.; GFP can be exchanged with YFP in this vector), which has been shown to effectively express TCR genes (Naito et al., Cancer Immunol Immunother. 2013; 62:347-357).

Figure 22:
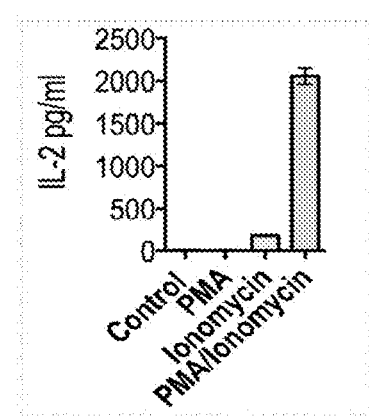
FIG. 22 illustrates that BW5147 cells produce IL2 in response to PMA/ionomycin.

To study the identified TCRs, the paired TCR α and β chains are expressed in a TCR-deficient reporter cell line. The reporter cell line may be constructed by transducing the murine TCR-deficient thymoma line BW5147.3 (ATCC TIB-47; BW) with multi-cistronic murine stem cell virus (MSCV)-based lentiviral constructs encoding the human CD3 complex and the human CD8 α and β chains. Both constructs contain an IRES and different antibiotic resistance markers. In addition, the reporter cell line is transduced with CFP controlled by the nuclear factor of activated T cells (NFAT-CFP reporter) similar to studies from others (Szymczak et al., Nat Biotechnol. 2004; 22:589-594; Jones et al., Hum Gene Ther. 2009; 20:630-640.). An advantage of using a murine cell line is that human TCRs positively selected for personal HLAs do not recognize murine MHC-molecules as allogeneic antigens. Furthermore, BW cells are functionally competent and secrete IL-2 upon antigen stimulation (FIG. 22). The lentiviral TCR constructs are introduced to create engineered BW T cells.

The expression of CD3 and CD8 is verified by flow cytometry with specific antibodies. The functionality of the NFAT-CFP reporter is confirmed by stimulating the parent reporter cells with PMA/ionomycin and monitoring CFP expression (FIG. 22).

Described is a method to screen the reactivity of engineered T cells against cognate antigens. To determine whether the TCRs isolated from tetramer+ T cells are reactive to M1 and mutFNDC3B peptides, BW cells transduced with specific TCRs are studied in two ways. First, flow cytometry is used to test for expression of antigen-specific TCR using fluorescent M1- or mutFNDC3B-specific tetramers. Second, CFP expression via NFAT signaling is monitored by flow cytometry after exposure of cells to cognate antigen on HLA-A2+ expressing antigen presenting cells (i.e. K562-A2+ cells, which have been previously used, Naito et al., 2013) (Rajasagi et al., Blood 2014, Jul. 17; 124(3):453-62; Sidney et al., Curr Protoc Immunol. 2013; Chapter 18:Unit 18 13). The antigen presenting cells are pulsed with M1 (GILGFVFTL (SEQ ID NO: 148)) or mutFNDC3B (VVMSWAPPV (SEQ ID NO: 149)) peptides or control peptides (i.e. the HTLV-1-derived Tar peptide LLFGYPVYV (SEQ ID NO: 150)), or transfected with an expression plasmid encoding minigenes for M1 or mutFNDC3B. Several TCR sequences recognizing each antigen are expected to be identified, and further studies are performed to address which TCRs are able to induce cytolysis on influenza-infected target cells (for M1-specific T cells) or tumor cells (mutFNDC3B-specific T cells).

Results with mutFNDC3B-tetramer+ T cells from a CLL patient showed that approximately half of neoantigen-reactive T cells appeared to be cytolytic to autologous tumor on the basis of surface expression of the standard marker CD107a, while the other half were negative for CD107a (FIG. 20C). To determine whether the TCRs with these different phenotypes are similar or different, CD107a-positive and -negative cells are sorted, and the sequences of paired TCR chains in each population are compared. These TCRs can then be directly tested to determine whether TCRs found in CD107a+ T cells are cytolytic for mutated FNDC3B-pulsed HLA-A2+ targets. While the murine thymoma line BW5147.3 is well-suited for initial TCR screening experiments, it lacks the cellular machinery for cytotoxicity studies. Primary peripheral blood lymphocytes (PBLs) are used for transduction with the paired TCRα/β chains (Cibulskis et al., Nat Biotechnol. 2013; 31:213-219) and are assessed for cytotoxic activity of TCR-transduced PBLs on pulsed targets with a standard chromium release assay.

The described methods are used to deconvolute complex T cell populations that target tumors following whole tumor cell vaccination. Described in FIG. 21B are methods to determine if CTL reactivity following tumor cell vaccination is directed against CLL neoantigens. The experimental framework in FIG. 21A may be used to identify TCRs and their target neoantigens in patients who have received autologous tumor cell vaccination.

Isolating tumor-reactive T cells for which the identity of the target antigens are unknown can be performed. Such patient tumor-specific T cells are enriched following stimulation with autologous tumor ex vivo (see Burkhardt et al, JCI 2013; Horowitz et al., Blood. 1990; 75:555-562). Based on limiting dilution experiments and patterns of reactivity of these T cell clones against a panel of target cells (FIG. 18C), it is estimated that 15-30% of clones are tumor-restricted. Thus, to further enrich for tumor-specific rather than alloantigen-specific T cells (resulting from transplantation), Applicants re-stimulate against three sets of targets: autologous tumor, recipient PHA blasts or recipient skin fibroblasts. For each stimulus, IFNγ+ cells can be isolated and processed as single cells for TCR profiling. Based on the sequences of paired TCRα/β chains in each group of T cells, TCRs that are reactive to tumor but not to non-malignant recipient cells (PHA blasts or skin cells) are identified.

Droplet sequencing and cloning of tumor-reactive TCRs is performed. Based on bulk IFNγ ELISpot data, if 1 million CD8+ T cells are processed, it can be expected that an average of 4000 IFNγ secreting cells are isolated. If 20% of these cells are tumor-reactive, then sequencing is expected to reveal fewer than 800 unique paired TCRα/β chains. 96 of the most abundant and unique paired TCRα/β chain sequences are cloned into a lentiviral expression vector for stable expression in BW T cells, using the same clone strategy described herein.

Neoepitopes are predicted based on tumor somatic mutations using the established discovery pipeline (Wang et al., N Engl J Med 2011, Dec. 29; 365(26):2497-506; Sorror et al., J Clin Oncol. 2008; 26:4912-4920). About 15-50 personal neoepitopes are predicted (IC50<500 nM) per subject (Rajasagi et al., Blood 2014, Jul. 17; 124(3):453-62). A single 8-10mer peptide for each personal neoantigen is synthesized.

Tumor-reactive TCRs can be screened against candidate neoantigens. To screen tumor-reactive TCRs for neoantigen specificity, the array of 96 distinct TCR-expressing BW cells are stimulated with irradiated autologous EBV-transformed B cells (APCs) pulsed with a mixture of 8-10mer predicted personal neopeptides. Neoantigen-reactive TCR-transduced BW cells (CFP+) are selected for further testing against individual neopeptides to match TCRs to neoepitopes (deconvolution).

The described methods can be used to test if the TCRs recognizing personal tumor neoepitopes lead to cytolysis of autologous CLL cells. To test for cytotoxicity against the tumor PBLs can be transduced with paired TCRα/β chains and the specificity of the cytotoxic activity can be assessed against: i) neoantigen- or unmutated native-antigen-pulsed HLA-matched targets; ii) autologous CLL cells; iii) HLA-matched CLL cells pulsed with native variants of neoantigens.

The described methods can be used to determine whether the tumor-specific TCR repertoire is similar in the marrow and periphery. Prior evidence leads to the hypothesis that tumor infiltrating T cells have higher avidity TCRs that are more reflective of an effective vaccination than peripheral blood T cells (Siewert et al., Nat Med. 2012; 18:824-828). Since the bone marrow is a common site of persistent CLL disease as well as a reservoir for memory T cells (Ohashi et al., Nature. 1985; 316:606-609; Melenhorst et al., Blood. 2009; 113:2238-2244), the TCR repertoire can be monitored in matched peripheral blood and marrow samples.

The described methods can be used to track the kinetics of the tumor-specific TCR repertoire. Based on CDR3 sequence of neoantigen-reactive cytolytic TCRs, quantitative real-time PCR assays can be designed with a probe to the highly diverse V-D-J junction region of each TCRβ CDR3 sequence (as done previously Zhang & Choi, Clin Cancer Res 2010, May 15; 16(10):2729-39; Feuerer et al., Nat Med. 2003; 9:1151-1157). These qPCR assays are used to quantify each T cell clone at various time points following transplant and whole tumor cell vaccination, as shown in the example of the Vβ11-restricted clone recognizing mutated FNDC3B (FIG. 20D). This allows a correlation of tumor regression with expansion of neoantigen-specific TCRs to be made.

Though the methods have focused on cytolytic CD8+ T cell responses (given the higher predictivity of MHC class I prediction algorithms and the more common cytolytic capabilities of CD8+ compared to CD4+ cells), there may be relevant CD4+ cells (cytolytic and helper).Therefore, a similar pipeline can be used to discover TCRs of CD4+ T cells and their target antigens.

Example 16

Figure 23:
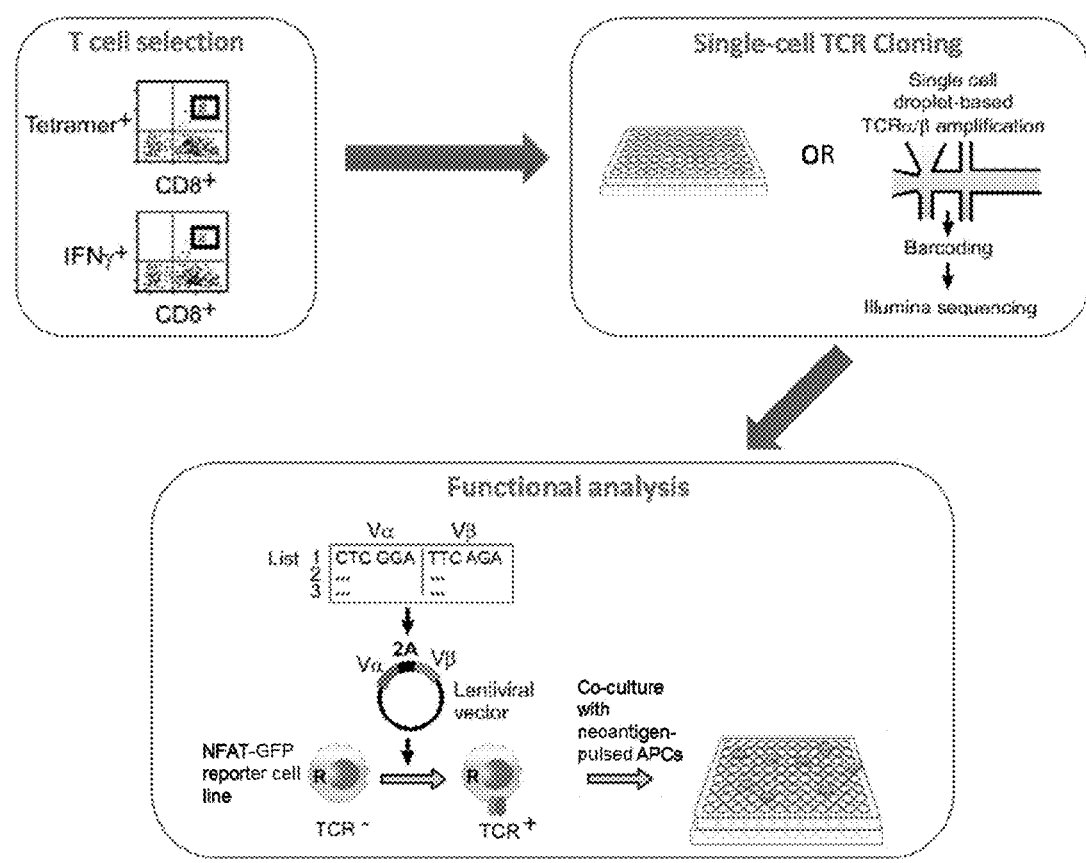
FIG. 23 illustrates an experimental workflow for determining identified TCRs that bind to antigen presenting cells expressing neoantigens.
Figure 24:
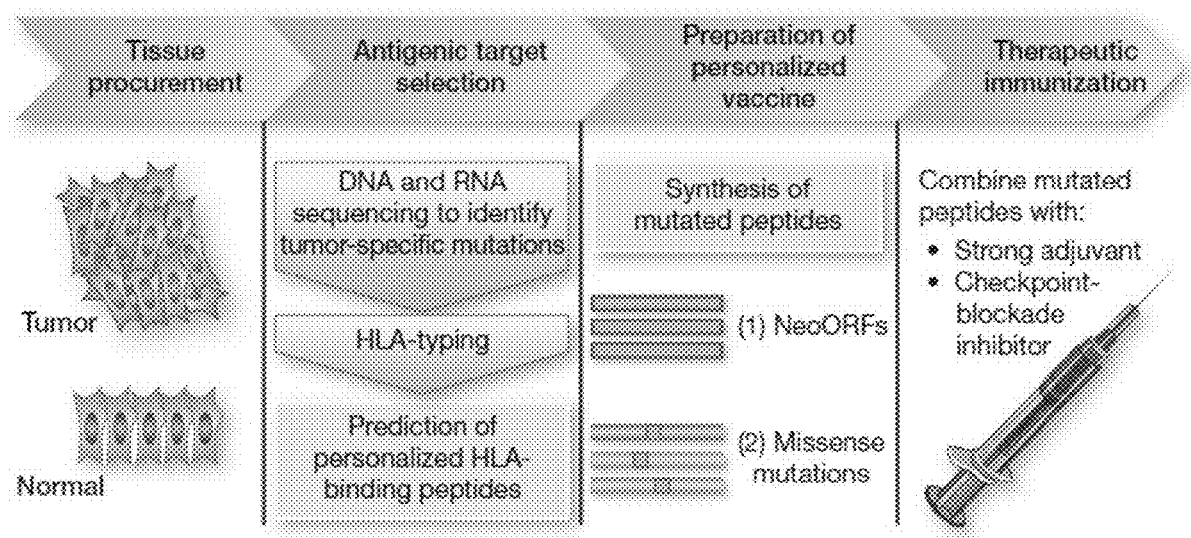
FIG. 24 illustrates a therapeutic vaccine strategy based on tumor neoantigens. First, tumor mutations are discovered rapidly through DNA and RNA sequencing of tumor and normal tissue. Second, personalized tumor-specific mutated peptides are identified on the basis of predictive HLA-binding algorithms. Third, peptides based on neoORFs and missense neoantigens are synthesized. Finally, the peptides are delivered to patients with a powerful immune adjuvant and coupled with complementary immunotherapeutics, such as checkpoint-blockade inhibitors. (Hacohen, Cancer Immunology Research. 2013; 1(1)).

FIG. 23 outlines a similar functional assay workflow. T cells are selected by FACS using tetramer analysis and IFNγ expression. Selected single cells are sequenced individually either by sub-cloning, sequencing cells sorted into separate wells of a plate or single cell microfluidic based methods. TCRs are cloned and inserted into lentiviral vectors. TCR deficient reporter T cells are transduced with lentiviruses expressing cloned TCRα/TCRβ pairs. The reporter cells are then incubated with antigen presenting cells (B cells) that were pulsed with neoantigens.
Protocol for Cloning TCRs Based on the sequences of the TCRα/TCRβ pairs, the corresponding Va an Vb plasmids are selected from a pre-made library and assembled with the synthesized CDR3 sequence. The detailed protocol is shown below.
Materials
phusion high fidelity PCR master (NEB M0531L)
NEB 5-alpha competent E. coli (C2987H)
NEB golden gate assembly mix (E1600S)
AgeI-HF (R3552L) 20,000 U/ml
SalI-HF (R3138L) 20,000 U/ml
T4 DNA ligase (M0202L) 400,000 U/ml
Annealing Single Strand Ultramer Oligos Ordered from IDT
Make STE buffer (10 mM Tris, 50 mM NaCl, 1 mM EDTA) by adding 2M NaCl (1.2 g NaCl into 10 ml dH2O, filter with 0.45 um, ×40) into 1×TE buffer from Qiagen kit (1 ml TE buffer+25 ul 2M NaCl)
Spin down the oligo tubes
Dissolve the oligo in 40 ul STE buffer to get 100 uM for all 4 oligos
Vortex and spin
Mix two strands in equal molarities (1 ul of top+1 ul of bottom+8 ul STE) in 1.5 ml eppendorf tube
94 C, 3 min on heat block
Cool gradually at RT
Golden Gate Assembly Protocol Using NEB Golden Gate Assembly Mix
1. Set up assembly reactions as follows:

| REAGENT | NEGATIVE CONTROL | ASSEMBLY REACTION |
|---|---|---|
| NEB Golden Gate Buffer (10X) | 2 μl | 2 μl |
| Destination Plasmid* (user provided) | 75 ng | 75 ng |
| Inserts (user provided): if precloned** if in amplicon form*** | — | 75-100 ng each plasmid 2:1 molar ratio (insert:vector backbone of destination plasmid) |
| NEB Golden Gate Assembly Mix | 1 μl | 1 μl |
| H2O | to 20 μl (make this to 25 ul) | to 20 μl (make this to 25 ul) |
| Total Volume | 20 μl (make this to 25 ul) | 20 μl (make this to 25 ul) |

*Destination plasmids must contain two BsaI restriction sites to define the sequence functioning as the vector backbone.
**Precloned inserts must possess BsaI restriction sites at both ends of the insert sequence.
***Amplicon inserts must possess 5' flanking bases and BsaI restriction sites at both ends of the amplicon.

3. Choose the appropriate assembly protocol.

| INSERT NUMBER | SUGGESTED ASSEMBLY PROTOCOL |
|---|---|
| For 1-4 Inserts | 37° C., 1 hr → 55° C., 5 min |

| | Concentration (ng/uL) | Dilution first | Mass (ng) | Volume (ul)* | Length (bp) |
|---|---|---|---|---|---|
| BMLF1 | | | | | |
| TRAV5 | 2787 | x100 | 75 | 2.7 | 937 |
| TRBV29-1 | 2278 | x100 | 75 | 3.3 | 3418 |
| CDR3a | 619.2 | x1000 | 3.3 | 5.3 | 75 |
| CDR3b | 719.6 | x1000 | 3.6 | 5 | 81 |
| EBNA3A | | | | | |
| TRAV8-1 | 197.8 | x10 | 75 | 3.8 | 966 |
| TRBV5-1 | 349.2 | x10 | 75 | 2.1 | 4228 |
| CDR3a | 715 | x1000 | 2.9 | 4.1 | 82 |
| CDR3b | 579.5 | x1000 | 2.7 | 4.7 | 75 |

Destination plasmid: Vb (75 ng/reaction)
Precloned inserts: Va (75 ng/reaction)
Amplicon form: CDR3a, CDR3b (2:1 molar ratio, insert:vector of destination plasmid) ex. 2 × 75 ng destination plasmid/3418 bp = Xng CDR3a/75 bp, X = 3.3 ng
* Volumes refer to diluted solutions
Dilutions
TRAV5        1 uL TRAV5 + 99 uL dH2O
TRBV29-1     1 uL TRBV29-1 + 99 uL dH2O
CDR3a        1 uL CDR3a + 9 uL dH2O Take 1 uL + 99 uL dH2O
CDR3b        1 uL CDR3b + 9 uL dH2O Take 1 uL + 99 uL dH2O Assembly Reactions for 4 (complete BMLF1 and negative control: no CDR3b, EBNA3A as positive control)
Mix 1: 5 uL Assembly Mix+10 uL NEB Golden Gate Buffer
Mix 2: 7 ul Mix 1+5.4 ul TRAV5+6.6 ul TRBV29-1+10.6 ul BMLF1 CDR3a
  split Mix 2 into 2 tubes, 14.8 ul/tube
  BMLF1 complete: 14.8 uL Mix+5 uL CDR3b+5.2 L dH2O (final 25 ul)
  BMLF1 negative control: 14.8 uL Mix+5 uL dH2O+5.2 L dH2O
Mix 3: 7 ul Mix 1+7.6 ul TRAV+4.2 ul TRBV+8.2 ul EBNA3A CDR3a
  split Mix 3 into 2 tubes, 13.5 ul/tube
  EBNA3A complete: 13.5 uL Mix+4.7 L CDR3b+6.8 L dH2O
  EBNA3A negative control: 13.5 uL Mix+4.7 L dH2O+6.8 L dH2O
Assembly Protocol
Incubate at 37 C for 1 hour, then 55 C for 5 minutes on PCR machine
Transformation Protocol
Thaw 50 ul of NEB 5-alpha competent *E. coli* on ice for 10 min
Add 2 ul of Assembly reaction, gently mix by flicking the tube 4-5 times
Incubate on ice for 30 min
Heat shock at 42 C for 30 sec
Place on ice for 5 min
Add 950 ul of RT SOC
37 C, 30 min, shake vigorously by using a rotation device
Plating Protocol
Warm LB agar plates containing kanamycin (50 ug/ml) at RT
Mix the cells thoroughly by flicking the tube and inverting
Add 75 ul of the 1 ml outgrowth onto each plate
Add 8 beads and shake,
Remove beads
Incubate the plate 16 h, 37 C (lid facing down), Mayer577
Pick Colonies and Colony PCR
  Confirm success of golden gate by PCR.
  The cloned TCR sequence specific for an antigen is encoded in a lentiviral vector, and transfected in 293T cells with second-generation viral packaging plasmids to generate lentivirus. This is used to transduce the Jurkat Δαβ cell line and express the TCR. Expression is verified by antibody surface staining for TCR and tetramer staining by flow cytometry. In addition, as CD3 expression is down regulated in TCR-deficient cell lines, successful expression of the TCR construct can be measured by CD3-rescue.

Sequence Listing

"master pUC57-Kan Cb1-F2A" = following sequence in pUC57-Kan backbone
ggtctctACCTGAACAAGGTGTTCCCACCCGAGGTCGCTGTGTTTGAGCCATCAGAAGCAGAGATCTCCCACACCCAAAAGGCCACACTGGTGTG
CCTGGCCACAGGCTTCTTCCCCGACCACGTGGAGCTGAGCTGGTGGGTGAATGGGAAGGAGGTGCACAGTGGGGTCAGCACGGACCCGCAGCCCC
TCAAGGAGCAGCCCGCCCTCAATGACTCCAGATACTGCCTGAGCAGCCGCCTGAGGGTtTCGGCCACCTTCTGGCAGAACCCCCGCAACCACTTC
CGCTGTCAAGTCCAGTTCTACGGGCTCTCGGAGAATGACGAGTGGACCCAGGATAGGGCCAAACCCGTCACCCAGATCGTCAGCGCCGAGGCCTG
GGGTAGAGCAGACTGTGGCTTTACCTCGGTGTCCTACCAGCAAGGGGTCCTGTCTGCCACCATCCTCTATGAGATCCTGCTAGGGAAGGCCACCC
TGTATGCTGTGCTGGTCAGCGCCCTTGTGTTGATGGCCATGGTCAAGAGAAAGGATTTCAGGAgGAGGAGGagcggcagtggagtgaaacagact
ttgaattttgaccttctcaagttggcgggagacgtggagtccaacccagggccc (SEQ ID NO: 151)

"master pUC57-Kan Cb2-F2A" = following sequence in pUC57-Kan backbone
ggtctctacctGAAAAACGTGTTCCCACCCGAGGTCGCTGTGTTTGAGCCATCAGAAGCAGAGATCTCCCACACCCAAAAGGCCACACTGGTGTG
CCTGGCCACAGGCTTCTACCCCGACCACGTGGAGCTGAGCTGGTGGGTGAATGGGAAGGAGGTGCACAGTGGGGTCAGCACAGACCCGCAGCCCC
TCAAGGAGCAGCCCGCCCTCAATGACTCCAGATACTGCCTGAGCAGCCGCCTGAGGGTtTCGGCCACCTTCTGGCAGAACCCCCGCAACCACTTC
CGCTGTCAAGTCCAGTTCTACGGGCTCTCGGAGAATGACGAGTGGACCCAGGATAGGGCCAAACCTGTCACCCAGATCGTCAGCGCCGAGGCCTG
GGGTAGAGCAGACTGTGGCTTCACCTCCGAGTCTTACCAGCAAGGGGTCCTGTCTGCCACCATCCTCTATGAGATCTTGCTAGGGAAGGCCACCT
TGTATGCCGTGCTGGTCAGTGCCCTCGTGCTGATGGCCATGGTCAAGAGAAAGGATTCCAGAGGCAGGAgGAGGAGGagcggcagtggagtgaaa
cagactttgaattttgaccttctcaagttggcgggagacgtggagtccaacccagggccc (SEQ ID NO: 152)

Full "master pUC57-Kan Cb1-F2A"
tcgcgcgtttcggtgatgacggtgaaaacctctgacacatgcagctcccggagacggtcacagcttgtctgtaagcggatgccgggagcagacaa
gcccgtcagggcgcgtcagcgggtgttggcgggtgtcggggctggcttaactatgcggcatcagagcagattgtactgagagtgcaccatatgcg
gtgtgaaataccgcacagatgcgtaaggagaaaataccgcatcaggcgccattcgccattcaggctgcgcaactgttgggaagggcgatcggtgc
gggcctcttcgctattacgccagctggcgaaaggggggatgtgctgcaaggcgattaagttgggtaacgccagggttttcccagtcacgacgttgt
aaaacgacggccagagaattcgagctcggtacctcgcgaatcactctagatggtctctACCTGAACAAGGTGTTCCCACCCGAGGTCGCTGTGTT
TGAGCCATCAGAAGCAGAGATCTCCCACACCCAAAAGGCCACACTGGTGTGCCTGGCCACAGGCTTCTTCCCCGACCACGTGGAGCTGAGCTGGT
GGGTGAATGGGAAGGAGGTGCACAGTGGGGTCAGCACGGACCCGCAGCCCCTCAAGGAGCAGCCCGCCCTCAATGACTCCAGATACTGCCGAGC
AGCCGCCTGAGGGTtTCGGCCACCTTCTGGCAGAACCCCCGCAACCACTTCCGCTGTCAAGTCCAGTTCTACGGGCTCTCGGAGAATGACGAGTG
GACCCAGGATAGGGCCAAACCCGTCACCCAGATCGTCAGCGCCGAGGCCTGGGGTAGAGCAGACTGTGGCTTTACCTCGGTGTCCTACCAGCAAG
GGGTCCTGTCTGCCACCATCCTCTATGAGATCCTGCTAGGGAAGGCCACCCTGTATGCTGTGCTGGTCAGCGCCCTTGTGTTGATGGCCATGGTC
AAGAGAAAGGATTTCAGGAgGAGGAGGagcggcagtggagtgaaacagactttgaattttgaccttctcaagttggcgggagacgtggagtccaa
cccagggcccatcggatcccgggcccgtcgactgcagaggcctgcatgcaagcttggtgtaatcatggtcatagctgtttcctgtgtgaaattgt
tatccgctcacaattccacacaacatacgagccggaagcataaagtgtaaagcctggggtgcctaatgagtgagctaactcacattaattgcgtt
gcgctcactgcccgctttccagtcgggaaacctgtcgtgccagctgcattaatgaatcggccaacgcgcggggagaggcggtttgcgtattgggc
gctcttccgcttcctcgctcactgactcgctgcgctcggtcgttcggctgcggcgagcggtatcagctcactcaaaggcggtaatacggttatcc
acagaatcaggggataacgcaggaaagaacatgtgagcaaaaggccagcaaaaggccaggaaccgtaaaaaggccgcgttgctggcgtttttcca
taggctccgcccccctgacgagcatcacaaaaatcgacgctcaagtcagaggtggcgaaacccgacaggactataaagataccaggcgtttcccc
ctggaagctccctcgtgcgctctcctgttccgaccctgccgcttaccggatacctgtccgcctttctcccttcgggaagcgtggcgctttctcat
agctcacgctgtaggtatctcagttcggtgtaggtcgttcgctccaagctgggctgtgtgcacgaaccccccgttcagcccgaccgctgcgcctt
atccggtaactatcgtcttgagtccaacccggtaagcacgacttatcgccactggcagcagccactggtaacaggattagcagagcgaggtatg
taggcggtgctacagagttcttgaagtggtggcctaactacggctacactagaagaacagtatttggtatctgcgctctgctgaagcagttacc
ttcggaaaaagagttggtagctcttgatccggcaaacaaaccaccgctggtagcggtggtttttttgtttgcaagcagcagattacgcgcagaaa
aaaaggatctcaagaagatcctttgatcttttctacggggtctgacgctcagtggaacgaaaactcacgttaagggattttggtcatgagattat
caaaaaggatcttcacctagatccttttaaattaaaaatgaagttttaaatcaagcccaatctgaataatgttacaaccaattaaccaattctga
ttagaaaaactcatcgagcatcaaatgaaactgcaatttattcatatcaggattatcaataccatattttgaaaaagccgtttctgtaatgaag
gagaaaactcaccgaggcagttccataggatggcaagatcctggtatcggtctgcgattccgactcgtccaacatcaatacaacctattaatttc
ccctcgtcaaaaataaggttatcaagtgagaaatcaccatgagtgacgactgaatccggtgagaatggcaaaagtttatgcatttattccagact
tgttcaacaggccagccattacgctcgtcatcaaaatcactcgcatcaaccaaaccgttattcattcgtgattgcgcctgagcgagacgaaatac -continued Sequence Listing

```
gcgatcgctgttaaaaggacaattacaaacaggaatcgaatgcaaccggcgcaggaacactgccagcgcatcaacaatattttcacctgaatcag
gatattcttctaatacctggaatgctgtttttccggggatcgcagtggtgagtaaccatgcatcatcaggagtacggataaaatgatgatggtcg
gaagaggcataaattccgtcagccagtttagtctgaccatctcatcgtgcaatcattggcaacgctaccttttgccatgtttcagaaacaactct
ggcgcatcgggcttcccatacaagcgatagattgtcgcacctgattgcccgacattatcgcgagcccatttatacccatataaatcagcatccat
gttggaatttaatcgcggcctcgacgtttcccgttgaatatggctcataacaccccttgtattactgtttatgtaagcagacagttttattgttc
atgatgatatatttttatcttgtgcaatgtaacatcagagattttgagacacgggccagagctgca (SEQ ID NO: 153)
```

Full "master pUC57-Kan Cb2-F2A"
```
tcgcgcgtttcggtgatgacggtgaaaacctctgacacatgcagctcccggagacggtcacagcttgtctgtaagcggatgccgggagcagacaa
gcccgtcagggcgcgtcagcgggtgttggcgggtgtcggggctggcttaactatgcggcatcagagcagattgtactgagagtgcaccatatgcg
gtgtgaaataccgcacagatgcgtaaggagaaaataccgcatcaggcgccattcgccattcaggctgcgcaactgttgggaagggcgatcggtgc
gggcctcttcgctattacgccagctggcgaaagggggatgtgctgcaaggcgattaagttgggtaacgccagggttttcccagtcacgacgttgt
aaaacgacggccagagaattcgagctcggtacctcgcgaatacatctagatggtctctacctGAAAAACGTGTTCCCACCCGAGGTCGCTGTGTT
TGAGCCATCAGAAGCAGAGATCTCCCACACCCAAAAGGCCACACTGGTGTGCCTGGCCACAGGCTTCTACCCCGACCACGTGGAGCTGAGCTGGT
GGGTGAATGGGAAGGAGGTGCACAGTGGGGTCAGCACAGACCCGCAGCCCCTCAAGGAGCAGCCCGCCTCAATGACTCCAGATACTGCCTGAGC
AGCCGCCTGAGGGTtTCGGCCACCTTCTGGCAGAACCCCCGCAACCACTTCCGCTGTCAAGTCCAGTTCTACGGGCTCTCGGAGAATGACGAGTG
GACCCAGGATAGGGCCAAACCTGTCACCCAGATCGTCAGCGCCGAGGCCTGGGGTAGAGCAGACTGTGGCTTCACCTCCGAGTCTTACCAGCAAG
GGGTCCTGTCTGCCACCATCCTCTATGAGATCTTGCTAGGGAAGGCCACCTTGTATGCCGTGCTGGTCAGTGCCCTCGTGCTGATGGCCATGGTC
AAGAGAAAGGATTCCAGAGGCAGGAgGAGGAGGagcggcagtggagtgaaacagactttgaattttgaccttctcaagttggcgggagacgtgga
gtccaacccagggcccatcggatcccgggccgtcgactgcagaggcctgcatgcaagcttggtgtaatcatggtcatagctgtttcctgtgtga
aattgttatccgctcacaattccacacaacatacgagccggaagcataaagtgtaaagcctggggtgcctaatgagtgagctaactcacattaat
tgcgttgcgctcactgcccgctttccagtcgggaaacctgtcgtgccagctgcattaatgaatcggccaacgcgcggggagaggcggtttgcgta
ttgggcgctcttccgcttcctcgctcactgactcgctgcgctcggtcgttcggctgcggcgagcggtatcagctcactcaaaggcggtaatacgg
ttatccacagaatcaggggataacgcaggaaagaacatgtgagcaaaaggccagcaaaaggccaggaaccgtaaaaaggccgcgttgctggcgtt
tttccataggctccgcccccctgacgagcatcacaaaaatcgacgctcaagtcagaggtggcgaaacccgacaggactataaagataccaggcgt
ttccccctggaagctccctcgtgcgctctcctgttccgaccctgccgcttaccggatacctgtccgcctttctcccttcgggaagcgtggcgctt
tctcatagctcacgctgtaggtatctcagttcggtgtaggtcgttcgctccaagctgggctgtgtgcacgaaccccccgttcagcccgaccgctg
cgccttatccggtaactatcgtcttgagtccaacccggtaagacacgacttatcgccactggcagcagccactggtaacaggattagcagagcga
ggtatgtaggcggtgctacagagttcttgaagtggtggcctaactacggctacactagaagaacagtatttggtatctgcgctctgctgaagcca
gttaccttcggaaaaagagttggtagctcttgatccggcaaacaaaccaccgctggtagcggtggtttttttgtttgcaagcagcagattacgcg
cagaaaaaaaggatctcaagaagatcctttgatcttttctacggggtctgacgctcagtggaacgaaaactcacgttaagggattttggtcatga
gattatcaaaaaggatcttcacctagatccttttaaattaaaaatgaagttttaaatcaagcccaatctgaataatgttacaaccaattaaccaa
ttctgattagaaaaactcatcgagcatcaaatgaaactgcaatttattcatatcaggattatcaataccatatttttgaaaaagccgtttctgta
atgaaggagaaaactcaccgaggcagttccataggatggcaagatcctggtatcggtctgcgattccgactcgtccaacatcaatacaacctatt
aatttccctcgtcaaaaataaggttatcaagtgagaaatcaccatgagtgacgactgaatccggtgagaatggcaaaagtttatgcatttcttt
ccagacttgttcaacaggccagccattacgctcgtcatcaaaatcactcgcatcaaccaaaccgttattcattcgtgattgcgcctgagcgagac
gaaatacgcgatcgctgttaaaaggacaattacaaacaggaatcgaatgcaaccggcgcaggaacactgccagcgcatcaacaatattttcacct
gaatcaggatattcttctaatacctggaatgctgtttttccggggatcgcagtggtgagtaaccatgcatcatcaggagtacggataaaatgatg
gatggtcggaagaggcataaattccgtcagccagtttagtctgaccatctcatctgtaacatcattggcaacgctaccttttgccatgtttcagaa
acaactctggcgcatcgggatcccatacaagcgatagattgtcgcacctgattgcccgacattatcgcgagcccatttatacccatataaatcag
catccatgttggaatttaatcgcggcctcgacgtttcccgttgaatatggctcataacacccttgtattactgtttatgtaagcagacagttttt
attgttcatgatgatatatttttatcttgtgcaatgtaacatcagagattttgagacacgggccagagctgca (SEQ ID NO: 154)
```

TRAV (46 total)
TRA V1-1
```
atgtggggagattccttctctatgtttccatgaagatgggaggcactgcaGGACAAAGCCTTGAGCAGCCCTCTGAAGTGACAGCTGTGGAAGGA
GCCATTGTCCAGATAAACTGCACGTACCAGACATCTGGGTTTATGGGCTGTCCTGGTACCAGCAACATGATGGCGGAGCACCCACATTTCTTTC
TTACAATGCTCTGGATGGTTTGGAGGAGACAGGTCGTTTTTCTTCATTCCTTAGTCGCTCTGATAGTTATGGTTACCTCCTTCTACAGGAGCTCC
AGATGAAAGACTCTGCCTCTTACtgagacc (SEQ ID NO: 155)
```

TRAV1-2
```
atgtggggagttttccttcttttatgtttccatgaagatgggaggcactacaGGACAAAACATTGACCAGCCCACTGAGATGACAGCTACGGAAGG
TGCCATTGTCCAGATCAACTGCACGTACCAGACATCTGGGTTCAACGGGCTGTTCTGGTACCAGCAACATGCTGGCGAAGCACCCACATTTCTGT
CTTACAATGTTCTGGATGGTTTGGAGGAGAAAGGTCGTTTTTCTTCATTCCTTAGTCGGTCTAAAGGGTACAGTTACCTCCTTTTGAAGGAGCTC
CAGATGAAAGACTCTGCCTCTTACtgagacc (SEQ ID NO: 156)
```

TRAV2
```
atggctttgcagagcactctggggcggtgtggctagggcttctcctcaactctctctggaaggttgcagaaagcAAGGACCAAGTGTTTCAGCC
TTCCACAGTGGCATCTTCAGAGGGAGCTGTGGTGGAAATCTTCTGTAATCACTCTGTGTCCAATGCTTACAACTTCTTCTGGTACCTTCACTTCC
CGGGATGTGCACCAAGACTCCTTGTTAAAGGCTCAAAGCCTTCTCAGCAGGGACGATACAACATGACCTATGAACGGTTCTCTTCATCGCTGCTC
ATCCTCCAGGTGCGGGAGGCAGATGCTGCTGTTTACtgagacc (SEQ ID NO: 157)
```

TRAV3
```
atggcctctgcacccatctcgatgcttgcgatgctcttcacattgagtgggctgagaGCTCAGTCAGTGGCTCAGCCGGAAGATCAGGTCAACGT
TGCTGAAGGGAATCCTCTGACTGTGAAATGCACCTATTCAGTCTCTGGAAACCCTTATCTTTTTTGGTATGTTCAATACCCCAACCGAGGCCTCC
AGTTCCTTCTGAAATACATCACAGGGGATAACCTGGTTAAAGGCAGCTATGGCTTTGAAGCTGAATTTAACAAGAGCCAAACCTCCTTCCACCTG
AAGAAACCATCTGCCCTTGTGAGCGACTCCGCTTTGTACtgagacc (SEQ ID NO: 158)
```

TRAV4
```
atgaggcaagtggcgagagtgatcgtgttcctgacccctgagtactttgagcCTTGCTAAGACCACCCAGCCCATCTCCATGGACTCATATGAAGG
ACAAGAAGTGAACATAACCTGTAGCCACAACAACATTGCTACAAATGATTATATCACGTGGTACCAACAGTTTCCCAGCCAAGGACCACGATTTA
TTATTCAAGGATACAAGACAAAAGTTACAAACGAAGTGGCCTCCCTGTTTATCCCTGCCGACAGAAAGTCCAGCACTCTGAGCCTGCCCCGGGTT
TCCCTGAGCGACACTGCTGTGTACtgagacc (SEQ ID NO: 159)
```

Sequence Listing

TRAV5
ATGAAGACATTTGCTGGATTTTCGTTCCTGTTTTTGTGGCTGCAGCTGGACTGTATGAGTAGAGGAGAGGATGTGGAGCAGAGTCTTTTCCTGAG
TGTCCGAGAGGGAGACAGCTCCGTTATAAACTGCACTTACACAGACAGCTCCTCCACCTACTTATACTGGTATAAGCAAGAACCTGGAGCAGGaC
TCCAGTTGCTGACGTATATTTTTTCAAATATGGACATGAAACAAGACCAAAGACTCACTGTTCTATTGAATAAAAAGGATAAACATCTGTCTCTG
CGCATTGCAGACACCCAGACTGGGGACTCAGCTATCTACtgagacc (SEQ ID NO: 160)

TRAV6
atggagtcattcctggggaggtgttttgctgattttgtggcttcaagtggactgggtgaagAGCCAAAAGATAGAACAGAATTCCGAGGCCCTGAA
CATTCAGGAGGGTAAAACGGCCACCCTGACCTGCAACTATACAAACTATTCCCCAGCATACTTACAGTGGTACCGACAAGATCCAGGAAGAGGCC
CTGTTTTCTTGCTACTCATACGTGAAAATGAGAAAGAAAAAGGAAAGAAAGACTGAAGGTCACCTTTGATACCACCCTTAAACAGAGTTTGTTT
CATATCACAGCCTCCCAGCCTGCAGACTCAGCTACCTACtgagacc (SEQ ID NO: 161)

TRAV7
atggagaagatgcggaggcctgtcctaattatattttgtctatgtcttggctgggcaaatggaGAAAACCAGGTGGAGCACAGCCCTCATTTTCT
GGGACCCCAGCAGGGAGACGTTGCCTCCATGAGCTGCACGTACTCTGTCAGTCGTTTTAACAATTTGCAGTGGTACAGGCAAATACAGGGATGG
GTCCCAAACACCTATTATCCATGTATTCAGCTGGATATGAGAAGCAGAAAGGAAGACTAAATGCTACATTACTGAAGAATGGAAGCAGCTTGTAC
ATTACAGCCGTGCAGCCTGAAGATTCAGCCACCTATtgagacc (SEQ ID NO: 162)

TRAV8-1
atgctcctgttgctcataccagtgctggggatgattttttgccctgagagatgccagaGCCCAGTCTGTGAGCCAGCATAACCACCACGTAATTCT
CTCTGAAGCAGCCTCACTGGAGTTGGGATGCAACTATTCCTATGGTGGAACTGTTAATCTCTTCTGGTATGTCCAGTACCCTGGTCAACACCTTC
AGCTTCTCCTCAAGTACTTTTCAGGGGATCCACTGGTTAAAGGCATCAAGGGCTTTGAGGCTGAATTTATAAAGAGTAAATTCTCCTTTAATCTG
AGGAAACCCTCTGTGCAGTGGAGTGACACAGCTGAGTACtgagacc (SEQ ID NO: 163)

TRAV8-2
atgctcctgctgctcgtcccagtgctcgaggtgattttttactctggggaggaaccagaGCCCAGTCGGTGACCCAGCTTGACAGCCACGTCTCTGT
CTCTGAAGGAACCCCGGTGCTGCTGAGGTGCAACTACTCATCTTCTTATTCACCATCTCTCTTCTGGTATGTGCAACACCCCAACAAAGGACTCC
AGCTTCTCCTGAAGTACACATCAGCGGCCACCCTGGTTAAAGGCATCAACGGTTTTGAGGCTGAATTTAAGAAGAGTGAAACCTCCTTCCACCTG
ACGAAACCCTCAGCCCATATGAGCGACGCGGCTGAGTACtgagacc (SEQ ID NO: 164)

TRAV8-3
atgctcctggagcttatcccactgctggggatacattttgtcctgagaactgccagaGCCCAGTCAGTGACCCAGCCTGACATCCACATCACTGT
CTCTGAAGGAGCCTCACTGGAGTTGAGATGTAACTATTCCTATGGGGCAACACCTTATCTCTTCTGGTATGTCCAGTCCCCCGGCCAAGGCCTCC
AGCTGCTCCTGAAGTACTTTTCAGGAGACACTCTGGTTCAAGGCATTAAAGGCTTTGAGGCTGAATTTAAGAGGAGTCAATCTTCCTTCAATCTG
AGGAAACCCTCTGTGCATTGGAGTGATGCTGCTGAGTACtgagacc (SEQ ID NO: 165)

TRAV8-4
atgctcctgctgctcgtcccagtgctcgaggtgattttttaccctggggaggaaccagaGCCCAGTCGGTGACCCAGCTTGGCAGCCACGTCTCTGT
CTCTGAAGGAGCCCTGGTTCTGCTGAGGTGCAACTACTCATCGTCTGTTCCACCATATCTCTTCTGGTATGTGCAATACCCCAACCAAGGACTCC
AGCTTCTCCTGAAGTACACATCAGCGGCCACCCTGGTTAAAGGCATCAACGGTTTTGAGGCTGAATTTAAGAAGAGTGAAACCTCCTTCCACCTG
ACGAAACCCTCAGCCCATATGAGCGACGCGGCTGAGTACtgagacc (SEQ ID NO: 166)

TRAV8-6
atgctcctgctgctcgtcccagcgttccaggtgattttttaccctgggaggaaccagaGCCCAGTCTGTGACCCAGCTTGACAGCCAAGTCCCTGT
CTTTGAAGAAGCCCCTGTGGAGCTGAGGTGCAACTACTCATCGTCTGTTTCAGTGTATCTCTTCTGGTATGTGCAATACCCCAACCAAGGACTCC
AGCTTCTCCTGAAGTATTTATCAGGATCCACCCTGGTTGAAAGCATCAACGGTTTTGAGGCTGAATTTAACAAGAGTCAAACTTCCTTCCACTTG
AGGAAACCCTCAGTCCATATAAGCGACACGGCTGAGTACtgagacc (SEQ ID NO: 167)

TRAV8-7
atgctcttagtggtcattctgctgcttggaatgttcttcacactgagaaccagaACCCAGTCGGTGACCCAGCTTGATGGCCACATCACTGTCTC
TGAAGAAGCCCCTCTGGAACTGAAGTGCAACTATTCCTATAGTGGAGTTCCTTCTCTCTTCTGGTATGTCCAATACTCTAGCCAAAGCCTCCAGC
TTCTCCTCAAAGACCTAACAGAGGCCACCCAGGTTAAAGGCATCAGAGGTTTTGAGGCTGAATTTAAGAAGAGCGAAACCTCCTTCTACCTGAGG
AAACCATCAACCCATGTGAGTGATGCTGCTGAGTACtgagacc (SEQ ID NO: 168)

TRAV9-1
atgaattatctccaggaccagcgattgcactattcttaatgtttgggggaatcaatGGAGATTCAGTGGTCCAGACAGAAGGCCAAGTGCTCCCC
TCTGAAGGGGATTCCCTGATTGTGAACTGCTCCTATGAAACCACACAGTACCCTTCCCTTTTTGGTATGTCCAATATCCTGGAGAAGGTCCACA
GCTCCACCTGAAAGCCATGAAGGCCAATGACAAGGGAAGGAACAAAGGTTTTGAAGCCATGTACCGTAAAGAAACCACTTCTTTCCACTTGGAGA
AAGACTCAGTTCAAGAGTCAGACTCCGCTGTGTACtgagacc (SEQ ID NO: 169)

TRAV9-2
atgaactattctccaggcttagtatctctgatactcttactgcttggaagaacccgtGGAAATTCAGTGACCCAGATGGAAGGGCCAGTGACTCT
CTCAGAAGAGGCCTTCCTGACTATAAACTGCACGTACACAGCCACAGGATACCCTTCCCTTTTCTGGTATGTCCAATATCCTGGAGAAGGTCTAC
AGCTCCTCCTGAAAGCCACGAAGGCTGATGACAAGGGAAGCAACAAAGGTTTTGAAGCCACATACCGTAAAGAAACCACTTCTTTCCACTTGGAG
AAAGGCTCAGTTCAAGTGTCAGACTCAGCGGTGTACtgagacc (SEQ ID NO: 170)

TRAV10
atgaaaaagcatctgacgaccttatggtgattttgtggctttatttttataggggaatggcAAAAACCAAGTGGAGCAGAGTCCTCAGTCCCTG
ATCATCCTGGAGGGAAAGAACTGCACTCTTCAATGCAATTATACAGTGAGCCCCTTCAGCAACTTAAGGTGGTATAAGCAAGATACTGGGAGAGG
TCCTGTTTCCCTGACAATCATGACTTTCAGTGAGAACACAAAGTCGAACGGAAGATATACAGCAACTCTGGATGCAGACACAAAGCAAAGCTCTC
TGCACATCACAGCCTCCCAGCTCAGCGATTCAGCCTCCTACtgagacc (SEQ ID NO: 171)

TRAV12-1
atgatatccttgagagttttactggtgatcctgtggcttcagttaagctgggtttggagccaaCGGAAGGAGGTGGAGCAGGATCCTGGACCCTT
CAATGTTCCAGAGGGAGCCACTGTCGCTTTCAACTGTACTTACAGCAACAGTGCTTCTCAGTCTTTCTTCTGGTACAGACAGGATTGCAGGAAG
AACCTAAGTTGCTGATGTCCGTATACTCCAGTGGTAATGAAGATGGAAGGTTTACAGCACAGCTCAATAGAGCCAGCCAGTATATTTCCCTGCTC
ATCAGAGACTCCAAGCTCAGTGATTCAGCCACCTACtgagacc (SEQ ID NO: 172)

Sequence Listing

TRAV12-2
atgaaatccttgagagttttactagtgatcctgtggcttcagttgagctgggtttggagccaaCAGAAGGAGGTGGAGCAGAATTCTGGACCCCT
CAGTGTTCCAGAGGGAGCCATTGCCTCTCTCAACTGCACTTACAGTGACCGAGGTTCCCAGTCCTTCTTCTGGTACAGACAATATTCTGGGAAAA
GCCCTGAGTTGATAATGTTCATATACTCCAATGGTGACAAAGAAGATGGAAGGTTTACAGCACAGCTCAATAAAGCCAGCCAGTATGTTTCTCTG
CTCATCAGAGACTCCCAGCCCAGTGATTCAGCCACCTACtgagacc (SEQ ID NO: 173)

TRAV12-3
atgatgaaatccttgagagttttactggtgatcctgtggcttcagttaagctgggtttggagccaaCAGAAGGAGGTGGAGCAGGATCCTGGACC
ACTCAGTGTTCCAGAGGGAGCCATTGTTTCTCTCAACTGCACTTACAGCAACAGTGCTTTTCAATACTTCATGTGGTACAGACAGTATTCCAGAA
AAGGCCCTGAGTTGCTGATGTACACATACTCCAGTGGTAACAAAGAAGATGGAAGGTTTACAGCACAGGTCGATAAATCCAGCAAGTATATCTCC
TTGTTCATCAGAGACTCACAGCCCAGTGATTCAGCCACCTACtgagacc (SEQ ID NO: 174)

TRAV13-1
atgacatccattcgagctgtatttatattcctgtggctgcagctggacttggtgaatGGAGAGAATGTGGAGCAGCATCCTTCAACCCTGAGTGT
CCAGGAGGGAGACAGCGCTGTTATCAAGTGTACTTATTCAGACAGTGCCTCAAACTACTTCCCTTGGTATAAGCAAGAACTTGGAAAAGGACCTC
AGCTTATTATAGACATTCGTTCAAATGTGGGCGAAAAGAAAGACCAACGAATTGCTGTTACATTGAACAAGACAGCCAAACATTTCTCCCTGCAC
ATCACAGAGACaCAACCTGAAGACTCGGCTGTCTACtgagacc (SEQ ID NO: 175)

TRAV13-2
atggcaggcattcgagctttatttatgtacttgtggctgcagctggactgggtgagcagaGGAGAGAGTGTGGGGCTGCATCTTCCTACCCTGAG
TGTCCAGGAGGGTGACAACTCTATTATCAACTGTGCTTATTCAAACAGCGCCTCAGACTACTTCATTTGGTACAAGCAAGAATCTGGAAAAGGTC
CTCAATTCATTATAGACATTCGTTCAAATATGGACAAAAGGCAAGGCCAAAGAGTCACCGTTTTATTGAATAAGACAGTGAAACATCTCTCTCTG
CAAATTGCAGCTACTCAACCTGGAGACTCAGCTGTCTACtgagacc (SEQ ID NO: 176)

TRAV14
atgtcactttctagcctgctgaaggtggtcacagcttcactgtggctaggacctggcattGCCCAGAAGATAACTCAAACCCAACCAGGAATGTT
CGTGCAGGAAAAGGAGGCTGTGACTCTGGACTGCACATATGACACCAGTGATCCAAGTTATGGTCTATTCTGGTACAAGCAGCCCAGCAGTGGGG
AAATGATTTTTCTTATTTATCAGGGGTCTTATGACCAGCAAAATGCAACAGAAGGTCGCTACTCATTGAATTTCCAGAAGGCAAGAAAATCCGCC
AACCTTGTCATCTCCGCTTCACAACTGGGGGACTCAGCAATGTACtgagacc (SEQ ID NO: 177)

TRAV16
atgaagcccaccctcatctcagtgcttgtgataatatttatactcagaggaacaagaGCCCAGAGAGTGACTCAGCCCGAGAAGCTCCTCTCTGT
CTTTAAAGGGGCCCCAGTGGAGCTGAAGTGCAACTATTCCTATTCTGGGAGTCCTGAACTCTTCTGGTATGTCCAGTACTCCAGACAACGCCTCC
AGTTACTCTTGAGACACATCTCTAGAGAGAGCATCAAAGGCTTCACTGCTGACCTTAACAAAGGCGAGACATCTTTCCACCTGAAGAAACCATTT
GCTCAAGAGGAAGACTCAGCCATGTATgagacc (SEQ ID NO: 178)

TRAV17
atggaaactctcctgggagtgtctttggtgattctatggcttcaactggctagggtgaacAGTCAACAGGGAGAAGAGGATCCTCAGGCCTTGAG
CATCCAGGAGGGTGAAAATGCCACCATGAACTGCAGTTACAAAACTAGTATAAACAATTTACAGTGGTATAGACAAAATTCAGGTAGAGGCCTTG
TCCACCTAATTTTAATACGTTCAAATGAAAGAGAGAAACACAGTGGAAGATTAAGAGTCACGCTTGACACTTCCAAGAAAAGCAGTTCCTTGTTG
ATCACGGCTTCCCGGGCAGCAGACACTGCTTCTTACtgagacc (SEQ ID NO: 179)

TRAV18
atgctgtctgatcctgctcaggacttgtgatcttgttgatattcagaaggaccagtGGAGACTCGGTTACCCAGACAGAAGGCCCAGTTACCCTC
CCTGAGAGGGCAGCTCTGACATTAAACTGCACTTATCAGTCCAGCTATTCAACTTTTCTATTCTGGTATGTCCAGTATCTAAACAAAGAGCCTGA
GCTCCTCCTGAAAAGTTCAGAAAACCAGGAGACGGACAGCAGAGGTTTTCAGGCCAGTCCTATCAAGAGTGACAGTTCCTTCCACCTGGAGAAGC
CCTCGGTGCAGCTGTCGGACTCTGCCGTGTACtgagacc (SEQ ID NO: 180)

TRAV19
atgctgactgccagcctgttgagggcagtcatagcctccatctgtgttgtatccagcatgGCTCAGAAGGTAACTCAAGCGCAGACTGAAATTTC
TGTGGTGGAGAAGGAGGATGTGACCTTGGACTGTGTGTATGAAACCCGTGATACTACTTATTACTTATTCTGGTACAAGCAACCACCAAGTGGAG
AATTGGTTTTCCTTATTCGTCGGAACTCTTTTGATGAGCAAAATGAAATAAGTGGTCGGTATTCTTGGAACTTCCAGAAATCCACCAGTTCCTTC
AACTTCACCATCACAGCCTCACAAGTCGTGGACTCAGCAGTATACtgagacc (SEQ ID NO: 181)

TRAV20
atggagaaaatgttggagtgtgcattcatagtatgtggatcagcttggctggttgagtggaGAAGACCAGGTGACGCAGAGTCCCGAGGCCCTGA
GACTCCAGGAGGGAGAGAGTAGCAGTCTTAACTGCAGTTACACAGTCAGCGGTTTAAGAGGGCTGTTCTGGTATAGGCAAGATCCTGGGAAAGGC
CCTGAATTCCTCTTCACCCTGTATTCAGCTGGGGAAGAAAAGGAGAAAGAAAGGCTAAAAGCCACATTAACAAAGAAGGAAAGCTTTCTGCACAT
CACAGCCCCTAAACCTGAAGACTCAGCCACTTATgagacc (SEQ ID NO: 182)

TRAV21
atggagacactcttgggcctgcttatcctttggctgcagctgcaatgggtgagcagcAAACAGGAGGTGACGCAGATTCCTGCAGCTCTGAGTGT
CCCAGAAGGAGAAACTTGGTTCTCAACTGCAGTTTCACTGATAGCGCTATTTACAACCTCCAGTGGTTTAGGCAGGACCCTGGGAAGGaCTCA
CATCTCTGTTGCTTATTCAGTCAAGTCAGAGAGAGCAAACAAGTGGAAGACTTAATGCCTCGCTGGATAAATCATCAGGACGTAGTACTTTATAC
ATTGCAGCTTCTCAGCCTGGTGACTCAGCCACCTACtgagacc (SEQ ID NO: 183)

TRAV22
atgaagaggatattgggagctctgctggggctcttgagtgcccaggtttgctgtgtgagaGGAATACAAGTGGAGCAGAGTCCTCCAGACCTGAT
TCTCCAGGAGGGAGCCAATTCCACGCTGCGGTGCAATTTTTCTGACTCTGTGAACAATTTGCAGTGGTTTCATCAAAACCCTTGGGGACAGCTCA
TCAACCTGTTTTACATTCCCTCAGGGACAAAACAGAATGGAAGATTAAGCGCCACGACTGTCGCTACGGAACGCTACAGCTTATTGTACATTTCC
TCTTCCCAGACCACAGACTCAGGCGTTTATtgagacc (SEQ ID NO: 184)

```
Sequence Listing

TRAV23
atggacaagatcttaggagcatcattttagttctgtggcttcaactatgctgggtgagtggccaacagaaggagaaaagtgacCAGCAGCAGGT
GAAACAAAGTCCTCAATCTTTGATAGTCCAGAAAGGAGGGATTTCAATTATAAACTGTGCTTATGAGAACACTGCGTTTGACTACTTTCCATGGT
ACCAACAATTCCCTGGGAAAGGCCCTGCATTATTGATAGCCATACGTCCAGATGTGAGTGAAAAGAAAGAAGGAAGATTCACAATCTCCTTCAAT
AAAAGTGCCAAGCAGTTCTCATTGCATATCATGGATTCCCAGCCTGGAGACTCAGCCACCTACtgagacc (SEQ ID NO: 185)

TRAV24
atggagaagaatcctttggcagcccccattactaatcctctggtttcatcttgactgcgtgagcagcATACTGAACGTGGAACAAAGTCCTCAGTC
ACTGCATGTTCAGGAGGGAGACAGCACCAATTTCACCTGCAGCTTCCCTTCCAGCAATTTTTTATGCCTTACACTGGTACAGATGGGAAACTGCAA
AAAGCCCCGAGGCCTTGTTTGTAATGACTTTAAATGGGGATGAAAAGAAGAAAGGACGAATAAGTGCCACTCTTAATACCAAGGAGGGTTACAGC
TATTTGTACATCAAAGGATCCCAGCCTGAAGACTCAGCCACATACtgagacc (SEQ ID NO: 186)

TRAV25
atgctactcatcacatcaatgttggtatatggatgcaattgtcacaggtgaatGGACAACAGGTAATGCAAATTCCTCAGTACCAGCATGTACAA
GAAGGAGAGGACTTCACCACGTACTGCAATTCCTCAACTACTTTAAGCAATATACAGTGGTATAAGCAAAGGCCTGGTGGACATCCCGTTTTTTT
GATACAGTTAGTGAAGAGTGGAGAAGTGAAGAAGCAGAAAAGACTGACATTTCAGTTTGGAGAAGCAAAAAAGAACAGCTCCCTGCACATCACAG
CCACCCAGACTACAGATGTAGGAACCTACtgagacc (SEQ ID NO: 187)

TRAV26-1
atgaggctggtggcaagagtaactgtgtttctgacctttggaactataattGATGCTAAGACCACCCAGCCCCCCTCCATGGATTGCGCTGAAGG
AAGAGCTGCAAACCTGCCTTGTAATCACTCTACCATCAGTGGAAATGAGTATGTGTATTGGTATCGACAGATTCACTCCCAGGGGCCACAGTATA
TCATTCATGGTCTAAAAAACAATGAAACCAATGAAATGGCCTCTCTGATCATCACAGAAGACAGAAAGTCCAGCACCTTGATCCTGCCCCACGCT
ACGCTGAGAGACACTGCTGTGTACtgagacc (SEQ ID NO: 188)

TRAV26-2
atgaagttggtgacaagcattactgtactcctatctttgggtattatgggtGATGCTAAGACCACACAGCCCAAATTCAATGGAGAGTAACGAAGA
AGAGCCTGTTCACTTGCCTTGTAACCACTCCACAATCAGTGGAACTGATTACATACATTGGTATCGACAGCTTCCCTCCCAGGGTCCAGAGTACG
TGATTCATGGTCTTACAAGCAATGTGAACAACAGAATGGCCTCTCTGGCAATCGCTGAAGACAGAAAGTCCAGTACCTTGATCCTGCACCGTGCT
ACCTTGAGAGATGCTGCTGTGTACtgagacc (SEQ ID NO: 189)

TRAV27
atggtcctgaaattctccgtgtccattctttggattcagttggcatgggtgagcACCCAGCTGCTGGAGCAGAGCCCTCAGTTTCTAAGCATCCA
AGAGGGAGAAAATCTCACTGTGTACTGCAACTCCTCAAGTGTTTTTTCCAGCTTACAATGGTACAGACAGGAGCCTGGGGAAGGTCCTGTCCTCC
TGGTGACAGTAGTTACGGGTGGAGAAGTGAAGAAGCTGAAGAGACTAACCTTTCAGTTTGGTGATGCAAGAAAGGACAGTTCTCTCCACATCACT
GCAGCCCAGCCTGGTGATACAGGCCTCTACtgagacc (SEQ ID NO: 190)

TRAV29
atggccatgctcctgggggcatcagtgctgattctgtggcttcagccagactgggtaaacagtcaacagaagaatgatGACCAGCAAGTTAAGCA
AAATTCACCATCCCTGAGCGTCCAGGAAGGAAGAATTTCTATTCTGAACTGTGACTATACTAACAGCATGTTTGATTATTTCCTATGGTACAAAA
ATACCCTGCTGAAGGTCCTACATTCCTGATATCTATAAGTTCCATTAAGGATAAAAATGAAGATGGAAGATTCACTGTCTTCTTAAACAAAAGT
GCCAAGCACCTCTCTCTGCACATTGTGCCCTCCCAGCCTGGAGACTCTGCAGTGTACtgagacc (SEQ ID NO: 191)

TRAV30
atggagactctcctgaaagtgcttttcaggcaccttgttgtggcagttgacctgggtgagaagcCAACAACCAGTGCAGAGTCCTCAAGCCGTGAT
CCTCCGAGAAGGGGAAGATGCTGTCATCAACTGCAGTTCCTCCAAGGCTTTATATTCTGTACACTGGTACAGGCAGAAGCATGGTGAAGCACCCG
TCTTCCTGATGATATTACTGAAGGGTGGAGAACAGAAGGGTCATGAAAAAATATCTGCTTCATTTAATGAAAAAAAAGCAGCAAAGCTCCCTGTAC
CTTACGGCCTCCCAGCTCAGTTACTCAGGAACCTACtgagacc (SEQ ID NO: 192)

TRAV34
atggagactgttctgcaagtactcctaggatattgggttccaagcagcctgggtcagtAGCCAAGAACTGGAGCAGAGTCCTCAGTCCTTGAT
CGTCCAAGAGGGAAGAATCTCACCATAAACTGCACGTCATCAAAGACGTTATATGGCTTATACTGGTATAAGCAAAGTATGGTGAAGGTCTTA
TCTTCTTGATGATGCTACAGAAAGGTGGGGAAGAGAAAAGTCATGAAAAGATAACTGCCAAGTTGGATGAGAAAAAGCAGCAAAGTTCCCTGCAT
ATCACAGCCTCCCAGCCCAGCCATGCAGGCATCTACtgagacc (SEQ ID NO: 193)

TRAV35
atgctccttgaacatttattaataatcttgtggatgcagctgacatgggtcagtGGTCAACAGCTGAATCAGAGTCCTCAATCTATGTTTATCCA
GGAAGGAGAAGATGTCTCCATGAACTGCACTTCTTCAAGCATATTTAACACCTGGCTATGGTACAAGCAGGAACCTGGGGAAGGTCCTGTCCTCT
TGATAGCCTTATATAAGGCTGGTGAATTGACCTCAAATGGAAGACTGACTGCTCAGTTTGGTATAACCAGAAAGGACAGCTTCCTGAATATCTCA
GCATCCATACCTAGTGATGTAGGCATCTACtgagacc (SEQ ID NO: 194)

TRAV36
atgatgaagtgtccacacaggctttactagctatcttttggcttctactgagctgggtgagcagtGAAGACAAGGTGGTACAAAGCCCTCTATCTCT
GGTTGTCCACGAGGGAGACACCGTAACTCTCAATTGCAGTTATGAAGTGACTAACTTTCGAAGCCTACTATGGTACAAGCAGGAAAAGAAAGCTC
CCACATTTCTATTTATGCTAACTTCAAGTGGAATTGAAAAGAAGTCAGGAAGACTAAGTAGCATATTAGATAAGAAAGAACTTTCCAGCATCCTG
AACATCACAGCCACCCAGACCGGAGACTCGGCCATCTACtgagacc (SEQ ID NO: 195)

TRAV38-1
atgacacgagttagcttgctgtgggcagtcgtggtgtccacctgtcttgaatccggcatgGCCCAGACAGTCACTCAGTCTCAACCAGAGATGTC
TGTGCAGGAGGCAGAGACTGTGACCCTGAGTTGCACATATGACACCAGTGAGAATAATTATTATTTGTTCTGGTACAAGCAGCCTCCCAGCAGGC
AGATGATTCTCGTTATTCGCCAAGAAGCTTATAAGCAACAGAATGCAACGGAGAATCGTTTCTCTGTGAACTTCCAGAAAGCAGCCAAATCCTTC
AGTCTCAAGATCTCAGACTCACAGCTGGGGGACACTGCGATGTATtgagacc (SEQ ID NO: 196)

TRAV38-2
atggcatgccctggatcctgtgggcacttgtgatctccacctgtcttgaatttagcatgGCTCAGACAGTCACTCAGTCTCAACCAGAGATGTCT
GTGCAGGAGGCAGAGACaGTGACCCTGAGCTGCACATATGACACCAGTGAGAGTGATTATTATTTATTCTGGTACAAGCAGCCTCCCAGCAGGCA
GATGATTCTCGTTATTCGCCAAGAAGCTTATAAGCAACAGAATGCAACAGAGAATCGTTTCTCTGTGAACTTCCAGAAAGCAGCCAAATCCTTCA
GTCTCAAGATCTCAGACTCACAGCTGGGGGATGCCGCGATGTATtgagacc (SEQ ID NO: 197)
```

Sequence Listing

TRAV39
atgaagaagctactagcaatgattctgtggcttcaactagaccgcttaagtggaGAGCTGAAAGTGGAACAAAACCCTCTGTTCCTGAGCATGCA
GGAGGGAAAAAACTATACCATCTACTGCAATTATTCAACCACTTCAGACAGACTGTATTGGTACAGGCAGGATCCTGGGAAAAGTCTGGAATCTC
TGTTTGTGTTGCTATCAAATGGAGCAGTGAAGCAGGAGGGACGATTAATGGCCTCACTTGATACCAAAGCCCGTCTCAGCACCCTCCACATCACA
GCTGCCGTGCATGACCTCTCTGCCACCTACtgagacc (SEQ ID NO: 198)

TRAV40
atgaactcctctctggactttctaattctgatcttaatgtttggaggaaccagcAGCAATTCAGTCAAGCAGACGGGCCAAATAACCGTCTCGGA
GGGAGCATCTGTGACTATGAACTGCACATACACATCCACGGGGTACCCTACCCTTTTCTGGTATGTGGAATACCCCAGCAAACCTCTGCAGCTTC
TTCAGAGAGAGACAATGGAAAACAGCAAAAACTTCGGAGGCGGAAATATTAAAGACAAAAACTCCCCCATTGTGAAATATTCAGTCCAGGTATCA
GACTCAGCCGTGTACtgagacc (SEQ ID NO: 199)

TRAV41
atggtgaagatccggcaattttttgttggctattttgtggcttcagctaagctgtgtaagtgccgccAAAAATGAAGTGGAGCAGAGTCCTCAGAA
CCTGACTGCCCAGGAAGGAGAATTTATCACAATCAACTGCAGTTACTCGGTAGGAATAAGTGCCTTACACTGGCTGCAACAGCATCCAGGAGGAG
GCATTGTTTCCTTGTTTATGCTGAGCTCAGGGAAGAAGAAGCATGGAAGATTAATTGCCACAATAAACATACAGGAAAAGCACAGCTCCCTGCAC
ATCCAGCCTCCCATCCCAGAGACTCTGCCGTCTACtgagacc (SEQ ID NO: 200)

"master pUC57-Kan Ca short" = following sequence in pUC57-Kan backbone
ggtggtggtggttctggttctggttctggtggtggttctggtggtggtctcTtGACCCTGCCGTGTACCAGCTGAGAGACTCTAAATCCAGTGAC
AAGTCTGTCTGCCTATTCACCGATTTTGATTCTCAAACAAATGTGTCACAAAGTAAGGATTCTGATGTGTATATCACAGACAAAACTGTGCTAGA
CATGAGGTCTATGGACTTCAAGAGCAACAGTGCTGTGGCCTGGAGCAACAAATCTGACTTTGCATGTGCAAACGCCTTCAACAACAGCATTATTC
CAGAAGAcACCTTCTTCCCCAGCCCAGAAAGTTCCTGTGATGTCAAGCTGGTCGAGAAAAGCTTTGAAACAGATACGAACCTAAACTTTCAAAAC
CTGTCAGTGATTGGGTTCCGAATCCTCCTCCTGAAAGTGGCCGGGTTTAATCTGCTCATGACGCTGCGGCTGTGGTCCAGCTAAagcggccgcgt
cgacaatcaa (SEQ ID NO: 201)

Full "master pUC57-Kan Ca short"
tcgcgcgtttcggtgatgacggtgaaaacctctgacacatgcagctcccggagacggtcacagcttgtctgtaagcggatgccgggagcagacaa
gcccgtcagggcgcgtcagcgggtgttggcgggtgtcggggctggcttaactatgcggcatcagagcagattgtactgagagtgcaccatatgcg
gtgtgaaataccgcacagatgcgtaaggagaaaataccgcatcaggcgccattcgccattcaggctgcgcaactgttgggaagggcgatcggtgc
gggcctcttcgctattacgccagctggcgaaaggggggatgtgctgcaaggcgattaagttgggtaacgccagggttttcccagtcacgacgttgt
aaaacgacggccagagaattcgagctcggtacctcgcgaatacatctagatggtggtggtggttctggttctggttctggtggtggttctggtgg
tggtctcTtGACCCTGCCGTGTACCAGCTGAGAGACTCTAAATCCAGTGACAAGTCTGTCTGCCTATTCACCGATTTTGATTCTCAAACAAATGT
GTCACAAAGTAAGGATTCTGATGTGTATATCACAGACAAAACTGTGCTAGACATGAGGTCTATGGACTTCAAGAGCAACAGTGCTGTGGCCTGGA
GCAACAAATCTGACTTTGCATGTGCAAACGCCTTCAACAACAGCATTATTCCAGAAGAcACCTTCTTCCCCAGCCCAGAAAGTTCCTGTGATGTC
AAGCTGGTCGAGAAAAGCTTTGAAACAGATACGAACCTAAACTTTCAAAACCTGTCAGTGATTGGGTTCCGAATCCTCCTCCTGAAAGTGGCCGG
GTTTAATCTGCTCATGACGCTGCGGCTGTGGTCCAGCTAAagcggccgcgtcgacaatcaaatcggatcccgggcccgtcgactgcagaggcctg
catgcaagcttggtgtaatcatggtcatagctgtttcctgtgtgaaattgttatccgctcacaattccacacaacatacgagccggaagcataaa
gtgtaaagcctggggtgcctaatgagtgagctaactcacattaattgcgttgcgctcactgcccgctttccagtcgggaaacctgtcgtgccagc
tgcattaatgaatcggccaacgcgcggggagaggcggtttgcgtattgggcgctcttccgcttcctcgctcactgactcgctgcgctcggtcgtt
cggctgcggcgagcggtatcagctcactcaaaggcggtaatacggttatccacagaatcaggggataacgcaggaaagaacatgtgagcaaaagg
ccagcaaaaggccaggaaccgtaaaaaggccgcgttgctggcgtttttccataggctccgcccccctgacgagcatcacaaaaatcgacgctcaa
gtcagaggtggcgaaacccgacaggactataaagataccaggcgtttccccctggaagctccctcgtgcgctctcctgttccgaccctgccgctt
accggatacctgtccgcctttctcccttcgggaagcgtggcgctttctcatagctcacgctgtaggtatctcagttcggtgtaggtcgttcgctc
caagctgggctgtgtgcacgaaccccccgttcagcccgaccgctgcgccttatccggtaactatcgtcttgagtccaacccggtaagacacgact
tatcgccactggcagcagccactggtaacaggattagcagagcgaggtatgtaggcggtgctacagagttcttgaagtggtggcctaactacggc
tacactagaagaacagtatttggtatctgcgctctgctgaagccagttaccttcggaaaaagagttggtagctcttgatccggcaaacaaaccac
cgctggtagcggtggtttttttgtttgcaagcagcagattacgcgcagaaaaaaaggatctcaagaagatcctttgatcttttctacgggggtctg
acgctcagtggaacgaaaactcacgttaagggattttggtcatgagattatcaaaaaggatcttcacctagatccttttaaattaaaaatgaagt
tttaaatcaagcccaatctgaataatgttacaaccaattaaccaattctgattagaaaaactcatcgagcatcaaatgaaactgcaatttattca
tatcaggattatcaataccatattttgaaaaagccgtttctgtaatgaaggagaaaactcaccgaggcagttccataggatggcaagatcctgg
tatcggtctgcgattccgactcgtccaacatcaatacaacctattaatttccctcgtcaaaaataaggttatcaagtgagaaatcaccatgagt
gacgactgaatccggtgagaatggcaaaagtttatgcatttctttccagacttgttcaacaggccagccattacgctcgtcatcaaaatcactcg
catcaaccaaaccgttattcattcgtgattgcgcctgagcgagacgaaatacgcgatcgctgttaaaaggacaattacaaacaggaatcgaatgc
aaccggcgcaggaacactgccagcgcatcaacaatatttcacctgaatcaggatattatctaatacctggaatgctgttttccggggatcgca
gtggtgagtaaccatgcatcatcaggagtacggataaaatgcttgatggtcggaagaggcataaattccgtcagccagtttagtctgaccatctca
tctgtaacatcattggcaacgctacctttgccatgtttcagaaacaactctggcgcatcgggcttcccatacaagcgatagattgtcgcacctga
ttgcccgacattatcgcgagcccatttataccatataaatcagcatccatgttggaatttaatcgcggcctcgacgtttcccgttgaatatggc
tcataacacccccttgtattactgtttatgtaagcagacagttttattgttcatgatgatatatttttatcttgtgcaatgtaacatcagagattt
tgagacacgggccagagctgca (SEQ ID NO: 202)

"master pUC57-Kan Ca" = following sequence in pUC57-Kan backbone
ggtggtggtggttctggttctggttctggtggtggttctggtggtggtctcTgaacCCTGACCCTGCCGTGTACCAGCTGAGAGACTCTAAATCC
AGTGACAAGTCTGTCTGCCTATTCACCGATTTTGATTCTCAAACAAATGTGTCACAAAGTAAGGATTCTGATGTGTATATCACAGACAAAACTGT
GCTAGACATGAGGTCTATGGACTTCAAGAGCAACAGTGCTGTGGCCTGGAGCAACAAATCTGACTTTGCATGTGCAAACGCCTTCAACAACAGCA
TTATTCCAGAAGAcACCTTCTTCCCCAGCCCAGAAAGTTCCTGTGATGTCAAGCTGGTCGAGAAAAGCTTTGAAACAGATACGAACCTAAACTTT
CAAAACCTGTCAGTGATTGGGTTCCGAATCCTCCTCCTGAAAGTGGCCGGGTTTAATCTGCTCATGACGCTGCGGCTGTGGTCCAGCTAAagcgg
ccgcgtcgacaatcaa (SEQ ID NO: 203)

Full "master pUC57-Kan Ca"
tcgcgcgtttcggtgatgacggtgaaaacctctgacacatgcagctcccggagacggtcacagcttgtctgtaagcggatgccgggagcagacaa
gcccgtcagggcgcgtcagcgggtgttggcgggtgtcggggctggcttaactatgcggcatcagagcagattgtactgagagtgcaccatatgcg
gtgtgaaataccgcacagatgcgtaaggagaaaataccgcatcaggcgccattcgccattcaggctgcgcaactgttgggaagggcgatcggtgc
gggcctcttcgctattacgccagctggcgaaaggggggatgtgctgcaaggcgattaagttgggtaacgccagggttttcccagtcacgacgttgt
aaaacgacggccagagaattcgagctcggtacctcgcgaatacatctagatggtggtggtggttctggttctggttctggtggtggttctggtgg

Sequence Listing

```
tggtctcTgaacCCTGACCCTGCCGTGTACCAGCTGAGAGACTCTAAATCCAGTGACAAGTCTGTCTGCCTATTCACCGATTTTGATTCTCAAAC
AAATGTGTCACAAAGTAAGGATTCTGATGTGTATATCACAGACAAAACTGTGCTAGACATGAGGTCTATGGACTTCAAGAGCAACAGTGCTGTGG
CCTGGAGCAACAAATCTGACTTTGCATGTGCAAACGCCTTCAACAACAGCATTATTCCAGAAGAcACCTTCTTCCCCAGCCCAGAAAGTTCCTGT
GATGTCAAGCTGGTCGAGAAAAGCTTTGAAACAGATACGAACCTAAACTTTCAAAACCTGTCAGTGATTGGGTTCCGAATCCTCCTCCTGAAAGT
GGCCGGGTTTAATCTGCTCATGACGCTGCGGCTGTGGTCCAGCTAAagcggccgcgtcgacaatcaaatcggatcccggcccgtcgactgcaga
ggcctgcatgcaagcttggtgtaatcatggtcatagctgtttcctgtgtgaaattgttatccgctcacaattccacacaacatacgagccggaag
cataaagtgtaaagcctggggtgcctaatgagtgagctaactcacattaattgcgttgcgctcactgcccgctttccagtcgggaaacctgtcgt
gccagctgcattaatgaatcggccaacgcgcggggagaggcggtttgcgtattgggcgctcttccgcttcctcgctcactgactcgctgcgctcg
gtcgttcggctgcggcgagcggtatcagctcactcaaaggcggtaatacggttatccacagaatcaggggataacgcaggaaagaacatgtgagc
aaaaggccagcaaaaggccaggaaccgtaaaaaggccgcgttgctggcgtttttccataggctccgcccccctgacgagcatcacaaaaatcgac
gctcaagtcagaggtggcgaaacccgacaggactataaagataccaggcgtttccccctggaagctccctcgtgcgctctcctgttccgaccctg
ccgcttaccggatacctgtccgcctttctcccttcgggaagcgtggcgctttctcatagctcacgctgtaggtatctcagttcggtgtaggtcgt
tcgctccaagctgggctgtgtgcacgaaccccccgttcagcccgaccgctgcgccttatccggtaactatcgtcttgagtccaacccggtaagac
acgacttatcgccactggcagcagccactggtaacaggattagcagagcgaggtatgtaggcggtgctacagagtcttgaagtggtggcctaac
tacggctacactagaagaacagtatttggtatctgcgctctgctgaagcagttaccttcggaaaaagagttggtagctcttgatccggcaaaca
aaccaccgctggtagcggtggtttttttgtttgcaagcagcagattacgcgcagaaaaaaaggatctcaagaagatcctttgatcttttctacgg
ggtctgacgctcagtggaacgaaaactcacgttaagggattttggtcatgagattatcaaaaaggatcttcacctagatccttttaaattaaaaa
tgaagttttaaatcaagcccaatctgaataatgttacaaccaattaaccaattctgattagaaaactcatcgagcatcaaatgaaactgcaatt
tattcatatcaggattatcaataccatattttgaaaaagccgtttctgtaatgaaggagaaaactcaccgaggcagttccataggatggcaaga
tcctggtatcggtctgcgattccgactcgtccaacatcaatacaacctattaatttccccctcgtcaaaaataaggttatcaagtgagaaatcacc
atgagtgacgactgaatccggtgagaatggcaaaagtttatgcatttctttccagacttgttcaacaggccagccattacgctcgtcatcaaaat
cactcgcatcaaccaaaccgttattcattcgtgattgcgcctgagcgagacgaaatacgcgatcgctgttaaaaggacaattacaaacaggaatc
gaatgcaaccggcgcaggaacactgccagcgcatcaacaatattttcacctgaatcaggatattatctaatacctggaatgctgttttccgggg
atcgcagtggtgagtaaccatgcatcatcaggagtacggataaaatgcttgatggtcggaagaggcataaattccgtcagccagtttagtctgac
catctcatctgtaacatcattggcaacgctacctttgccatgtttcagaaacaactctggcgcatcgggcttcccataccaagcgatagattgtcg
cacctgattgcccgacattatcgcgagcccatttatacccatataaatcagcatccatgttggaatttaatcgcggcctcgacgtttcccgttga
atatggctcataacaccccatgtattactgtttatgtaagcagacagttttattgttcatgatgatatattttatcttgtgcaatgtaacatcag
agattttgagacacgggccagagctgca (SEQ ID NO: 204)
```

TRBV (54 total)

TRBV2
```
ggggatccaccggtcgccaccatggatacctggctcgtatgctgggcaattttttagtctcttgaaagcaggactcacagaaCCTGAAGTCACCCA
GACTCCCAGCCATCAGGTCACACAGATGGGACAGGAAGTGATCTTGCGCTGTGTCCCCATCTCTAATCACTTATACTTCTATTGGTACAGACAAA
TCTTGGGGCAGAAAGTCGAGTTTCTGGTTTCCTTTTATAATAATGAAATCTCAGAGAAGTCTGAAATATTCGATGATCAATTCTCAGTTGAAAGG
CCTGATGGATCAAATTTCACTCTGAAGATCCGGTCCACAAAGCTGGAGGACTCAGCCATGTACgagacctaa (SEQ ID NO: 205)
```

TRBV3-1
```
ggggatccaccggtcgccaccatgggctgcaggctcctctgctgtggtcttctgcctcctccaagcaggtcccttgGACACAGCTGTTTCCCA
GACTCCAAAATACCTGGTCACACAGATGGGAAACGACAAGTCCATTAAATGTGAACAAAATCTGGGCCATGATACTATGTATTGGTATAAACAGG
ACTCTAAGAAATTTCTGAAGATAATGTTTAGCTACAATAATAAGGAGCTCATTATAAATGAAACAGTTCCAAATCGCTTCTCACCTAAATCTCCA
GACAAAGCTCACTTAAATCTTCACATCAATTCCCTGGAGCTTGGTGACTCTGCTGTGTATgagacctaa (SEQ ID NO: 206)
```

TRBV4-1
```
ggggatccaccggtcgccaccatgggctgcaggctgctctgctgtgcggttctctgtctcctgggagcagttcccataGACACTGAAGTTACCCA
GACACCAAAACACCTGGTCATGGGAATGACAAATAAGAAGTCTTTGAAATGTGAACAACATATGGGGCACAGGGCTATGTATTGGTACAAGCAGA
AAGCTAAGAAGCCACCGGAGCTCATGTTTGTCTACAGCTATGAGAAATCTCTATAAATGAAAGTGTGCCAAGTCGCTTCTCACCTGAATGCCCC
AACAGCTCTCTCTTAAACCTTCACCTACACGCCCTGCAGCCAGAAGACTCAGCCCTGTATgagacctaa (SEQ ID NO: 207)
```

TRBV4-2
```
ggggatccaccggtcgccaccatgggctgcaggctgctctgctgtgcggttctctgtctcctgggagcggtcccatgGAAACGGGAGTTACGCA
GACACCAAGACACCTGGTCATGGGAATGACAAATAAGAAGTCTTTGAAATGTGAACAACATCTGGGGCATAACGCTATGTATTGGTACAAGCAAA
GTGCTAAGAAGCCACTGGAGCTCATGTTTGTCTACAACTTTAAAGAACAGACTGAAAACAACAGTGTGCCAAGTCGCTTCTCACCTGAATGCCCC
AACAGCTCTCACTTATTCCTTCACCTACACACCCTGCAGCCAGAAGACTCGGCCCTGTATgagacctaa (SEQ ID NO: 208)
```

TRBV4-3
```
ggggatccaccggtcgccaccatgggctgcaggctgctctgctgtgcggttctctgtctcctgggagcggtcccatgGAAACGGGAGTTACGCA
GACACCAAGACACCTGGTCATGGGAATGACAAATAAGAAGTCTTTGAAATGTGAACAACATCTGGGTCATAACGCTATGTATTGGTACAAGCAA
GTGCTAAGAAGCCACTGGAGCTCATGTTTGTCTACAGTCTTGAAGACGGGTTGAAAACAACAGTGTGCCAAGTCGCTTCTCACCTGAATGCCCC
AACAGCTCTCACTTATTCCTTCACCTACACACCCTGCAGCCAGAAGACTCGGCCCTGTATgagacctaa (SEQ ID NO: 209)
```

TRBV5-1
```
ggggatccaccggtcgccaccatgggctccaggctgctctgttgggctgctgctttgtctcctgggagcaggcccagtaAAGGCTGGAGTCACTCA
AACTCCAAGATATCTGATCAAAACGAGAGGACAGCAAGTGACACTGAGCTGCTCCCCTATCTCTGGGCATAGGAGTGTATCCTGGTACCAACAGA
CCCCAGGACAGGGCCTTCAGTTCCTCTTTGAATACTTCAGTGAGACACAGAGAAACAAAGGAAACTTCCCTGGTCGATTCTCAGGGCGCCAGTTC
TCTAACTCTCGCTCTGAGATGAATGTGAGCACCTTGGAGCTGGGGGACTCGGCCCTTTATgagacctaa (SEQ ID NO: 210)
```

TRBV5-3
```
ggggatccaccggtcgccaccatgggcccgggctcctctgctgggaactgctttatctcctgggagcaggcccagtgGAGGCTGGAGTCACCCA
AAGTCCCACACACCTGATCAAAACGAGAGGACAGCAAGTGACTCTGAGATGCTCTCCTATCTCTGGGCACAGCAGTGTGTCCTGGTACCAACAGG
CCCCGGGTCAGGGGCCCCAGTTTATCTTTGAATATGCTAATGAGTTAAGGAGATCAGAAGGAAACTTCCCTAATCGATTCTCAGGGCGCCAGTTC
CATGACTGTTGCTCTGAGATGAATGTGAGTGCCTTGGAGCTGGGGGACTCGGCCCTGTATgagacctaa (SEQ ID NO: 211)
```

TRBV5-4
```
ggggatccaccggtcgccaccatgggccctgggctcctctgctgggtgctgctttgtctcctgggagcaggctcagtgGAGACTGGAGTCACCCA
AAGTCCCACACACCTGATCAAAACGAGAGGACAGCAAGTGACTCTGAGATGCTCTTCTCAGTCTGGGCACAACACTGTGTCCTGGTACCAACAGG
CCCTGGGTCAGGGGCCCCAGTTTATCTTTCAGTATTATAGGGGAGGAAGAGAATGGCAGAGGAAACTTCCCTCCTAGATTCTCAGGaCTCAGTTC
CCTAATTATAGCTCTGAGCTGAATGTGAACGCCTTGGAGCTGGACGACTCGGCCCTGTATgagacctaa (SEQ ID NO: 212)
```

```
TRBV5-5
ggggatccaccggtcgccaccatgggccctgggctcctctgctgggtgctgctttgtctcctgggagcaggcccagtgGACGCTGGAGTCACCCA
AAGTCCCACACACCTGATCAAAACGAGAGGACAGCAAGTGACTCTGAGATGCTCTCCTATCTCTGGGCACAAGAGTGTGTCCTGGTACCAACAGG
TCCTGGGTCAGGGGCCCCAGTTTATCTTTCAGTATTATGAGAAAGAAGAGAGGAGGAAGAGGGAAACTTCCCTGATCGATTCTCAGCTCGCCAGTTC
CCTAACTATAGCTCTGAGCTGAATGTGAACGCCTTGTTGCTGGGGGACTCGGCCCTGTATgagacctaa (SEQ ID NO: 213)

TRBV5-6
ggggatccaccggtcgccaccatgggccccgggctcctctgctgggcactgctttgtctcctgggagcaggcttagtGACGCTGGAGTCACCCA
AAGTCCCACACACCTGATCAAAACGAGAGGACAGCAAGTGACTCTGAGATGCTCTCCTAAGTCTGGGCATGACACTGTGTCCTGGTACCAACAGG
CCCTGGGTCAGGGGCCCCAGTTTATCTTTCAGTATTATGAGGAGGAAGAGAGACAGAGAGGCAACTTCCCTGATCGATTCTCAGGTCACCAGTTC
CCTAACTATAGCTCTGAGCTGAATGTGAACGCCTTGTTGCTGGGGGACTCGGCCCTCTATgagacctaa (SEQ ID NO: 214)

TRBV5-7
ggggatccaccggtcgccaccatgggccccgggctcctctgctgggtgctgctttgtccctaggagaaggcccagtgGACGCTGGAGTCACCCA
AAGTCCCACACACCTGATCAAAACGAGAGGACAGCACGTGACTCTGAGATGCTCTCCTATCTCTGGGCACACCAGTGTGTCCTCGTACCAACAGG
CCCTGGGTCAGGGGCCCCAGTTTATCTTTCAGTATTATGAGAAAGAAGAGAGGAGGAAGAGGGAAACTTCCCTGATCAATTCTCAGGTCACCAGTTC
CCTAACTATAGCTCTGAGCTGAATGTGAACGCCTTGTTGCTAGGGGACTCGGCCCTCTATgagacctaa (SEQ ID NO: 215)

TRBV5-8
ggggatccaccggtcgccaccatgggacccaggctcctatctgggcactgattgtctcctcggaacaggcccagtgGAGGCTGGAGTCACACAAA
GTCCCACACACCTGATCAAAACGAGAGGACAGCAAGCGACTCTGAGATGCTCTCCTATCTCTGGGCACACCAGTGTGTACTGGTACCAACAGGCC
CTGGGTCTGGGCCTCCAGTTCCTCCTTTGGTATGACGAGGGTGAAGAGAGAAACAGAGGGAAACTTCCCTCCTAGATTTTCAGGTCGCCAGTTCCC
TAATTATAGCTCTGAGCTGAATGTGAACGCCTTGGAGCTGGAGGACTCGGCCCTGTATgagacctaa (SEQ ID NO: 216)

TRBV6-1
ggggatccaccggtcgccaccatgagcatcgggctcctgtgctgtgtggcttttctctcctgtgggcaagtccagtgAATGCTGGTGTCACTCA
GACCCCAAAATTCCAGGTCCTGAAGACAGGACAGAGCATGACACTGCAGTGTGCCCAGGATATGAACCATAACTCCATGTACTGGTATCGACAAG
ACCCAGGCATGGGACTGAGGCTGATTTATTACTCAGCTTCTGAGGGTACCACTGACAAAGGAGAAGTCCCCAATGGCTACAATGTCTCCAGATTA
AACAAACGGGAGTTCTCGCTCAGGCTGGAGTCGGCTGCTCCCTCCCAGACATCTGTGTACgagacctaa (SEQ ID NO: 217)

TRBV6-2
ggggatccaccggtcgccaccatgagcctcgggctcctgtgctgtgcagcctttttctctcctgtgggcaggtccagtgAATGCTGGTGTCACTCA
GACCCCAAAATTCCGGGTCCTGAAGACAGGACAGAGCATGACACTGCTGTGTGCCCAGGATATGAACCATGAATACATGTACTGGTATCGACAAG
ACCCAGGCATGGGGCTGAGGCTGATTCATTACTCAGTTGGTGAGGGTACAACTGCCAAAGGAGAGGTCCCTGATGGCTACAATGTCTCCAGATTA
AAAAAACAGAATTTCCTGCTGGGGTTGGAGTCGGCTGCTCCCTCCCAAACATCTGTGTACgagacctaa (SEQ ID NO: 218)

TRBV6-3
ggggatccaccggtcgccaccatgaaatacctattgcctacggcagccgctggattgttattactcgcggcccagccggccatggccAATGCTGG
TGTCACTCAGACCCCAAAATTCCGGGTCCTGAAGACAGGACAGAGCATGACACTGCTGTGTGCCCAGGATATGAACCATGAATACATGTACTGGT
ATCGACAAGACCCAGGCATGGGGCTGAGGCTGATTCATTACTCAGTTGGTGAGGGTACAACTGCCAAAGGAGAGGTCCCTGATGGCTACAATGTC
TCCAGATTAAAAAAAACAGAATTTCCTGCTGGGGTTGGAGTCGGCTGCTCCCTCCCAAACATCTGTGTACgagacctaa (SEQ ID NO: 219)

TRBV6-4
ggggatccaccggtcgccaccatgagaatcaggctcctgtgctgtgtggccttttctctcctgtgggcaggtccagtgATTGCTGGGATCACCCA
GGCACCAACATCTCAGATCCTGGCAGCAGGACGGCGCATGACACTGAGATGTACCCAGGATATGAGACATAATGCCATGTACTGGTATAGACAAG
ATCTAGGACTGGGGCTAAGGCTCATCCATTATTCAAATACTGCAGGTACCACTGGCAAAGGAGAAGTCCCTGATGGTTATAGTGTCTCCAGAGCA
AACACAGATGATTTCCCCCTCACGTTGGCGTCTGCTGTACCCTCTCAGACATCTGTGTACgagacctaa (SEQ ID NO: 220)

TRBV6-5
ggggatccaccggtcgccaccatgagcatcggcctcctgtgctgtgtcagccttgtctctcctgtgggcaggtccagtgAATGCTGGTGTCACTCA
GACCCCAAAATTCCAGGTCCTGAAGACAGGACAGAGCATGACACTGCAGTGTGCCCAGGATATGAACCATGAATACATGTCCTGGTATCGACAAG
ACCCAGGCATGGGGCTGAGGCTGATTCATTACTCAGTTGGTGCTGGTATCACTGACCAAGGAGAAGTCCCCAATGGCTACAATGTCTCCAGATCA
ACCACAGAGGATTTCCCGCTCAGGCTGCTGTCGGCTGCTCCCTCCCAGACATCTGTGTACgagacctaa (SEQ ID NO: 221)

TRBV6-6
ggggatccaccggtcgccaccatgagcatcagcctcctgtgctgtgcagcctttcctctcctgtgggcaggtccagtgAATGCTGGTGTCACTCA
GACCCCAAAATTCCGCATCCTGAAGATAGGACAGAGCATGACACTGCAGTGTACCCAGGATATGAACCATAACTACATGTACTGGTATCGACAAG
ACCCAGGCATGGGGCTGAAGCTGATTTATTATTCAGTTGGTGCTGGTATCACTGATAAAGGAGAAGTCCCGAATGGCTACAACGTCTCCAGATCA
ACCACAGAGGATTTCCCGCTCAGGCTGGAGTTGGCTGCTCCCTCCCAGACATCTGTGTACgagacctaa (SEQ ID NO: 222)

TRBV6-7
ggggatccaccggtcgccaccatgagcctcgggctcctgtgctgtgtggccttttctctcctgtgggcaggtccaatgAATGCTGGTGTCACTCA
GACCCCAAAATTCCACGTCCTGAAGACAGGACAGAGCATGACTCTGCTGTGTGCCCAGGATATGAACCATGAATACATGTATCGGTATCGACAAG
ACCCAGGCAAGGGGCTGAGGCTGATTTACTACTCAGTTGCTGCTGCTCTCACTGACAAAGGAGAAGTTCCCAATGGCTACAATGTCTCCAGATCA
AACACAGAGGATTTCCCCCTCAAGCTGGAGTCAGCTGCTCCCTCTCAGACTTCTGTTTACgagacctaa (SEQ ID NO: 223)

TRBV6-8
ggggatccaccggtcgccaccatgagcctcgggctcctgtgctgtgcggccttttctctcctgtgggcaggtcccgtgAATGCTGGTGTCACTCA
GACCCCAAAATTCCACATCCTGAAGACAGGACAGAGCATGACACTGCAGTGTGCCCAGGATATGAACCATATACTCGGTATCGACAAG
ACCCAGGCATGGGGCTGAGACTGATTTACTACTCAGCTGCTGCTGGTACTACTGACAAAGAAGTCCCCAATGGCTACAATGTCTCTAGATTAAAC
ACAGAGGATTTCCCACTCAGGCTGGTGTCGGCTGCTCCCTCCCAGACATCTGTGTACgagacctaa (SEQ ID NO: 224)

TRBV6-9
ggggatccaccggtcgccaccatgagcatcgggctcctgtgctgtgtggccttttctctcctgtgggcaggtccagtgAATGCTGGTGTCACTCA
GACCCCAAAATTCCACATCCTGAAGACAGGACAGAGCATGACACTGCAGTGTGCCCAGGATATGAACCATGGATACTTGTCCTGGTATCGACAAG
```

```
ACCCAGGCATGGGGCTGAGGCGCATTCATTACTCAGTTGCTGCTGGTATCACTGACAAAGGAGAAGTCCCCGATGGCTACAATGTATCCAGATCA
AACACAGAGGATTTCCCGCTCAGGCTGGAGTCAGCTGCTCCCTCCCAGACATCTGTATACgagacctaa (SEQ ID NO: 225)

TRBV7-1
ggggatccaccggtcgccaccatgggcacaaggctcctctgctgggcagccatatgtctcctgggggcagatcacacaGGTGCTGGAGTCTCCCA
GTCCCTGAGACACAAGGTAGCAAAGAAGGGAAAGGATGTAGCTCTCAGATATGATCCAATTTCAGGTCATAATGCCCTTTATTGGTACCGACAGA
GCCTGGGGCAGGGCCTGGAGTTTCCAATTTACTTCCAAGGCAAGGATGCAGCAGACAAATCGGGGCTTCCCCGTGATCGGTTCTCTGCACAGAGG
TCTGAGGGATCCATCTCCACTCTGAAGTTCCAGCGCACACAGCAGGGGGACTTGGCTGTGTATgagacctaa (SEQ ID NO: 226)

TRBV7-2
ggggatccaccggtcgccaccatgggcaccaggctcctatctgggtggccttctgtctcctgggggcagatcacacaGGAGCTGGAGTCTCCCAG
TCCCCCAGTAACAAGGTCACAGAGAAGGGAAAGGATGTAGAGCTCAGGTGTGATCCAATTTCAGGTCATACTGCCCTTTACTGGTACCGACAGAG
CCTGGGGCAGGGCCTGGAGTTTTTAATTTACTTCCAAGGCAACAGTGCACCAGACAAATCAGGGCTGCCCAGTGATCGCTTCTCTGCAGAGAGGA
CTGGGGGATCCGTCTCCACTCTGACGATCCAGCGCACACAGCAGGAGGACTCGGCCGTGTATgagacctaa (SEQ ID NO: 227)

TRBV7-3
ggggatccaccggtcgccaccatgggcaccaggctcctctgctgggcagccctgtgcctcctgggggcagatcacacaGGTGCTGGAGTCTCCCA
GACCCCCAGTAACAAGGTCACAGAGAAGGGAAAATATGTAGAGCTCAGGTGTGATCCAATTTCAGGTCATACTGCCCTTTACTGGTACCGACAAA
GCCTGGGGCAGGGCCCAGAGTTTCTAATTTACTTCCAAGGCACGGGTGCGGCAGATGACTCAGGGCTGCCCAACGATCGGTTCTTTGCAGTCAGG
CCTGAGGGATCCGTCTCTACTCTGAAGATCCAGCGCACAGAGCGGGGGGACTCAGCCGTGTATgagacctaa (SEQ ID NO: 228)

TRBV7-4
ggggatccaccggtcgccaccatgggcaccaggctcctctgctgggtggtcctgggtttcctagggacagatcacacaGGTGCTGGAGTCTCCCA
GTCCCCAAGGTACAAAGTCGCAAAGAAGGGACGGGATGTAGCTCTCAGGTGTGATTCAATTTCGGGTCATGTAACCCTTTATTGGTACCGACAGA
CCCTGGGGCAGGGCTCAGAGGTTCTGACTTACTCCCAGAGTGATGCTCAACGAGACAAATCAGGGCGGCCCAGTGGTCGGTTCTCTGCAGAGAGG
CCTGAGAGATCCGTCTCCACTCTGAAGATCCAGCGCACAGAGCAGGGGGACTCAGCTGTGTATgagacctaa (SEQ ID NO: 229)

TRBV7-6
ggggatccaccggtcgccaccatgggcaccagtctcctatgctgggtggtcctgggtttcctagggacagatcacacaGGTGCTGGAGTCTCCCA
GTCTCCCAGGTACAAAGTCACAAAGAGGGGACAGGATGTAGCTCTCAGGTGTGATCCAATTTCGGGTCATGTATCCCTTTATTGGTACCGACAGG
CCCTGGGGCAGGGCCCAGAGTTTCTGACTTACTTCAATTATGAAGCCCAACAAGACAAATCAGGGCTGCCCAATGATCGGTTCTCTGCAGAGAGG
CCTGAGGGATCCATCTCCACTCTGACGATCCAGCGCACAGAGCAGCGGGACTCGGCCATGTATgagacctaa (SEQ ID NO: 230)

TRBV7-7
ggggatccaccggtcgccaccatgggtaccagtctcctatgctgggtggtcctgggtttcctagggacagatcacacaGGTGCTGGAGTCTCCCA
GTCTCCCAGGTACAAAGTCACAAAGAGGGGACAGGATGTAACTCTCAGGTGTGATCCAATTTCGAGTCATGCAACCCTTTATTGGTATCAACAGG
CCCTGGGGCAGGGCCCAGAGTTTCTGACTTACTTCAATTATGAAGCTCAACCAGACAAATCAGGGCTGCCCAGTGATCGGTTCTCTGCAGAGAGG
CCTGAGGGATCCATCTCCACTCTGACGATTCAGCGCACAGAGCAGCGGGACTCAGCCATGTATgagacctaa (SEQ ID NO: 231)

TRBV7-8
ggggatccaccggtcgccaccatgggcaccaggctcctctgctgggtggtcctgggtttcctagggacagatcacacaGGTGCTGGAGTCTCCCA
GTCCCCTAGGTACAAAGTCGCAAAGAGAGGACAGGATGTAGCTCTCAGGTGTGATCCAATTTCGGGTCATGTATCCCTTTTTTGGTACCAACAGG
CCCTGGGGCAGGGGCCAGAGTTTCTGACTTATTTCCAGAATGAAGCTCAACTAGACAAATCGGGGCTGCCCAGTGATCGCTTCTTTGCAGAAAGG
CCTGAGGGATCCGTCTCCACTCTGAAGATCCAGCGCACACAGCAGGAGGACTCCGCCGTGTATgagacctaa (SEQ ID NO: 232)

TRBV7-9
ggggatccaccggtcgccaccatgggcaccagcctcctctgctggatggccctgtgtctcctgggggcagatcacgcaGATACTGGAGTCTCCCA
GAACCCCAGACACAAGATCACAAAGAGGGGACAGAATGTAACTTTCAGGTGTGATCCAATTTCTGAACACAACCGCCTTTATTGGTACCGACAGA
CCCTGGGGCAGGGCCCAGAGTTTCTGACTTACTTCCAGAATGAAGCTCAACTAGAAAAATCAAGGCTGCTCAGTGATCGGTTCTCTGCAGAGAGG
CCTAAGGGATCTTTCTCCACCTTGGAGATCCAGCGCACAGAGCAGGGGGACTCGGCCATGTATgagacctaa (SEQ ID NO: 233)

TRBV9
ggggatccaccggtcgccaccatgggatcaggctcctctgctgtgtggccttttgtctcctgggagcaggcccagtgGATTCTGGAGTCACACAA
ACCCCAAAGCACCTGATCACAGCAACTGGACAGCAGGTGAGTGACCTGGTTCCCCTAGGTCTGGAGAtCTCTCTGTGTACTGGTACCAACAGAG
CCTGGACCAGGGCCTCCAGTTCCTCATTCAGTATTATAATGGAGAAGAGAGAGCAAAAGGAAACATTCTTGAACGATTCTCCGCACAACAGTTCC
CTGACTTGCACTCTGAACTAAACCTGAGCTCTCTGGAGCTGGGGGACTCAGCTTTGTATgagacctaa (SEQ ID NO: 234)

TRBV10-1
ggggatccaccggtcgccaccatgggcacgaggctatatctatgtggccattgtctgctgtgggcaggacacaggGATGCTGAAATCACCCAGAG
CCCAAGACACAAGATCACAGAGACAGGAAGGCAGGTGACCTTGGCGTGTCACCAGACTTGGAACCACAACAATATGTTCTGGTATCGACAAGACC
TGGGACATGGGCTGAGGCTGATCCATTACTCATATGGTGTTCAAGACACTAACAAAGGAGAAGTCTCAGATGGCTACAGTGTCTCTAGATCAAAC
ACAGAGGACCTCCCCCTCACTCTGGAGTCTGCTGCCTCCTCCCAGACATCTGTATATgagacctaa (SEQ ID NO: 235)

TRBV10-2
ggggatccaccggtcgccaccatgggcaccaggctatatctatgtggccattgtctgctgtgggcaggacacaggGATGCTGGAATCACCCAGAG
CCCAAGATACAAGATCACAGAGACAGGAAGGCAGGTGACCTTGATGTGTCACCAGACTTGGAGCCACAGCTATATGTTCTGGTATCGACAAGACC
TGGGACATGGGCTGAGGCTGATCTATTACTCAGCAGCTGCTGATATTACAGATAAAGGAGAAGTCCCCGATGGCTATGTTGTCTCCAGATCAAG
ACAGAGAATTTCCCCCTCACTCTGGAGTCAGCTACCCGCTCCCAGACATCTGTGTATgagacctaa (SEQ ID NO: 236)

TRBV10-3
ggggatccaccggtcgccaccatgggcacaaggttgttatctatgtggccattgtctcctgtggacaggacacatgGATGCTGGAATCACCCAGA
GCCCAAGACACAAGGTCACAGAGACAGGAACACCAGTGACTCTGAGATGTCACCAGACTGAGAACCACCGCTATATGTACTGGTATCGACAAGAC
CCGGGGCATGGGCTGAGGCTGATCCATTACTCATATGGTGTTAAAGATACTGACAAAGGAGAAGTCTCAGATGGCTATAGTGTCTCTAGATCAAA
GACAGAGGATTTCCTCCTCACTCTGGAGTCCGCTACCAGCTCCCAGACATCTGTGTACgagacctaa (SEQ ID NO: 237)
```

Sequence Listing

TRBV11-1
ggggatccaccggtcgccaccatgagcaccaggatctctgctggatggccctctgtctcctgggggcagaactctcaGAAGCTGAAGTTGCCCAG
TCCCCCAGATATAAGATTACAGAGAAAAGCCAGGCTGTGGCTTTTTGGTGTGATCCTATTTCTGGCCATGCTACCCTTTACTGGTACCGGCAGAT
CCTGGGACAGGGCCCGGAGCTTCTGGTTCAATTTCAGGATGAGAGTGTAGTAGATGATTCACAGTTGCCTAAGGATCGATTTTCTGCAGAGAGGC
TCAAAGGAGTAGACTCCACTCTCAAGATCCAGCCTGCAGAGCTTGGGGACTCGGCCATGTATgagacctaa (SEQ ID NO: 238)

TRBV11-2
ggggatccaccggtcgccaccatgggcaccaggctcctctgctgggcggccctctgtctcctgggagcagaactcacaGAAGCTGGAGTTGCCCA
GTCTCCCAGATATAAGATTATAGAGAAAAGGCAGAGTGTGGCTTTTTGGTGCAATCCTATATCTGGCCATGCTACCCTTTACTGGTACCAGCAGA
TCCTGGGACAGGGCCCAAAGCTTCTGATTCAGTTTCAGAATAACGGTGTAGTGGATGATTCACAGTTGCCTAAGGATCGATTTTCTGCAGAGAGG
CTCAAAGGAGTAGACTCCACTCTCAAGATCCAGCCTGCAAAGCTTGAGGACTCGGCCGTGTATgagacctaa (SEQ ID NO: 239)

TRBV11-3
ggggatccaccggtcgccaccatgggtaccaggctcctctgctgggtggccttctgtctcctggtggaagaactcataGAAGCTGGAGTGGTTCA
GTCTCCCAGATATAAGATTATAGAGAAAAAACAGCCTGTGGCTTTTTGGTGCAATCCTATTTCTGGCCACAATACCCTTTACTGGTACCTGCAGA
ACTTGGGACAGGGCCCGGAGCTTCTGATTCGATATGAGAATGAGGAAGCAGTAGACGATTCACAGTTGCCTAAGGATCGATTTTCTGCAGAGAGG
CTCAAAGGAGTAGACTCCACTCTCAAGATCCAGCCTGCAGAGCTTGGGGACTCGGCCGTGTATgagacctaa (SEQ ID NO: 240)

TRBV12-3
ggggatccaccggtcgccaccatggactcctggaccttctgctgtgtgtcccttTGCATCCTGGTAGCGAAGCATACAGATGCTGGAGTTATCCA
GTCACCCCGCCATGAGGTGACAGAGATGGGACAAGAAGTGACTCTGAGATGTAAACCAATTTCAGGCCACAACTCCCTTTTCTGGTACAGACAGA
CCATGATGCGGGGACTGGAGTTGCTCATTTACTTTAACAACAACGTTCCGATAGATGATTCAGGGATGCCCGAGGATCGATTCTCAGCTAAGATG
CCTAATGCATCATTCTCCACTCTGAAGATCCAGCCCTCAGAACCCAGGGACTCAGCTGTGTACgagacctaa (SEQ ID NO: 241)

TRBV12-4
ggggatccaccggtcgccaccatgggctcctggaccctctgctgtgtgtcccttTGCATCCTGGTAGCAAAGCACACAGATGCTGGAGTTATCCA
GTCACCCCGGCACGAGGTGACAGAGATGGGACAAGAAGTGACTCTGAGATGTAAACCAATTTCAGGACACGACTACCTTTTCTGGTACAGACAGA
CCATGATGCGGGGACTGGAGTTGCTCATTTACTTTAACAACAACGTTCCGATAGATGATTCAGGGATGCCCGAGGATCGATTCTCAGCTAAGATG
CCTAATGCATCATTCTCCACTCTGAAGATCCAGCCCTCAGAACCCAGGGACTCAGCTGTGTACgagacctaa (SEQ ID NO: 242)

TRBV12-5
ggggatccaccggtcgccaccatggccaccaggctcctctgctgtgtggttctttgtctcctgggagaagacgcttataGATGCTAGAGTCACCCA
GACACCAAGGCACAAGGTGACAGAGATGGGACAAGAAGTAACAATGAGATGTCAGCCAATTTTAGGCCACAATACTGTTTTCTGGTACAGACAGA
CCATGATGCAAGGACTGGAGTTGCTGGCTTACTTCCGCAACCGGGCTCCTCTAGATGATTCGGGGATGCCGAAGGATCGATTCTCAGCAGAGATG
CCTGATGCAACTTTAGCCACTCTGAAGATCCAGCCCTCAGAACCCAGGGACTCAGCTGTGTATgagacctaa (SEQ ID NO: 243)

TRBV13
ggggatccaccggtcgccaccatgcttagtcctgacctgcctgactctgcctggaacaccaggctcctctgccgtgtcatgctttgtctcctggg
agcaggttcagtgGCTGCTGGAGTCATCCAGTCCCCAAGACATCTGATCAAAGAAAAGAGGGAAACAGCCACTCTGAAATGCTATCCTATCCCTA
GACACGACACTGTCTACTGGTACCAGCAGGGTCCAGGTCAGGACCCCCAGTTCCTCATTTCGTTTTATGAAAAGATGCAGAGCGATAAAGGAAGC
ATCCCTGATCGATTCTCAGCTCAACAGTTCAGTGACTATCATTCTGAACTGAACATGAGCTCCTTGGAGCTGGGGGACTCAGCCCTGTACgagac
ctaa (SEQ ID NO: 244)

TRBV14
ggggatccaccggtcgccaccatggtttccaggatctcagtttagtgtccctttgtctcctgggagcaaagcacataGAAGCTGGAGTTACTCAG
TTCCCCAGCCACAGCGTAATAGAGAAGGCCAGACTGTGACTCTGAGATGTGACCCAATTTCTGGACATGATAATCTTTATTGGTATCGACGTGT
TATGGGAAAGAAATAAAATTTCTGTTACATTTTGTGAAAGAGTCTAAACAGGATGAGTCCGGTATGCCCAACAATCGATTCTTAGCTGAAAGGA
CTGGAGGGACGTATTCTACTCTGAAGGTGCAGCCTGCAGAACTGGAGGATTCTGGAGTTTATgagacctaa (SEQ ID NO: 245)

TRBV15
ggggatccaccggtcgccaccatgggtcctgggcttctccactggatggccctttgtctccttggaacaggtcatgggGATGCCATGGTCATCCA
GAACCCAAGATACCAGGTTACCCAGTTTGGAAAGCCAGTGACCCTGAGTTGTTCTCAGACTTTGAACCATAACGTCATGTACTGGTACCAGCAGA
AGTCAAGTCAGGCCCCAAAGCTGCTGTTCCACTACTATGACAAAGATTTTAACAATGAAGCAGACACCCCTGATAACTTCCAATCCAGGAGGCCG
AACACTTCTTTCTGCTTTCTTGACATCCGCTCACCAGGCCTGGGGGACACAGCCATGTACgagacctaa (SEQ ID NO: 246)

TRBV16
ggggatccaccggtcgccaccatgagcccaatattccactgcatcacaatcctttgtctgctggctgcaggttctcctGGTGAAGAAGTCGCCCA
GACTCCAAAACATCTTGTCAGAGGGGAAGGACAGAAAGCAAAATTATATTGTGCCCCAATAAAAGGACACAGTTATGTTTTTGGTACCAACAGG
TCCTGAAAAACGAGTTCAAGTTCTTGATTTCCTTCCAGAATGAAAATGTCTTTGATGAAACAGGTATGCCCAAGGAAAGATTTTCAGCTAAGTGC
CTCCCAAATTCACCCTGTAGCCTTGAGATCCAGGCTACGAAGCTTGAGGATTCAGCAGTGTATgagacctaa (SEQ ID NO: 247)

TRBV17
ggggatccaccggtcgccaccatggatatctggcctctctgctgggtgaccctgtgtctcttggcggcaggacactcgGAGCCTGGAGTCAGCCA
GACCCCCAGACACAAGGTCACCAACATGGGACAGGAGGTGATTCTGAGGTGCGATCCATCTTCTGGTCACATGTTTGTTCACTGGTACCGACAGA
ATCTGAGGCAAGAAATGAAGTTGCTGATTTCCTTCCAGTACCAAAACATTGCAGTTGATTCAGGGATGCCCAAGGAACGATTCACAGCTGAAAGA
CCTAACGGAACGTCTTCCACGCTGAAGATCCATCCCGCAGAGCCGAGGGACTCAGCCGTGTATgagacctaa (SEQ ID NO: 248)

TRBV19
ggggatccaccggtcgccaccatgagcaaccaggtgctctgctgtgtggtccttTGTTTCCTGGGAGCAAACACCGTGGATGGTGGAATCACTCA
GTCCCCAAAGTACCTGTTCAGAAAGGAAGGACAGAATGTGACCCTGAGTTGTGAACAGAATTTGAACCACGATGCCATGTACTGGTACCGACAGG
ACCCAGGGCAAGGGCTGAGATTGATCTACTACTCACAGATAGTAAATGACTTTCAGAAAGGAGATATAGCTGAAGGGTACAGCGTCTCTCGGGAG
AAGAAGGAATCCTTTCCTCTCACTGTGACATCGGCCCAAAAGAACCCGACAGCTTTCTATgagacctaa (SEQ ID NO: 249)

TRBV18
ggggatccaccggtcgccaccatggacgccagagtactctgctgtgcggtcatctgtatctggggggcaggactctcaAATGCCGGCGTCATGCAG
AACCCAAGACACCTGGTCAGGAGGAGGGACAGGAGGCAAGACTGAGATGCAGCCCAATGAAGGACACAGTCATGTTTACTGGTATCGGCAGCT

```
CCCAGAGGAAGGTCTGAAATTCATGGTTTATCTCCAGAAAGAAAATATCATAGATGAGTCAGGAATGCCAAAGGAACGATTTTCTGCTGAATTTC
CCAAAGAGGGCCCCAGCATCCTGAGGATCCAGCAGGTAGTGCGAGGAGATTCGGCAGCTTATgagacctaa (SEQ ID NO: 250)

TRBV20-1
ggggatccaccggtcgccaccatgctgctgatctgctgatctggggccagcaggctccgggcttGGTGCTGTCGTCTCTCAACATCCGAGCTGGG
TTATCTGTAAGAGTGGAACCTCTGTGAAGATCGAGTGCCGTTCCCTGGACTTTCAGGCCACAACTATGTTTTGGTATCGTCAGTTCCCGAAACAG
AGTCTCATGCTGATGGCAACTTCCAATGAGGGCTCCAAGGCCACATACGAGCAAGGCGTCGAGAAGGACAAGTTTCTCATCAACCATGCAAGCCT
GACCTTGTCCACTCTGACAGTGACCAGTGCCCATCCTGAAGACAGCAGCTTCTACgagacctaa (SEQ ID NO: 251)

TRBV23-1
ggggatccaccggtcgccaccatgggcaccaggctcctcggctgtgcagccctgtgtctcctgacagcagactcttttCATGCCAAAGTCACACA
GACTCCAGGACATTTGGTCAAAGGAAAAGGACAGAAAACAAAGATGGATTGTACCCCGAAAAAGGACATACTTTTGTTTATTGGTATCAACAGA
ATCAGAATAAAGAGTTTATGCTTTTGATTTCCTTTCAGAATGAACAAGTTCTTCAAGAAACGGAGATGCACAAGAAGCGATTCTCATCTCAATGC
CCCAAGAACGCACCCTGCAGCCTGGCAATCCTGTCCTCAGAACCGGGAGACACGGCACTGTATgagacctaa (SEQ ID NO: 252)

TRBV24-1
ggggatccaccggtcgccaccatggcctccctgctcttcttctgtggggcctttatctcctgggaacagggtccatgGATGCTGATGTTACCCA
GACCCCAAGGAATAGGATCACAAAGACAGGAAAGAGGATTATGCTGGAATGTTCTCAGACTAAGGGTCATGATAGAATGTACTGGTATCGACAAG
ACCCAGGACTGGGCCTACGGTTGATCTATTACTCCTTTGATGTCAAAGATATAAACAAAGGAGAGATCTCTGATGGATACAGTGTCTCTCGACAG
GCACAGGCTAAATTCTCCCTGTCCCTAGAGTCTGCCATCCCCAACCAGACAGCTCTTTACgagacctaa (SEQ ID NO: 253)

TRBV25-1
ggggatccaccggtcgccaccatgactatcaggctcctctgctacatgggcttttattttctggggcaggcctcatgGAAGCTGACATCTACCA
GACCCCAAGATACCTTGTTATAGGGACAGGAAAGAAGATCACTCTGGAATGTTCTCAAACCATGGGCCATGACAAATGTACTGGTATCAACAAG
ATCCAGGAATGGAACTACACCTCATCCACTATTCCTATGGAGTTAATTCCACAGAGAAGGGAGATCTTTCCTCTGAGTCAACAGTCTCCAGAATA
AGGACGGAGCATTTTCCCCTGACCCTGGAGTCTGCCAGGCCCTCACATACCTCTCAGTACgagacctaa (SEQ ID NO: 254)

TRBV27
ggggatccaccggtcgccaccatgggcccccagctccttggctatgtggtcctttgccttctaggagcaggcccctgGAAGCCCAAGTGACCCA
GAACCCAAGATACCTCATCACAGTGACTGGAAAGAAGTTAACAGTGACTTGTTCTCAGAATATGAACCATGAGTATATGTCCTGGTATCGACAAG
ACCCAGGGCTGGGCTTAAGGCAGATCTACTATTCAATGAATGTTGAGGTGACTGATAAGGGAGATGTTCCTGAAGGGTACAAAGTCTCTCGAAAA
GAGAAGAGGAATTTCCCCCTGATCCTGGAGTCGCCCAGCCCCAACCAGACCTCTCTGTACgagacctaa (SEQ ID NO: 255)

TRBV28
ggggatccaccggtcgccaccatgggaatcaggctcctctgtcgtgtggccttttgtttcctggctgtaggcctcgtaGATGTGAAAGTAACCCA
GAGCTCGAGATATCTAGTCAAAAGGACGGGAGAGAAAGTTTTTCTGGAATGTGTCCAGGATATGGACCATGAAAATATGTTCTGGTATCGACAAG
ACCCAGGTCTGGGGCTACGGCTGATCTATTTCTCATATGATGTTAAAATGAAAGAAAAAGGAGATATTCCTGAGGGGTACAGTGTCTCTAGAGAG
AAGAAGGAGCGCTTCTCCCTGATTCTGGAGTCCGCCAGCACCAACCAGACATCTATGTACgagacctaa (SEQ ID NO: 256)

TRBV29-1
ggggatccaccggtcgccaccatgctgagtcttctgctccttctcctgggactaggctctgtgttcAGTGCTGTCATCTCTCAAAAGCCAAGCAG
GGATATCTGTCAACGTGGAACCTCCCTGACGATCCAGTGTCAAGTCGATAGCCAAGTCACCATGATGTTCTGGTACCGTCAGCAACCTGGACAGA
GCCTGACACTGATCGCAACTGCAAATCAGGGCTCTGAGGCCACATATGAGAGTGGATTTGTCATTGACAAGTTTCCCATCAGCCGCCCAAACCTA
ACATTCTCAACTCTGACTGTGAGCAACATGAGCCCTGAAGACAGCAGCATATATgagacctaa (SEQ ID NO: 257)

TRBV30
ggggatccaccggtcgccaccatgctctgctctctccttgcccttctcctgggcactttcttggggtcagaTCTCAGACTATTCATCAATGGCC
AGCGACCCTGGTGCAGCCTGTGGGCAGCCCGCTCTCTCTGGAGTGCACTGTGGAGGGAACATCAAACCCCAACCTATACTGGTACCGACAGGCTG
CAGGCAGGGGCCTCCAGCTGCTCTTCTACTCCGTTGGTATTGGCCAGATCAGCTCTGAGGTGCCCCAGAATCTCTCAGCCTCCAGACCCCAGGAC
CGGCAGTTCATCCTGAGTTCTAAGAAGCTCCTTCTCAGTGACTCTGGCTTCTATgagacctaa (SEQ ID NO: 258)
```

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of selecting a T cell receptor (TCR) or one or more subject-specific antigenic peptides targeted by a TCR for preparing a personal pharmaceutical composition for administration to a human subject with a disease or condition, the method comprising:
 (a) obtaining a biological sample from the human subject, wherein the biological sample comprises a plurality of T cells comprising T cells that are reactive against one or more subject-specific antigenic peptides;
 (b) obtaining at least 1,000 paired TCR-alpha and TCR-beta chain nucleic acid sequences, wherein each pair of the paired TCR-alpha and TCR-beta chain nucleic acid sequences are distinct and have originated from a single T cell of the biological sample of (a);
 (c) cloning CDR3 alpha and CDR3 beta sequences of each of the 1,000 paired TCR-alpha and TCR-beta chain nucleic acid sequences into a pre-assembled variable chain library of recombinant expression vectors to assemble a plurality of recombinant TCR expression vectors, wherein the recombinant expression vectors of the pre-assembled variable chain library comprises
  (i) a first set of recombinant expression vectors, each recombinant expression vector of the first set comprising a different TCR-alpha variable fragment and a constant beta (V alpha-C beta), and
  (ii) a second set of recombinant expression vectors, each recombinant expression vector of the second set comprising a different TCR-beta variable fragment and a constant alpha (V beta-C alpha);
 (d) introducing the plurality of recombinant TCR expression vectors comprising each of the at least 1,000 paired TCR-alpha and TCR-beta chain nucleic acid sequences into reporter T cells, wherein the at least 1,000 paired TCR-alpha and TCR-beta chain nucleic acid sequences comprise paired TCR-alpha and TCR-beta chain nucleic acid sequences that occur at a frequency of 0.3% or less of the plurality of T cells of the biological sample of (a);
 (e) assaying recombinant TCRs encoded by the recombinant expression vectors of (d) that are expressed by the reporter T cells, wherein assaying comprises
  (i) incubating the reporter T cells with antigen presenting cells (APCs) that (A) express an HLA encoded by the human subject's genome and (B) present one or more subject-specific antigenic peptides expressed by diseased cells of the human subject;
  (ii) measuring activation of a reporter in the reporter T cells that is activated upon binding of the recombinant TCRs encoded by the recombinant expression vectors of (d) to HLA-peptide complexes of the APCs; and
 (f) selecting
  (i) at least one of the one or more subject-specific antigenic peptides that when in complex with the HLA encoded by the human subject's genome binds to at least one of the recombinant TCRs encoded by the recombinant expression vectors of (d) based on (e)(ii), or
  (ii) at least one of the recombinant TCRs encoded by the recombinant expression vectors of (d) that binds to the one or more subject-specific antigenic peptide based on (e)(ii).

2. The method of claim 1, wherein the method further comprises immunizing the subject with a vaccine comprising the at least one of the antigenic peptides selected in (f) prior to identifying the plurality of paired TCR chain sequences.

3. The method of claim 1, wherein the method further comprises stimulating peripheral blood mononuclear cells (PBMCs) in the biological sample of (a) with the at least one of the antigenic peptides prior to identifying the plurality of paired TCR chain sequences, wherein the PBMCs comprise the single T cell.

4. The method of claim 1, wherein T cells comprising the single T cell from which the plurality of paired TCR chain sequences are identified are selected by detecting stimulation by autologous tumor.

5. The method of claim 1, wherein a reporter T cell comprising the TCR-alpha and TCR-beta chain sequences is selected by detecting stimulation by at least one of the one or more subject-specific antigenic peptides that is expressed by a tumor of the subject, when presented as bound to one or more HLA molecules expressed by the subject in (e).

6. The method of claim 1, wherein the method further comprises sequencing the polynucleotides from the single T cell that encode the plurality of paired TCR chain sequences.

7. The method of claim 1, wherein the reporter T cells expressing the plurality of paired TCR chain sequences express at least one activation marker selected from CD25, CD54, CD69, CD38, CD45RO, CD49d, CD40L, CD137, IFN-γ, IL-2, IL-4, CD107a, and CD134.

8. The method of claim 1, further comprising expressing the at least 1,000 paired TCR-alpha and TCR-beta chain sequences in reporter T cells prior to step (e).

9. The method of claim 1, wherein the recombinant expression vector is a plasmid.

10. The method of claim 1, wherein the recombinant expression vector is a viral vector.

11. The method of claim 10, wherein the viral vector is selected from the group consisting of a lentiviral vector, an adenoviral vector and an adeno-associated viral vector.

12. The method of claim 1, wherein the method further comprises
 selecting the one or more paired TCR chain sequences from step (f)(ii) that targets one or more autologous tumor cells.

13. The method of claim 12, wherein selecting comprises:
 (a) cloning the one or more paired TCR chain sequences;
 (b) expressing the one or more paired TCR chain sequences in T cells; and
 (c) incubating the one or more autologous tumor cells with the T cells expressing the one or more paired TCR chain sequences.

14. The method of claim 12, wherein selecting comprises:
(a) cloning the one or more paired TCR chain sequences;
(b) expressing the one or more paired TCR chain sequences in T cells, wherein the T cells are activated; and
(c) incubating one or more antigen presenting cells (APCs) presenting at least one of the antigenic peptides with the T cells expressing the one or more paired TCR chain sequences.

15. The method of claim 12, wherein selecting comprises:
(a) cloning the one or more paired TCR chain sequences;
(b) generating one or more soluble recombinant versions of the one or more paired TCR chain sequences; and
(c) incubating at least one of the antigenic peptides bound to an HLA molecule with the one or more soluble recombinant versions of the one or more paired TCR chain sequences.

16. The method of claim 1, further comprising determining from the plurality of T cells after step (a) the sequences encoding at least 1,000 paired TCR-alpha and TCR-beta chains, wherein said sequencing comprises:
(a) emulsifying (i) single T cells of the plurality of T cells and (ii) deformable beads in a population of approximately uniformly-sized aqueous droplets at respective frequencies of less than about 0.1 cells/droplet on average and at least about 0.5 beads/droplet or greater on average, wherein the deformable beads comprise sequencing-compatible barcodes;
(b) lysing a single T cell within a droplet;
(c) performing RT-PCR upon the plurality of droplet such that the RT-PCR amplified cDNA of the single lysed T cell bound to a sequencing-compatible barcodest.

17. The method of claim 16, further comprising obtaining sequences for at least two cDNAs and the bound sequencing-compatible barcode, wherein the bound sequencing-compatible barcode identifies the at least two cDNA sequences as of a single T cell, thereby obtaining nucleic acid sequence information for two or more transcripts of a single T cell within the plurality of T cells in the biological sample of 1(a), wherein the two or more transcripts comprise the paired TCR-alpha and TCR-beta chains.

18. The method of claim 1, further comprising determining by single cell sequencing after step (a) the sequences encoding at least 1,000 paired TCR-alpha and TCR-beta chains, wherein said single cell sequencing comprises sorting T cell into single T cells and sequencing the single T cells.

19. The method of claim 1, wherein identifying comprises sequencing polynucleotides encoding the plurality of paired TCR chains, wherein sequencing comprises high-throughput sequencing, massively parallel sequencing or next generation sequencing.

20. The method of claim 19, wherein sequencing comprises sequencing polynucleotides from single T cells.

21. The method of claim 20, wherein sequencing comprises sequencing polynucleotides from single T cells that have not been expanded ex vivo.

22. The method of claim 1, wherein the human subject has cancer, an autoimmune disease or an infection.

23. The method of claim 1, wherein the biological sample from the human subject comprises a tumor biopsy, tumor infiltrating lymphocytes (TILS) or peripheral blood.

24. The method of claim 22, wherein the human subject has cancer, and wherein the one or more subject-specific antigenic peptides are expressed by cancer cells of the human subject and are not encoded by non-cancer cells of the human subject.

25. The method of claim 1, wherein the reporter T cells are a cell line.

26. The method of claim 25, wherein the reporter T cells are deficient for endogenous TCRs and comprise a reporter gene that is activated upon binding of a TCR to an antigenic peptide.

27. The method of claim 26, wherein the reporter cells comprise a fluorescent reporter gene.

28. The method of claim 1, wherein the reporter T cells are T cells from a biological sample from the human subject.

29. The method of claim 1, wherein the human subject has been immunized with the one or more subject-specific antigenic peptides.

30. The method of claim 1, wherein the APCs of step (e)(i) (A) are tumor cells from the human subject.

31. The method of claim 1, wherein the peptide (e)(i) (B) comprise a mutation that is (i) encoded by cancer cells of the human subject and (ii) not encoded by non-cancer cells of the human subject.

32. The method of claim 31, wherein the method comprises sequencing the whole genome or whole exome of cancer cells and non-cancer cells of the human subject and identifying the peptides that comprise a mutation that is encoded by cancer cells of the human subject and not encoded by non-cancer cells of the human subject.

33. The method of claim 16, wherein each of the 1,000 paired TCR-alpha and TCR-beta chain sequences comprise a unique barcode sequence.

34. The method of claim 16, wherein the polynucleotides comprise RNAs from single cells lysed within droplets that are used to make cDNAs.

35. The method of claim 1, wherein the plurality of paired TCR chain sequences comprises at least 10,000 paired TCR-alpha and TCR-beta chain sequences.

36. The method of claim 1, wherein the method further comprises measuring (e)(i) (A) binding affinities of TCRs encoded by the recombinant expression vectors to HLA-peptide complexes of the APCs or (e)(i) (B) cytolytic activity of the reporter cells to the APCs.

37. The method of claim 1, wherein the method further comprises:
(II) preparing the personal pharmaceutical composition, wherein the personal pharmaceutical composition comprises a pharmaceutically acceptable excipient and:
(i) at least one of the one or more subject-specific antigenic peptides selected based on (f)(i); or
(ii) a T cell comprising a polynucleotide encoding at least one of the TCRs selected based on (f)(ii).

38. The method according to claim 1, wherein selecting in (f)(i) or (f)(ii) is based on incubating a T cell comprising a paired TCR with one of the one or more subject-specific antigenic peptide.

39. The method according to claim 1, wherein selecting in (f)(i) or (f)(ii) is based on incubating a T cell comprising a paired TCR with different pools of subject-specific antigenic peptides.

40. The method according to claim 1, wherein the human subject's T cells are $CD8^+$ or $CD4^+$ T cells.

41. The method according to claim 1, wherein the one or more subject-specific antigenic peptides are cancer-specific.

* * * * *

SEQUENCE LISTING

<160> NUMBER OF SEQ ID NOS: 291

<210> SEQ ID NO 1
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 1

His His His His His His
1               5

<210> SEQ ID NO 2
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 2
ctgcacgtac cagacatctg ggtt                                          24

<210> SEQ ID NO 3
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 3
ggctcaaagc cttctcagca gg                                            22

<210> SEQ ID NO 4
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 4
ggataacctg gttaaaggca gcta                                          24

<210> SEQ ID NO 5
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 5
ggatacaaga caaaagttac aaacga                                        26

<210> SEQ ID NO 6
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 6
gctgacgtat attttttcaa atatgga                                       27

<210> SEQ ID NO 7
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

-continued

```
<400> SEQUENCE: 7
ggaagaggcc ctgttttctt gct                                          23

<210> SEQ ID NO 8
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
gctggatatg agaagcagaa agga                                         24

<210> SEQ ID NO 9
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
aggactccag cttctcctga agta                                         24

<210> SEQ ID NO 10
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
gtatgtccaa tatcctggag aaggt                                        25

<210> SEQ ID NO 11
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
cagtgagaac acaaagtcga acgg                                         24

<210> SEQ ID NO 12
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
cctaagttgc tgatgtccgt atac                                         24

<210> SEQ ID NO 13
<211> LENGTH: 25
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 13
gggaaaagcc ctgagttgat aatgt                                   25

<210> SEQ ID NO 14
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 14
gctgatgtac acatactcca gtgg                                    24

<210> SEQ ID NO 15
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 15
cccttggtat aagcaagaac ttgg                                    24

<210> SEQ ID NO 16
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 16
cctcaattca ttatagacat tcgttc                                  26

<210> SEQ ID NO 17
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 17
gcaaaatgca acagaaggtc gcta                                    24

<210> SEQ ID NO 18
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 18
tagagagagc atcaaaggct tcac                                    24

<210> SEQ ID NO 19
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
cgttcaaatg aaagagagaa acacag                                          26

<210> SEQ ID NO 20
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
cctgaaaagt tcagaaaacc aggag                                           25

<210> SEQ ID NO 21
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ggtcggtatt cttggaactt ccag                                            24

<210> SEQ ID NO 22
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
gctggggaag aaaaggagaa agaaa                                           25

<210> SEQ ID NO 23
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
gtcagagaga gcaaacaagt ggaa                                            24

<210> SEQ ID NO 24
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic primer"

<400> SEQUENCE: 24
ggacaaaaca gaatggaaga ttaagc                                        26

<210> SEQ ID NO 25
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
ccagatgtga gtgaaaagaa agaag                                         25

<210> SEQ ID NO 26
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
gactttaaat ggggatgaaa agaaga                                        26

<210> SEQ ID NO 27
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
ggagaagtga agaagcagaa aagac                                         25

<210> SEQ ID NO 28
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ccaatgaaat ggcctctctg atca                                          24

<210> SEQ ID NO 29
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
gcaatgtgaa caacagaatg gcct                                          24

<210> SEQ ID NO 30
<211> LENGTH: 24

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
ggtggagaag tgaagaagct gaag                                            24

<210> SEQ ID NO 31
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
ggataaaaat gaagatggaa gattcac                                         27

<210> SEQ ID NO 32
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
cctgatgata ttactgaagg gtgga                                           25

<210> SEQ ID NO 33
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
ggtggggaag agaaaagtca tgaa                                            24

<210> SEQ ID NO 34
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
ggtgaattga cctcaaatgg aagac                                           25

<210> SEQ ID NO 35
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
```

```
gctaacttca agtggaattg aaaaga                                         26
```

<210> SEQ ID NO 36
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36

```
gaagcttata agcaacagaa tgcaac                                         26
```

<210> SEQ ID NO 37
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37

```
ggagcagtga agcaggaggg ac                                             22
```

<210> SEQ ID NO 38
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38

```
gagagacaat ggaaaacagc aaaaac                                         26
```

<210> SEQ ID NO 39
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39

```
gctgagctca gggaagaaga agc                                            23
```

<210> SEQ ID NO 40
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40

```
aggtcgtttt tcttcattcc ttagtc                                         26
```

<210> SEQ ID NO 41
<211> LENGTH: 25
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 41
acgatacaac atgacctatg aacgg                                            25

<210> SEQ ID NO 42
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
ctttgaagct gaatttaaca agagcc                                           26

<210> SEQ ID NO 43
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
ctccctgttt atccctgccg ac                                               22

<210> SEQ ID NO 44
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
aaacaagacc aaagactcac tgttc                                            25

<210> SEQ ID NO 45
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
aagactgaag gtcacctttg atacc                                            25

<210> SEQ ID NO 46
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
actaaatgct acattactga agaatgg                                          27

<210> SEQ ID NO 47
```

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gcatcaacgg ttttgaggct gaatttaa                                          28

<210> SEQ ID NO 48
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
gaaaccactt ctttccactt ggagaa                                            26

<210> SEQ ID NO 49
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
tacagcaact ctggatgcag acac                                              24

<210> SEQ ID NO 50
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
gaagatggaa ggtttacagc aca                                               23

<210> SEQ ID NO 51
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
gacattcgtt caaatgtggg cgaa                                              24

<210> SEQ ID NO 52
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
```

```
ggcaaggcca aagagtcacc gt                                              22

<210> SEQ ID NO 53
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
tccagaaggc aagaaaatcc gcca                                            24

<210> SEQ ID NO 54
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
gctgacctta acaaaggcga gaca                                            24

<210> SEQ ID NO 55
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
ttaagagtca cgcttgacac ttcca                                           25

<210> SEQ ID NO 56
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
gcagaggttt tcaggccagt cct                                             23

<210> SEQ ID NO 57
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
tccaccagtt ccttcaactt cacc                                            24

<210> SEQ ID NO 58
<211> LENGTH: 25
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 58
gccacattaa caaagaagga aagct                                            25

<210> SEQ ID NO 59
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
gcctcgctgg ataaatcatc agga                                             24

<210> SEQ ID NO 60
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
acgactgtcg ctacggaacg cta                                              23

<210> SEQ ID NO 61
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
cacaatctcc ttcaataaaa gtgcca                                           26

<210> SEQ ID NO 62
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
acgaataagt gccactctta atacca                                           26

<210> SEQ ID NO 63
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
gtttggagaa gcaaaaaaga acagct                                           26
```

```
<210> SEQ ID NO 64
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
cagaagacag aaagtccagc acct                                           24

<210> SEQ ID NO 65
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
atcgctgaag acagaaagtc cagt                                           24

<210> SEQ ID NO 66
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
actaaccttt cagtttggtg atgcaa                                         26

<210> SEQ ID NO 67
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
cttaaacaaa agtgccaagc acctc                                          25

<210> SEQ ID NO 68
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
aatatctgct tcatttaatg aaaaaaagc                                      29

<210> SEQ ID NO 69
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 69
ccaagttgga tgagaaaaag cagca                                          25

<210> SEQ ID NO 70
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
ctcagtttgg tataaccaga aagga                                          25

<210> SEQ ID NO 71
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
ggaagactaa gtagcatatt agataag                                        27

<210> SEQ ID NO 72
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
ctgtgaactt ccagaaagca gcca                                           24

<210> SEQ ID NO 73
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
cctcacttga taccaaagcc cgt                                            23

<210> SEQ ID NO 74
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
aggcggaaat attaaagaca aaaactc                                        27

<210> SEQ ID NO 75
<211> LENGTH: 27
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 75
gattaattgc cacaataaac atacagg                                              27

<210> SEQ ID NO 76
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76
ctgaaatatt cgatgatcaa ttctcag                                              27

<210> SEQ ID NO 77
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
tcattataaa tgaaacagtt ccaaatcg                                             28

<210> SEQ ID NO 78
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
agtgtgccaa gtcgcttctc ac                                                   22

<210> SEQ ID NO 79
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
gagacacaga gaaacaaagg aaacttc                                              27

<210> SEQ ID NO 80
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
cagaggaaac tyccctccta gatt                                                 24
```

```
<210> SEQ ID NO 81
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
ggtaccactg acaaaggaga agtcc                                          25

<210> SEQ ID NO 82
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
gagggtacaa ctgccaaagg agaggt                                         26

<210> SEQ ID NO 83
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
ggcaaaggag aagtccctga tggtt                                          25

<210> SEQ ID NO 84
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
aaggagaagt cccsaatggc tacaa                                          25

<210> SEQ ID NO 85
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
ctgacaaaga agtccccaat ggctac                                         26

<210> SEQ ID NO 86
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 86
cactgacaaa ggagaagtcc ccgat 25

<210> SEQ ID NO 87
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
agacaaatca gggctgccca gtga 24

<210> SEQ ID NO 88
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
gactcagggc tgcccaacga t 21

<210> SEQ ID NO 89
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
ggttctctgc agagaggcct gag 23

<210> SEQ ID NO 90
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
ggctgcccag tgatcggttc tc 22

<210> SEQ ID NO 91
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
ccagaatgaa gctcaactag acaa 24

<210> SEQ ID NO 92
<211> LENGTH: 27
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
gacttacttc cagaatgaag ctcaact                                         27

<210> SEQ ID NO 93
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
gagcaaaagg aaacattctt gaacgatt                                        28

<210> SEQ ID NO 94
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
ggctratcca ttactcatat ggtgtt                                          26

<210> SEQ ID NO 95
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
gataaaggag aagtccccga tggct                                           25

<210> SEQ ID NO 96
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
gattcacagt tgcctaagga tcgat                                           25

<210> SEQ ID NO 97
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
gattcaggga tgcccgagga tcg                                             23
```

<210> SEQ ID NO 98
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 98
gattcgggga tgccgaagga tcg         23

<210> SEQ ID NO 99
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 99
gcagagcgat aaaggaagca tccct         25

<210> SEQ ID NO 100
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 100
tccggtatgc ccaacaatcg attct         25

<210> SEQ ID NO 101
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 101
gattttaaca atgaagcaga cacccct         27

<210> SEQ ID NO 102
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 102
gatgaaacag gtatgcccaa ggaaag         26

<210> SEQ ID NO 103
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 103
tatcatagat gagtcaggaa tgccaaag                               28

<210> SEQ ID NO 104
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
gactttcaga aaggagatat agctgaa                                27

<210> SEQ ID NO 105
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
caaggccaca tacgagcaag gcgtc                                  25

<210> SEQ ID NO 106
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
caaagatata aacaaaggag agatctct                               28

<210> SEQ ID NO 107
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
agagaaggga gatctttcct ctgagt                                 26

<210> SEQ ID NO 108
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
gactgataag ggagatgttc ctgaag                                 26

<210> SEQ ID NO 109
<211> LENGTH: 28

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
ggctgatcta tttctcatat gatgttaa                                         28

<210> SEQ ID NO 110
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
gccacatatg agagtggatt tgtcatt                                          27

<210> SEQ ID NO 111
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
ggtgccccag aatctctcag cct                                              23

<210> SEQ ID NO 112
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
gcctgatgga tcaaatttca ctctg                                            25

<210> SEQ ID NO 113
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113
tctcacctaa atctccagac aaagct                                           26

<210> SEQ ID NO 114
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
```
cctgaatgcc ccaacagctc tc                                              22

<210> SEQ ID NO 115
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
cgattctcag ggcgccagtt ctct                                            24

<210> SEQ ID NO 116
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 116
ctctgagctg aatgtgaacg cct                                             23

<210> SEQ ID NO 117
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 117
tggctacaat gtctccagat taaacaa                                         27

<210> SEQ ID NO 118
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
ccctgatggc tacaatgtct ccaga                                           25

<210> SEQ ID NO 119
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
gtgtctccag agcaaacaca gatgatt                                         27

<210> SEQ ID NO 120
<211> LENGTH: 24
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 120
gtctccagat caaccacaga ggat                                              24

<210> SEQ ID NO 121
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
gtctctagat taaacacaga ggatttc                                           27

<210> SEQ ID NO 122
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
ggctacaatg tatccagatc aaaca                                             25

<210> SEQ ID NO 123
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
tcgcttctct gcagagagga ctgg                                              24

<210> SEQ ID NO 124
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 124
cggttctttg cagtcaggcc tga                                               23

<210> SEQ ID NO 125
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 125
tctccactct gamgatccag cgca                                              24

<210> SEQ ID NO 126
```

<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 126
gcagagaggc ctgagggatc cat                                              23

<210> SEQ ID NO 127
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 127
ccagtgatcg cttctttgca gaaa                                             24

<210> SEQ ID NO 128
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 128
ctgcagagag gcctaaggga tct                                              23

<210> SEQ ID NO 129
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 129
ctccgcacaa cagttccctg actt                                             24

<210> SEQ ID NO 130
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 130
cagatggcta yagtgtctct agatcaaa                                         28

<210> SEQ ID NO 131
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 131

```
gttgtctcca gatccaagac agagaa                                        26

<210> SEQ ID NO 132
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 132
gcagagaggc tcaaaggagt agact                                         25

<210> SEQ ID NO 133
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 133
gctaagatgc ctaatgcatc attctc                                        26

<210> SEQ ID NO 134
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 134
ctcagcagag atgcctgatg caact                                         25

<210> SEQ ID NO 135
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 135
tctcagctca acagttcagt gacta                                         25

<210> SEQ ID NO 136
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 136
gctgaaagga ctggagggac gtat                                          24

<210> SEQ ID NO 137
<211> LENGTH: 24
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 137
gataacttcc aatccaggag gccg                                           24

<210> SEQ ID NO 138
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 138
gctaagtgcc tcccaaattc accc                                           24

<210> SEQ ID NO 139
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 139
ggaacgattt tctgctgaat ttccca                                         26

<210> SEQ ID NO 140
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 140
ggtacagcgt ctctcgggag aaga                                           24

<210> SEQ ID NO 141
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 141
ggacaagttt ctcatcaacc atgcaa                                         26

<210> SEQ ID NO 142
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 142
tggatacagt gtctctcgac aggc                                           24
```

```
<210> SEQ ID NO 143
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 143
caacagtctc cagaataagg acgga                                              25

<210> SEQ ID NO 144
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 144
tacaaagtct ctcgaaaaga gaagagga                                           28

<210> SEQ ID NO 145
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 145
ggggtacagt gtctctagag aga                                                23

<210> SEQ ID NO 146
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 146
gtttcccatc agccgcccaa accta                                              25

<210> SEQ ID NO 147
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147
cagaccccag gaccggcagt tcat                                               24

<210> SEQ ID NO 148
<211> LENGTH: 9
<212> TYPE: PRT
<213> ORGANISM: Influenza A virus

<400> SEQUENCE: 148

Gly Ile Leu Gly Phe Val Phe Thr Leu
1               5
```

<210> SEQ ID NO 149
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Val Val Met Ser Trp Ala Pro Pro Val
1               5

<210> SEQ ID NO 150
<211> LENGTH: 9
<212> TYPE: PRT
<213> ORGANISM: Human T-lymphotropic virus 1

<400> SEQUENCE: 150

Leu Leu Phe Gly Tyr Pro Val Tyr Val
1               5

<210> SEQ ID NO 151
<211> LENGTH: 624
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 151

```
ggtctctacc tgaacaaggt gttcccaccc gaggtcgctg tgtttgagcc atcagaagca      60
gagatctccc acacccaaaa ggccacactg gtgtgcctgg ccacaggctt cttccccgac     120
cacgtggagc tgagctggtg ggtgaatggg aaggaggtgc acagtggggt cagcacggac     180
ccgcagcccc tcaaggagca gcccgccctc aatgactcca gatactgcct gagcagccgc     240
ctgagggttt cggccacctt ctggcagaac ccccgcaacc acttccgctg tcaagtccag     300
ttctacgggc tctcggagaa tgacgagtgg acccaggata gggccaaacc cgtcacccag     360
atcgtcagcg ccgaggcctg ggtagagcag actgtggct ttacctcggt gtcctaccag     420
caaggggtcc tgtctgccac catcctctat gagatcctgc tagggaaggc caccctgtat     480
gctgtgctgg tcagcgccct tgtgttgatg gccatggtca agagaaagga tttcaggagg     540
aggaggagcg gcagtggagt gaaacagact ttgaattttg accttctcaa gttggcggga     600
gacgtggagt ccaacccagg gccc                                            624
```

<210> SEQ ID NO 152
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 152

```
ggtctctacc tgaaaaacgt gttcccaccc gaggtcgctg tgtttgagcc atcagaagca      60
gagatctccc acacccaaaa ggccacactg gtgtgcctgg ccacaggctt ctaccccgac     120
cacgtggagc tgagctggtg ggtgaatggg aaggaggtgc acagtggggt cagcacagac     180
```

```
ccgcagcccc tcaaggagca gcccgccctc aatgactcca gatactgcct gagcagccgc    240
ctgagggttt cggccacctt ctggcagaac ccccgcaacc acttccgctg tcaagtccag    300
ttctacgggc tctcggagaa tgacgagtgg acccaggata gggccaaacc tgtcacccag    360
atcgtcagcg ccgaggcctg ggtagagca gactgtggct tcacctccga gtcttaccag    420 caagggtcc tgtctgccac catcctctat gagatcttgc tagggaaggc caccttgtat    480
gccgtgctgg tcagtgccct cgtgctgatg gccatggtca agagaaagga ttccagaggc    540
aggaggagga ggagcggcag tggagtgaaa cagactttga attttgacct tctcaagttg    600
gcgggagacg tggagtccaa cccagggccc                                    630
```

<210> SEQ ID NO 153
<211> LENGTH: 3203
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 153

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagagaatt cgagctcggt acctcgcgaa    420
tacatctaga tggtctctac ctgaacaagg tgttcccacc cgaggtcgct gtgtttgagc    480
catcagaagc agagatctcc cacacccaaa aggccacact ggtgtgcctg gccacaggct    540
tcttccccga ccacgtggag ctgagctggt gggtgaatgg aaggaggtg cacagtgggg    600 tcagcacgga cccgcagccc ctcaaggagc agcccgccct caatgactcc agatactgcc    660
tgagcagccg cctgagggtt cggccacct ctggcagaa ccccgcaac cacttccgct    720 gtcaagtcca gttctacggg ctctcggaga atgacgagtg gacccaggat agggccaaac    780
ccgtcaccca gatcgtcagc gccgaggcct ggggtagagc agactgtggc tttacctcgg    840
tgtcctacca gcaagggtc ctgtctgcca ccatcctcta tgagatcctg ctagggaagg    900
ccaccctgta tgctgtgctg gtcagcgccc ttgtgttgat ggccatggtc aagagaaagg    960
atttcaggag gaggaggagc ggcagtggag tgaaacagac tttgaattt gaccttctca   1020 agttggcggg agacgtggag tccaacccag ggcccatcgg atcccgggcc cgtcgactgc   1080
agaggcctgc atgcaagctt ggtgtaatca tggtcatagc tgtttcctgt gtgaaattgt   1140
tatccgctca caattccaca caacatacga gccgaagca taaagtgtaa agcctggggt   1200
gcctaatgag tgagctaact cacattaatt gcgttgcgct cactgcccgc tttccagtcg   1260
ggaaacctgt cgtgccagct gcattaatga atcggccaac gcgcgggag aggcggtttg   1320 cgtattgggc gctcttccgc ttcctcgctc actgactcgc tgcgctcggt cgttcggctg   1380
cggcgagcgg tatcagctca ctcaaaggcg gtaatacggt tatccacaga atcaggggat   1440
aacgcaggaa agaacatgtg agcaaaaggc cagcaaaagg ccaggaaccg taaaaaggcc   1500
gcgttgctgg cgtttttcca taggctccgc cccctgacg agcatcacaa aatcgacgc   1560
```

| | |
|---|---:|
| tcaagtcaga ggtggcgaaa cccgacagga ctataaagat accaggcgtt tccccctgga | 1620 |
| agctccctcg tgcgctctcc tgttccgacc ctgccgctta ccggatacct gtccgccttt | 1680 |
| ctcccttcgg gaagcgtggc gctttctcat agctcacgct gtaggtatct cagttcggtg | 1740 |
| taggtcgttc gctccaagct gggctgtgtg cacgaacccc ccgttcagcc cgaccgctgc | 1800 |
| gccttatccg gtaactatcg tcttgagtcc aacccggtaa gacacgactt atcgccactg | 1860 |
| gcagcagcca ctggtaacag gattagcaga gcgaggtatg taggcggtgc tacagagttc | 1920 |
| ttgaagtggt ggcctaacta cggctacact agaagaacag tatttggtat ctgcgctctg | 1980 |
| ctgaagccag ttaccttcgg aaaaagagtt ggtagctctt gatccggcaa acaaaccacc | 2040 |
| gctggtagcg gtggtttttt tgtttgcaag cagcagatta cgcgcagaaa aaaggatct | 2100 |
| caagaagatc ctttgatctt ttctacgggg tctgacgctc agtggaacga aaactcacgt | 2160 |
| taagggattt tggtcatgag attatcaaaa aggatcttca cctagatcct tttaaattaa | 2220 |
| aaatgaagtt ttaaatcaag cccaatctga ataatgttac aaccaattaa ccaattctga | 2280 |
| ttagaaaaac tcatcgagca tcaaatgaaa ctgcaattta ttcatatcag gattatcaat | 2340 |
| accatatttt tgaaaaagcc gtttctgtaa tgaaggagaa aactcaccga ggcagttcca | 2400 |
| taggatggca agatcctggt atcggtctgc gattccgact cgtccaacat caatacaacc | 2460 |
| tattaatttc ccctcgtcaa aaataaggtt atcaagtgag aaatcaccat gagtgacgac | 2520 |
| tgaatccggt gagaatggca aaagtttatg catttctttc cagacttgtt caacaggcca | 2580 |
| gccattacgc tcgtcatcaa aatcactcgc atcaaccaaa ccgttattca ttcgtgattg | 2640 |
| cgcctgagcg agacgaaata cgcgatcgct gttaaaagga caattacaaa caggaatcga | 2700 |
| atgcaaccgg cgcaggaaca ctgccagcgc atcaacaata ttttcacctg aatcaggata | 2760 |
| ttcttctaat acctggaatg ctgttttttcc ggggatcgca gtggtgagta accatgcatc | 2820 |
| atcaggagta cggataaaat gcttgatggt cggaagaggc ataaattccg tcagccagtt | 2880 |
| tagtctgacc atctcatctg taacatcatt ggcaacgcta cctttgccat gtttcagaaa | 2940 |
| caactctggc gcatcgggct tcccatacaa gcgatagatt gtcgcacctg attgcccgac | 3000 |
| attatcgcga gcccatttat acccatataa atcagcatcc atgttggaat ttaatcgcgg | 3060 |
| cctcgacgtt tcccgttgaa tatggctcat aacacccctt gtattactgt ttatgtaagc | 3120 |
| agacagtttt attgttcatg atgatatatt tttatcttgt gcaatgtaac atcagagatt | 3180 |
| ttgagacacg ggccagagct gca | 3203 |

<210> SEQ ID NO 154
<211> LENGTH: 3209
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 154

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |

```
tacgccagct ggcgaaaggg ggatgtgctg caaggcgatt aagttgggta acgccagggt      360
tttcccagtc acgacgttgt aaaacgacgg ccagagaatt cgagctcggt acctcgcgaa      420
tacatctaga tggtctctac ctgaaaaacg tgttcccacc cgaggtcgct gtgtttgagc      480
catcagaagc agagatctcc cacacccaaa aggccacact ggtgtgcctg gccacaggct      540
tctacgccga ccacgtggag ctgagctggt gggtgaatgg gaaggaggtg cacagtgggg      600
tcagcacaga cccgcagccc ctcaaggagc agcccgccct caatgactcc agatactgcc      660
tgagcagccg cctgagggtt tcggccacct tctggcagaa cccccgcaac cacttccgct      720
gtcaagtcca gttctacggg ctctcggaga tgacgagtg gacccaggat agggccaaac       780
ctgtcaccca gatcgtcagc gccgaggcct ggggtagagc agactgtggc ttcacctccg      840
agtcttacca gcaaggggtc ctgtctgcca ccatcctcta tgagatcttg ctagggaagg      900
ccaccttgta tgccgtgctg gtcagtgccc tcgtgctgat ggccatggtc aagagaaagg      960
attccagagg caggaggagg aggagcggca gtggagtgaa acagactttg aattttgacc     1020
ttctcaagtt ggcgggagac gtggagtcca acccagggcc catcggatcc cgggcccgtc     1080
gactgcagag gcctgcatgc aagcttggtg taatcatggt catagctgtt cctgtgtga     1140 aattgttatc cgctcacaat tccacacaac atacgagccg gaagcataaa gtgtaaagcc     1200
tggggtgcct aatgagtgag ctaactcaca ttaattgcgt tgcgctcact gcccgctttc     1260
cagtcgggaa acctgtcgtg ccagctgcat taatgaatcg ccaacgcgc ggggagaggc      1320 ggtttgcgta ttgggcgctc ttccgcttcc tcgctcactg actcgctgcg ctcggtcgtt     1380
cggctgcggc gagcggtatc agctcactca aaggcggtaa tacggttatc cacagaatca     1440
ggggataacg caggaaagaa catgtgagca aaaggccagc aaaaggccag gaaccgtaaa     1500
aaggccgcgt tgctggcgtt ttccatagg ctccgccccc ctgacgagca tcacaaaaat      1560
cgacgctcaa gtcagaggtg gcgaaaccg acaggactat aaagatacca ggcgtttccc      1620
cctggaagct ccctcgtgcg ctctcctgtt ccgaccctgc cgcttaccgg atacctgtcc     1680
gcctttctcc cttcgggaag cgtggcgctt tctcatagct cacgctgtag gtatctcagt     1740
tcggtgtagg tcgttcgctc caagctgggc tgtgtgcacg aacccccgt tcagcccgac      1800 cgctgcgcct tatccggtaa ctatcgtctt gagtccaacc cggtaagaca cgacttatcg     1860
ccactggcag cagccactgg taacaggatt agcagagcga ggtatgtagg cggtgctaca     1920
gagttcttga agtggtggcc taactacggc tacactagaa gaacagtatt tggtatctgc     1980
gctctgctga agccagttac cttcggaaaa agagttggta gctcttgatc cggcaaacaa     2040
accaccgctg gtagcggtgg tttttttgtt tgcaagcagc agattacgcg cagaaaaaaa     2100
ggatctcaag aagatccttt gatcttttct acggggtctg acgctcagtg gaacgaaaac     2160
tcacgttaag ggattttggt catgagatta tcaaaaagga tcttcaccta gatcctttta     2220
aattaaaaat gaagttttaa atcaagccca atctgaataa tgttacaacc aattaaccaa     2280
ttctgattag aaaaactcat cgagcatcaa atgaaactgc aatttattca tatcaggatt     2340
atcaatacca tatttttgaa aaagccgttt ctgtaatgaa ggagaaaact caccgaggca     2400
gttccatagg atggcaagat cctggtatcg gtctgcgatt ccgactcgtc caacatcaat     2460
acaacctatt aatttcccct cgtcaaaaat aaggttatca agtgagaaat caccatgagt     2520
gacgactgaa tccggtgaga atggcaaaag tttatgcatt tctttccaga cttgttcaac     2580
aggccagcca ttacgctcgt catcaaaatc actcgcatca accaaaccgt tattcattcg     2640
tgattgcgcc tgagcgagac gaaatacgcg atcgctgtta aaaggacaat acaaacagg      2700
```

| | |
|---|---|
| aatcgaatgc aaccggcgca ggaacactgc cagcgcatca acaatatttt cacctgaatc | 2760 |
| aggatattct tctaatacct ggaatgctgt ttttccgggg atcgcagtgg tgagtaacca | 2820 |
| tgcatcatca ggagtacgga taaaatgctt gatggtcgga agaggcataa attccgtcag | 2880 |
| ccagtttagt ctgaccatct catctgtaac atcattggca acgctacctt tgccatgttt | 2940 |
| cagaaacaac tctggcgcat cgggcttccc atacaagcga tagattgtcg cacctgattg | 3000 |
| cccgacatta tcgcgagccc atttataccc atataaatca gcatccatgt tggaatttaa | 3060 |
| tcgcggcctc gacgtttccc gttgaatatg gctcataaca ccccttgtat tactgtttat | 3120 |
| gtaagcagac agttttattg ttcatgatga tatattttta tcttgtgcaa tgtaacatca | 3180 |
| gagattttga gacacgggcc agagctgca | 3209 |

<210> SEQ ID NO 155
<211> LENGTH: 316
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 155

| | |
|---|---|
| atgtggggag ctttccttct ctatgtttcc atgaagatgg gaggcactgc aggacaaagc | 60 |
| cttgagcagc cctctgaagt gacagctgtg gaaggagcca ttgtccagat aaactgcacg | 120 |
| taccagacat ctgggtttta tgggctgtcc tggtaccagc aacatgatgg cggagcaccc | 180 |
| acatttcttt cttacaatgc tctggatggt ttggaggaga caggtcgttt ttcttcattc | 240 |
| cttagtcgct ctgatagtta tggttacctc cttctacagg agctccagat gaaagactct | 300 |
| gcctcttact gagacc | 316 |

<210> SEQ ID NO 156
<211> LENGTH: 316
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 156

| | |
|---|---|
| atgtggggag ttttccttct ttatgtttcc atgaagatgg gaggcactac aggacaaaac | 60 |
| attgaccagc ccactgagat gacagctacg gaaggtgcca ttgtccagat caactgcacg | 120 |
| taccagacat ctgggttcaa cgggctgttc tggtaccagc aacatgctgg cgaagcaccc | 180 |
| acatttctgt cttacaatgt tctggatggt ttggaggaga aggtcgtttt tcttcattc | 240 |
| cttagtcggt ctaaagggta cagttacctc cttttgaagg agctccagat gaaagactct | 300 |
| gcctcttact gagacc | 316 |

<210> SEQ ID NO 157
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 157

```
atggctttgc agagcactct gggggcggtg tggctagggc ttctcctcaa ctctctctgg      60
aaggttgcag aaagcaagga ccaagtgttt cagccttcca cagtggcatc ttcagaggga     120
gctgtggtgg aaatcttctg taatcactct gtgtccaatg cttacaactt cttctggtac    180
cttcacttcc cgggatgtgc accaagactc cttgttaaag ctcaaagcc ttctcagcag     240 ggacgataca acatgaccta tgaacggttc tcttcatcgc tgctcatcct ccaggtgcgg    300
gaggcagatg ctgctgttta ctgagacc                                        328
```

<210> SEQ ID NO 158
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 158

```
atggcctctg cacccatctc gatgcttgcg atgctcttca cattgagtgg gctgagagct      60
cagtcagtgg ctcagccgga agatcaggtc aacgttgctg aagggaatcc tctgactgtg    120
aaatgcacct attcagtctc tggaaaccct tatcttttt ggtatgttca ataccccaac     180
cgaggcctcc agttccttct gaaatacatc acaggggata acctggttaa aggcagctat    240
ggctttgaag ctgaatttaa caagagccaa acctccttcc acctgaagaa accatctgcc    300
cttgtgagcg actccgcttt gtactgagac c                                    331
```

<210> SEQ ID NO 159
<211> LENGTH: 316
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 159

```
atgaggcaag tggcgagagt gatcgtgttc ctgaccctga gtactttgag ccttgctaag      60
accacccagc ccatctccat ggactcatat gaaggacaag aagtgaacat aacctgtagc    120
cacaacaaca ttgctacaaa tgattatatc acgtggtacc aacagtttcc cagccaagga    180
ccacgattta ttattcaagg atacaagaca aaagttacaa acgaagtggc ctccctgttt    240
atccctgccg acagaaagtc cagcactctg agcctgcccc gggtttccct gagcgacact    300
gctgtgtact gagacc                                                     316
```

<210> SEQ ID NO 160
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160

```
atgaagacat tgctggatt ttcgttcctg tttttgtggc tgcagctgga ctgtatgagt       60
agaggagagg atgtggagca gagtctttc ctgagtgtcc gagagggaga cagctccgtt     120
ataaactgca cttacacaga cagctcctcc acctacttat actggtataa gcaagaacct    180
ggagcaggac tccagttgct gacgtatatt ttttcaaata tggacatgaa acaagaccaa    240
```

```
agactcactg ttctattgaa taaaaaggat aaacatctgt ctctgcgcat tgcagacacc    300
cagactgggg actcagctat ctactgagac c                                  331

<210> SEQ ID NO 161
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 161
atggagtcat tcctgggagg tgttttgctg attttgtggc ttcaagtgga ctgggtgaag    60
agccaaaaga tagaacagaa ttccgaggcc ctgaacattc aggagggtaa aacggccacc   120
ctgacctgca actatacaaa ctattcccca gcatacttac agtggtaccg acaagatcca   180
ggaagaggcc ctgttttctt gctactcata cgtgaaaatg agaaagaaaa aaggaaagaa   240
agactgaagg tcacctttga taccaccctt aaacagagtt tgtttcatat cacagcctcc   300
cagcctgcag actcagctac ctactgagac c                                  331

<210> SEQ ID NO 162
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 162
atggagaaga tgcggaggcc tgtcctaatt atattttgtc tatgtcttgg ctgggcaaat    60
ggagaaaacc aggtggagca cagccctcat tttctgggac cccagcaggg agacgttgcc   120
tccatgagct gcacgtactc tgtcagtcgt tttaacaatt tgcagtggta caggcaaaat   180
acagggatgg gtcccaaaca cctattatcc atgtattcag ctggatatga gaagcagaaa   240
ggaagactaa atgctacatt actgaagaat ggaagcagct tgtacattac agccgtgcag   300
cctgaagatt cagccaccta ttgagacc                                      328

<210> SEQ ID NO 163
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 163
atgctcctgt tgctcatacc agtgctgggg atgattttg ccctgagaga tgccagagcc    60
cagtctgtga gccagcataa ccaccacgta attctctctg aagcagcctc actggagttg   120
ggatgcaact attcctatgg tggaactgtt aatctcttct ggtatgtcca gtaccctggt   180
caacaccttc agcttctcct caagtacttt tcagggatc cactggttaa aggcatcaag   240
ggctttgagg ctgaatttat aaagagtaaa ttctccttta atctgaggaa accctctgtg   300
cagtggagtg acacagctga gtactgagac c                                  331

<210> SEQ ID NO 164
```

```
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
atgctcctgc tgctcgtccc agtgctcgag gtgattttta ctctgggagg aaccagagcc    60
cagtcggtga cccagcttga cagccacgtc tctgtctctg aaggaacccc ggtgctgctg   120
aggtgcaact actcatcttc ttattcacca tctctcttct ggtatgtgca acaccccaac   180
aaaggactcc agcttctcct gaagtacaca tcagcggcca ccctggttaa aggcatcaac   240
ggttttgagg ctgaatttaa gaagagtgaa acctccttcc acctgacgaa accctcagcc   300
catatgagcg acgcggctga gtactgagac c                                  331

<210> SEQ ID NO 165
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 165
atgctcctgg agcttatccc actgctgggg atacattttg tcctgagaac tgccagagcc    60
cagtcagtga cccagcctga catccacatc actgtctctg aaggagcctc actggagttg   120
agatgtaact attcctatgg ggcaacacct tatctcttct ggtatgtcca gtccccggc    180 caaggcctcc agctgctcct gaagtacttt tcaggagaca ctctggttca aggcattaaa   240
ggctttgagg ctgaatttaa gaggagtcaa tcttccttca atctgaggaa accctctgtg   300
cattggagtg atgctgctga gtactgagac c                                  331

<210> SEQ ID NO 166
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 166
atgctcctgc tgctcgtccc agtgctcgag gtgatttttta ccctgggagg aaccagagcc   60
cagtcggtga cccagcttgg cagccacgtc tctgtctctg aaggagccct ggttctgctg   120
aggtgcaact actcatcgtc tgttccacca tatctcttct ggtatgtgca ataccccaac   180
caaggactcc agcttctcct gaagtacaca tcagcggcca ccctggttaa aggcatcaac   240
ggttttgagg ctgaatttaa gaagagtgaa acctccttcc acctgacgaa accctcagcc   300
catatgagcg acgcggctga gtactgagac c                                  331

<210> SEQ ID NO 167
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 167

```
atgctcctgc tgctcgtccc agcgttccag gtgattttta ccctgggagg aaccagagcc    60
cagtctgtga cccagcttga cagccaagtc cctgtctttg aagaagcccc tgtggagctg   120
aggtgcaact actcatcgtc tgtttcagtg tatctcttct ggtatgtgca ataccccaac   180
caaggactcc agcttctcct gaagtattta tcaggatcca ccctggttga aagcatcaac   240
ggttttgagg ctgaatttaa caagagtcaa acttccttcc acttgaggaa accctcagtc   300
catataagcg acacggctga gtactgagac c                                  331
```

<210> SEQ ID NO 168
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 168

```
atgctcttag tggtcattct gctgcttgga atgttcttca cactgagaac cagaacccag    60
tcggtgaccc agcttgatgg ccacatcact gtctctgaag aagcccctct ggaactgaag   120
tgcaactatt cctatagtgg agttccttct ctccttctggt atgtccaata ctctagccaa   180
agcctccagc ttctcctcaa agacctaaca gaggccaccc aggttaaagg catcagaggt   240
tttgaggctg aatttaagaa gagcgaaacc tccttctacc tgaggaaacc atcaacccat   300
gtgagtgatg ctgctgagta ctgagacc                                      328
```

<210> SEQ ID NO 169
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 169

```
atgaattctt ctccaggacc agcgattgca ctattcttaa tgtttggggg aatcaatgga    60
gattcagtgg tccagacaga aggccaagtg ctcccctctg aagggattcc ctgattgtg   120
aactgctcct atgaaaccac acagtaccct tcccttttttt ggtatgtcca atatcctgga   180
gaaggtccac agctccacct gaaagccatg aaggccaatg acaagggaag gaacaaaggt   240
tttgaagcca tgtaccgtaa agaaaccact tctttccact ggagaaaaga ctcagttcaa   300
gagtcagact ccgctgtgta ctgagacc                                      328
```

<210> SEQ ID NO 170
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 170

```
atgaactatt ctccaggctt agtatctctg atactcttac tgcttggaag aacccgtgga    60
aattcagtga cccagatgga agggccagtg actctctcag aagaggcctt cctgactata   120
```

```
aactgcacgt acacagccac aggatacoct tcccttttct ggtatgtcca atatcctgga    180
gaaggtctac agctcctcct gaaagccacg aaggctgatg acaagggaag caacaaaggt    240
tttgaagcca cataccgtaa agaaaccact tctttccact tggagaaagg ctcagttcaa    300
gtgtcagact cagcggtgta ctgagacc                                       328
```

```
<210> SEQ ID NO 171
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 171
```

```
atgaaaaagc atctgacgac cttcttggtg attttgtggc tttatttta taggggaat     60 ggcaaaaacc aagtggagca gagtcctcag tccctgatca tcctggaggg aaagaactgc   120
actcttcaat gcaattatac agtgagcccc ttcagcaact taaggtggta taagcaagat   180
actgggagag gtcctgtttc cctgacaatc atgactttca gtgagaacac aaagtcgaac   240
ggaagatata cagcaactct ggatgcagac acaaagcaaa gctctctgca catcacagcc   300
tcccagctca gcgattcagc tcctactga gacc                                334
```

```
<210> SEQ ID NO 172
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 172
```

```
atgatatcct tgagagtttt actggtgatc ctgtggcttc agttaagctg ggtttggagc    60
caacggaagg aggtggagca ggatcctgga cccttcaatg ttccagaggg agccactgtc   120
gctttcaact gtacttacag caacagtgct tctcagtctt tcttctggta cagacaggat   180
tgcaggaaag aacctaagtt gctgatgtcc gtatactcca gtggtaatga agatggaagg   240
tttacagcac agctcaatag agccagccag tatatttccc tgctcatcag agactccaag   300
ctcagtgatt cagccaccta ctgagacc                                       328
```

```
<210> SEQ ID NO 173
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 173
```

```
atgaaatcct tgagagtttt actagtgatc ctgtggcttc agttgagctg ggtttggagc    60
caacagaagg aggtggagca gaattctgga cccctcagtg ttccagaggg agccattgcc   120
tctctcaact gcacttacag tgaccgaggt tcccagtcct tcttctggta cagacaatat   180
tctgggaaaa gccctgagtt gataatgttc atatactcca atggtgacaa agaagatgga   240
aggtttacag cacagctcaa taagccagcc agtatgtttt ctctgctcat cagagactcc   300
cagcccagtg attcagccac ctactgagac c                                   331
```

<210> SEQ ID NO 174
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 174

```
atgatgaaat ccttgagagt tttactggtg atcctgtggc ttcagttaag ctgggtttgg      60
agccaacaga aggaggtgga gcaggatcct ggaccactca gtgttccaga gggagccatt     120
gtttctctca actgcactta cagcaacagt gcttttcaat acttcatgtg gtacagacag     180
tattccagaa aaggccctga gttgctgatg tacacatact ccagtggtaa caaagaagat     240
ggaaggttta cagcacaggt cgataaatcc agcaagtata tctccttgtt catcagagac     300
tcacagccca gtgattcagc cacctactga gacc                                 334
```

<210> SEQ ID NO 175
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 175

```
atgacatcca ttcgagctgt atttatattc ctgtggctgc agctggactt ggtgaatgga      60
gagaatgtgg agcagcatcc ttcaaccctg agtgtccagg agggagacag cgctgttatc     120
aagtgtactt attcagacag tgcctcaaac tacttccctt ggtataagca agaacttgga     180
aaaggacctc agcttattat agacattcgt tcaaatgtgg gcgaaaagaa agaccaacga     240
attgctgtta cattgaacaa gacagccaaa catttctccc tgcacatcac agagacacaa     300
cctgaagact cggctgtcta ctgagacc                                        328
```

<210> SEQ ID NO 176
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 176

```
atggcaggca ttcgagcttt atttatgtac ttgtggctgc agctggactg ggtgagcaga      60
ggagagagtg tggggctgca tcttcctacc ctgagtgtcc aggagggtga caactctatt     120
atcaactgtg cttattcaaa cagcgcctca gactacttca tttggtacaa gcaagaatct     180
ggaaaaggtc ctcaattcat tatagacatt cgttcaaata tggacaaaag gcaaggccaa     240
agagtcaccg ttttattgaa taagacagtg aaacatctct ctctgcaaat tgcagctact     300
caacctggag actcagctgt ctactgagac c                                    331
```

<210> SEQ ID NO 177
<211> LENGTH: 337
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 177
atgtcacttt ctagcctgct gaaggtggtc acagcttcac tgtggctagg acctggcatt      60
gcccagaaga taactcaaac ccaaccagga atgttcgtgc aggaaaagga ggctgtgact     120
ctggactgca catatgacac cagtgatcca agttatggtc tattctggta caagcagccc     180
agcagtgggg aaatgatttt tcttatttat cagggtgtct tatgaccagca aaatgcaaca     240 gaaggtcgct actcattgaa tttccagaag gcaagaaaat ccgccaacct tgtcatctcc     300
gcttcacaac tgggggactc agcaatgtac tgagacc                              337

<210> SEQ ID NO 178
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 178
atgaagccca ccctcatctc agtgcttgtg ataatattta tactcagagg aacaagagcc      60
cagagagtga ctcagcccga gaagctcctc tctgtcttta aggggcccc agtggagctg      120 aagtgcaact attcctattc tgggagtcct gaactcttct ggtatgtcca gtactccaga     180
caacgcctcc agttactctt gagacacatc tctagagaga gcatcaaagg cttcactgct     240
gaccttaaca aggcgagac atctttccac ctgaagaaac catttgctca gaggaagac      300 tcagccatgt attgagacc                                                  319

<210> SEQ ID NO 179
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 179
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta ctgagacc                                        328

<210> SEQ ID NO 180
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 180
atgctgtctg cttcctgctc aggacttgtg atcttgttga tattcagaag gaccagtgga      60
```

```
gactcggtta cccagacaga aggcccagtt accctccctg agagggcagc tctgacatta    120
aactgcactt atcagtccag ctattcaact tttctattct ggtatgtcca gtatctaaac    180
aaagagcctg agctcctcct gaaaagttca gaaaaccagg agacggacag cagaggtttt    240
caggccagtc ctatcaagag tgacagttcc ttccacctgg agaagccctc ggtgcagctg    300
tcggactctg ccgtgtactg agacc                                          325

<210> SEQ ID NO 181
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 181
atgctgactg ccagcctgtt gagggcagtc atagcctcca tctgtgttgt atccagcatg     60
gctcagaagg taactcaagc gcagactgaa atttctgtgg tggagaagga ggatgtgacc    120
ttggactgtg tgtatgaaac ccgtgatact acttattact tattctgtgta caagcaacca    180 ccaagtggag aattggtttt ccttattcgt cggaactctt ttgatgagca aaatgaaata    240
agtggtcggt attcttggaa cttccagaaa tccaccagtt ccttcaactt caccatcaca    300
gcctcacaag tcgtggactc agcagtatac tgagacc                             337

<210> SEQ ID NO 182
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182
atggagaaaa tgttggagtg tgcattcata gtcttgtggc ttcagcttgg ctggttgagt     60
ggagaagacc aggtgacgca gagtcccgag gccctgagac tccaggaggg agagagtagc    120
agtcttaact gcagttacac agtcagcggt ttaagagggc tgttctggta taggcaagat    180
cctgggaaag gccctgaatt cctcttcacc ctgtattcag ctggggaaga aaaggagaaa    240
gaaaggctaa agccacatt aacaaagaag gaaagctttc tgcacatcac agcccctaaa    300
cctgaagact cagccactta ttgagacc                                       328

<210> SEQ ID NO 183
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183
atggagacac tcttgggcct gcttatcctt tggctgcagc tgcaatgggt gagcagcaaa     60
caggaggtga cgcagattcc tgcagctctg agtgtcccag aaggagaaaa cttggttctc    120
aactgcagtt tcactgatag cgctatttac aacctccagt ggtttaggca ggaccctggg    180 aaggactca catctctgtt gcttattcag tcaagtcaga gagagcaaac aagtggaaga    240
```

```
cttaatgcct cgctggataa atcatcagga cgtagtactt tatacattgc agcttctcag    300
cctggtgact cagccaccta ctgagacc                                      328

<210> SEQ ID NO 184
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184
atgaagagga tattgggagc tctgctgggg ctcttgagtg cccaggtttg ctgtgtgaga     60
ggaatacaag tggagcagag tcctccagac ctgattctcc aggagggagc caattccacg    120
ctgcggtgca attttctga ctctgtgaac aatttgcagt ggtttcatca aaacccttgg     180
ggacagctca tcaacctgtt ttacattccc tcagggacaa acagaatgg aagattaagc     240 gccacgactg tcgctacgga acgctacagc ttattgtaca tttcctcttc ccagaccaca    300
gactcaggcg tttattgaga cc                                            322

<210> SEQ ID NO 185
<211> LENGTH: 355
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 185
atggacaaga tcttaggagc atcattttta gttctgtggc ttcaactatg ctgggtgagt     60
ggccaacaga aggagaaaag tgaccagcag caggtgaaac aaagtcctca atctttgata    120
gtccagaaag gagggatttc aattataaac tgtgcttatg agaacactgc gtttgactac    180
tttccatggt accaacaatt ccctgggaaa ggccctgcat tattgatagc catacgtcca    240
gatgtgagtg aaaagaaaga aggaagattc acaatctcct tcaataaaag tgccaagcag    300
ttctcattgc atatcatgga ttcccagcct ggagactcag ccacctactg agacc         355

<210> SEQ ID NO 186
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 186
atggagaaga tcctttggc agccccatta ctaatcctct ggtttcatct tgactgcgtg      60
agcagcatac tgaacgtgga acaaagtcct cagtcactgc atgttcagga gggagacagc    120
accaatttca cctgcagctt cccttccagc aattttttatg ccttacactg gtacagatgg    180
gaaactgcaa aaagccccga ggccttgttt gtaatgactt aaatgggga tgaaaagaag     240 aaaggacgaa taagtgccac tcttaatacc aaggagggtt acagctattt gtacatcaaa    300
ggatcccagc tgaagactc agccacatac tgagacc                              337

<210> SEQ ID NO 187
<211> LENGTH: 322
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 187
atgctactca tcacatcaat gttggtctta tggatgcaat tgtcacaggt gaatggacaa      60
caggtaatgc aaattcctca gtaccagcat gtacaagaag gagaggactt caccacgtac     120
tgcaattcct caactacttt aagcaatata cagtggtata agcaaaggcc tggtggacat     180
cccgtttttt tgatacagtt agtgaagagt ggagaagtga agaagcagaa aagactgaca     240
tttcagtttg agaagcaaa aaagaacagc tccctgcaca tcacagccac ccagactaca      300
gatgtaggaa cctactgaga cc                                              322

<210> SEQ ID NO 188
<211> LENGTH: 316
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 188
atgaggctgg tggcaagagt aactgtgttt ctgacctttg aactataat tgatgctaag      60 accacccagc cccctccat ggattgcgct gaaggaagag ctgcaaacct gccttgtaat     120
cactctacca tcagtggaaa tgagtatgtg tattggtatc gacagattca ctcccagggg    180
ccacagtata tcattcatgg tctaaaaaac aatgaaacca atgaaatggc ctctctgatc    240
atcacagaag acagaaagtc cagcaccttg atcctgcccc acgctacgct gagagacact   300
gctgtgtact gagacc                                                    316

<210> SEQ ID NO 189
<211> LENGTH: 316
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 189
atgaagttgg tgacaagcat tactgtactc ctatctttgg gtattatggg tgatgctaag      60
accacacagc caaattcaat ggagagtaac gaagaagagc ctgttcactt gccttgtaac     120
cactccacaa tcagtggaac tgattacata cattggtatc gacagcttcc ctcccagggt    180
ccagagtacg tgattcatgg tcttacaagc aatgtgaaca acagaatggc ctctctggca    240
atcgctgaag acagaaagtc cagtaccttg atcctgcacc gtgctacctt gagagatgct    300
gctgtgtact gagacc                                                    316

<210> SEQ ID NO 190
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 190

```
atggtcctga aattctccgt gtccattctt tggattcagt tggcatgggt gagcacccag    60
ctgctggagc agagccctca gtttctaagc atccaagagg gagaaaatct cactgtgtac   120
tgcaactcct caagtgtttt ttccagctta caatggtaca gacaggagcc tggggaaggt   180
cctgtcctcc tggtgacagt agttacgggt ggagaagtga agaagctgaa gagactaacc   240
tttcagtttg gtgatgcaag aaaggacagt tctctccaca tcactgcagc ccagcctggt   300
gatacaggcc tctactgaga cc                                            322
```

<210> SEQ ID NO 191
<211> LENGTH: 349
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 191

```
atggccatgc tcctgggggc atcagtgctg attctgtggc ttcagccaga ctgggtaaac    60
agtcaacaga gaatgatga ccagcaagtt aagcaaaatt caccatccct gagcgtccag    120
gaaggaagaa tttctattct gaactgtgac tatactaaca gcatgtttga ttatttccta   180
tggtacaaaa ataccctgc tgaaggtcct acattcctga tatctataag ttccattaag   240
gataaaaatg aagatggaag attcactgtc ttcttaaaca aaagtgccaa gcacctctct   300
ctgcacattg tgccctccca gcctggagac tctgcagtgt actgagacc               349
```

<210> SEQ ID NO 192
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 192

```
atggagactc tcctgaaagt gctttcaggc accttgttgt ggcagttgac ctgggtgaga    60
agccaacaac cagtgcagag tcctcaagcc gtgatcctcc gagaagggga agatgctgtc   120
atcaactgca gttcctccaa ggctttatat tctgtacact ggtacaggca aagcatggt    180
gaagcacccg tcttcctgat gatattactg aagggtggag aacagaaggg tcatgaaaaa   240
atatctgctt catttaatga aaaaaagcag caaagctccc tgtaccttac ggcctcccag   300
ctcagttact caggaaccta ctgagacc                                      328
```

<210> SEQ ID NO 193
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 193

```
atggagactg ttctgcaagt actcctaggg atattggggt tccaagcagc ctgggtcagt    60
agccaagaac tggagcagag tcctcagtcc ttgatcgtcc aagagggaaa gaatctcacc   120
ataaactgca cgtcatcaaa gacgttatat ggcttatact ggtataagca aaagtatggt   180
```

```
gaaggtctta tcttcttgat gatgctacag aaaggtgggg aagagaaaag tcatgaaaag    240
ataactgcca agttggatga aaaaagcag caaagttccc tgcatatcac agcctcccag    300
cccagccatg caggcatcta ctgagacc                                      328
```

<210> SEQ ID NO 194
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 194

```
atgctccttg aacatttatt aataatcttg tggatgcagc tgacatgggt cagtggtcaa     60
cagctgaatc agagtcctca atctatgttt atccaggaag agaagatgt ctccatgaac     120 tgcacttctt caagcatatt aacacctgg ctatggtaca agcaggaacc tggggaaggt     180
cctgtcctct tgatagcctt atataaggct ggtgaattga cctcaaatgg aagactgact    240
gctcagtttg gtataaccag aaaggacagc ttcctgaata tctcagcatc catacctagt    300
gatgtaggca tctactgaga cc                                             322
```

<210> SEQ ID NO 195
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 195

```
atgatgaagt gtccacaggc tttactagct atcttttggc ttctactgag ctgggtgagc     60
agtgaagaca aggtggtaca aagccctcta tctctggttg tccacgaggg agacaccgta    120
actctcaatt gcagttatga agtgactaac tttcgaagcc tactatggta caagcaggaa    180
aagaaagctc ccacatttct atttatgcta acttcaagtg gaattgaaaa gaagtcagga    240
agactaagta gcatattaga taagaaagaa cttttccagca tcctgaacat cacagccacc    300
cagaccggag actcggccat ctactgagac c                                   331
```

<210> SEQ ID NO 196
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 196

```
atgacacgag ttagcttgct gtgggcagtc gtggtgtcca cctgtcttga atccggcatg     60
gcccagacag tcactcagtc tcaaccagag atgtctgtgc aggaggcaga gactgtgacc    120
ctgagttgca catatgacac cagtgagaat aattattatt tgttctggta caagcagcct    180
cccagcaggc agatgattct cgttattcgc caagaagctt ataagcaaca gaatgcaacg    240
gagaatcgtt tctctgtgaa cttccagaaa gcagccaaat ccttcagtct caagatctca    300
gactcacagc tggggacac tgcgatgtat tgagacc                              337
```

<210> SEQ ID NO 197
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 197

```
atggcatgcc ctggcttcct gtgggcactt gtgatctcca cctgtcttga atttagcatg      60
gctcagacag tcactcagtc tcaaccagag atgtctgtgc aggaggcaga gacagtgacc     120
ctgagctgca catatgacac cagtgagagt gattattatt tattctggta caagcagcct     180
cccagcaggc agatgattct cgttattcgc caagaagctt ataagcaaca gaatgcaaca     240
gagaatcgtt tctctgtgaa cttccagaaa gcagccaaat ccttcagtct caagatctca     300
gactcacagc tgggggatgc cgcgatgtat tgagacc                              337
```

<210> SEQ ID NO 198
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 198

```
atgaagaagc tactagcaat gattctgtgg cttcaactag accgcttaag tggagagctg      60
aaagtggaac aaaaccctct gttcctgagc atgcaggagg gaaaaaacta taccatctac     120
tgcaattatt caaccacttc agacagactg tattggtaca ggcaggatcc tgggaaaagt     180
ctggaatctc tgtttgtgtt gctatcaaat ggagcagtga agcaggaggg acgattaatg     240
gcctcacttg ataccaaagc ccgtctcagc accctccaca tcacagctgc cgtgcatgac     300
ctctctgcca cctactgaga cc                                              322
```

<210> SEQ ID NO 199
<211> LENGTH: 307
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 199

```
atgaactcct ctctggactt tctaattctg atcttaatgt ttggaggaac cagcagcaat      60
tcagtcaagc agacgggcca ataaccgtc tcggagggag catctgtgac tatgaactgc      120
acatacacat ccacgggta ccctacccctt ttctggtatg tggaataccc cagcaaacct     180
ctgcagcttc ttcagagaga gacaatggaa aacagcaaaa acttcggagg cggaaatatt     240
aaagacaaaa actcccccat tgtgaaatat tcagtccagg tatcagactc agccgtgtac     300
tgagacc                                                                307
```

<210> SEQ ID NO 200
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 200

```
atggtgaaga tccggcaatt tttgttggct attttgtggc ttcagctaag ctgtgtaagt    60
gccgccaaaa atgaagtgga gcagagtcct cagaacctga ctgcccagga aggagaattt   120
atcacaatca actgcagtta ctcggtagga ataagtgcct acactggct gcaacagcat    180
ccaggaggag gcattgtttc cttgtttatg ctgagctcag ggaagaagaa gcatggaaga   240
ttaattgcca caataaacat acaggaaaag cacagctccc tgcacatcac agcctcccat   300
cccagagact ctgccgtcta ctgagacc                                       328
```

<210> SEQ ID NO 201
<211> LENGTH: 485
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 201

```
ggtggtggtg gttctggttc tggttctggt ggtggttctg gtggtggtct cttgaccctg    60
ccgtgtacca gctgagagac tctaaatcca gtgacaagtc tgtctgccta ttcaccgatt   120
ttgattctca aacaaatgtg tcacaaagta aggattctga tgtgtatatc acagacaaaa   180
ctgtgctaga catgaggtct atggacttca agagcaacag tgctgtggcc tggagcaaca   240
aatctgactt tgcatgtgca aacgccttca acaacagcat tattccagaa gacaccttct   300
tccccagccc agaaagttcc tgtgatgtca agctggtcga aaaagctttg aaacagata   360
cgaacctaaa ctttcaaaac ctgtcagtga ttgggttccg aatcctcctc tgaaagtgg   420
ccgggtttaa tctgctcatg acgctgcggc tgtggtccag ctaaagcggc cgcgtcgaca   480
atcaa                                                               485
```

<210> SEQ ID NO 202
<211> LENGTH: 3064
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 202

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagagaatt cgactcggt acctcgcgaa   420
tacatctaga tggtggtggt ggttctggtt ctggttctgg tggtggttct ggtggtggtc   480
tcttgaccct gccgtgtacc agctgagaga ctctaaatcc agtgacaagt ctgtctgcct   540
attcaccgat tttgattctc aaacaaatgt gtcacaaagt aaggattctg atgtgtatat   600
```

```
cacagacaaa actgtgctag acatgaggtc tatggacttc aagagcaaca gtgctgtggc    660
ctggagcaac aaatctgact ttgcatgtgc aaacgcctTc aacaacagca ttattccaga    720
agacaccttc ttccccagcc cagaaagttc ctgtgatgtc aagctggtcg agaaaagctt    780
tgaaacagat acgaacctaa actttcaaaa cctgtcagtg attgggttcc gaatcctcct    840
cctgaaagtg gccgggttta atctgctcat gacgctgcgg ctgtggtcca gctaaagcgg    900
ccgcgtcgac aatcaaatcg gatcccgggc ccgtcgactg cagaggcctg catgcaagct    960
tggtgtaatc atggtcatag ctgtttcctg tgtgaaattg ttatccgctc acaattccac   1020
acaacatacg agccggaagc ataaagtgta agcctggggt gcctaatga gtgagctaac    1080
tcacattaat tgcgttgcgc tcactgcccg ctttccagtc gggaaacctg tcgtgccagc   1140
tgcattaatg aatcggccaa cgcgcgggga gaggcggttt gcgtattggg cgctcttccg   1200
cttcctcgct cactgactcg ctgcgctcgg tcgttcggct gcggcgagcg gtatcagctc   1260
actcaaaggc ggtaatacgg ttatccacag aatcagggga taacgcagga agaacatgt   1320
gagcaaaagg ccagcaaaag gccaggaacc gtaaaaaggc cgcgttgctg gcgttttttcc   1380
ataggctccg cccccctgac gagcatcaca aaaatcgacg ctcaagtcag aggtggcgaa   1440
acccgacagg actataaaga taccaggcgt ttccccctgg aagctccctc gtgcgctctc   1500
ctgttccgac cctgccgctt accggatacc tgtccgcctt tctcccttcg ggaagcgtgg   1560
cgctttctca tagctcacgc tgtaggtatc tcagttcggt gtaggtcgtt cgctccaagc   1620
tgggctgtgt gcacgaaccc cccgttcagc ccgaccgctg cgccttatcc ggtaactatc   1680
gtcttgagtc caacccggta agacacgact tatcgccact ggcagcagcc actggtaaca   1740
ggattagcag agcgaggtat gtaggcggtg ctacagagtt cttgaagtgg tggcctaact   1800
acggctacac tagaagaaca gtatttggta tctgcgctct gctgaagcca gttaccttcg   1860
gaaaaagagt tggtagctct tgatccggca aacaaaccac cgctggtagc ggtggttttt   1920
ttgtttgcaa gcagcagatt acgcgcagaa aaaaaggatc tcaagaagat cctttgatct   1980
tttctacggg gtctgacgct cagtggaacg aaaactcacg ttaagggatt ttggtcatga   2040
gattatcaaa aaggatcttc acctagatcc ttttaaatta aaaatgaagt tttaaatcaa   2100
gcccaatctg aataatgtta caaccaatta accaattctg attagaaaaa ctcatcgagc   2160
atcaaatgaa actgcaattt attcatatca ggattatcaa taccatattt ttgaaaaagc   2220
cgtttctgta atgaaggaga aaactcaccg aggcagttcc ataggatggc aagatcctgg   2280
tatcggtctg cgattccgac tcgtccaaca tcaatacaac ctattaattt cccctcgtca   2340
aaaataaggt tatcaagtga gaaatcacca tgagtgacga ctgaatccgg tgagaatggc   2400
aaaagtttat gcatttcttt ccagacttgt tcaacaggcc agccattacg ctcgtcatca   2460
aaatcactcg catcaaccaa accgttattc attcgtgatt gcgcctgagc gagacgaaat   2520
acgcgatcgc tgttaaaagg acaattacaa acaggaatcg aatgcaaccg gcgcaggaac   2580
actgccagcg catcaacaat attttcacct gaatcaggat attcttctaa tacctggaat   2640
gctgttttc cggggatcgc agtggtgagt aaccatgcat catcaggagt acggataaaa   2700
tgcttgatgg tcgaagagg cataaattcc gtcagccagt ttagtctgac catctcatct   2760
gtaacatcat tggcaacgct acctttgcca tgtttcagaa acaactctgg cgcatcgggc   2820
ttcccataca agcgatagat tgtcgcacct gattgcccga cattatcgcg agcccattta   2880
tacccatata aatcagcatc catgttggaa tttaatcgcg gcctcgacgt ttcccgttga   2940
atatggctca taacaccccT tgtattactg tttatgtaag cagacagttt tattgttcat   3000
```

```
gatgatatat ttttatcttg tgcaatgtaa catcagagat tttgagacac gggccagagc    3060
tgca                                                                3064

<210> SEQ ID NO 203
<211> LENGTH: 491
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 203
ggtggtggtg gttctggttc tggttctggt ggtggttctg gtggtggtct ctgaaccctg      60
accctgccgt gtaccagctg agagactcta aatccagtga caagtctgtc tgcctattca     120
ccgattttga ttctcaaaca aatgtgtcac aaagtaagga ttctgatgtg tatatcacag     180
acaaaactgt gctagacatg aggtctatgg acttcaagag caacagtgct gtggcctgga     240
gcaacaaatc tgactttgca tgtgcaaacg ccttcaacaa cagcattatt ccagaagaca     300
ccttcttccc cagcccagaa agttcctgtg atgtcaagct ggtcgagaaa agctttgaaa     360
cagatacgaa cctaaacttt caaaacctgt cagtgattgg gttccgaatc ctcctcctga     420
aagtggccgg gtttaatctg ctcatgacgc tgcggctgtg gtccagctaa agcggccgcg     480
tcgacaatca a                                                         491

<210> SEQ ID NO 204
<211> LENGTH: 3070
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 204
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagagaatt cgagctcggt acctcgcgaa     420
tacatctaga tggtggtggt ggttctggtt ctggttctgg tggtggttct ggtggtggtc     480
tctgaaccct gaccctgccg tgtaccagct gagagactct aaatccagtg acaagtctgt     540
ctgcctattc accgattttg attctcaaac aaatgtgtca caaagtaagg attctgatgt     600
gtatatcaca gacaaaactg tgctagacat gaggtctatg gacttcaaga gcaacagtgc     660
tgtggcctgg agcaacaaat ctgactttgc atgtgcaaac gccttcaaca acagcattat     720
tccagaagac accttcttcc ccagcccaga agttcctgtg atgtcaagc tggtcgagaa     780 aagctttgaa acagatacga acctaaactt tcaaaacctg tcagtgattg gttccgaat      840 cctcctcctg aaagtggccg ggtttaatct gctcatgacg ctgcggctgt ggtccagcta     900
aagcggccgc gtcgacaatc aaatcggatc ccgggcccgt cgactgcaga ggcctgcatg     960
```

```
caagcttggt gtaatcatgg tcatagctgt ttcctgtgtg aaattgttat ccgctcacaa    1020
ttccacacaa catacgagcc ggaagcataa agtgtaaagc ctggggtgcc taatgagtga    1080
gctaactcac attaattgcg ttgcgctcac tgcccgcttt ccagtcggga aacctgtcgt    1140
gccagctgca ttaatgaatc ggccaacgcg cggggagagg cggtttgcgt attgggcgct    1200
cttccgcttc ctcgctcact gactcgctgc gctcggtcgt tcggctgcgg cgagcggtat    1260
cagctcactc aaaggcggta atacggttat ccacagaatc aggggataac gcaggaaaga    1320
acatgtgagc aaaaggccag caaaaggcca ggaaccgtaa aaaggccgcg ttgctggcgt    1380
ttttccatag gctccgcccc cctgacgagc atcacaaaaa tcgacgctca agtcagaggt    1440
ggcgaaaccc gacaggacta taaagatacc aggcgtttcc ccctggaagc tccctcgtgc    1500
gctctcctgt tccgaccctg ccgcttaccg gatacctgtc cgcctttctc ccttcgggaa    1560
gcgtggcgct ttctcatagc tcacgctgta ggtatctcag ttcggtgtag tcgttcgct    1620 ccaagctggg ctgtgtgcac gaaccccccg ttcagcccga ccgctgcgcc ttatccggta    1680
actatcgtct tgagtccaac ccggtaagac acgacttatc gccactggca gcagccactg    1740
gtaacaggat tagcagagcg aggtatgtag gcggtgctac agagttcttg aagtggtggc    1800
ctaactacgg ctacactaga agaacagtat ttggtatctg cgctctgctg aagccagtta    1860
ccttcggaaa aagagttggt agctcttgat ccggcaaaca aaccaccgct ggtagcggtg    1920
gtttttttgt ttgcaagcag cagattacgc gcagaaaaaa aggatctcaa gaagatcctt    1980
tgatcttttc tacggggtct gacgctcagt ggaacgaaaa ctcacgttaa gggattttgg    2040
tcatgagatt atcaaaaagg atcttcacct agatcctttt aaattaaaaa tgaagtttta    2100
aatcaagccc aatctgaata atgttacaac caattaacca attctgatta gaaaaactca    2160
tcgagcatca aatgaaactg caatttattc atatcaggat tatcaatacc atatttttga    2220
aaaagccgtt tctgtaatga aggagaaaac tcaccgaggc agttccatag gatggcaaga    2280
tcctggtatc ggtctgcgat tccgactcgt ccaacatcaa tacaacctat aatttcccc    2340 tcgtcaaaaa taaggttatc aagtgagaaa tcaccatgag tgacgactga atccggtgag    2400
aatggcaaaa gtttatgcat ttcttttcag acttgttcaa caggccagcc attacgctcg    2460
tcatcaaaat cactcgcatc aaccaaaccg ttattcattc gtgattgcgc ctgagcgaga    2520
cgaaatacgc gatcgctgtt aaaaggacaa ttacaaacag gaatcgaatg caaccggcgc    2580
aggaacactg ccagcgcatc aacaatattt tcacctgaat caggatattc ttctaatacc    2640
tggaatgctg ttttccgggg atcgcagtg gtgagtaacc atgcatcatc aggagtacgg    2700
ataaaatgct tgatggtcgg aagaggcata aattccgtca gccagtttag tctgaccatc    2760
tcatctgtaa catcattggc aacgctacct ttgccatgtt tcagaaacaa ctctggcgca    2820
tcgggcttcc catacaagcg atagattgtc gcacctgatt gcccgacatt atcgcgagcc    2880
catttatacc catataaatc agcatccatg ttggaattta atcgcggcct cgacgtttcc    2940
cgttgaatat ggctcataac accccttgta ttactgttta tgtaagcaga cagttttatt    3000
gttcatgatg atatattttt atcttgtgca atgtaacatc agagattttg agacacgggc    3060
cagagctgca                                                          3070
```

<210> SEQ ID NO 205
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 205

| gggatccac cggtcgccac catggatacc tggctcgtat gctgggcaat ttttagtctc | 60 |
| ttgaaagcag gactcacaga acctgaagtc acccagactc ccagccatca ggtcacacag | 120 |
| atgggacagg aagtgatctt gcgctgtgtc cccatctcta atcacttata cttctattgg | 180 |
| tacagacaaa tcttggggca gaaagtcgag tttctggttt ccttttataa taatgaaatc | 240 |
| tcagagaagt ctgaaatatt cgatgatcaa ttctcagttg aaaggcctga tggatcaaat | 300 |
| ttcactctga agatccggtc cacaaagctg gaggactcag ccatgtacga gacctaa | 357 |

<210> SEQ ID NO 206
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 206

| ggggatccac cggtcgccac catgggctgc aggctcctct gctgtgtggt cttctgcctc | 60 |
| ctccaagcag gtcccttgga cacagctgtt tcccagactc caaaatacct ggtcacacag | 120 |
| atgggaaacg acaagtccat taaatgtgaa caaaatctgg gccatgatac tatgtattgg | 180 |
| tataaacagg actctaagaa atttctgaag ataatgttta gctacaataa taaggagctc | 240 |
| attataaatg aaacagttcc aaatcgcttc tcacctaaat ctccagacaa agctcactta | 300 |
| aatcttcaca tcaattccct ggagcttggt gactctgctg tgtatgagac ctaa | 354 |

<210> SEQ ID NO 207
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 207

| ggggatccac cggtcgccac catgggctgc aggctgctct gctgtgcggt tctctgtctc | 60 |
| ctgggagcag ttcccataga cactgaagtt acccagacac caaaacacct ggtcatggga | 120 |
| atgacaaata gaagtctttt gaatgtgaa caacatatgg ggcacagggc tatgtattgg | 180 |
| tacaagcaga aagctaagaa gccaccggag ctcatgtttg tctacagcta tgagaaactc | 240 |
| tctataaatg aaagtgtgcc aagtcgcttc tcacctgaat gccccaacag ctctctctta | 300 |
| aaccttcacc tacacgccct gcagccagaa gactcagccc tgtatgagac ctaa | 354 |

<210> SEQ ID NO 208
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 208

| ggggatccac cggtcgccac catgggctgc aggctgctct gctgtgcggt tctctgtctc | 60 |

```
ctgggagcgg tccccatgga acgggagtt acgcagacac caagacacct ggtcatggga    120
atgacaaata agaagtcttt gaaatgtgaa caacatctgg ggcataacgc tatgtattgg   180
tacaagcaaa gtgctaagaa gccactggag ctcatgtttg tctacaactt aaagaacag    240 actgaaaaca acagtgtgcc aagtcgcttc tcacctgaat gccccaacag ctctcactta   300
ttccttcacc tacacaccct gcagccagaa gactcggccc tgtatgagac ctaa         354
```

<210> SEQ ID NO 209
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 209

```
ggggatccac cggtcgccac catgggctgc aggctgctct gctgtgcggt tctctgtctc    60
ctgggagcgg tccccatgga acgggagtt acgcagacac caagacacct ggtcatggga    120
atgacaaata agaagtcttt gaaatgtgaa caacatctgg gtcataacgc tatgtattgg   180
tacaagcaaa gtgctaagaa gccactggag ctcatgtttg tctacagtct gaagaacgg    240 gttgaaaaca acagtgtgcc aagtcgcttc tcacctgaat gccccaacag ctctcactta   300
ttccttcacc tacacaccct gcagccagaa gactcggccc tgtatgagac ctaa         354
```

<210> SEQ ID NO 210
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 210

```
ggggatccac cggtcgccac catgggctcc aggctgctct gttgggtgct gctttgtctc    60
ctgggagcag gcccagtaaa ggctggagtc actcaaactc caagatatct gatcaaaacg   120
agaggacagc aagtgacact gagctgctcc cctatctctg ggcataggag tgtatcctgg   180
taccaacaga ccccaggaca gggccttcag ttcctctttg aatacttcag tgagacacag   240
agaaacaaag gaaacttccc tggtcgattc tcagggcgcc agttctctaa ctctcgctct   300
gagatgaatg tgagcacctt ggagctgggg gactcggccc tttatgagac ctaa         354
```

<210> SEQ ID NO 211
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 211

```
ggggatccac cggtcgccac catgggcccc gggctcctct gctgggaact gctttatctc    60
ctgggagcag gcccagtgga ggctggagtc acccaaagtc ccacacacct gatcaaaacg   120
agaggacagc aagtgactct gagatgctct cctatctctg gcacagcag tgtgtcctgg    180 taccaacagg ccccgggtca ggggcccag tttatctttg aatatgctaa tgagttaagg    240
agatcagaag gaaacttccc taatcgattc tcagggcgcc agttccatga ctgttgctct   300
```
gagatgaatg tgagtgcctt ggagctgggg gactcggccc tgtatgagac ctaa    354

```
<210> SEQ ID NO 212
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 212
```
ggggatccac cggtcgccac catgggccct gggctcctct gctgggtgct gctttgtctc    60
ctgggagcag gctcagtgga gactggagtc acccaaagtc ccacacacct gatcaaaacg    120
agaggacagc aagtgactct gagatgctct tctcagtctg gcacaacac tgtgtcctgg    180 taccaacagg ccctgggtca ggggccccag tttatctttc agtattatag ggaggaagag    240
aatggcagag gaaactttcc cctagattc tcaggactcc agttccctaa ttatagctct    300
gagctgaatg tgaacgcctt ggagctggac gactcggccc tgtatgagac ctaa    354

```
<210> SEQ ID NO 213
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213
```
ggggatccac cggtcgccac catgggccct gggctcctct gctgggtgct gctttgtctc    60
ctgggagcag gcccagtgga cgctggagtc acccaaagtc ccacacacct gatcaaaacg    120
agaggacagc aagtgactct gagatgctct cctatctctg gcacaagag tgtgtcctgg    180 taccaacagg tcctgggtca ggggccccag tttatctttc agtattatga gaaagaagag    240
agaggaagag gaaactttcc tgatcgattc tcagctcgcc agttccctaa ctatagctct    300
gagctgaatg tgaacgcctt gttgctgggg gactcggccc tgtatgagac ctaa    354

```
<210> SEQ ID NO 214
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 214
```
ggggatccac cggtcgccac catgggcccc gggctcctct gctgggcact gctttgtctc    60
ctgggagcag gcttagtgga cgctggagtc acccaaagtc ccacacacct gatcaaaacg    120
agaggacagc aagtgactct gagatgctct cctaagtctg gcatgacac tgtgtcctgg    180 taccaacagg ccctgggtca ggggccccag tttatctttc agtattatga ggaggaagag    240
agacagagag gcaacttccc tgatcgattc tcaggtcacc agttccctaa ctatagctct    300
gagctgaatg tgaacgcctt gttgctgggg gactcggccc tctatgagac ctaa    354

```
<210> SEQ ID NO 215
<211> LENGTH: 354
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 215

```
ggggatccac cggtcgccac catgggcccc gggctcctct gctgggtgct gctttgtccc      60
ctaggagaag gcccagtgga cgctggagtc acccaaagtc ccacacacct gatcaaaacg     120
agaggacagc acgtgactct gagatgctct cctatctctg gcacaccag tgtgtcctcg      180 taccaacagg ccctgggtca ggggccccag tttatctttc agtattatga gaaagaagag     240
agaggaagag gaaacttccc tgatcaattc tcaggtcacc agttccctaa ctatagctct     300
gagctgaatg tgaacgcctt gttgctaggg gactcggccc tctatgagac ctaa           354
```

<210> SEQ ID NO 216
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 216

```
ggggatccac cggtcgccac catgggaccc aggctcctct tctgggcact gctttgtctc      60
ctcggaacag gcccagtgga ggctggagtc acacaaagtc ccacacacct gatcaaaacg     120
agaggacagc aagcgactct gagatgctct cctatctctg gcacaccag tgtgtactgg      180 taccaacagg ccctgggtct gggcctccag ttcctccttt ggtatgacga gggtgaagag     240
agaaacagag gaaacttccc tcctagattt tcaggtcgcc agttccctaa ttatagctct     300
gagctgaatg tgaacgcctt ggagctggag gactcggccc tgtatgagac ctaa           354
```

<210> SEQ ID NO 217
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 217

```
ggggatccac cggtcgccac catgagcatc gggctcctgt gctgtgtggc cttttctctc      60
ctgtgggcaa gtccagtgaa tgctggtgtc actcagaccc caaaattcca ggtcctgaag     120
acaggacaga gcatgacact gcagtgtgcc caggatatga accataactc catgtactgg     180
tatcgacaag acccaggcat gggactgagg ctgatttatt actcagcttc tgagggtacc     240
actgacaaag agaagtccc caatggctac aatgtctcca gattaaacaa acgggagttc      300
tcgctcaggc tggagtcggc tgctccctcc cagacatctg tgtacgagac ctaa           354
```

<210> SEQ ID NO 218
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218

```
ggggatccac cggtcgccac catgagcctc gggctcctgt gctgtgcagc ctttctctc    60 ctgtgggcag gtccagtgaa tgctggtgtc actcagaccc caaaattccg ggtcctgaag   120
acaggacaga gcatgacact gctgtgtgcc caggatatga accatgaata catgtactgg   180
tatcgacaag acccaggcat ggggctgagg ctgattcatt actcagttgg tgagggtaca   240
actgccaaag gagaggtccc tgatggctac aatgtctcca gattaaaaaa acagaatttc   300
ctgctggggt tggagtcggc tgctccctcc caaacatctg tgtacgagac ctaa         354
```

<210> SEQ ID NO 219
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 219

```
ggggatccac cggtcgccac catgaaatac ctattgccta cggcagccgc tggattgtta   60
ttactcgcgg cccagccggc catggccaat gctggtgtca ctcagacccc aaaattccgg   120
gtcctgaaga caggacagag catgacactg ctgtgtgccc aggatatgaa ccatgaatac   180
atgtactggt atcgacaaga cccaggcatg gggctgaggc tgattcatta ctcagttggt   240
gagggtacaa ctgccaaagg agaggtccct gatggctaca atgtctccag attaaaaaaa   300
cagaatttcc tgctggggtt ggagtcggct gctccctccc aaacatctgt gtacgagacc   360
taa                                                                363
```

<210> SEQ ID NO 220
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 220

```
ggggatccac cggtcgccac catgagaatc aggctcctgt gctgtgtggc cttttctctc   60
ctgtgggcag gtccagtgat tgctgggatc acccaggcac caaacatctca gatcctggca   120 gcaggacggc gcatgacact gagatgtacc caggatatga gacataatgc catgtactgg   180
tatagacaag atctaggact ggggctaagg ctcatccatt attcaaatac tgcaggtacc   240
actggcaaag gagaagtccc tgatggttat agtgtctcca gagcaaacac agatgatttc   300
cccctcacgt tggcgtctgc tgtaccctct cagacatctg tgtacgagac ctaa         354
```

<210> SEQ ID NO 221
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 221

```
ggggatccac cggtcgccac catgagcatc ggcctcctgt gctgtgcagc cttgtctctc   60
ctgtgggcag gtccagtgaa tgctggtgtc actcagaccc caaaattcca ggtcctgaag   120
```

| | |
|---|---|
| acaggacaga gcatgacact gcagtgtgcc caggatatga accatgaata catgtcctgg | 180 |
| tatcgacaag acccaggcat ggggctgagg ctgattcatt actcagttgg tgctggtatc | 240 |
| actgaccaag gagaagtccc caatggctac aatgtctcca gatcaaccac agaggatttc | 300 |
| ccgctcaggc tgctgtcggc tgctccctcc cagacatctg tgtacgagac ctaa | 354 |

<210> SEQ ID NO 222
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222

| | |
|---|---|
| ggggatccac cggtcgccac catgagcatc agcctcctgt gctgtgcagc ctttcctctc | 60 |
| ctgtgggcag gtccagtgaa tgctggtgtc actcagaccc caaaattccg catcctgaag | 120 |
| ataggacaga gcatgacact gcagtgtacc caggatatga accataacta catgtactgg | 180 |
| tatcgacaag acccaggcat ggggctgaag ctgatttatt attcagttgg tgctggtatc | 240 |
| actgataaag gagaagtccc gaatggctac aacgtctcca gatcaaccac agaggatttc | 300 |
| ccgctcaggc tggagttggc tgctccctcc cagacatctg tgtacgagac ctaa | 354 |

<210> SEQ ID NO 223
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 223

| | |
|---|---|
| ggggatccac cggtcgccac catgagcctc gggctcctgt gctgtgtggc cttttctctc | 60 |
| ctgtgggcag gtccaatgaa tgctggtgtc actcagaccc caaaattcca cgtcctgaag | 120 |
| acaggacaga gcatgactct gctgtgtgcc caggatatga accatgaata catgtatcgg | 180 |
| tatcgacaag acccaggcaa ggggctgagg ctgatttact actcagttgc tgctgctctc | 240 |
| actgacaaag gagaagttcc caatggctac aatgtctcca gatcaaacac agaggatttc | 300 |
| cccctcaagc tggagtcagc tgctccctct cagacttctg tttacgagac ctaa | 354 |

<210> SEQ ID NO 224
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224

| | |
|---|---|
| ggggatccac cggtcgccac catgagcctc gggctcctgt gctgtgcggc cttttctctc | 60 |
| ctgtgggcag gtcccgtgaa tgctggtgtc actcagaccc caaaattcca catcctgaag | 120 |
| acaggacaga gcatgacact gcagtgtgcc caggatatga accatggata catgtcctgg | 180 |
| tatcgacaag acccaggcat ggggctgaga ctgatttact actcagctgc tgctggtact | 240 |
| actgacaaag aagtccccaa tggctacaat gtctctagat aaacacaga ggatttccca | 300 |
| ctcaggctgg tgtcggctgc tccctcccag acatctgtgt acgagaccta a | 351 |

<210> SEQ ID NO 225
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 225

```
ggggatccac cggtcgccac catgagcatc gggctcctgt gctgtgtggc cttttctctc    60
ctgtgggcag gtccagtgaa tgctggtgtc actcagaccc caaaattcca catcctgaag   120
acaggacaga gcatgacact gcagtgtgcc caggatatga accatggata cttgtcctgg   180
tatcgacaag acccaggcat ggggctgagg cgcattcatt actcagttgc tgctggtatc   240
actgacaaag gagaagtccc cgatggctac aatgtatcca gatcaaacac agaggatttc   300
ccgctcaggc tggagtcagc tgctccctcc cagacatctg tatacgagac ctaa         354
```

<210> SEQ ID NO 226
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 226

```
ggggatccac cggtcgccac catgggcaca aggctcctct gctgggcagc catatgtctc    60
ctgggggcag atcacacagg tgctggagtc tcccagtccc tgagacacaa ggtagcaaag   120
aagggaaagg atgtagctct cagatatgat ccaatttcag gtcataatgc cctttattgg   180
taccgacaga gcctggggca gggcctggag tttccaattt acttccaagg caaggatgca   240
gcagacaaat cggggcttcc ccgtgatcgg ttctctgcac agaggtctga gggatccatc   300
tccactctga agttccagcg cacacagcag ggggacttgg ctgtgtatga gacctaa     357
```

<210> SEQ ID NO 227
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 227

```
ggggatccac cggtcgccac catgggcacc aggctcctct tctgggtggc cttctgtctc    60 ctggggcag atcacacagg agctggagtc tcccagtccc ccagtaacaa ggtcacagag   120
aagggaaagg atgtagagct caggtgtgat ccaatttcag gtcatactgc cctttactgg   180
taccgacaga gcctggggca gggcctggag tttttaattt acttccaagg caacagtgca   240
ccagacaaat cagggctgcc cagtgatcgc ttctctgcag agaggactgg gggatccgtc   300
tccactctga cgatccagcg cacacagcag gaggactcgg ccgtgtatga gacctaa    357
```

<210> SEQ ID NO 228
<211> LENGTH: 357
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 228

```
ggggatccac cggtcgccac catgggcacc aggctcctct gctgggcagc cctgtgcctc    60 ctggggcag atcacacagg tgctggagtc tcccagaccc ccagtaacaa ggtcacagag    120
aagggaaaat atgtagagct caggtgtgat ccaatttcag gtcatactgc cctttactgg    180
taccgacaaa gcctggggca gggcccagag tttctaattt acttccaagg cacgggtgcg    240
gcagatgact cagggctgcc caacgatcgg ttctttgcag tcaggcctga gggatccgtc    300
tctactctga agatccagcg cacagagcgg ggggactcag ccgtgtatga gacctaa     357
```

<210> SEQ ID NO 229
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 229

```
ggggatccac cggtcgccac catgggcacc aggctcctct gctgggtggt cctgggtttc    60
ctagggacag atcacacagg tgctggagtc tcccagtccc caaggtacaa agtcgcaaag    120
aggggacggg atgtagctct caggtgtgat tcaatttcgg gtcatgtaac cctttattgg    180
taccgacaga ccctggggca gggctcagag gttctgactt actcccagag tgatgctcaa    240
cgagacaaat cagggcggcc cagtggtcgg ttctctgcag agaggcctga gagatccgtc    300
tccactctga agatccagcg cacagagcag ggggactcag ctgtgtatga gacctaa     357
```

<210> SEQ ID NO 230
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230

```
ggggatccac cggtcgccac catgggcacc agtctcctat gctgggtggt cctgggtttc    60
ctagggacag atcacacagg tgctggagtc tcccagtctc ccaggtacaa agtcacaaag    120
aggggacagg atgtagctct caggtgtgat ccaatttcgg gtcatgtatc cctttattgg    180
taccgacagg ccctggggca gggcccagag tttctgactt acttcaatta tgaagcccaa    240
caagacaaat cagggctgcc caatgatcgg ttctctgcag agaggcctga gggatccatc    300
tccactctga cgatccagcg cacagagcag cgggactcgg ccatgtatga gacctaa     357
```

<210> SEQ ID NO 231
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 231

```
ggggatccac cggtcgccac catgggtacc agtctcctat gctgggtggt cctgggtttc    60
```

```
ctagggacag atcacacagg tgctggagtc tcccagtctc ccaggtacaa agtcacaaag    120
aggggacagg atgtaactct caggtgtgat ccaatttcga gtcatgcaac cctttattgg    180
tatcaacagg ccctggggca gggcccagag tttctgactt acttcaatta tgaagctcaa    240
ccagacaaat cagggctgcc cagtgatcgg ttctctgcag agaggcctga gggatccatc    300
tccactctga cgattcagcg cacagagcag cgggactcag ccatgtatga gacctaa      357
```

<210> SEQ ID NO 232
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 232

```
ggggatccac cggtcgccac catgggcacc aggctcctct gctgggtggt cctgggtttc     60
ctagggacag atcacacagg tgctggagtc tcccagtccc ctaggtacaa agtcgcaaag    120
agaggacagg atgtagctct caggtgtgat ccaatttcgg gtcatgtatc ccttttttgg    180
taccaacagg ccctggggca ggggccagag tttctgactt atttccagaa tgaagctcaa    240
ctagacaaat cggggctgcc cagtgatcgc ttctttgcag aaaggcctga gggatccgtc    300
tccactctga agatccagcg cacacagcag gaggactccg ccgtgtatga gacctaa      357
```

<210> SEQ ID NO 233
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 233

```
ggggatccac cggtcgccac catgggcacc agcctcctct gctggatggc cctgtgtctc     60
ctgggggcag atcacgcaga tactggagtc tcccagaacc ccagacacaa gatcacaaag    120
aggggacaga atgtaacttt caggtgtgat ccaatttctg aacacaaccg cctttattgg    180
taccgacaga ccctggggca gggcccagag tttctgactt acttccagaa tgaagctcaa    240
ctagaaaaat caaggctgct cagtgatcgg ttctctgcag agaggcctaa gggatctttc    300
tccaccttgg agatccagcg cacagagcag ggggactcgg ccatgtatga gacctaa      357
```

<210> SEQ ID NO 234
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 234

```
ggggatccac cggtcgccac catgggcttc aggctcctct gctgtgtggc cttttgtctc     60
ctgggagcag gcccagtgga ttctggagtc acacaaaccc caaagcacct gatcacagca    120
actggacagc gagtgacgct gagatgctcc cctaggtctg agatctctct tgtgtactgg    180
taccaacaga gcctggacca gggcctccag ttcctcattc agtattataa tggagaagag    240
```

| | |
|---|---|
| agagcaaaag gaaacattct tgaacgattc tccgcacaac agttccctga cttgcactct | 300 |
| gaactaaacc tgagctctct ggagctgggg gactcagctt tgtatgagac ctaa | 354 |

<210> SEQ ID NO 235
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 235

| | |
|---|---|
| ggggatccac cggtcgccac catgggcacg aggctcttct tctatgtggc cctttgtctg | 60 |
| ctgtgggcag gacacaggga tgctgaaatc acccagagcc caagacacaa gatcacagag | 120 |
| acaggaaggc aggtgacctt ggcgtgtcac cagacttgga accacaacaa tatgttctgg | 180 |
| tatcgacaag acctgggaca tgggctgagg ctgatccatt actcatatgg tgttcaagac | 240 |
| actaacaaag gagaagtctc agatggctac agtgtctcta gatcaaacac agaggacctc | 300 |
| cccctcactc tggagtctgc tgcctcctcc cagacatctg tatatgagac ctaa | 354 |

<210> SEQ ID NO 236
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 236

| | |
|---|---|
| ggggatccac cggtcgccac catgggcacc aggctcttct tctatgtggc cctttgtctg | 60 |
| ctgtgggcag gacacaggga tgctggaatc acccagagcc caagatacaa gatcacagag | 120 |
| acaggaaggc aggtgacctt gatgtgtcac cagacttgga gccacagcta tatgttctgg | 180 |
| tatcgacaag acctgggaca tgggctgagg ctgatctatt actcagcagc tgctgatatt | 240 |
| acagataaag gagaagtccc cgatggctat gttgtctcca gatccaagac agagaatttc | 300 |
| cccctcactc tggagtcagc tacccgctcc cagacatctg tgtatgagac ctaa | 354 |

<210> SEQ ID NO 237
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 237

| | |
|---|---|
| ggggatccac cggtcgccac catgggcaca aggttgttct tctatgtggc cctttgtctc | 60 |
| ctgtggacag gacacatgga tgctggaatc acccagagcc caagacacaa ggtcacagag | 120 |
| acaggaacac cagtgactct gagatgtcac cagactgaga accaccgcta tatgtactgg | 180 |
| tatcgacaag acccggggca tgggctgagg ctgatccatt actcatatgg tgttaaagat | 240 |
| actgacaaag gagaagtctc agatggctat agtgtctcta gatcaaagac agaggatttc | 300 |
| ctcctcactc tggagtccgc taccagctcc cagacatctg tgtacgagac ctaa | 354 |

<210> SEQ ID NO 238
<211> LENGTH: 357

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 238

```
ggggatccac cggtcgccac catgagcacc aggcttctct gctggatggc cctctgtctc    60 ctggggcag aactctcaga agctgaagtt gcccagtccc ccagatataa gattacagag    120
aaaagccagg ctgtggcttt tggtgtgat cctatttctg gccatgctac cctttactgg    180
taccggcaga tcctgggaca gggcccggag cttctggttc aatttcagga tgagagtgta    240
gtagatgatt cacagttgcc taaggatcga ttttctgcag agaggctcaa aggagtagac    300
tccactctca agatccagcc tgcagagctt ggggactcgg ccatgtatga gacctaa    357
```

<210> SEQ ID NO 239
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 239

```
ggggatccac cggtcgccac catgggcacc aggctcctct gctgggcggc cctctgtctc    60
ctgggagcag aactcacaga agctggagtt gcccagtctc ccagatataa gattatagag    120
aaaaggcaga gtgtggcttt tggtgcaat cctatatctg gccatgctac cctttactgg    180
taccagcaga tcctgggaca gggcccaaag cttctgattc agtttcagaa taacggtgta    240
gtggatgatt cacagttgcc taaggatcga ttttctgcag agaggctcaa aggagtagac    300
tccactctca agatccagcc tgcaaagctt gaggactcgg ccgtgtatga gacctaa    357
```

<210> SEQ ID NO 240
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 240

```
ggggatccac cggtcgccac catgggtacc aggctcctct gctgggtggc cttctgtctc    60
ctggtggaag aactcataga agctggagtg gttcagtctc ccagatataa gattatagag    120
aaaaaacagc ctgtggcttt tggtgcaat cctatttctg gccacaatac cctttactgg    180
tacctgcaga acttgggaca gggcccggag cttctgattc gatatgagaa tgaggaagca    240
gtagacgatt cacagttgcc taaggatcga ttttctgcag agaggctcaa aggagtagac    300
tccactctca agatccagcc tgcagagctt ggggactcgg ccgtgtatga gacctaa    357
```

<210> SEQ ID NO 241
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 241

```
ggggatccac cggtcgccac catggactcc tggaccttct gctgtgtgtc cctttgcatc      60
ctggtagcga agcatacaga tgctggagtt atccagtcac cccgccatga ggtgacagag     120
atgggacaag aagtgactct gagatgtaaa ccaatttcag ccacaactc cctttctgg       180
tacagacaga ccatgatgcg gggactggag ttgctcattt actttaacaa caacgttccg    240
atagatgatt cagggatgcc cgaggatcga ttctcagcta agatgcctaa tgcatcattc     300
tccactctga agatccagcc ctcagaaccc agggactcag ctgtgtacga gacctaa       357
```

<210> SEQ ID NO 242
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 242

```
ggggatccac cggtcgccac catgggctcc tggaccctct gctgtgtgtc cctttgcatc      60
ctggtagcaa agcacacaga tgctggagtt atccagtcac cccggcacga ggtgacagag     120
atgggacaag aagtgactct gagatgtaaa ccaatttcag gacacgacta cctttctgg      180
tacagacaga ccatgatgcg gggactggag ttgctcattt actttaacaa caacgttccg    240
atagatgatt cagggatgcc cgaggatcga ttctcagcta agatgcctaa tgcatcattc     300
tccactctga agatccagcc ctcagaaccc agggactcag ctgtgtacga gacctaa       357
```

<210> SEQ ID NO 243
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 243

```
ggggatccac cggtcgccac catggccacc aggctcctct gctgtgtggt tctttgtctc      60
ctgggagaag agcttataga tgctagagtc acccagacac caaggcacaa ggtgacagag     120
atgggacaag aagtaacaat gagatgtcag ccaattttag gccacaatac tgttttctgg    180
tacagacaga ccatgatgca aggactggag ttgctggctt acttccgcaa ccgggctcct    240
ctagatgatt cggggatgcc gaaggatcga ttctcagcag agatgcctga tgcaacttta    300
gccactctga agatccagcc ctcagaaccc agggactcag ctgtgtatga gacctaa       357
```

<210> SEQ ID NO 244
<211> LENGTH: 384
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 244

```
ggggatccac cggtcgccac catgcttagt cctgacctgc ctgactctgc ctggaacacc      60
aggctcctct gccgtgtcat gctttgtctc ctgggagcag gttcagtggc tgctggagtc    120
atccagtccc caagacatct gatcaaagaa aagagggaaa cagccactct gaaatgctat    180
```

```
cctatcccta gacacgacac tgtctactgg taccagcagg gtccaggtca ggaccccag    240 ttcctcattt cgttttatga aaagatgcag agcgataaag gaagcatccc tgatcgattc    300
tcagctcaac agttcagtga ctatcattct gaactgaaca tgagctcctt ggagctgggg    360
gactcagccc tgtacgagac ctaa                                          384
```

<210> SEQ ID NO 245
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245

```
ggggatccac cggtcgccac catggtttcc aggcttctca gtttagtgtc cctttgtctc     60
ctgggagcaa agcacataga agctggagtt actcagttcc ccagccacag cgtaatagag    120
aagggccaga ctgtgactct gagatgtgac ccaatttctg acatgataa tctttattgg    180 tatcgacgtg ttatgggaaa agaaataaaa tttctgttac attttgtgaa agagtctaaa    240
caggatgagt ccggtatgcc caacaatcga ttcttagctg aaaggactgg agggacgtat    300
tctactctga aggtgcagcc tgcagaactg gaggattctg agtttatga gacctaa       357
```

<210> SEQ ID NO 246
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 246

```
ggggatccac cggtcgccac catgggtcct gggcttctcc actggatggc cctttgtctc     60
cttggaacag gtcatgggga tgccatggtc atccagaacc caagatacca ggttacccag    120
tttggaaagc cagtgaccct gagttgttct cagactttga accataacgt catgtactgg    180
taccagcaga agtcaagtca ggccccaaag ctgctgttcc actactatga caaagatttt    240
aacaatgaag cagacacccc tgataacttc aatccagga gccgaacac ttctttctgc     300 tttcttgaca tccgctcacc aggcctgggg gacacagcca tgtacgagac ctaa          354
```

<210> SEQ ID NO 247
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 247

```
ggggatccac cggtcgccac catgagccca atattcacct gcatcacaat cctttgtctg     60
ctggctgcag gttctcctgg tgaagaagtc gcccagactc aaaacatct tgtcagaggg    120 gaaggacaga aagcaaaatt atattgtgcc ccaataaaag gacacagtta tgtttttgg    180 taccaacagg tcctgaaaaa cgagttcaag ttcttgattt ccttccagaa tgaaaatgtc    240
tttgatgaaa caggtatgcc caaggaaaga ttttcagcta agtgcctccc aaattcaccc    300
```
tgtagccttg agatccaggc tacgaagctt gaggattcag cagtgtatga gacctaa    357

<210> SEQ ID NO 248
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248
ggggatccac cggtcgccac catggatatc tggctcctct gctgggtgac cctgtgtctc    60
ttggcggcag gacactcgga gcctggagtc agccagaccc ccagacacaa ggtcaccaac   120
atgggacagg aggtgattct gaggtgcgat ccatcttctg gtcacatgtt tgttcactgg   180
taccgacaga atctgaggca agaaatgaag ttgctgattt ccttccagta ccaaaacatt   240
gcagttgatt cagggatgcc caaggaacga ttcacagctg aaagacctaa cggaacgtct   300
tccacgctga agatccatcc cgcagagccg agggactcag ccgtgtatga gacctaa      357

<210> SEQ ID NO 249
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 249
ggggatccac cggtcgccac catgagcaac caggtgctct gctgtgtggt cctttgtttc    60
ctgggagcaa acaccgtgga tgtggaatc actcagtccc caaagtacct gttcagaaag   120
gaaggacaga atgtgaccct gagttgtgaa cagaatttga accacgatgc catgtactgg   180
taccgacagg acccagggca agggctgaga ttgatctact actcacagat agtaaatgac   240
tttcagaaag gagatatagc tgaagggtac agcgtctctc gggagaagaa ggaatccttt   300
cctctcactg tgacatcggc ccaaaagaac ccgacagctt tctatgagac ctaa         354

<210> SEQ ID NO 250
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 250
ggggatccac cggtcgccac catggacgcc agagtactct gctgtgcggt catctgtctt    60
ctgggggcag gactctcaaa tgccggcgtc atgcagaacc caagacacct ggtcaggagg   120
aggggacagg aggcaagact gagatgcagc ccaatgaaag gacacagtca tgtttactgg   180
tatcggcagc tcccagagga aggtctgaaa ttcatggttt atctccagaa agaaaatatc   240
atagatgagt caggaatgcc aaaggaacga ttttctgctg aatttcccaa agagggcccc   300
agcatcctga ggatccagca ggtagtgcga ggagattcgg cagcttatga gacctaa      357

<210> SEQ ID NO 251
<211> LENGTH: 351
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 251
ggggatccac cggtcgccac catgctgctg cttctgctgc ttctggggcc agcaggctcc      60
gggcttggtg ctgtcgtctc tcaacatccg agctgggtta tctgtaagag tggaacctct    120
gtgaagatcg agtgccgttc cctggacttt caggccacaa ctatgttttg gtatcgtcag    180
ttcccgaaac agagtctcat gctgatggca acttccaatg agggctccaa ggccacatac    240
gagcaaggcg tcgagaagga caagtttctc atcaaccatg caagcctgac cttgtccact    300
ctgacagtga ccagtgccca tcctgaagac agcagcttct acgagaccta a              351

<210> SEQ ID NO 252
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 252
ggggatccac cggtcgccac catgggcacc aggctcctcg gctgtgcagc cctgtgtctc      60
ctgacagcag actcttttca tgccaaagtc acacagactc caggacattt ggtcaaagga    120
aaaggacaga aaacaaagat ggattgtacc cccgaaaaag acatactttt gtttattgg     180 tatcaacaga atcagaataa agagtttatg cttttgattt cctttcagaa tgaacaagtt    240
cttcaagaaa cggagatgca caagaagcga ttctcatctc aatgccccaa gaacgcaccc    300
tgcagcctgg caatcctgtc ctcagaaccg ggagacacgg cactgtatga gacctaa       357

<210> SEQ ID NO 253
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 253
ggggatccac cggtcgccac catggcctcc ctgctcttct tctgtggggc cttttatctc      60
ctgggaacag gtccatgga tgctgatgtt acccagaccc caaggaatag atcacaaag      120 acaggaaaga ggattatgct ggaatgttct cagactaagg gtcatgatag aatgtactgg    180
tatcgacaag acccaggact gggcctacgg ttgatctatt actcctttga tgtcaaagat    240
ataaacaaag gagagatctc tgatggatac agtgtctctc gacaggcaca ggctaaattc    300
tccctgtccc tagagtctgc catccccaac cagacagctc tttacgagac ctaa           354

<210> SEQ ID NO 254
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 254
```

| | |
|---|---|
| ggggatccac cggtcgccac catgactatc aggctcctct gctacatggg cttttatttt | 60 |
| ctggggcag gcctcatgga agctgacatc taccagaccc caagatacct tgttataggg | 120 |
| acaggaaaga agatcactct ggaatgttct caaaccatgg ccatgacaa aatgtactgg | 180 |
| tatcaacaag atccaggaat ggaactacac ctcatccact attcctatgg agttaattcc | 240 |
| acagagaagg gagatctttc ctctgagtca acagtctcca gaataaggac ggagcatttt | 300 |
| cccctgaccc tggagtctgc caggccctca catacctctc agtacgagac ctaa | 354 |

<210> SEQ ID NO 255
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 255

| | |
|---|---|
| ggggatccac cggtcgccac catgggcccc cagctccttg ctatgtggt cctttgcctt | 60 |
| ctaggagcag gccccctgga agcccaagtg acccagaacc caagatacct catcacagtg | 120 |
| actggaaaga agttaacagt gacttgttct cagaatatga accatgagta tatgtcctgg | 180 |
| tatcgacaag acccagggct gggcttaagg cagatctact attcaatgaa tgttgaggtg | 240 |
| actgataagg gagatgttcc tgaagggtac aaagtctctc gaaaagagaa gaggaatttc | 300 |
| cccctgatcc tggagtcgcc cagccccaac cagacctctc tgtacgagac ctaa | 354 |

<210> SEQ ID NO 256
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 256

| | |
|---|---|
| ggggatccac cggtcgccac catgggaatc aggctcctct gtcgtgtggc cttttgtttc | 60 |
| ctggctgtag gcctcgtaga tgtgaaagta acccagagct cgagatatct agtcaaaagg | 120 |
| acgggagaga aagttttttct ggaatgtgtc caggatatgg accatgaaaa tatgttctgg | 180 |
| tatcgacaag acccaggtct ggggctacgg ctgatctatt tctcatatga tgttaaaatg | 240 |
| aaagaaaaag gagatattcc tgaggggtac agtgtctcta gagagaagaa ggagcgcttc | 300 |
| tccctgatte tggagtccgc cagcaccaac cagacatcta tgtacgagac ctaa | 354 |

<210> SEQ ID NO 257
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 257

| | |
|---|---|
| ggggatccac cggtcgccac catgctgagt cttctgctcc ttctcctggg actaggctct | 60 |
| gtgttcagtg ctgtcatctc tcaaaagcca agcagggata tctgtcaacg tggaacctcc | 120 |
| ctgacgatcc agtgtcaagt cgatagccaa gtcaccatga tgttctggta ccgtcagcaa | 180 |
| cctggacaga gcctgacact gatcgcaact gcaaatcagg gctctgaggc cacatatgag | 240 |

```
agtggatttg tcattgacaa gtttcccatc agccgcccaa acctaacatt ctcaactctg    300
actgtgagca acatgagccc tgaagacagc agcatatatg agacctaa                 348
```

<210> SEQ ID NO 258
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 258

```
ggggatccac cggtcgccac catgctctgc tctctccttg cccttctcct gggcactttc    60
tttggggtca gatctcagac tattcatcaa tggccagcga ccctggtgca gcctgtgggc   120
agcccgctct ctctggagtg cactgtggag ggaacatcaa accccaacct atactggtac   180
cgacaggctg caggcagggg cctccagctg ctcttctact ccgttggtat tggccagatc   240
agctctgagg tgccccagaa tctctcagcc tccagacccc aggaccggca gttcatcctg   300
agttctaaga agctccttct cagtgactct ggcttctatg agacctaa                 348
```

<210> SEQ ID NO 259
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 259

```
Ala Gly Arg Leu Val Asp Gln Gly Gly Lys Leu Ile Phe
1               5                   10
```

<210> SEQ ID NO 260
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 260

```
Ala Ser Ser Ile Gly Leu Ala Gly Tyr Glu Gln Tyr Phe
1               5                   10
```

<210> SEQ ID NO 261
<211> LENGTH: 9
<212> TYPE: PRT
<213> ORGANISM: Influenza A virus

<400> SEQUENCE: 261

```
Val Ser Asp Gly Gly Pro Asn Leu Tyr
1               5
```

<210> SEQ ID NO 262
<211> LENGTH: 9
<212> TYPE: PRT
<213> ORGANISM: Influenza A virus

<400> SEQUENCE: 262

```
Cys Thr Glu Leu Lys Leu Ser Asp Tyr
```

```
1               5

<210> SEQ ID NO 263
<211> LENGTH: 9
<212> TYPE: PRT
<213> ORGANISM: Influenza A virus

<400> SEQUENCE: 263

Phe Met Tyr Ser Asp Phe His Phe Ile
1               5

<210> SEQ ID NO 264
<211> LENGTH: 9
<212> TYPE: PRT
<213> ORGANISM: Epstein-Barr virus

<400> SEQUENCE: 264

Cys Leu Gly Gly Leu Leu Thr Met Val
1               5

<210> SEQ ID NO 265
<211> LENGTH: 9
<212> TYPE: PRT
<213> ORGANISM: Epstein-Barr virus

<400> SEQUENCE: 265

Gly Leu Cys Thr Leu Val Ala Met Leu
1               5

<210> SEQ ID NO 266
<211> LENGTH: 9
<212> TYPE: PRT
<213> ORGANISM: Human cytomegalovirus

<400> SEQUENCE: 266

Asn Leu Val Pro Met Val Ala Thr Val
1               5

<210> SEQ ID NO 267
<211> LENGTH: 9
<212> TYPE: PRT
<213> ORGANISM: Influenza A virus

<400> SEQUENCE: 267

Lys Thr Gly Gly Pro Ile Tyr Lys Arg
1               5

<210> SEQ ID NO 268
<211> LENGTH: 10
<212> TYPE: PRT
<213> ORGANISM: Influenza A virus

<400> SEQUENCE: 268

Arg Val Leu Ser Phe Ile Lys Gly Thr Lys
1               5                   10

<210> SEQ ID NO 269
<211> LENGTH: 9
<212> TYPE: PRT
<213> ORGANISM: Influenza A virus

<400> SEQUENCE: 269

Ile Leu Arg Gly Ser Val Ala His Lys
1               5
```

<210> SEQ ID NO 270
<211> LENGTH: 9
<212> TYPE: PRT
<213> ORGANISM: Epstein-Barr virus

<400> SEQUENCE: 270

Arg Val Arg Ala Tyr Thr Tyr Ser Lys
1               5

<210> SEQ ID NO 271
<211> LENGTH: 9
<212> TYPE: PRT
<213> ORGANISM: Epstein-Barr virus

<400> SEQUENCE: 271

Arg Leu Arg Ala Glu Ala Gln Val Lys
1               5

<210> SEQ ID NO 272
<211> LENGTH: 9
<212> TYPE: PRT
<213> ORGANISM: Influenza A virus

<400> SEQUENCE: 272

Ser Ile Ile Pro Ser Gly Pro Leu Lys
1               5

<210> SEQ ID NO 273
<211> LENGTH: 10
<212> TYPE: PRT
<213> ORGANISM: Epstein-Barr virus

<400> SEQUENCE: 273

Ala Val Phe Asp Arg Lys Ser Asp Ala Lys
1               5                   10

<210> SEQ ID NO 274
<211> LENGTH: 9
<212> TYPE: PRT
<213> ORGANISM: Epstein-Barr virus

<400> SEQUENCE: 274

Ile Val Thr Asp Phe Ser Val Ile Lys
1               5

<210> SEQ ID NO 275
<211> LENGTH: 9
<212> TYPE: PRT
<213> ORGANISM: Epstein-Barr virus

<400> SEQUENCE: 275

Ala Thr Ile Gly Thr Ala Met Tyr Lys
1               5

<210> SEQ ID NO 276
<211> LENGTH: 10
<212> TYPE: PRT
<213> ORGANISM: Epstein-Barr virus

<400> SEQUENCE: 276

Asp Tyr Cys Asn Val Leu Asn Lys Glu Phe
1               5                   10

<210> SEQ ID NO 277

<211> LENGTH: 9
<212> TYPE: PRT
<213> ORGANISM: Influenza A virus

<400> SEQUENCE: 277

Leu Pro Phe Asp Lys Thr Thr Val Met
1               5

<210> SEQ ID NO 278
<211> LENGTH: 9
<212> TYPE: PRT
<213> ORGANISM: Epstein-Barr virus

<400> SEQUENCE: 278

Arg Pro Pro Ile Phe Ile Arg Arg Leu
1               5

<210> SEQ ID NO 279
<211> LENGTH: 9
<212> TYPE: PRT
<213> ORGANISM: Influenza A virus

<400> SEQUENCE: 279

Glu Leu Arg Ser Arg Tyr Trp Ala Ile
1               5

<210> SEQ ID NO 280
<211> LENGTH: 8
<212> TYPE: PRT
<213> ORGANISM: Epstein-Barr virus

<400> SEQUENCE: 280

Arg Ala Lys Phe Lys Gln Leu Leu
1               5

<210> SEQ ID NO 281
<211> LENGTH: 9
<212> TYPE: PRT
<213> ORGANISM: Epstein-Barr virus

<400> SEQUENCE: 281

Phe Leu Arg Gly Arg Ala Tyr Gly Leu
1               5

<210> SEQ ID NO 282
<211> LENGTH: 9
<212> TYPE: PRT
<213> ORGANISM: Epstein-Barr virus

<400> SEQUENCE: 282

Gln Ala Lys Trp Arg Leu Gln Thr Leu
1               5

<210> SEQ ID NO 283
<211> LENGTH: 12
<212> TYPE: PRT
<213> ORGANISM: Human cytomegalovirus

<400> SEQUENCE: 283

Ser Asp Glu Glu Glu Ala Ile Val Ala Tyr Thr Leu
1               5                   10

<210> SEQ ID NO 284
<211> LENGTH: 9
<212> TYPE: PRT

```
<213> ORGANISM: Influenza A virus

<400> SEQUENCE: 284

Ser Arg Tyr Trp Ala Ile Arg Thr Arg
1               5

<210> SEQ ID NO 285
<211> LENGTH: 8
<212> TYPE: PRT
<213> ORGANISM: Influenza A virus

<400> SEQUENCE: 285

Ala Ser Cys Met Gly Leu Ile Tyr
1               5

<210> SEQ ID NO 286
<211> LENGTH: 9
<212> TYPE: PRT
<213> ORGANISM: Epstein-Barr virus

<400> SEQUENCE: 286

Arg Arg Ile Tyr Asp Leu Ile Glu Leu
1               5

<210> SEQ ID NO 287
<211> LENGTH: 9
<212> TYPE: PRT
<213> ORGANISM: Epstein-Barr virus

<400> SEQUENCE: 287

Tyr Pro Leu His Glu Gln His Gly Met
1               5

<210> SEQ ID NO 288
<211> LENGTH: 9
<212> TYPE: PRT
<213> ORGANISM: Cytomegalovirus

<400> SEQUENCE: 288

Ile Pro Ser Ile Asn Val His His Tyr
1               5

<210> SEQ ID NO 289
<211> LENGTH: 10
<212> TYPE: PRT
<213> ORGANISM: Epstein-Barr virus

<400> SEQUENCE: 289

Glu Glu Asn Leu Leu Asp Phe Val Arg Phe
1               5                   10

<210> SEQ ID NO 290
<211> LENGTH: 10
<212> TYPE: PRT
<213> ORGANISM: Human cytomegalovirus

<400> SEQUENCE: 290

Glu Phe Phe Trp Asp Ala Asn Asp Ile Tyr
1               5                   10

<210> SEQ ID NO 291
<211> LENGTH: 10
<212> TYPE: PRT
<213> ORGANISM: Human cytomegalovirus
```

```
<400> SEQUENCE: 291

Thr Pro Arg Val Thr Gly Gly Gly Ala Met
1               5                   10
```